United States Patent
Veal et al.

(10) Patent No.: US 11,939,335 B2
(45) Date of Patent: Mar. 26, 2024

(54) SUBSTITUTED IMIDAZO[1,2-A]QUINAZOLINES AND IMIDAZO[1,2-A]PYRIDO[4,3-E]PYRIMIDINES AS INHIBITORS OF PARG

(71) Applicant: 858 Therapeutics, Inc., San Diego, CA (US)

(72) Inventors: James M. Veal, Solana Beach, CA (US); Jeffrey A. Stafford, Rancho Santa Fe, CA (US); Donald S. Karanewsky, Escondido, CA (US); Shyama Herath, San Diego, CA (US)

(73) Assignee: 858 THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 18/199,900

(22) Filed: May 19, 2023

(65) Prior Publication Data
US 2023/0374022 A1    Nov. 23, 2023

Related U.S. Application Data

(63) Continuation of application No. PCT/US2023/022390, filed on May 16, 2023.

(60) Provisional application No. 63/343,005, filed on May 17, 2022.

(51) Int. Cl.
| | | |
|---|---|---|
| A61K 31/519 | (2006.01) | |
| C07D 487/04 | (2006.01) | |
| C07D 487/14 | (2006.01) | |
| C07D 491/147 | (2006.01) | |
| C07D 491/20 | (2006.01) | |
| C07D 519/00 | (2006.01) | |

(52) U.S. Cl.
CPC ....... *C07D 487/04* (2013.01); *C07D 491/147* (2013.01); *C07D 491/20* (2013.01); *C07D 519/00* (2013.01); *C07B 2200/05* (2013.01)

(58) Field of Classification Search
CPC .......................... A61K 31/519; C07D 487/14
USPC ............................................ 514/267; 544/252
See application file for complete search history.

(56) References Cited

U.S. PATENT DOCUMENTS

| | | | |
|---|---|---|---|
| 5,846,514 | A | 12/1998 | Foster et al. |
| 6,334,997 | B1 | 1/2002 | Foster et al. |
| 2015/0353526 | A1 | 12/2015 | Angibaud et al. |
| 2018/0016242 | A1 | 1/2018 | Mcgonagle et al. |
| 2021/0355103 | A1 | 11/2021 | Yu et al. |

FOREIGN PATENT DOCUMENTS

| | | |
|---|---|---|
| WO | WO-2016092326 A1 | 6/2016 |
| WO | WO-2016097749 A1 | 6/2016 |
| WO | WO-2018237296 A1 | 12/2018 |
| WO | WO-2020023802 A1 | 1/2020 |
| WO | WO-2020205646 A2 | 10/2020 |
| WO | WO-2021055744 A1 | 3/2021 |
| WO | WO-2023052363 A1 | 4/2023 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag Gmbh & Co. KGaA, 2005, Preface.*
Vippagunta, et al. Advanced Drug Delivery Reviews, 48, 2001, 18.*
Berge et al. Pharmaceutical Salts. Journal of Pharmaceutical Sciences 66(1):1-19 (Jan. 1977).
Dean. Recent Advances in the Synthesis and Applications of Radiolabeled Compounds for Drug Discovery and Development. In: Curr. Pharm. Des., 6(10):110 (2000) (Preface only).
Ding et al., Two B-Box Domain Proteins, BBX18 and BBX23, Interact with ELF3 and Regulate Thermomorphogenesis in *Arabidopsis*. Cell Reports 25(7):1718-1728.e4 (2018).
Evans. Synthesis of radiolabeled compounds. J Radioanal Chem 64(1-2):9-32 (1981).
Kabalka et al. The Synthesis of Radiolabeled Compounds via Organometallic Intermediates. Tetrahedron 45(21):6601-6621 (1989).

(Continued)

*Primary Examiner* — Douglas M Willis
(74) *Attorney, Agent, or Firm* — WILSON SONSINI GOODRICH & ROSATI

(57) ABSTRACT

Provided herein are inhibitors of PARG, pharmaceutical compositions comprising the inhibitory compounds, and methods for using the PARG inhibitory compounds for the treatment of disease. Said inhibitors of PARG have the structure provided in Formula (I):

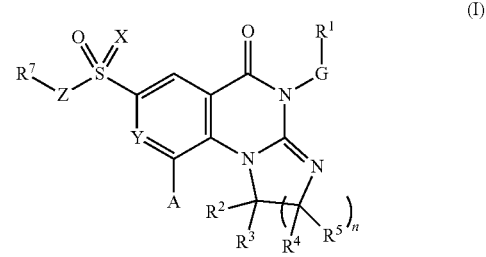

as represented, for example, by Example 1:

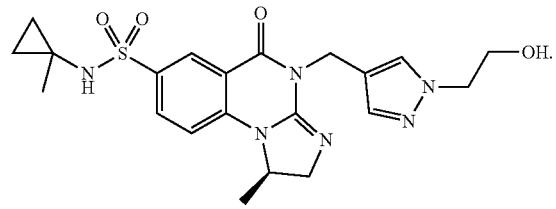

28 Claims, No Drawings

(56) References Cited

OTHER PUBLICATIONS

Pilger et al., Interfaces between cellular responses to DNA damage and cancer immunotherapy. Genes Dev. 35(9-10):602-618 (2021).
Reislander et al., BRCA2 abrogation triggers innate immune responses potentiated by treatment with PARP inhibitors. Nature Comm 10(1):3143 (2019).
SciFinder Chemical Structure Search 1 dated May 16, 2023.
SciFinder Chemical Structure Search 2 dated May 16, 2023.
SciFinder Chemical Structure Search 3 dated May 16, 2023.
Houl et al. Selective small molecule PARG inhibitor causes replication fork stalling and cancer cell death. Nat Commun 10(1):5654 (2019).
PCT/US2023/022390 International Search Report and Written Opinion dated Aug. 24, 2023.

* cited by examiner

SUBSTITUTED IMIDAZO[1,2-A]QUINAZOLINES AND IMIDAZO [1,2-A]PYRIDO[4,3-E]PYRIMIDINES AS INHIBITORS OF PARG

CROSS-REFERENCE TO RELATED APPLICATION

This application is a continuation of PCT International Application No. PCT/US23/22390, filed May 16, 2023, which claims the benefit of U.S. Patent Application No. 63/343,005, filed on May 17, 2022, each of which is incorporated by reference in their entirety.

BACKGROUND

Poly(ADP-ribose)glycohydrolase (PARG) is an enzyme involved in DNA replication and repair, and PARG depleted or inhibited cells show an increased sensitivity to DNA damaging agents. PARG inhibitors are anticipated to have utility as a cancer treatment both as single agents and in combination with therapeutic agents and radiotherapy.

BRIEF SUMMARY OF THE INVENTION

Provided herein are inhibitors of PARG, pharmaceutical compositions comprising said inhibitory compounds, and methods for using said inhibitory compounds for the treatment of disease.

One embodiment provides a compound, or a pharmaceutically acceptable salt or solvate thereof, having the structure of Formula (I):

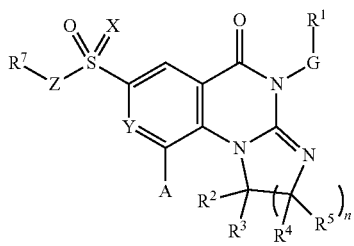

(I)

wherein,
  A is selected from the group consisting of hydrogen, halo, —OH, —CN, optionally substituted C1-C6 alkoxy, —N($R^9$)$_2$, optionally substituted C1-C6 alkyl, optionally substituted C2-C6 alkenyl, optionally substituted C2-C6 alkynyl, optionally substituted C3-C7 carbocyclyl, optionally substituted carbocyclylalkyl, optionally substituted (carbocyclyl)alkynyl, optionally substituted heterocyclyl, optionally substituted heterocyclylalkyl, optionally substituted heteroaryl, and optionally substituted aryl;
  n is 1, 2, or 3;
  X is O, or $NR^6$;
  Y is N, C—H, or C—F;
  Z is —N(H)— or —CH($R^8$)—;
  G is a bond, optionally substituted cycloalkylene, or optionally substituted heterocycloalkylene;
  $R^1$ is selected from the group consisting of optionally substituted alkyl, optionally substituted alkenyl, optionally substituted alkynyl, optionally substituted cycloalkylalkyl, optionally substituted aralkyl, optionally substituted heterocyclylalkyl, and optionally substituted heteroaralkyl;
  $R^2$ and $R^3$ are independently selected from the group consisting of hydrogen, halo, —OH, —CN, optionally substituted alkyl, optionally substituted alkenyl, optionally substituted alkynyl, optionally substituted cycloalkyl, optionally substituted cycloalkylalkyl, optionally substituted (cycloalkyl)alkynyl, optionally substituted heterocyclyl, optionally substituted heterocyclylalkyl, optionally substituted heteroaryl, and optionally substituted aryl; optionally, $R^2$ and $R^3$ combine to form an optionally substituted carbocyclic or heterocyclic ring;
  $R^4$ and $R^5$ are independently selected from the group consisting of hydrogen, halo, —OH, —CN, optionally substituted alkyl, optionally substituted alkenyl, optionally substituted alkynyl, optionally substituted cycloalkyl, optionally substituted cycloalkylalkyl, optionally substituted (cycloalkyl)alkynyl, optionally substituted heterocyclyl, optionally substituted heterocyclylalkyl, optionally substituted heteroaryl, and optionally substituted aryl; optionally, $R^4$ and $R^5$ combine to form an optionally substituted carbocyclic or heterocyclic ring, or $R^3$ and $R^4$ combine to form an optionally substituted carbocyclic or heterocyclic ring;
  $R^6$ is selected from hydrogen, OH, or optionally substituted C1-C5 alkyl;
  $R^7$ is optionally substituted alkyl, optionally substituted cycloalkyl, or an optionally substituted 1,1'-bi(cyclopropan)-1-yl;
  $R^8$ is hydrogen, halo, or an optionally substituted alkyl; and
  each $R^9$ is independently hydrogen or an optionally substituted C1-C6 alkyl.

One embodiment provides a pharmaceutical composition comprising a compound of Formula (I), or a pharmaceutically acceptable salt or solvate thereof, and at least one pharmaceutically acceptable excipient.

One embodiment provides a method of treating a disease or disorder in a patient in need thereof comprising administering to the patient a compound of Formula (I), or a pharmaceutically acceptable salt or solvate thereof. Another embodiment provides the method wherein the disease or disorder is cancer.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_8$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl). In certain embodiments, an optionally substituted alkyl is a haloalkyl. In other embodiments, an optionally substituted alkyl is a fluoroalkyl. In other embodiments, an optionally substituted alkyl is a —$CF_3$ group.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_8$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises two carbon atoms (e.g., $C_2$ alkenylene). In other embodiments, an alkenylene comprises five to eight carbon atoms (e.g., $C_5$-$C_8$ alkenylene). In other embodiments, an alkenylene comprises three to five carbon atoms (e.g., $C_3$-$C_5$ alkenylene).

Unless stated otherwise specifically in the specification, an alkenylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—

$R^a$, —$N(R^a)_2$, —$C(O)R^a$, —$C(O)OR^a$, —$C(O)N(R^a)_2$, —$N(R^a)C(O)OR^a$, —$OC(O)$—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from optionally substituted alkyl, optionally substituted alkenyl, optionally substituted alkynyl, halo, cyano, nitro, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from optionally substituted alkyl, optionally substituted alkenyl, optionally substituted alkynyl, halo, oxo, thioxo, cyano, nitro, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic, or tetracyclic ring system, which optionally includes spiro, fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In some embodiments, the heterocyclyl radical includes 2-oxa-7-azaspiro[3.5]nonanyl. Unless stated otherwise specifically in the specification, the term "heterocyclyl" is meant to include heterocyclyl radicals as defined above that are optionally substituted by one or more substituents selected from optionally substituted alkyl, optionally substituted alkenyl, optionally substituted alkynyl, halo, fluoroalkyl, oxo, thioxo, cyano, nitro, —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N(R^a)S(O)$_t$R^a$ (where t is 1 or 2), —$R^b$—S(O)$_t$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen, and sulfur. As used herein, the heteroaryl radical is a monocyclic, bicyclic, tricyclic, or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). In some embodiments, the heteroaryl includes 5,6-dihydro-4H-pyrrolo[1,2-b]pyrazol-3-yl and 6,7-dihydro-5H-pyrazolo[5,1-b][1,3]oxazin-3-yl. Unless stated otherwise specifically in the specification, the term "heteroaryl" is meant to include heteroaryl radicals as defined above which are optionally substituted by one or more substituents selected from optionally substituted alkyl, optionally substituted cycloalkylalkyl, optionally substituted heterocyclylalkyl, optionally substituted alkenyl, optionally substituted alkynyl, halo, optionally substituted fluoroalkyl, optionally substituted haloalkenyl, optionally substituted haloalkynyl, oxo, thioxo, cyano, nitro, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

As used herein, "carboxylic acidbioisostere" refers to a functional group or moiety that exhibits similar physical, biological and/or chemical properties as a carboxylic acid moiety. Examples of carboxylic acid bioisosteres include, but are not limited to,

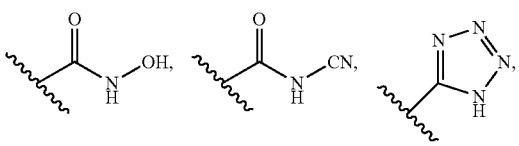

-continued

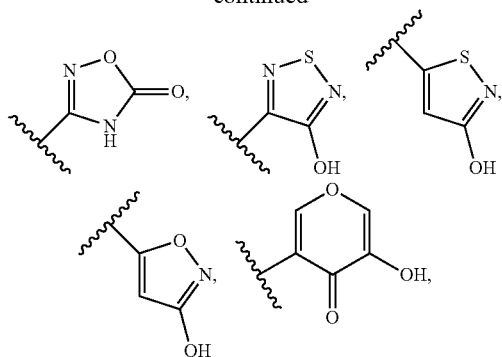

and the like.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. In some embodiments, isotopic substitution with $^{18}F$ is contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

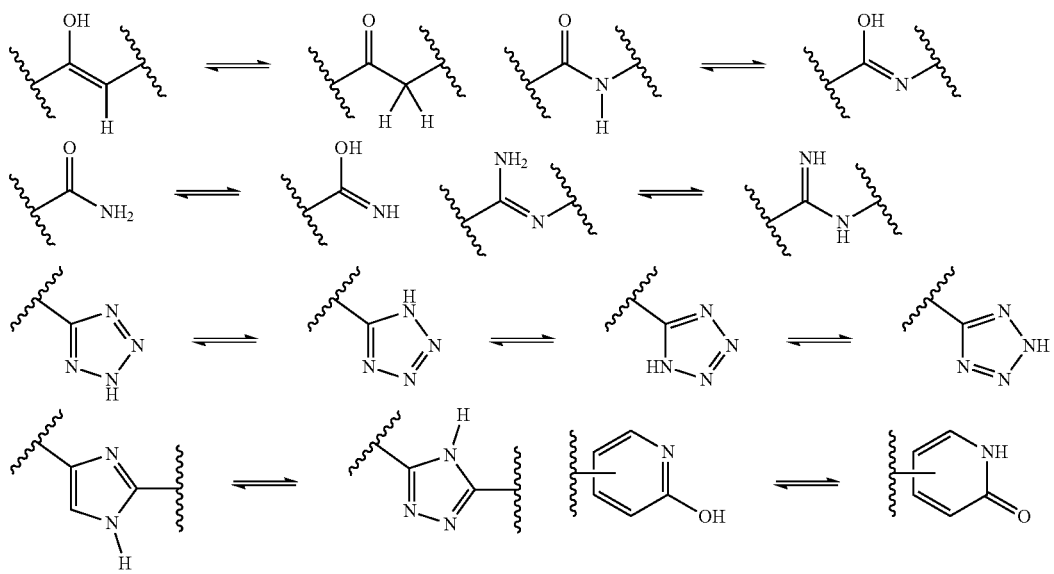

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-$d_3$ ($CD_3I$), are readily available and may be employed to transfer a deuterium-substituted carbon atom under nucleophilic substitution reaction conditions to the reaction substrate. The use of $CD_3I$ is illustrated, by way of example only, in the reaction schemes below.

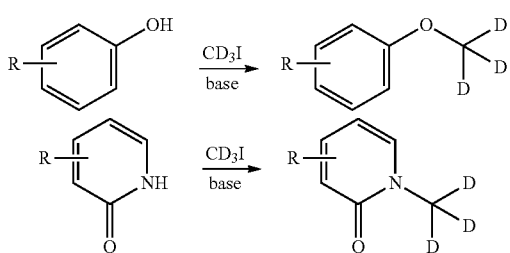

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the reaction schemes below.

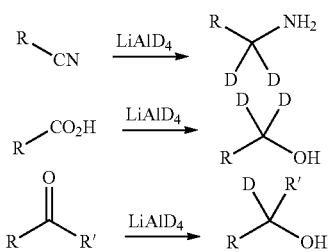

Deuterium gas and palladium catalyst are employed to reduce unsaturated carbon-carbon linkages and to perform a reductive substitution of aryl carbon-halogen bonds as illustrated, by way of example only, in the reaction schemes below.

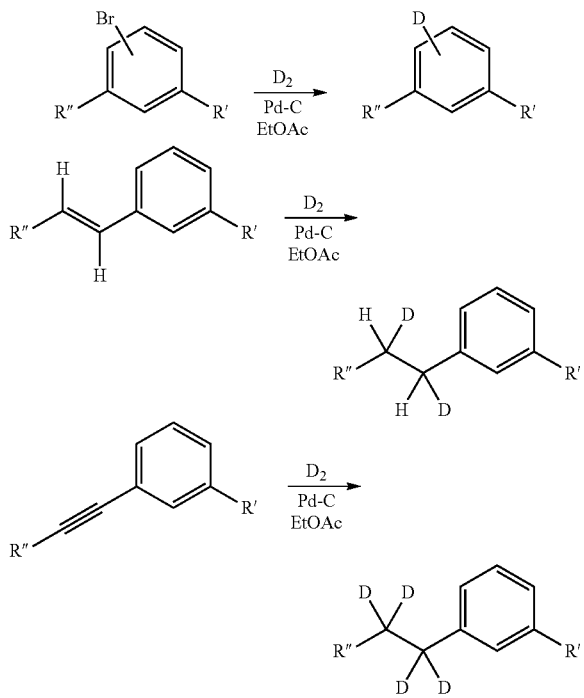

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1$H hydrogen atoms. In one embodiment, the level of deuterium incorporation is determined by synthetic methods in which a deuterated synthetic building block is used as a starting material.

"A pharmaceutically acceptable salt" includes both acid and base addition salts. A pharmaceutically acceptable salt of any one of the PARG inhibitory compounds described herein is intended to encompass any and all pharmaceutically suitable salt forms. Preferred a pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are notbiologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. The compounds provided herein exist in either unsolvated or solvated forms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

Poly(ADP-ribose) Glycohydrolase

DNA single-strand breaks (SSBs) are the most common type of lesion arising in cells and poly (ADP-ribose) glycohydrolase (PARG), together with poly(ADP-ribose) polymerase (PARP), is involved, along with a number of other proteins, in SSB repair and another repair mechanism called base excision repair. PARG, as well as PARP, is involved in DNA replication and repair, and PARG depleted or inhibited cells show an increased sensitivity to DNA damaging agents. PARG can reverse the action of PARP enzymes by hydrolyzing the ribose bonds present in poly(ADP-ribose) (PAR). PARG is the primary hydrolase involved in the degradation of PAR, with endo-glycohydrolase and exo-glycohydrolase activity, and is one of the hydrolases responsible for rapid removal of ADP-ribose moieties from modified proteins to recycle $NAD^+$ back into the cellular system.

PARG inhibition may provide a therapeutic advantage in PARP inhibitor resistant cells. Furthermore, depletion of PARG has been reported to lead to a markedly different gene expression pattern to that of PARP depletion in breast cancer cells. Although current models show that PARG depletion leads to PARP-dependent effects on DNA repair, recent research has shown a mechanistic differentiation from PARP inhibition. Following a genotoxic stimulus depletion of PARG, in contrast to PARP depletion, leads to a drop in NAD levels. This leads to lung cancer cell death that may be as a result of energy failure.

PARG exists as a single gene with isoforms that reside in the nucleus, mitochondria, and cytosol. The only other known protein with glycohydrolase activity is ARH3 which is localized to the mitochondria. Although, known primarily for its direct role in DNA repair, PARG impacts PAR signaling in splicing, transcriptional and epigenetic pathways. PARG can play a role in preventing the accumulation of cytoplasmic PAR, and also parthanatos, a PAR-mediated type of cell death. Accumulation of perturbed replication intermediates can lead to synthetic lethality in certain situations. PARG inhibitors can have uses as a cancer treatment both as single agents and in combination with therapeutic agents and radiotherapy.

Cancer cells may thrive from the utilization of a specific DNA repair pathway when other mechanisms of DNA repair are non-functional. Tumors carrying mutations in proteins involved in double strand break repair are often more sensitive to PARP inhibitors of SSB repair. There is already some evidence that PARG depletion inhibits SSB repair and reduces survival of BRCA2-deficient cells. However, other tumor mutations may give rise to deficiencies in double strand DNA repair mechanisms (so-called "BRCA-ness") thereby sensitizing tumor cells to PARG inhibition.

PARG depletion has been studied in a number of murine and human model systems. Murine cells that are null or depleted for PARG display an increased sensitivity to experimental and clinical DNA damaging agents. However, as deficiency in PARG does not sensitize to all agents (e.g. gemcitabine, camptothecin) this suggests a specificity for PARG function with certain pathways of DNA damage repair and chemo- and radiotherapies. In humans, PARG depletion sensitizes lung, cervical and pancreatic cancer cells to γ-irradiation or experimental DNA damaging agents (e.g. hydrogen peroxide, methylmethanesulfonate).

In humans, the PARG gene is in a single chromosome, at the locus 10q11.23-21, but can be subjected to alternative splicing, resulting in different PARG isoforms, such as $PARG_{111}$, $PARG_{102}$, $PARG_{99}$, $PARG_{60}$, $PARG_{55}$. Different PARG isoforms can be localized in different subcellular locations. For example, $PARG_{111}$, which is the largest isoform, can be localized in the nucleus and translocate to the cytoplasm. $PARG_{111}$ has four domains, the PARG catalytic domain, a macrodomain, an intrinsically disordered regulatory region, and a hinge domain. $PARG_{102}$ and $PARG_{99}$, which lack part of the N-terminal domain, can be localized in the cytoplasm, and have perinuclear distribution which can translate to the nucleus. $PARG_{102}$ and $PARG_{99}$ have a greater degree of whole cell activity. $PARG_{60}$ and $PARG_{55}$ can be localized in the mitochondria and lack catalytic activity.

PARG can function along with PARP for DNA repair. The PARP family of enzymes have at least 17 members, of which PARP1-3 are localized to the nucleus and implicated in many cellular processes. The nuclear PARP enzymes are part of the DNA repair, as well as in transcription, chromatin modification, and cell death pathways. PARP1-3 contain DNA binding domains to facilitate interactions with DNA and are activated by DNA damage. One of the ways PARP1-3 function is through addition of a large post-translation modification onto other proteins and themselves, which PARG can reverse. By inhibiting PARG, it can alter the kinetics of dePARylation, which results in proteins being inappropriately modified.

PARG Enzyme Function

PARG and PARP can co-operate together to facilitate downstream cellular processes. Exo-glycohydrolase activity of PARG includes binding to the two most distal ADP-ribose residues within the PARG chain, resulting in free PAR and mono-ADP-ribose moieties. The mono-ADP-ribose is the metabolized by ADP-ribose pyrophosphohydrolase into AMP and ribose 5' phosphate. AMP is then utilized in the cell signaling pathway while ribose can be utilized for other biomolecules such as, but not limited to DNA and RNA. The PARG endo-glycohydrolase activity can occur through hyper-PARP activity, which results in free PAR chains produced. The free PAR chains may be linked to apoptosis and function to signal cellular death.

PARG also functions to maintain stable levels of PAR to protect the cell against parthanatos, which is triggered by the release of the apoptosis-inducing factor (AIF) from the mitochondria to the nucleus. Within the nucleus chromatin environment, AIF can lead to large-scale DNA fragmentation and chromatic condensation, leading to cell death. Depletion of PARG can prevent release of AIF from the mitochondria, to protect against the oxidative stress-induced parthanatos. PARG can also have a useful function in telomere maintenance by negatively regulating access to telomeric DNA by reversing ADP-ribosylation of telomeric-specific protein TRF1. This leads to PARG contributing to the regulation of telomere repair and replication.

Inhibitors of PARP have been studied for cancers with defects in the DNA damage response mechanism as PARP enzymes can fulfill many functions of DNA repair, such as, but not limited to DNA single-strand breaks (Pilger et. al., Genes Dev. 2021). Immune response of PARP has been linked to DNA repairs, wherein DNA lesions can activate antitumor immunity. (Pilger et. al., Genes Dev. 2021). Studies have shown that PARP inhibitors can impact cellular innate and adaptive immune responses through the DNA damage and repair mechanism, highlighting the implication of PARP inhibitors for use in DNA damage response for therapeutic uses of immune checkpoint inhibitors, or use as biomarkers.

PARP enzymes can catalyze the addition of PAR subunits onto acceptor proteins and themselves. PARP inhibitors have been studied for cancer therapy, with success in treating ovarian, breast, and prostate cancer. PARP inhibitors have been found to treat defects in the homologous recombination DNA repair pathway, especially for BRCA1 and BRCA2 mutated tumors (Ding et al., Cell Reports 2018; Reislander et. al., Nature Comm. 2019). The BRCA-mutated cells may then be reliant on PARP mediated DNA repair and survival, and therefore sensitive to PARP inhibition.

Inhibitors of PARP have also shown clinical efficacy for subjects with BRCA mutations. PARP inhibitors can trigger local and systemic antitumor immunity can involve innate immune responses through a stimulator of interferon genes (STING) dependent pathway (Ding et al., Cell Reports 2018; Reislander et. al., Nature Comm. 2019). Studies have found that the STING-dependent type I interferons (IFN) signal may mediate the therapeutic effects of PARP inhibition in BRCA1 deficient tumors. Further, it was found that treatment with PARP inhibitors can stimulation the upregulation of IFN signaling genes in vitro and in vivo and can accelerate upregulation of innate immune responses in BRCA1 or BRCA 2 deficient tumors (Reislander et al., Nature Comm. 2019).

PARP inhibitors exhibit synthetic lethality with BRCA loss of function, which can be exploited for therapeutic treatment in ovarian cancer for monotherapy treatment in patents with germline or somatic BRCA 1 and BRCA 2 mutations or can be utilized as maintenance therapy after platinum chemotherapy for subjects which platinum-sensitive recurrent disease (Ding et al., Cell Reports 2018). Further studies suggest that addition of PD-1 blockade can prolong activity of PARP inhibitors by overcoming the increased expression of PD-LI on tumor cells which occur when the cells are treated with PARP inhibitors alone (Ding et al., Cell Reports 2018).

Prior Art PARG Inhibitors

PARG inhibitors have not been studied to the extent of PARP inhibitors. Clinical resistance to PARP inhibitors has already been described and therefore there is a need to discover alternative inhibitors targeting the DNA damage repair pathways. Previously described PARG inhibitors include bicyclic aryl and heteroaryl compounds as described in WO 2016/092326, WO 2016/097749, WO 2021/055744, WO 2018/237296, WO 2020/023802, and WO 2020/205646. There remains a need to find alternative PARG inhibitors that have potent stand-alone efficacy for DNA break repair cycle and also synergy with PARP inhibitors.

PARG Inhibitory Compounds

In one aspect, provided herein is a PARG inhibitory compound.

One embodiment provides a compound, or a pharmaceutically acceptable salt or solvate thereof, having the structure of Formula (I):

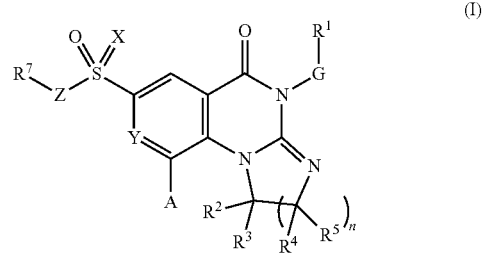

wherein,
- A is selected from the group consisting of hydrogen, halo, —OH, —CN, optionally substituted C1-C6 alkoxy, —N(R$^9$)$_2$, optionally substituted C1-C6 alkyl, optionally substituted C2-C6 alkenyl, optionally substituted C2-C6 alkynyl, optionally substituted C3-C7 carbocyclyl, optionally substituted carbocyclylalkyl, optionally substituted (carbocyclyl)alkynyl, optionally substituted heterocyclyl, optionally substituted heterocyclylalkyl, optionally substituted heteroaryl, and optionally substituted aryl;
- n is 1, 2, or 3;
- X is O, or NR$^6$;
- Y is N, C—H, or C—F;
- Z is —N(H)— or —CH(R$^8$)—;
- G is a bond, optionally substituted cycloalkylene, or optionally substituted heterocycloalkylene;

R[1] is selected from the group consisting of optionally substituted alkyl, optionally substituted alkenyl, optionally substituted alkynyl, optionally substituted cycloalkylalkyl, optionally substituted aralkyl, optionally substituted heterocyclylalkyl, and optionally substituted heteroaralkyl;

R[2] and R[3] are independently selected from the group consisting of hydrogen, halo, —OH, —CN, optionally substituted alkyl, optionally substituted alkenyl, optionally substituted alkynyl, optionally substituted cycloalkyl, optionally substituted cycloalkylalkyl, optionally substituted (cycloalkyl)alkynyl, optionally substituted heterocyclyl, optionally substituted heterocyclylalkyl, optionally substituted heteroaryl, and optionally substituted aryl; optionally, R[2] and R[3] combine to form an optionally substituted carbocyclic or heterocyclic ring;

R[4] and R[5] are independently selected from the group consisting of hydrogen, halo, —OH, —CN, optionally substituted alkyl, optionally substituted alkenyl, optionally substituted alkynyl, optionally substituted cycloalkyl, optionally substituted cycloalkylalkyl, optionally substituted (cycloalkyl)alkynyl, optionally substituted heterocyclyl, optionally substituted heterocyclylalkyl, optionally substituted heteroaryl, and optionally substituted aryl; optionally, R[4] and R[5] combine to form an optionally substituted carbocyclic or heterocyclic ring, or R[3] and R[4] combine to form an optionally substituted carbocyclic or heterocyclic ring;

R[6] is selected from hydrogen, OH, or optionally substituted C1-C5 alkyl;

R[7] is optionally substituted alkyl, optionally substituted cycloalkyl, or an optionally substituted 1,1'-bi(cyclopropan)-1-yl;

R[8] is hydrogen, halo, or an optionally substituted alkyl; and each R[9] is independently hydrogen or an optionally substituted C1-C6 alkyl.

Another embodiment provides the compound of Formula (I), or a pharmaceutically acceptable salt or solvate thereof, wherein A is hydrogen.

Another embodiment provides the compound of Formula (I), or a pharmaceutically acceptable salt or solvate thereof, wherein A is halo, —OH, or —CN.

Another embodiment provides the compound of Formula (I), or a pharmaceutically acceptable salt or solvate thereof, wherein A is optionally substituted C1-C6 alkoxy or —N(R[9])$_2$.

Another embodiment provides the compound of Formula (I), or a pharmaceutically acceptable salt or solvate thereof, wherein A is selected from the group consisting optionally substituted C1-C6 alkyl, optionally substituted C3-C7 carbocyclyl, and optionally substituted carbocyclylalkyl.

Another embodiment provides the compound of Formula (I), or a pharmaceutically acceptable salt or solvate thereof, wherein A is optionally substituted heterocyclyl or optionally substituted heterocyclylalkyl.

Another embodiment provides the compound of Formula (I), or a pharmaceutically acceptable salt or solvate thereof, wherein A is selected from optionally substituted heteroaryl or optionally substituted aryl.

One embodiment provides a compound, or a pharmaceutically acceptable salt or solvate thereof, of Formula (I) having the structure of Formula (Ia):

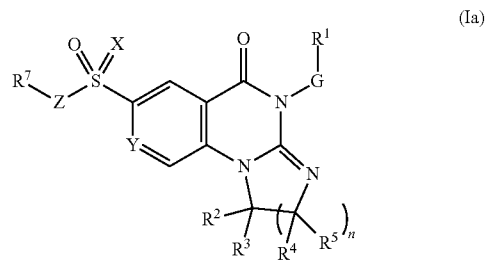

wherein,
n is 1, 2, or 3;
X is O, or NR[6];
Y is N, C—H, or C—F;
Z is —N(H)— or —CH(R[8])—;
G is a bond, optionally substituted cycloalkylene, or optionally substituted heterocycloalkylene;

R[1] is selected from the group consisting of optionally substituted alkyl, optionally substituted alkenyl, optionally substituted alkynyl, optionally substituted cycloalkylalkyl, optionally substituted aralkyl, optionally substituted heterocyclylalkyl, and optionally substituted heteroaralkyl;

R[2] and R[3] are independently selected from the group consisting of hydrogen, halo, —OH, —CN, optionally substituted alkyl, optionally substituted alkenyl, optionally substituted alkynyl, optionally substituted cycloalkyl, optionally substituted cycloalkylalkyl, optionally substituted (cycloalkyl)alkynyl, optionally substituted heterocyclyl, optionally substituted heterocyclylalkyl, optionally substituted heteroaryl, and optionally substituted aryl; optionally, R[2] and R[3] combine to form an optionally substituted carbocyclic or heterocyclic ring;

R[4] and R[5] are independently selected from the group consisting of hydrogen, halo, —OH, —CN, optionally substituted alkyl, optionally substituted alkenyl, optionally substituted alkynyl, optionally substituted cycloalkyl, optionally substituted cycloalkylalkyl, optionally substituted (cycloalkyl)alkynyl, optionally substituted heterocyclyl, optionally substituted heterocyclylalkyl, optionally substituted heteroaryl, and optionally substituted aryl; optionally, R[4] and R[5] combine to form an optionally substituted carbocyclic or heterocyclic ring, or R[3] and R[4] combine to form an optionally substituted carbocyclic or heterocyclic ring;

R[6] is selected from hydrogen, OH, or optionally substituted C1-C5 alkyl;

R[7] is optionally substituted alkyl, optionally substituted cycloalkyl, or an optionally substituted 1,1'-bi(cyclopropan)-1-yl; and R[8] is hydrogen, halo, or an optionally substituted alkyl.

Another embodiment provides the compound of Formula (I) or (Ia), or a pharmaceutically acceptable salt or solvate thereof, wherein n is 1. Another embodiment provides the compound of Formula (I) or (Ia), or a pharmaceutically acceptable salt or solvate thereof, wherein n is 2 or 3.

Another embodiment provides the compound of Formula (I) or (Ia), or a pharmaceutically acceptable salt or solvate thereof, wherein X is O. Another embodiment provides the compound of Formula (I) or (Ia), or a pharmaceutically acceptable salt or solvate thereof, wherein X is NR[6].

Another embodiment provides the compound of Formula (I) or (Ia), or a pharmaceutically acceptable salt or solvate thereof, wherein Y is N. Another embodiment provides the compound of Formula (I) or (Ia), or a pharmaceutically acceptable salt or solvate thereof, wherein Y is C—H. Another embodiment provides the compound of Formula (I) or (Ia), or a pharmaceutically acceptable salt or solvate thereof, wherein Y is C—F.

Another embodiment provides the compound of Formula (I) or (Ia), or a pharmaceutically acceptable salt or solvate thereof, wherein $R^1$ is optionally substituted alkyl. Another embodiment provides the compound of Formula (I) or (Ia), or a pharmaceutically acceptable salt or solvate thereof, wherein $R^1$ is optionally substituted C1-C4 alkyl. Another embodiment provides the compound of Formula (I) or (Ia), or a pharmaceutically acceptable salt or solvate thereof, wherein $R^1$ is optionally substituted C1-C4 alkyl and is substituted with at least one substituent selected from —CN, —$OR^8$, halo, oxo, —$N(R^8)_2$, or —$CON(R^8)_2$; wherein each $R^8$ is independently hydrogen, or optionally substituted C1-C4 alkyl.

Another embodiment provides the compound of Formula (I) or (Ia), or a pharmaceutically acceptable salt or solvate thereof, wherein $R^1$ is optionally substituted heteroaralkyl. Another embodiment provides the compound of Formula (I) or (Ia), or a pharmaceutically acceptable salt or solvate thereof, wherein $R^1$ is an optionally substituted heteroaralkyl, and the heteroaryl is selected from a 5- or a 6-membered heteroaryl. Another embodiment provides the compound of Formula (I) or (Ia), or a pharmaceutically acceptable salt or solvate thereof, wherein $R^1$ is an optionally substituted heteroaralkyl and the heteroaryl is selected from a 5-membered nitrogen-containing heteroaryl. Another embodiment provides the compound of Formula (I) or (Ia), or a pharmaceutically acceptable salt or solvate thereof, wherein the optionally substituted 5-membered nitrogen-containing heteroaryl is selected from optionally substituted thiazole, optionally substituted oxazole, optionally substituted imidazole, optionally substituted pyrazole, optionally substituted isoxazole, optionally substituted pyrrole, optionally substituted oxadiazole, optionally substituted triazole, optionally substituted thiadiazole, or optionally substituted isothiazole. Another embodiment provides the compound of Formula (I) or (Ia), or a pharmaceutically acceptable salt or solvate thereof, wherein the optionally substituted 5-membered nitrogen-containing heteroaryl is an optionally substituted pyrazole. Another embodiment provides the compound of Formula (I) or (Ia), or a pharmaceutically acceptable salt or solvate thereof, wherein the optionally substituted 5-membered nitrogen-containing heteroaryl is substituted with at least an optionally substituted C1-C5 alkyl. Another embodiment provides the compound of Formula (I) or (Ia), or a pharmaceutically acceptable salt or solvate thereof, wherein the optionally substituted C1-C5 alkyl is an optionally substituted C1 alkyl.

Another embodiment provides the compound of Formula (I) or (Ia), or a pharmaceutically acceptable salt or solvate thereof, wherein $R^1$ is optionally substituted heteroaralkyl and the alkylene is an optionally substituted C1-C4 alkylene. Another embodiment provides the compound of Formula (I) or (Ia), or a pharmaceutically acceptable salt or solvate thereof, wherein the optionally substituted C1-C4 alkylene is a —$CH_2$—.

Another embodiment provides the compound of Formula (I) or (Ia), or a pharmaceutically acceptable salt or solvate thereof, wherein $R^1$ is optionally substituted aralkyl. Another embodiment provides the compound of Formula (I) or (Ia), or a pharmaceutically acceptable salt or solvate thereof, wherein the optionally substituted aralkyl comprises an optionally substituted phenyl. Another embodiment provides the compound of Formula (I) or (Ia), or a pharmaceutically acceptable salt or solvate thereof, wherein the optionally substituted aralkyl comprises an optionally substituted C1-C4 alkylene. Another embodiment provides the compound of Formula (I) or (Ia), or a pharmaceutically acceptable salt or solvate thereof, wherein the optionally substituted C1-C4 alkylene is a —$CH_2$—. Another embodiment provides the compound of Formula (I) or (Ia), or a pharmaceutically acceptable salt or solvate thereof, wherein the heteroaryl is a 6-membered nitrogen-containing heteroaryl. Another embodiment provides the compound of Formula (I) or (Ia), or a pharmaceutically acceptable salt or solvate thereof, wherein the 6-membered nitrogen-containing heteroaryl is an optionally substituted pyridine or pyrazine.

Another embodiment provides the compound of Formula (I) or (Ia), or a pharmaceutically acceptable salt or solvate thereof, wherein $R^1$ is an optionally substituted C4-C7 cycloalkylalkyl. Another embodiment provides the compound of Formula (I) or (Ia), or a pharmaceutically acceptable salt or solvate thereof, wherein the optionally substituted cycloalkylalkyl is an optionally substituted cyclopropylmethyl.

Another embodiment provides the compound of Formula (I) or (Ia), or a pharmaceutically acceptable salt or solvate thereof, wherein $R^1$ is an optionally substituted heterocyclylalkyl. Another embodiment provides the compound of Formula (I) or (Ia), or a pharmaceutically acceptable salt or solvate thereof, wherein the optionally substituted heterocyclylalkyl is an optionally substituted oxetanylmethyl or optionally substituted pyrazolonylmethyl.

Another embodiment provides the compound of Formula (I) or (Ia), or a pharmaceutically acceptable salt or solvate thereof, wherein $R^4$ is hydrogen.

Another embodiment provides the compound of Formula (I) or (Ia), or a pharmaceutically acceptable salt or solvate thereof, wherein $R^5$ is hydrogen.

Another embodiment provides the compound of Formula (I) or (Ia), or a pharmaceutically acceptable salt or solvate thereof, wherein $R^3$ is hydrogen.

Another embodiment provides the compound of Formula (I) or (Ia), or a pharmaceutically acceptable salt or solvate thereof, wherein $R^2$ is not hydrogen. Another embodiment provides the compound of Formula (I) or (Ia), or a pharmaceutically acceptable salt or solvate thereof, wherein $R^2$ is an optionally substituted C1-C5 alkyl. Another embodiment provides the compound of Formula (I) or (Ia), or a pharmaceutically acceptable salt or solvate thereof, wherein the optionally substituted C1-C5 alkyl is an optionally substituted C1-C2 alkyl.

Another embodiment provides the compound of Formula (I) or (Ia), or a pharmaceutically acceptable salt or solvate thereof, wherein $R^2$ and $R^3$ are both optionally substituted C1-C5 alkyl.

Another embodiment provides the compound of Formula (I) or (Ia), or a pharmaceutically acceptable salt or solvate thereof, wherein $R^2$ and $R^3$ combine to form an optionally substituted carbocyclic or heterocyclic ring.

Another embodiment provides the compound of Formula (I) or (Ia), or a pharmaceutically acceptable salt or solvate thereof, wherein $R^2$ is an optionally substituted C1-C5 alkynyl.

Another embodiment provides the compound of Formula (I) or (Ia), or a pharmaceutically acceptable salt or solvate thereof, wherein $R^2$ is an optionally substituted heterocyclyl.

Another embodiment provides the compound of Formula (I) or (Ia), or a pharmaceutically acceptable salt or solvate thereof, wherein $R^7$ is optionally substituted C3-C5 cycloalkyl. Another embodiment provides the compound of Formula (I) or (Ia), or a pharmaceutically acceptable salt or solvate thereof, wherein the optionally substituted cycloalkyl is:

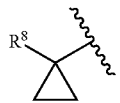

wherein $R^8$ is selected from the group consisting of hydrogen, —$CH_3$, —$CH_2F$, —$CHF_2$, —$CF_3$, —CN, cyclopropyl, —$CH_2CH_3$, —$CH(CH_3)_2$, and —$C(CH_3)_3$.

Another embodiment provides the compound of Formula (I) or (Ia), or a pharmaceutically acceptable salt or solvate thereof, wherein G is a bond. Another embodiment provides the compound of Formula (I) or (Ia), or a pharmaceutically acceptable salt or solvate thereof, wherein G is an optionally substituted cycloalkylene. Another embodiment provides the compound of Formula (I) or (Ia), or a pharmaceutically acceptable salt or solvate thereof, wherein G is an optionally substituted heterocycloalkylene.

Another embodiment provides the compound of Formula (I), or a pharmaceutically acceptable salt or solvate thereof, wherein Z is —N(H)—.

One embodiment provides an PARG inhibitory compound, or a pharmaceutically acceptable salt or solvate thereof, having a structure presented in Table 1.

TABLE 1

| Synthetic Chemistry Example | Compound Structure | Compound Name |
|---|---|---|
| 1 | 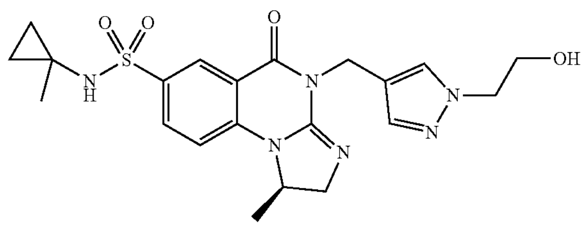 [SMILES: C[C@@H]1CN=C2N(Cc3cnn(CCO)c3)C(=O)c3cc(S(=O)(=O)NC4(C)CC4)ccc3N21] | (R)-4-((1-(2-hydroxyethyl)-1H-pyrazol-4-yl)methyl)-1-methyl-N-(1-methylcyclopropyl)-5-oxo-1,2,4,5-tetrahydroimidazo[1,2-a]quinazoline-7-sulfonamide |
| 2 | 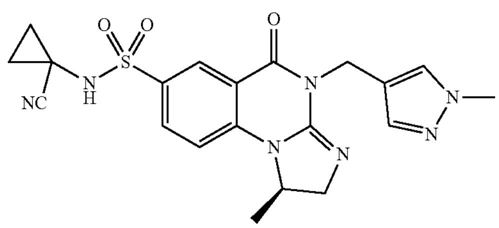 [SMILES: C[C@@H]1CN=C2N(Cc3cnn(C)c3)C(=O)c3cc(S(=O)(=O)NC4(C#N)CC4)ccc3N21] | (R)-N-(1-cyanocyclopropyl)-1-methyl-4-((1-methyl-1H-pyrazol-4-yl)methyl)-5-oxo-1,2,4,5-tetrahydroimidazo-[1,2-a]quinazoline-7-sulfonamide |
| 3 | 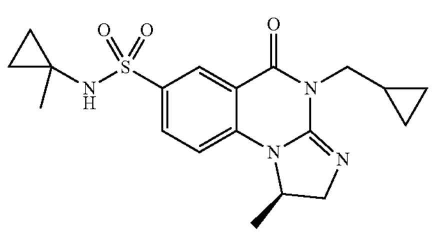 [SMILES: C[C@@H]1CN=C2N(CC3CC3)C(=O)c3cc(S(=O)(=O)NC4(C)CC4)ccc3N21] | (R)-4-(cyclopropylmethyl)-1-methyl-N-(1-methylcyclopropyl)-5-oxo-1,2,4,5-tetrahydroimidazo[1,2-a]quinazoline-7-sulfonamide |
| 4 | 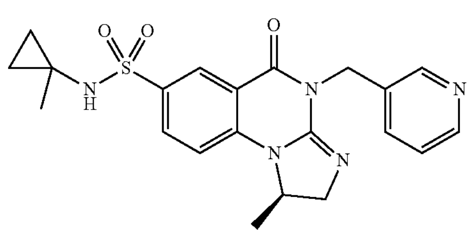 [SMILES: C[C@@H]1CN=C2N(Cc3cccnc3)C(=O)c3cc(S(=O)(=O)NC4(C)CC4)ccc3N21] | (R)-1-methyl-N-(1-methylcyclopropyl)-5-oxo-4-(pyridin-3-ylmethyl)-1,2,4,5-tetrahydroimidazo[1,2-a]-quinazoline-7-sulfonamide |

TABLE 1-continued

| Synthetic Chemistry Example | Compound Structure | Compound Name |
|---|---|---|
| 5 | 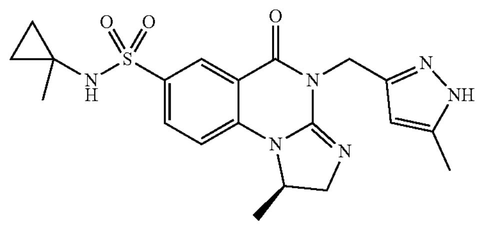 [SMILES: Cc1cc(CN2C(=O)c3cc(S(=O)(=O)NC4(C)CC4)ccc3N3C2=NC[C@H]3C)n[nH]1] | (R)-1-methyl-4-((5-methyl-1H-pyrazol-3-yl)methyl)-N-(1-methylcyclopropyl)-5-oxo-1,2,4,5-tetrahydroimidazo[1,2-a]quinazoline-7-sulfonamide |
| 6 | 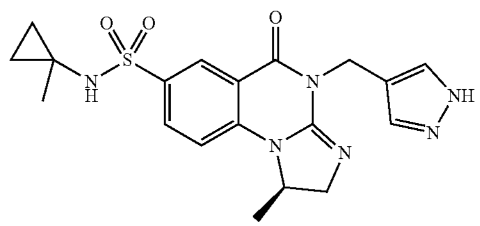 [SMILES: C[C@@H]1CN=C2N(Cc3cn[nH]c3)C(=O)c3cc(S(=O)(=O)NC4(C)CC4)ccc3N21] | (R)-4-((1H-pyrazol-4-yl)methyl)-1-methyl-N-(1-methylcyclopropyl)-5-oxo-1,2,4,5-tetrahydroimidazo[1,2-a]quinazoline-7-sulfonamide |
| 7 | 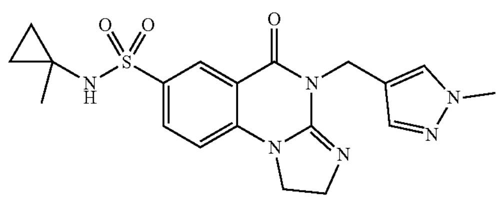 [SMILES: Cn1cc(CN2C(=O)c3cc(S(=O)(=O)NC4(C)CC4)ccc3N3CCN=C23)cn1] | 4-((1-methyl-1H-pyrazol-3-yl)methyl)-N-(1-methylcyclopropyl)-5-oxo-1,2,4,5-tetrahydroimidazo[1,2-a]quinazoline-7-sulfonamide |
| 8 | 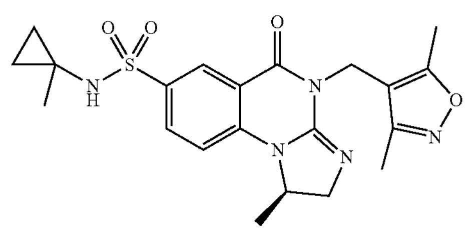 [SMILES: Cc1noc(C)c1CN1C(=O)c2cc(S(=O)(=O)NC3(C)CC3)ccc2N2C1=NC[C@H]2C] | (R)-4-((3,5-dimethylisoxazol-4-yl)methyl)-1-methyl-N-(1-methylcyclopropyl)-5-oxo-1,2,4,5-tetrahydroimidazo[1,2-a]quinazoline-7-sulfonamide |
| 9 | 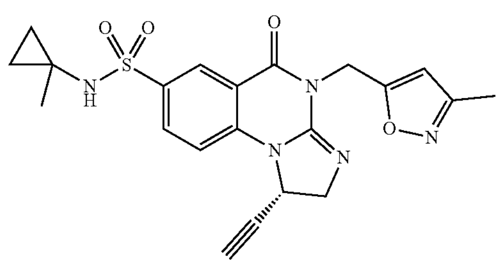 [SMILES: C#C[C@H]1CN=C2N(Cc3cc(C)no3)C(=O)c3cc(S(=O)(=O)NC4(C)CC4)ccc3N21] | (S)-1-ethynyl-N-(1-methylcyclopropyl)-4-((3-methylisoxazol-5-yl)methyl)-5-oxo-1,2,4,5-tetrahydroimidazo[1,2-a]quinazoline-7-sulfonamide |
| 10 | 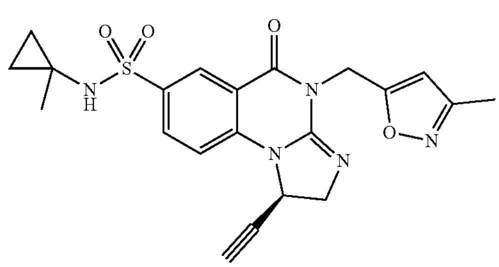 [SMILES: C#C[C@@H]1CN=C2N(Cc3cc(C)no3)C(=O)c3cc(S(=O)(=O)NC4(C)CC4)ccc3N21] | (R)-1-ethynyl-N-(1-methylcyclopropyl)-4-((3-methylisoxazol-5-yl)methyl)-5-oxo-1,2,4,5-tetrahydroimidazo[1,2-a]quinazoline-7-sulfonamide |

TABLE 1-continued

| Synthetic Chemistry Example | Compound Structure | Compound Name |
|---|---|---|
| 11 | 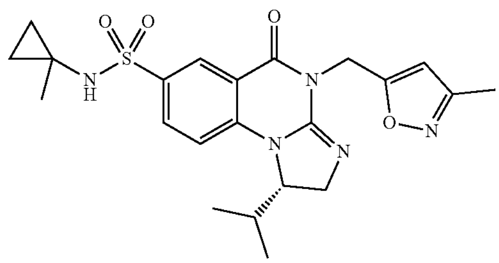 [SMILES: Cc1cc(CN2C(=O)c3cc(S(=O)(=O)NC4(C)CC4)ccc3N3C2=NC[C@@H]3C(C)C)on1] | (S)-1-isopropyl-N-(1-methyl-cyclopropyl)-4-((3-methyl-isoxazol-5-yl)methyl)-5-oxo-1,2,4,5-tetrahydroimidazo[1,2-a]quinazoline-7-sulfonamide |
| 12 | 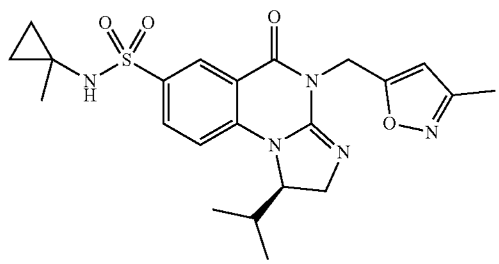 [SMILES: Cc1cc(CN2C(=O)c3cc(S(=O)(=O)NC4(C)CC4)ccc3N3C2=NC[C@H]3C(C)C)on1] | (R)-1-isopropyl-N-(1-methyl-cyclopropyl)-4-((3-methyl-isoxazol-5-yl)methyl)-5-oxo-1,2,4,5-tetrahydroimidazo[1,2-a]quinazoline-7-sulfonamide |
| 13 | 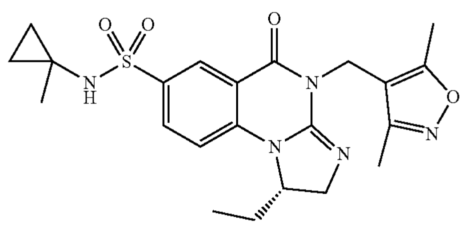 [SMILES: CC[C@H]1CN=C2N(Cc3c(C)noc3C)C(=O)c3cc(S(=O)(=O)NC4(C)CC4)ccc3N21] | (S)-4-((3,5-dimethylisoxazol-4-yl)methyl)-1-ethyl-N-(1-methylcyclopropyl)-5-oxo-1,2,4,5-tetrahydroimidazo[1,2-a]quinazoline-7-sulfonamide |
| 14 | 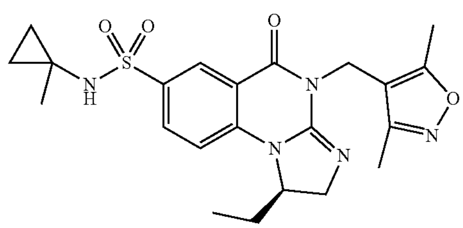 [SMILES: CC[C@@H]1CN=C2N(Cc3c(C)noc3C)C(=O)c3cc(S(=O)(=O)NC4(C)CC4)ccc3N21] | (R)-4-((3,5-dimethylisoxazol-4-yl)methyl)-1-ethyl-N-(1-methylcyclopropyl)-5-oxo-1,2,4,5-tetrahydroimidazo-[1,2-a]quinazoline-7-sulfonamide |
| 15 | 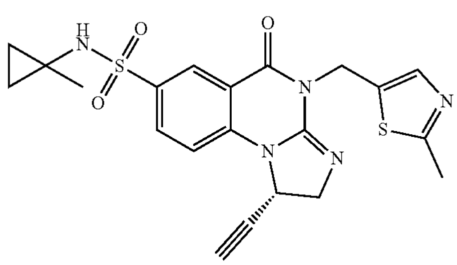 [SMILES: C#C[C@H]1CN=C2N(Cc3cnc(C)s3)C(=O)c3cc(S(=O)(=O)NC4(C)CC4)ccc3N21] | (S)-1-ethynyl-N-(1-methylcyclopropyl)-4-((2-methylthiazol-5-yl)methyl)-5-oxo-1,2,4,5-tetrahydroimidazo[1,2-a]quinazoline-7-sulfonamide |
| 16 | 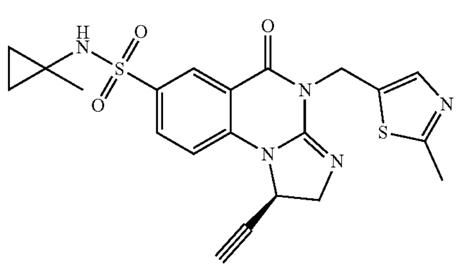 [SMILES: C#C[C@@H]1CN=C2N(Cc3cnc(C)s3)C(=O)c3cc(S(=O)(=O)NC4(C)CC4)ccc3N21] | (R)-1-ethynyl-N-(1-methylcyclopropyl)-4-((2-methylthiazol-5-yl)methyl)-5-oxo-1,2,4,5-tetrahydroimidazo[1,2-a]quinazoline-7-sulfonamide |

TABLE 1-continued

| Synthetic Chemistry Example | Compound Structure | Compound Name |
|---|---|---|
| 17 | 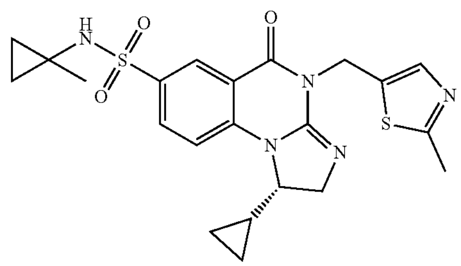 [SMILES: Cc1ncc(CN2C(=O)c3cc(S(=O)(=O)NC4(C)CC4)ccc3N3C2=NC[C@@H]3C2CC2)s1] | (S)-1-cyclopropyl-N-(1-methyl-cyclopropyl)-4-((2-methylthiazol-5-yl)methyl)-5-oxo-1,2,4,5-tetrahydroimidazo[1,2-a]-quinazoline-7-sulfonamide |
| 18 | 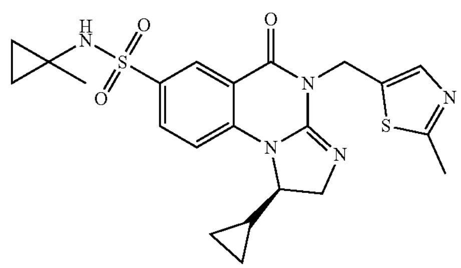 [SMILES: Cc1ncc(CN2C(=O)c3cc(S(=O)(=O)NC4(C)CC4)ccc3N3C2=NC[C@H]3C2CC2)s1] | (R)-1-cyclopropyl-N-(1-methyl-cyclopropyl)-4-((2-methylthiazol-5-yl)methyl)-5-oxo-1,2,4,5-tetrahydroimidazo[1,2-a]-quinazoline-7-sulfonamide |
| 19 | 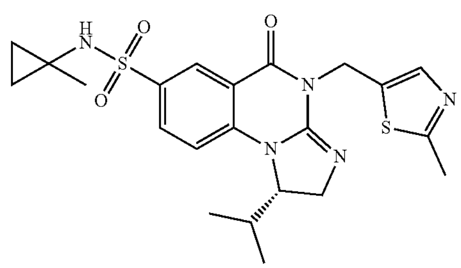 [SMILES: Cc1ncc(CN2C(=O)c3cc(S(=O)(=O)NC4(C)CC4)ccc3N3C2=NC[C@@H]3C(C)C)s1] | (S)-1-isopropyl-N-(1-methyl-cyclopropyl)-4-((2-methylthiazol-5-yl)methyl)-5-oxo-1,2,4,5-tetrahydroimidazo[1,2-a]-quinazoline-7-sulfonamide |
| 20 | 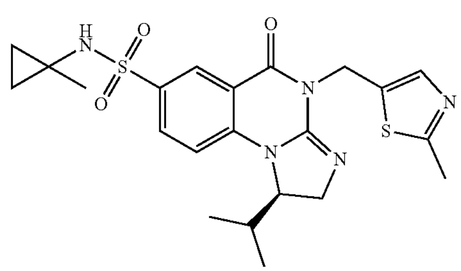 [SMILES: Cc1ncc(CN2C(=O)c3cc(S(=O)(=O)NC4(C)CC4)ccc3N3C2=NC[C@H]3C(C)C)s1] | (R)-1-isopropyl-N-(1-methyl-cyclopropyl)-4-((2-methylthiazol-5-yl)methyl)-5-oxo-1,2,4,5-tetrahydroimidazo[1,2-a]-quinazoline-7-sulfonamide |
| 21 | 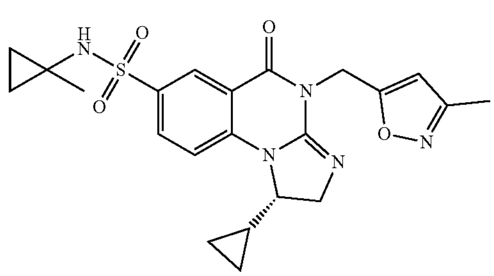 [SMILES: Cc1cc(CN2C(=O)c3cc(S(=O)(=O)NC4(C)CC4)ccc3N3C2=NC[C@@H]3C2CC2)on1] | (S)-1-cyclopropyl-N-(1-methyl-cyclopropyl)-4-((3-methyl-isoxazol-5-yl)methyl)-5-oxo-1,2,4,5-tetrahydroimidazo[1,2-a]-quinazoline-7-sulfonamide |

TABLE 1-continued

| Synthetic Chemistry Example | Compound Structure | Compound Name |
|---|---|---|
| 22 | 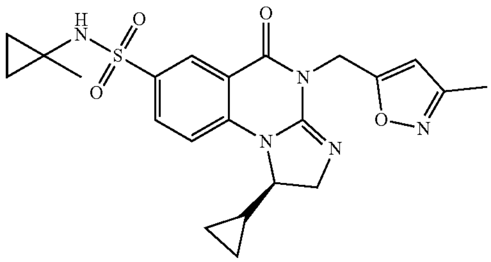 [SMILES: Cc1cc(CN2C(=O)c3cc(S(=O)(=O)NC4(C)CC4)ccc3N3C2=NC[C@H]3C2CC2)on1] | (R)-1-cyclopropyl-N-(1-methyl-cyclopropyl)-4-((3-methyl-isoxazol-5-yl)methyl)-5-oxo-1,2,4,5-tetrahydroimidazo[1,2-a]quinazoline-7-sulfonamide |
| 23 | 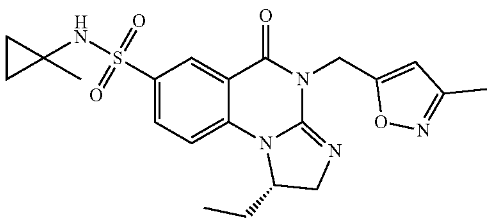 [SMILES: CC[C@H]1CN=C2N(Cc3cc(C)no3)C(=O)c3cc(S(=O)(=O)NC4(C)CC4)ccc3N21] | (S)-1-ethyl-N-(1-methylcyclo-propyl)-4-((3-methylisoxazol-5-yl)methyl)-5-oxo-1,2,4,5-tetra-hydroimidazo[1,2-a]quinazoline-7-sulfonamide |
| 24 | 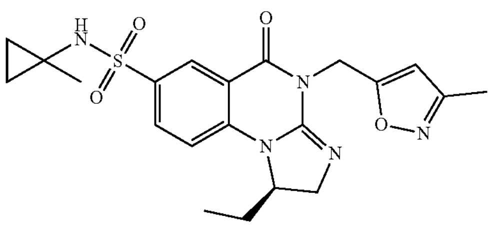 [SMILES: CC[C@@H]1CN=C2N(Cc3cc(C)no3)C(=O)c3cc(S(=O)(=O)NC4(C)CC4)ccc3N21] | (R)-1-ethyl-N-(1-methylcyclo-propyl)-4-((3-methylisoxazol-5-yl)methyl)-5-oxo-1,2,4,5-tetra-hydroimidazo[1,2-a]quinazoline-7-sulfonamide |
| 25 | 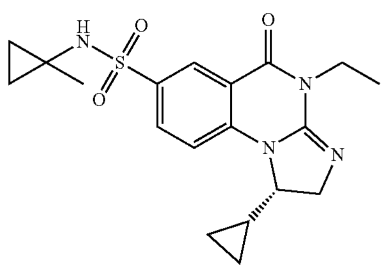 [SMILES: CCN1C(=O)c2cc(S(=O)(=O)NC3(C)CC3)ccc2N2C1=NC[C@@H]2C1CC1] | (S)-1-cyclopropyl-4-ethyl-N-(1-methylcyclopropyl)-5-oxo-1,2,4,5-tetrahydroimidazo[1,2-a]quinazoline-7-sulfonamide |
| 26 | 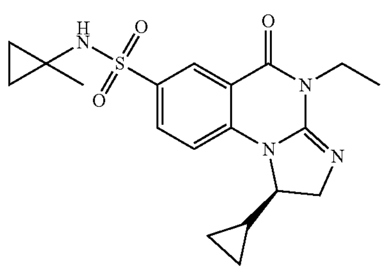 [SMILES: CCN1C(=O)c2cc(S(=O)(=O)NC3(C)CC3)ccc2N2C1=NC[C@H]2C1CC1] | (R)-1-cyclopropyl-4-ethyl-N-(1-methylcyclopropyl)-5-oxo-1,2,4,5-tetrahydroimidazo[1,2-a]quinazoline-7-sulfonamide |
| 27 | 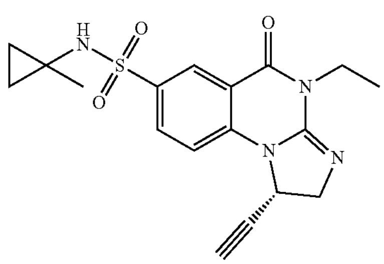 [SMILES: C#C[C@H]1CN=C2N(CC)C(=O)c3cc(S(=O)(=O)NC4(C)CC4)ccc3N21] | (S)-4-ethyl-1-ethynyl-N-(1-methylcyclopropyl)-5-oxo-1,2,4,5-tetrahydroimidazo[1,2-a]quinazoline-7-sulfonamide |

TABLE 1-continued

| Synthetic Chemistry Example | Compound Structure | Compound Name |
|---|---|---|
| 28 | 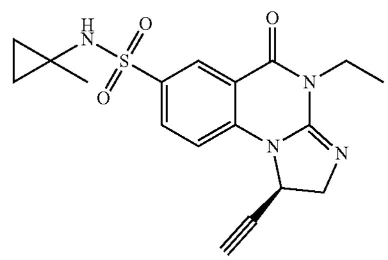 [SMILES: C#C[C@@H]1CN=C2N(CC)C(=O)c3cc(S(=O)(=O)NC4(C)CC4)ccc3N21] | (R)-4-ethyl-1-ethynyl-N-(1-methylcyclopropyl)-5-oxo-1,2,4,5-tetrahydroimidazo[1,2-a]quinazoline-7-sulfonamide |
| 29 | 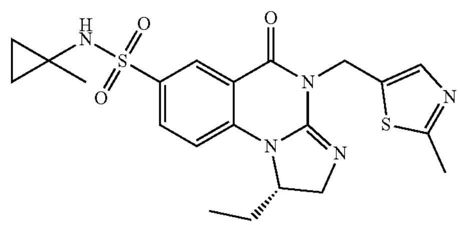 [SMILES: CC[C@H]1CN=C2N(Cc3cnc(C)s3)C(=O)c3cc(S(=O)(=O)NC4(C)CC4)ccc3N21] | (S)-1-ethyl-N-(1-methylcyclopropyl)-4-((2-methylthiazol-5-yl)methyl)-5-oxo-1,2,4,5-tetrahydroimidazo[1,2-a]-quinazoline-7-sulfonamide |
| 30 | 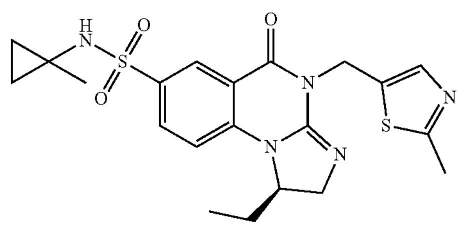 [SMILES: CC[C@@H]1CN=C2N(Cc3cnc(C)s3)C(=O)c3cc(S(=O)(=O)NC4(C)CC4)ccc3N21] | (R)-1-ethyl-N-(1-methylcyclopropyl)-4-((2-methylthiazol-5-yl)methyl)-5-oxo-1,2,4,5-tetrahydroimidazo[1,2-a]quinazoline-7-sulfonamide |
| 31 | 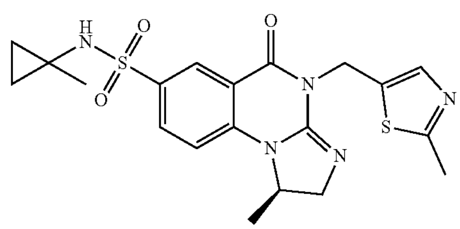 [SMILES: Cc1ncc(CN2C(=O)c3cc(S(=O)(=O)NC4(C)CC4)ccc3N3C2=NC[C@H]3C)s1] | (R)-1-methyl-N-(1-methylcyclopropyl)-4-((2-methylthiazol-5-yl)methyl)-5-oxo-1,2,4,5-tetrahydroimidazo[1,2-a]quinazoline-7-sulfonamide |
| 32 | 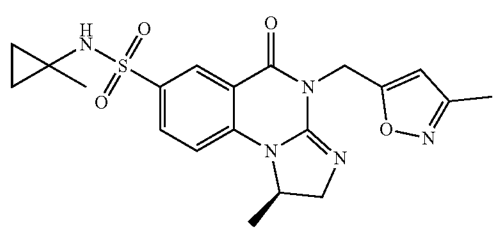 [SMILES: Cc1cc(CN2C(=O)c3cc(S(=O)(=O)NC4(C)CC4)ccc3N3C2=NC[C@H]3C)on1] | (R)-1-methyl-N-(1-methylcyclopropyl)-4-((3-methylisoxazol-5-yl)methyl)-5-oxo-1,2,4,5-tetrahydroimidazo[1,2-a]quinazoline-7-sulfonamide |
| 33 | 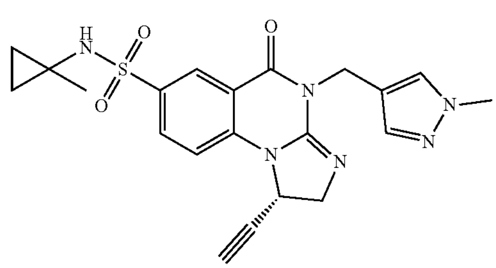 [SMILES: C#C[C@H]1CN=C2N(Cc3cnn(C)c3)C(=O)c3cc(S(=O)(=O)NC4(C)CC4)ccc3N21] | (S)-1-ethynyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |

TABLE 1-continued

| Synthetic Chemistry Example | Compound Structure | Compound Name |
|---|---|---|
| 34 | 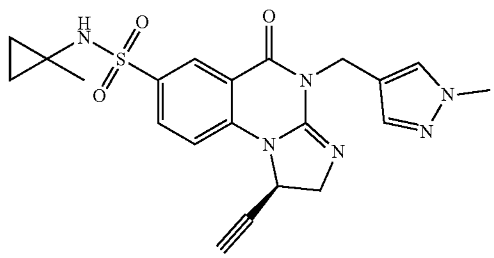 [SMILES: C#C[C@@H]1CN=C2N(Cc3cnn(C)c3)C(=O)c3cc(S(=O)(=O)NC4(C)CC4)ccc3N21] | (R)-1-ethynyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 35 | 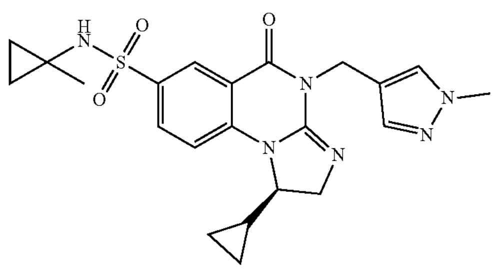 [SMILES: Cn1cc(CN2C(=O)c3cc(S(=O)(=O)NC4(C)CC4)ccc3N3C2=NC[C@H]3C2CC2)cn1] | (R)-1-cyclopropyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 36 | 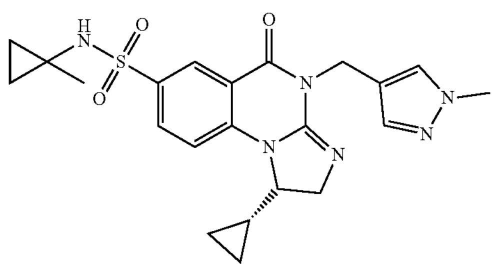 | (S)-1-cyclopropyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 37 | 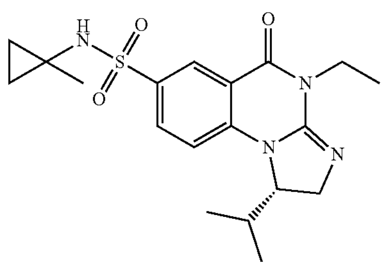 [SMILES: CCN1C(=O)c2cc(S(=O)(=O)NC3(C)CC3)ccc2N2C1=NC[C@@H]2C(C)C] | (S)-4-ethyl-1-isopropyl-N-(1-methylcyclopropyl)-5-oxo-1,2,4,5-tetrahydroimidazo[1,2-a]quinazoline-7-sulfonamide |
| 38 | 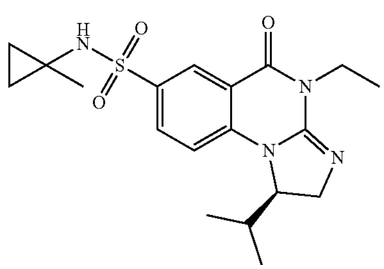 [SMILES: CCN1C(=O)c2cc(S(=O)(=O)NC3(C)CC3)ccc2N2C1=NC[C@H]2C(C)C] | (R)-4-ethyl-1-isopropyl-N-(1-methylcyclopropyl)-5-oxo-1,2,4,5-tetrahydroimidazo[1,2-a]quinazoline-7-sulfonamide |

TABLE 1-continued

| Synthetic Chemistry Example | Compound Structure | Compound Name |
|---|---|---|
| 39 | 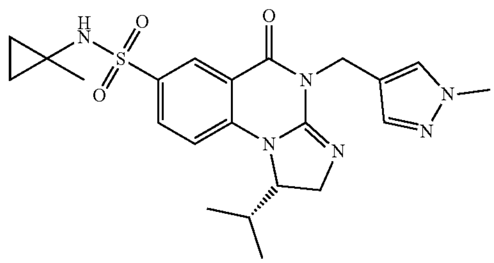 | (S)-1-isopropyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 40 | 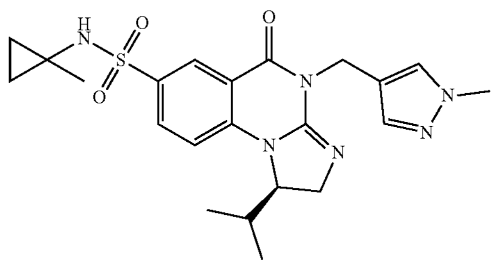 [SMILES: CC(C)[C@@H]1CN=C2N(Cc3cnn(C)c3)C(=O)c3cc(S(=O)(=O)NC4(C)CC4)ccc3N21] | (R)-1-isopropyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 41 | 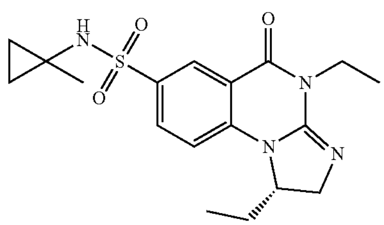 [SMILES: CC[C@H]1CN=C2N(CC)C(=O)c3cc(S(=O)(=O)NC4(C)CC4)ccc3N21] | (S)-1,4-diethyl-N-(1-methyl-cyclopropyl)-5-oxo-1,2,4,5-tetrahydroimidazo[1,2-a]-quinazoline-7-sulfonamide |
| 42 | 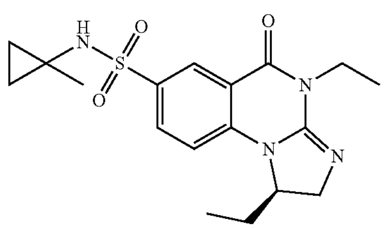 [SMILES: CC[C@@H]1CN=C2N(CC)C(=O)c3cc(S(=O)(=O)NC4(C)CC4)ccc3N21] | (R)-1,4-diethyl-N-(1-methyl-cyclopropyl)-5-oxo-1,2,4,5-tetrahydroimidazo[1,2-a]-quinazoline-7-sulfonamide |
| 43 | 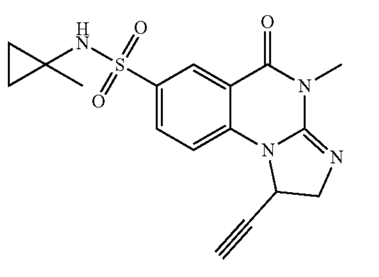 [SMILES: C#CC1CN=C2N(C)C(=O)c3cc(S(=O)(=O)NC4(C)CC4)ccc3N21] | 1-ethynyl-4-methyl-N-(1-methylcyclopropyl)-5-oxo-1,2,4,5-tetrahydroimidazo[1,2-a]quinazoline-7-sulfonamide |
| 44 | 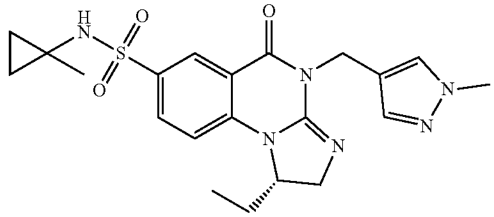 [SMILES: CC[C@H]1CN=C2N(Cc3cnn(C)c3)C(=O)c3cc(S(=O)(=O)NC4(C)CC4)ccc3N21] | (S)-1-ethyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |

TABLE 1-continued

| Synthetic Chemistry Example | Compound Structure | Compound Name |
|---|---|---|
| 45 | 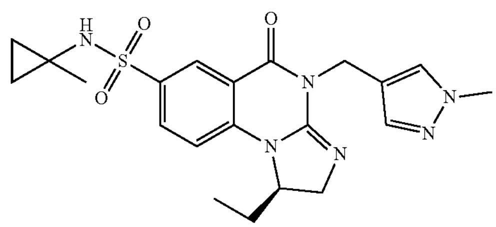 [SMILES: CC[C@@H]1CN=C2N(Cc3cnn(C)c3)C(=O)c3cc(S(=O)(=O)NC4(C)CC4)ccc3N21] | (R)-1-ethyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 46 | 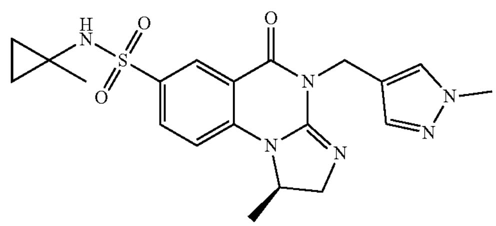 [SMILES: C[C@@H]1CN=C2N(Cc3cnn(C)c3)C(=O)c3cc(S(=O)(=O)NC4(C)CC4)ccc3N21] | (R)-1-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 47 | 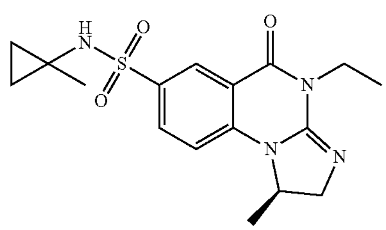 [SMILES: CCN1C(=O)c2cc(S(=O)(=O)NC3(C)CC3)ccc2N2C1=NC[C@H]2C] | (R)-4-ethyl-1-methyl-N-(1-methylcyclopropyl)-5-oxo-1,2,4,5-tetrahydroimidazo[1,2-a]quinazoline-7-sulfonamide |
| 48 | 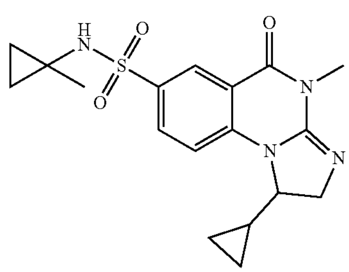 [SMILES: CN1C(=O)c2cc(S(=O)(=O)NC3(C)CC3)ccc2N2C1=NCC2C1CC1] | 1-cyclopropyl-4-methyl-N-(1-methylcyclopropyl)-5-oxo-1,2,4,5-tetrahydroimidazo[1,2-a]quinazoline-7-sulfonamide |
| 49 | 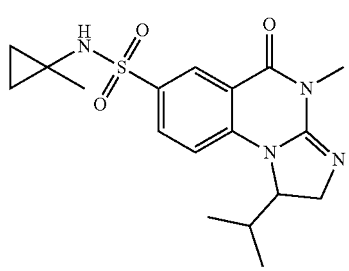 [SMILES: CC(C)C1CN=C2N(C)C(=O)c3cc(S(=O)(=O)NC4(C)CC4)ccc3N21] | 1-isopropyl-4-methyl-N-(1-methylcyclopropyl)-5-oxo-1,2,4,5-tetrahydroimidazo[1,2-a]quinazoline-7-sulfonamide |
| 50 | 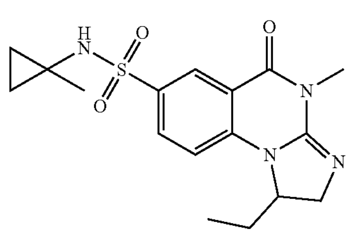 [SMILES: CCC1CN=C2N(C)C(=O)c3cc(S(=O)(=O)NC4(C)CC4)ccc3N21] | 1-ethyl-4-methyl-N-(1-methyl-cyclopropyl)-5-oxo-1,2,4,5-tetrahydroimidazo[1,2-a]quinazoline-7-sulfonamide |

TABLE 1-continued

| Synthetic Chemistry Example | Compound Structure | Compound Name |
|---|---|---|
| 51 | 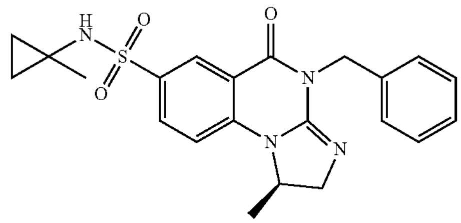 [SMILES: C[C@@H]1CN=C2N(Cc3ccccc3)C(=O)c3cc(S(=O)(=O)NC4(C)CC4)ccc3N21] | (R)-4-benzyl-1-methyl-N-(1-methylcyclopropyl)-5-oxo-1,2,4,5-tetrahydroimidazo[1,2-a]quinazoline-7-sulfonamide |
| 52 | 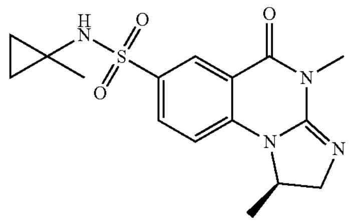 [SMILES: C[C@@H]1CN=C2N(C)C(=O)c3cc(S(=O)(=O)NC4(C)CC4)ccc3N21] | (R)-1,4-dimethyl-N-(1-methylcyclopropyl)-5-oxo-1,2,4,5-tetrahydroimidazo[1,2-a]quinazoline-7-sulfonamide |
| 53 | 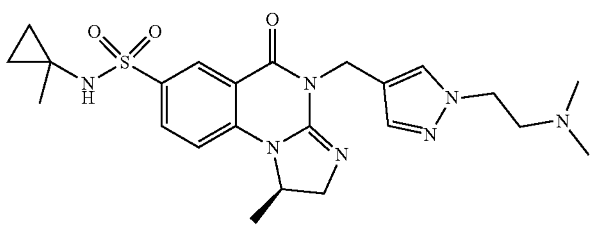 [SMILES: C[C@@H]1CN=C2N(Cc3cnn(CCN(C)C)c3)C(=O)c3cc(S(=O)(=O)NC4(C)CC4)ccc3N21] | (R)-4-((1-(2-(dimethylamino)ethyl)-1H-pyrazol-4-yl)methyl)-1-methyl-N-(1-methylcyclopropyl)-5-oxo-1,2,4,5-tetrahydroimidazo[1,2-a]quinazoline-7-sulfonamide |
| 54 | 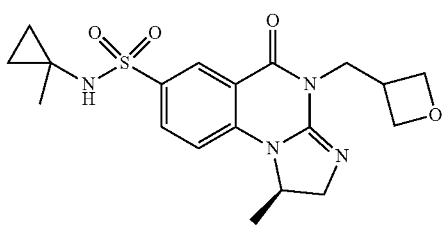 [SMILES: C[C@@H]1CN=C2N(CC3COC3)C(=O)c3cc(S(=O)(=O)NC4(C)CC4)ccc3N21] | (R)-1-methyl-N-(1-methylcyclopropyl)-4-(oxetan-3-ylmethyl)-5-oxo-1,2,4,5-tetrahydroimidazo[1,2-a]quinazoline-7-sulfonamide |
| 55 | 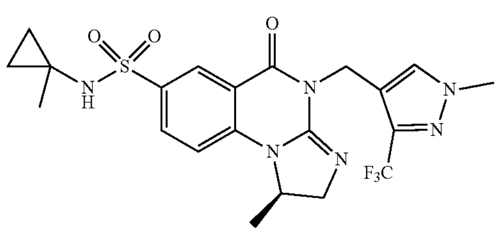 [SMILES: C[C@@H]1CN=C2N(Cc3cn(C)nc3C(F)(F)F)C(=O)c3cc(S(=O)(=O)NC4(C)CC4)ccc3N21] | (R)-1-methyl-4-((1-methyl-3-(trifluoromethyl)-1H-pyrazol-4-yl)methyl)-N-(1-methylcyclopropyl)-5-oxo-1,2,4,5-tetrahydroimidazo[1,2-a]quinazoline-7-sulfonamide |
| 56 | 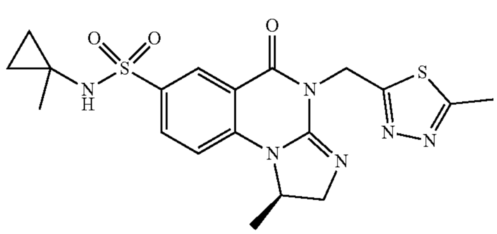 [SMILES: Cc1nnc(CN2C(=O)c3cc(S(=O)(=O)NC4(C)CC4)ccc3N3C2=NC[C@H]3C)s1] | (R)-1-methyl-4-((5-methyl-1,3,4-thiadiazol-2-yl)methyl)-N-(1-methylcyclopropyl)-5-oxo-1,2,4,5-tetrahydroimidazo[1,2-a]quinazoline-7-sulfonamide |

TABLE 1-continued

| Synthetic Chemistry Example | Compound Structure | Compound Name |
|---|---|---|
| 57 | 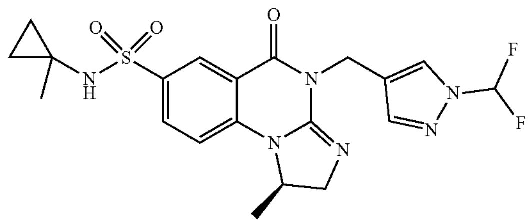 [SMILES: C[C@@H]1CN=C2N(Cc3cnn(C(F)F)c3)C(=O)c3cc(S(=O)(=O)NC4(C)CC4)ccc3N21] | (R)-4-((1-(difluoromethyl)-1H-pyrazol-4-yl)methyl)-1-methyl-N-(1-methylcyclopropyl)-5-oxo-1,2,4,5-tetrahydroimidazo[1,2-a]quinazoline-7-sulfonamide |
| 58 | 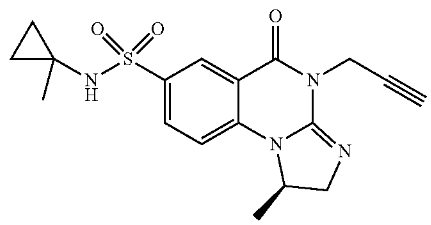 [SMILES: C#CCN1C(=O)c2cc(S(=O)(=O)NC3(C)CC3)ccc2N2C1=NC[C@H]2C] | (R)-1-methyl-N-(1-methylcyclopropyl)-5-oxo-4-(prop-2-yn-1-yl)-1,2,4,5-tetrahydroimidazo-[1,2-a]quinazoline-7-sulfonamide |
| 59 | 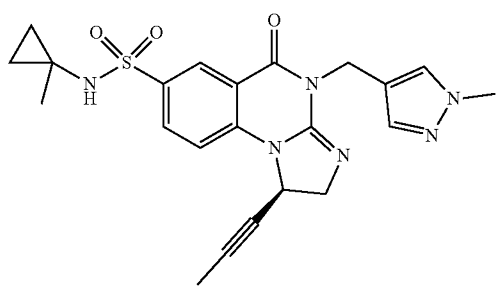 [SMILES: CC#C[C@@H]1CN=C2N(Cc3cnn(C)c3)C(=O)c3cc(S(=O)(=O)NC4(C)CC4)ccc3N21] | (R)-4-((1-methyl-1H-pyrazol-4-yl)methyl)-N-(1-methylcyclopropyl)-5-oxo-1-(prop-1-yn-1-yl)-1,2,4,5-tetrahydroimidazo-[1,2-a]quinazoline-7-sulfonamide |
| 60 | 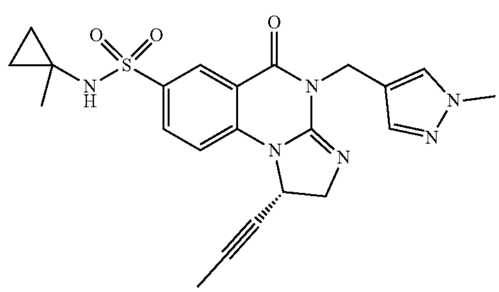 [SMILES: CC#C[C@H]1CN=C2N(Cc3cnn(C)c3)C(=O)c3cc(S(=O)(=O)NC4(C)CC4)ccc3N21] | (S)-4-((1-methyl-1H-pyrazol-4-yl)methyl)-N-(1-methylcyclopropyl)-5-oxo-1-(prop-1-yn-1-yl)-1,2,4,5-tetrahydroimidazo-[1,2-a]quinazoline-7-sulfonamide |
| 61 | 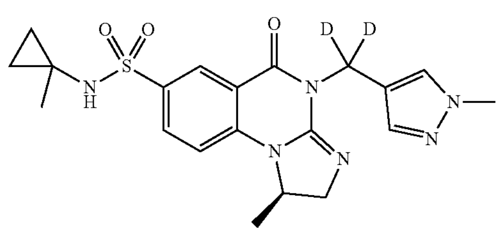 [SMILES: [2H]C([2H])(c1cnn(C)c1)N1C(=O)c2cc(S(=O)(=O)NC3(C)CC3)ccc2N2C1=NC[C@H]2C] | (R)-1-methyl-4-((1-methyl-1H-pyrazol-4-yl)methyl-d2)-N-(1-methylcyclopropyl)-5-oxo-1,2,4,5-tetrahydroimidazo[1,2-a]quinazoline-7-sulfonamide |
| 62 | 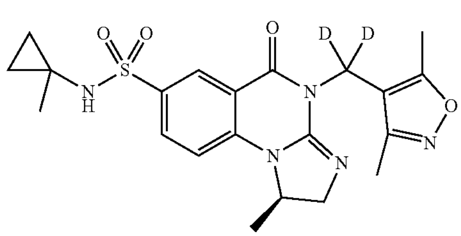 [SMILES: [2H]C([2H])(c1c(C)noc1C)N1C(=O)c2cc(S(=O)(=O)NC3(C)CC3)ccc2N2C1=NC[C@H]2C] | (R)-4-((3,5-dimethylisoxazol-4-yl)methyl-d2)-1-methyl-N-(1-methylcyclopropyl)-5-oxo-1,2,4,5-tetrahydroimidazo[1,2-a]quinazoline-7-sulfonamide |

TABLE 1-continued

| Synthetic Chemistry Example | Compound Structure | Compound Name |
|---|---|---|
| 63 | 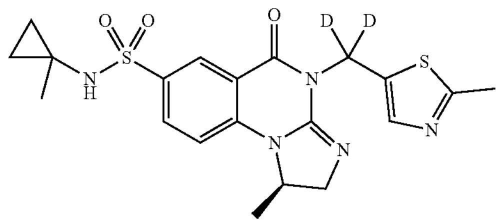 [SMILES: [2H]C([2H])(c1cnc(C)s1)N1C(=O)c2cc(S(=O)(=O)NC3(C)CC3)ccc2N2C1=NC[C@H]2C] | (R)-1-methyl-N-(1-methylcyclopropyl)-4-((2-methylthiazol-5-yl)methyl-d2)-5-oxo-1,2,4,5-tetrahydroimidazo[1,2-a]-quinazoline-7-sulfonamide |
| 64 | 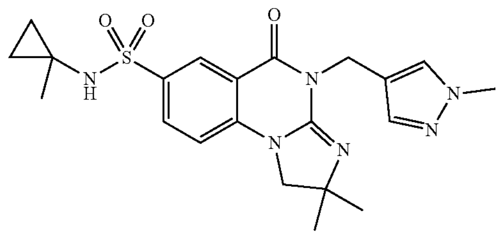 [SMILES: Cn1cc(CN2C(=O)c3cc(S(=O)(=O)NC4(C)CC4)ccc3N3CC(C)(C)N=C23)cn1] | 2,2-dimethyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 65 | 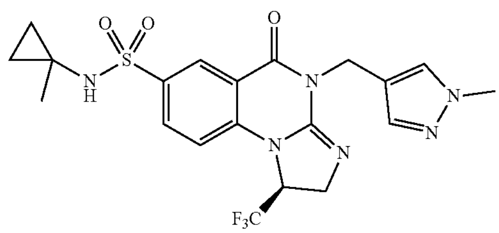 [SMILES: Cn1cc(CN2C(=O)c3cc(S(=O)(=O)NC4(C)CC4)ccc3N3C2=NC[C@H]3C(F)(F)F)cn1] | (S)-1-trifluoromethyl-4-((1-methyl-1H-pyrazol-4-yl)-methyl)-N-(1-methylcyclopropyl)-5-oxo-1,2,4,5-tetrahydroimidazo-[1,2-a]quinazoline-7-sulfonamide |
| 66 | 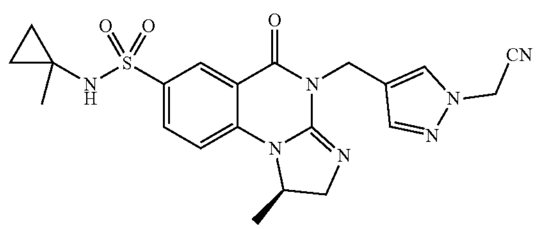 [SMILES: C[C@@H]1CN=C2N(Cc3cnn(CC#N)c3)C(=O)c3cc(S(=O)(=O)NC4(C)CC4)ccc3N21] | (R)-1-methyl-4-((1-cyanomethyl-1H-pyrazol-4-yl)methyl)-N-(1-methylcyclopropyl)-5-oxo-1,2,4,5-tetrahydroimidazo[1,2-a]quinazoline-7-sulfonamide |
| 67 | 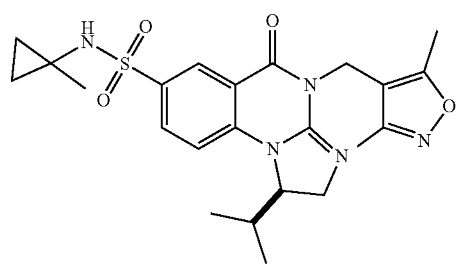 [SMILES: Cc1noc(C)c1CN1C(=O)c2cc(S(=O)(=O)NC3(C)CC3)ccc2N2C1=NC[C@H]2C(C)C] | (R)-4-((3,5-dimethylisoxazol-4-yl)methyl)-1-isopropyl-N-(1-methylcyclopropyl)-5-oxo-1,2,4,5-tetrahydroimidazo[1,2-a]quinazoline-7-sulfonamide |
| 68 | 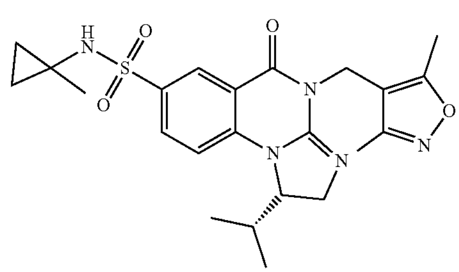 | (S)-4-((3,5-dimethylisoxazol-4-yl)methyl)-1-isopropyl-N-(1-methylcyclopropyl)-5-oxo-1,2,4,5-tetrahydroimidazo[1,2-a]quinazoline-7-sulfonamide |

TABLE 1-continued

| Synthetic Chemistry Example | Compound Structure | Compound Name |
|---|---|---|
| 69 | 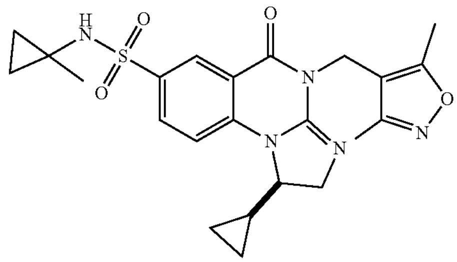 [SMILES: Cc1noc(C)c1CN1C(=O)c2cc(S(=O)(=O)NC3(C)CC3)ccc2N2C1=NC[C@H]2C1CC1] | (R)-1-cyclopropyl-4-((3,5-dimethylisoxazol-4-yl)methyl)-N-(1-methylcyclopropyl)-5-oxo-1,2,4,5-tetrahydroimidazo-[1,2-a]quinazoline-7-sulfonamide |
| 70 | 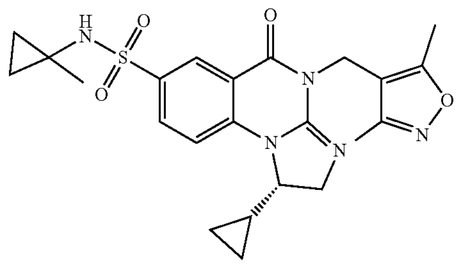 [SMILES: Cc1noc(C)c1CN1C(=O)c2cc(S(=O)(=O)NC3(C)CC3)ccc2N2C1=NC[C@@H]2C1CC1] | (S)-1-cyclopropyl-4-((3,5-dimethylisoxazol-4-yl)methyl)-N-(1-methylcyclopropyl)-5-oxo-1,2,4,5-tetrahydroimidazo[1,2-a]quinazoline-7-sulfonamide |
| 71 | 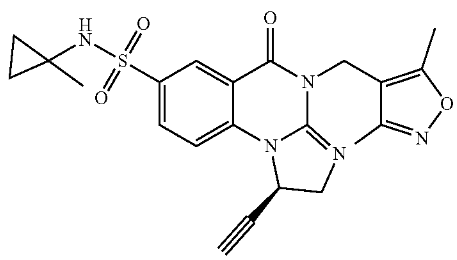 [SMILES: C#C[C@@H]1CN=C2N(Cc3c(C)noc3C)C(=O)c3cc(S(=O)(=O)NC4(C)CC4)ccc3N21] | (R)-4-((3,5-dimethylisoxazol-4-yl)methyl)-1-ethynyl-N-(1-methylcyclopropyl)-5-oxo-1,2,4,5-tetrahydroimidazo[1,2-a]quinazoline-7-sulfonamide |
| 72 | 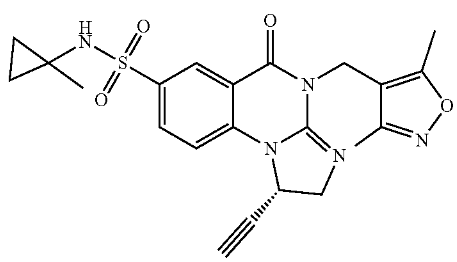 [SMILES: C#C[C@H]1CN=C2N(Cc3c(C)noc3C)C(=O)c3cc(S(=O)(=O)NC4(C)CC4)ccc3N21] | (S)-4-((3,5-dimethylisoxazol-4-yl)methyl)-1-ethynyl-N-(1-methylcyclopropyl)-5-oxo-1,2,4,5-tetrahydroimidazo[1,2-a]quinazoline-7-sulfonamide |
| 73 | 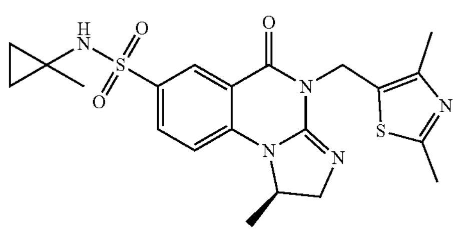 [SMILES: Cc1nc(C)c(CN2C(=O)c3cc(S(=O)(=O)NC4(C)CC4)ccc3N3C2=NC[C@H]3C)s1] | (R)-4-((2,4-dimethylthiazol-5-yl)methyl)-1-methyl-N-(1-methylcyclopropyl)-5-oxo-1,2,4,5-tetrahydroimidazo[1,2-a]quinazoline-7-sulfonamide |
| 74 | 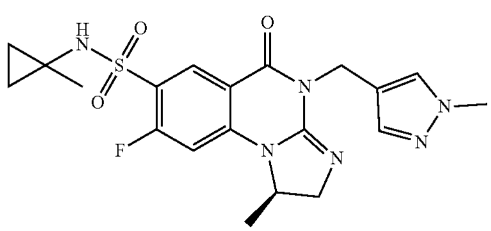 [SMILES: C[C@@H]1CN=C2N(Cc3cnn(C)c3)C(=O)c3cc(S(=O)(=O)NC4(C)CC4)c(F)cc3N21] | (R)-8-fluoro-1-methyl-4-((1-methyl-1H-pyrazol-4-yl)methyl)-N-(1-methylcyclopropyl)-5-oxo-1,2,4,5-tetrahydroimidazo-[1,2-a]quinazoline-7-sulfonamide |

TABLE 1-continued

| Synthetic Chemistry Example | Compound Structure | Compound Name |
|---|---|---|
| 75 | 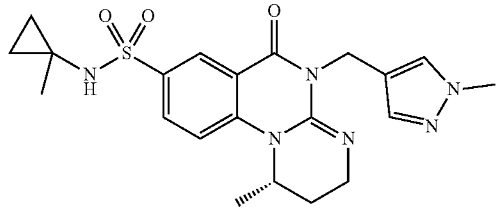 [SMILES: C[C@H]1CCN=C2N(Cc3cnn(C)c3)C(=O)c3cc(S(=O)(=O)NC4(C)CC4)ccc3N21] | (S)-1-methyl-5-((1-methyl-1H-pyrazol-4-yl)methyl)-N-(1-methylcyclopropyl)-6-oxo-2,3,5,6-tetrahydro-1H-pyrimido-[1,2-a]quinazoline-8-sulfonamide |
| 76 | 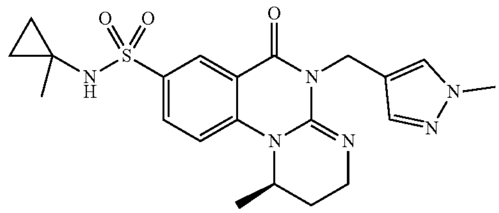 [SMILES: C[C@@H]1CCN=C2N(Cc3cnn(C)c3)C(=O)c3cc(S(=O)(=O)NC4(C)CC4)ccc3N21] | (R)-1-methyl-5-((1-methyl-1H-pyrazol-4-yl)methyl)-N-(1-methylcyclopropyl)-6-oxo-2,3,5,6-tetrahydro-1H-pyrimido-[1,2-a]quinazoline-8-sulfonamide |
| 77 | 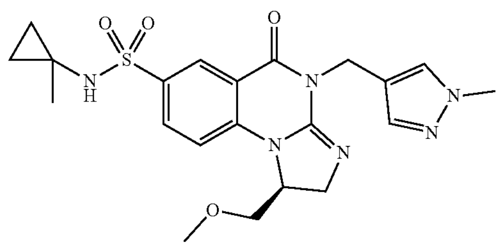 [SMILES: COC[C@@H]1CN=C2N(Cc3cnn(C)c3)C(=O)c3cc(S(=O)(=O)NC4(C)CC4)ccc3N21] | (S)-1-(methoxymethyl)-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 78 | 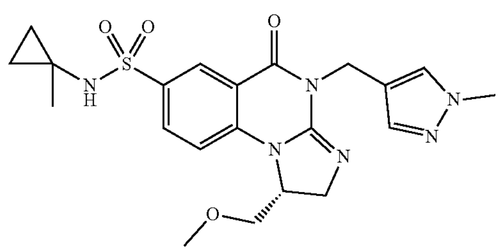 [SMILES: COC[C@H]1CN=C2N(Cc3cnn(C)c3)C(=O)c3cc(S(=O)(=O)NC4(C)CC4)ccc3N21] | (R)-1-(methoxymethyl)-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 79 | 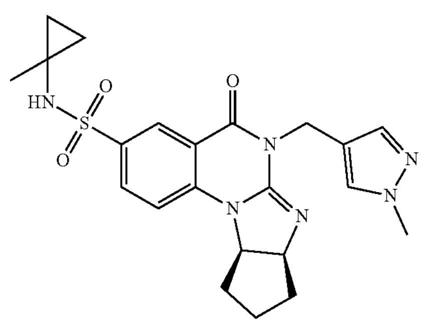 [SMILES: Cn1cc(CN2C(=O)c3cc(S(=O)(=O)NC4(C)CC4)ccc3N3C2=N[C@H]2CCC[C@H]23)cn1] | (7aS,10aR)-6-((1-methyl-1H-pyrazol-4-yl)methyl)-N-(1-methylcyclopropyl)-5-oxo-6,7a,8,9,10,10a-hexahydro-5H-cyclopenta[4,5]imidazo[1,2-a]quinazoline-3-sulfonamide |
| 80 | 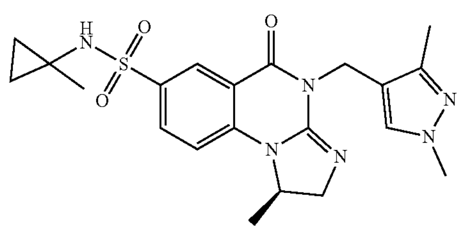 [SMILES: Cc1nn(C)cc1CN1C(=O)c2cc(S(=O)(=O)NC3(C)CC3)ccc2N2C1=NC[C@H]2C] | (R)-4-((1,3-dimethyl-1H-pyrazol-4-yl)methyl)-1-methyl-N-(1-methylcyclopropyl)-5-oxo-1,2,4,5-tetrahydroimidazo[1,2-a]quinazoline-7-sulfonamide |

TABLE 1-continued

| Synthetic Chemistry Example | Compound Structure | Compound Name |
|---|---|---|
| 81 | 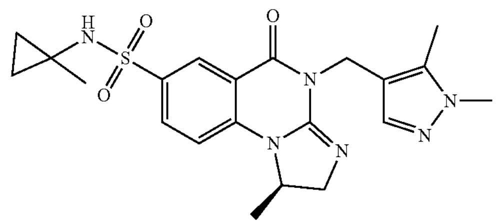 [SMILES: Cc1c(CN2C(=O)c3cc(S(=O)(=O)NC4(C)CC4)ccc3N3C2=NC[C@H]3C)cnn1C] | (R)-4-((1,5-dimethyl-1H-pyrazol-4-yl)methyl)-1-methyl-N-(1-methylcyclopropyl)-5-oxo-1,2,4,5-tetrahydroimidazo-[1,2-a]quinazoline-7-sulfonamide |
| 82 | 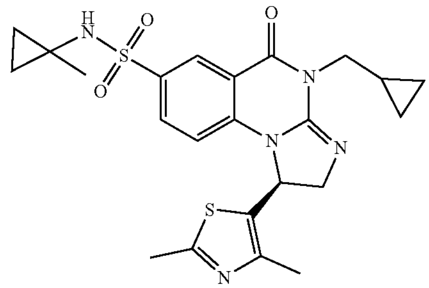 [SMILES: Cc1nc(C)c([C@@H]2CN=C3N(CC4CC4)C(=O)c4cc(S(=O)(=O)NC5(C)CC5)ccc4N32)s1] | (S)-4-(cyclopropylmethyl)-1-(2,4-dimethylthiazol-5-yl)-N-(1-methylcyclopropyl)-5-oxo-1,2,4,5-tetrahydroimidazo[1,2-a]quinazoline-7-sulfonamide |
| 83 | 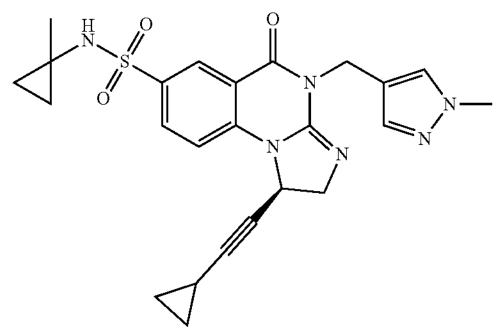 [SMILES: Cn1cc(CN2C(=O)c3cc(S(=O)(=O)NC4(C)CC4)ccc3N3C2=NC[C@H]3C#CC2CC2)cn1] | (R)-1-(cyclopropylethynyl)-4-((1-methyl-1H-pyrazol-4-yl)-methyl)-N-(1-methylcyclopropyl)-5-oxo-1,2,4,5-tetrahydro-imidazo[1,2-a]quinazoline-7-sulfonamide |
| 84 | 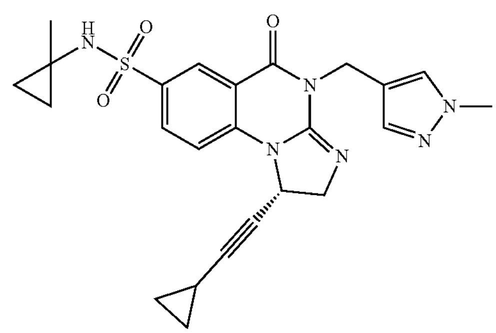 [SMILES: Cn1cc(CN2C(=O)c3cc(S(=O)(=O)NC4(C)CC4)ccc3N3C2=NC[C@@H]3C#CC2CC2)cn1] | (S)-1-(cyclopropylethynyl)-4-((1-methyl-1H-pyrazol-4-yl)methyl)-N-(1-methylcyclopropyl)-5-oxo-1,2,4,5-tetrahydroimidazo[1,2-a]quinaz-oline-7-sulfonamide |
| 85 | 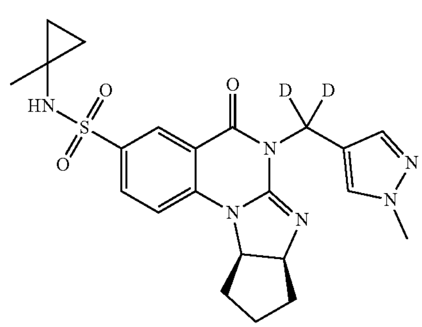 [SMILES: [2H]C([2H])(c1cnn(C)c1)N1C(=O)c2cc(S(=O)(=O)NC3(C)CC3)ccc2N2C1=N[C@H]1CCC[C@H]12] | (7aS,10aR)-6-(dideutero(1-methyl-1H-pyrazol-4-yl)meth-yl)-N-(1-methylcyclopropyl)-5-oxo-6,7a,8,9,10,10a-hexahydro-5H-cyclopenta[4,5]imidazo[1,2-a]quinazoline-3-sulfonamide |

TABLE 1-continued

| Synthetic Chemistry Example | Compound Structure | Compound Name |
|---|---|---|
| 86 | 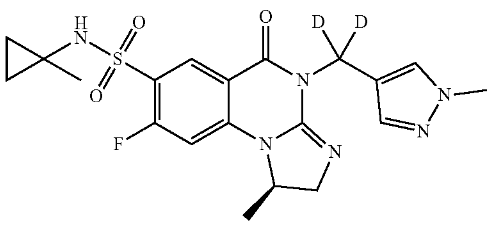 [SMILES: [2H]C([2H])(c1cnn(C)c1)N1C(=O)c2cc(S(=O)(=O)NC3(C)CC3)c(F)cc2N2C1=NC[C@H]2C] | (R)-4-(dideutero(1-methyl-1H-pyrazol-4-yl)methyl)-8-fluoro-1-methyl-N-(1-methylcyclopropyl)-5-oxo-1,2,4,5-tetrahydroimidazo[1,2-a]quinazoline-7-sulfonamide |
| 87 | 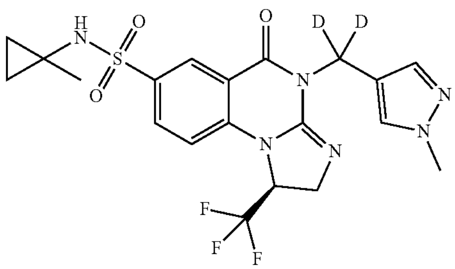 [SMILES: [2H]C([2H])(c1cnn(C)c1)N1C(=O)c2cc(S(=O)(=O)NC3(C)CC3)ccc2N2C1=NC[C@H]2C(F)(F)F] | (S)-4-(dideutero(1-methyl-1H-pyrazol-4-yl)methyl)-N-(1-methylcyclopropyl)-5-oxo-1-(trifluoromethyl)-1,2,4,5-tetrahydroimidazo[1,2-a]quinazoline-7-sulfonamide |
| 88 | 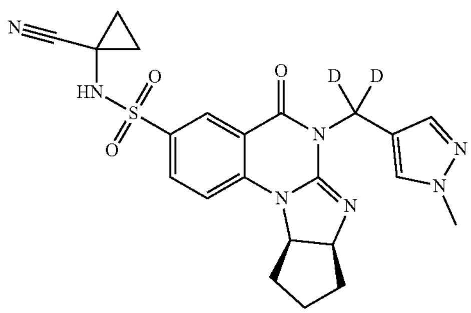 [SMILES: [2H]C([2H])(c1cnn(C)c1)N1C(=O)c2cc(S(=O)(=O)NC3(C#N)CC3)ccc2N2C1=N[C@H]1CCC[C@H]12] | (7aS,10aR)-N-(1-cyanocyclopropyl)-6-(dideutero(1-methyl-1H-pyrazol-4-yl)methyl)-5-oxo-6,7a,8,9,10,10a-hexahydro-5H-cyclopenta[4,5]imidazo[1,2-a]quinazoline-3-sulfonamide |
| 89 | 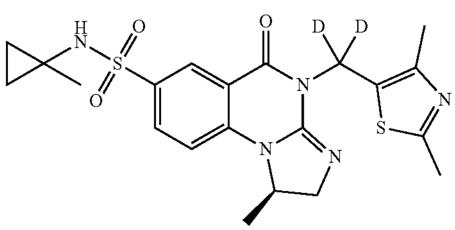 [SMILES: [2H]C([2H])(c1sc(C)nc1C)N1C(=O)c2cc(S(=O)(=O)NC3(C)CC3)ccc2N2C1=NC[C@H]2C] | (R)-4-(dideutero(2,4-dimethyl-thiazol-5-yl)methyl)-1-methyl-N-(1-methylcyclopropyl)-5-oxo-1,2,4,5-tetrahydroimidazo[1,2-a]quinazoline-7-sulfonamide |
| 90 | 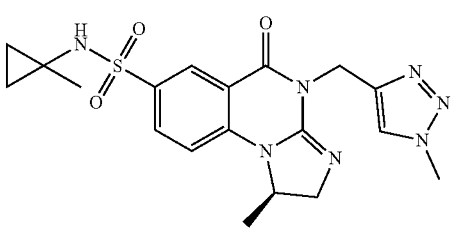 [SMILES: C[C@@H]1CN=C2N(Cc3cn(C)nn3)C(=O)c3cc(S(=O)(=O)NC4(C)CC4)ccc3N21] | (R)-1-methyl-4-((1-methyl-1H-1,2,3-triazol-4-yl)methyl)-N-(1-methylcyclopropyl)-5-oxo-1,2,4,5-tetrahydroimidazo[1,2-a]quinazoline-7-sulfonamide |
| 91 | 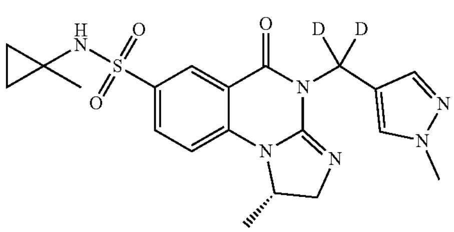 [SMILES: [2H]C([2H])(c1cnn(C)c1)N1C(=O)c2cc(S(=O)(=O)NC3(C)CC3)ccc2N2C1=NC[C@@H]2C] | (S)-4-(dideutero(1-methyl-1H-pyrazol-4-yl)methyl)-1-methyl-N-(1-methylcyclopropyl)-5-oxo-1,2,4,5-tetrahydroimidazo[1,2-a]quinazoline-7-sulfonamide |

TABLE 1-continued

| Synthetic Chemistry Example | Compound Structure | Compound Name |
|---|---|---|
| 92 | 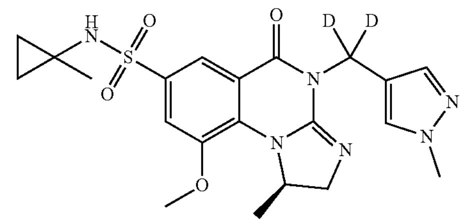 [SMILES: [2H]C([2H])(c1cnn(C)c1)N1C(=O)c2cc(S(=O)(=O)NC3(C)CC3)cc(OC)c2N2C1=NC[C@H]2C] | (R)-4-(dideutero(1-methyl-1H-pyrazol-4-yl)methyl)-9-methoxy-1-methyl-N-(1-methylcyclopropyl)-5-oxo-1,2,4,5-tetrahydroimidazo[1,2-a]quinazoline-7-sulfonamide |
| 93 | 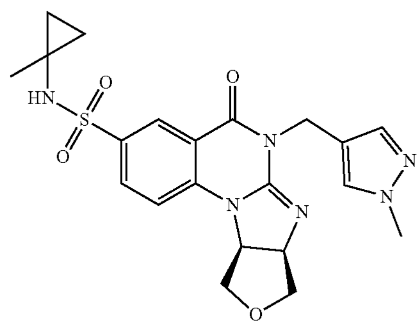 [SMILES: Cn1cc(CN2C(=O)c3cc(S(=O)(=O)NC4(C)CC4)ccc3N3C2=N[C@H]2COC[C@H]23)cn1] | (7aR,10aS)-6-((1-methyl-1H-pyrazol-4-yl)methyl)-N-(1-methylcyclopropyl)-5-oxo-5,6,7a,8,10,10a-hexahydrofuro[3',4':4,5]imidazo[1,2-a]quinazoline-3-sulfonamide |
| 94 | 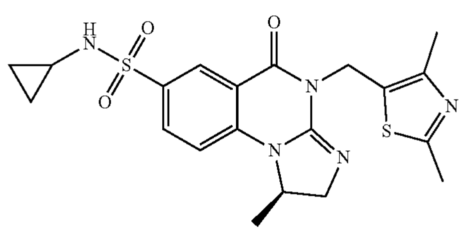 [SMILES: Cc1nc(C)c(CN2C(=O)c3cc(S(=O)(=O)NC4CC4)ccc3N3C2=NC[C@H]3C)s1] | (R)-N-cyclopropyl-4-((2,4-dimethylthiazol-5-yl)methyl)-1-methyl-5-oxo-1,2,4,5-tetrahydroimidazo[1,2-a]quinazoline-7-sulfonamide |
| 95 | 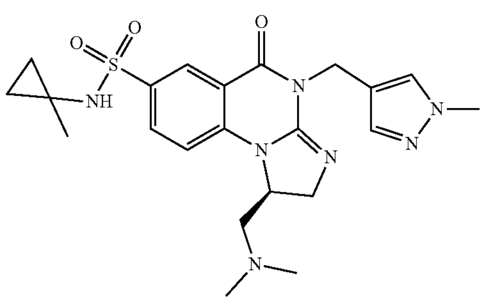 [SMILES: CN(C)C[C@@H]1CN=C2N(Cc3cnn(C)c3)C(=O)c3cc(S(=O)(=O)NC4(C)CC4)ccc3N21] | (R)-1-((dimethylamino)methyl)-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 96 | 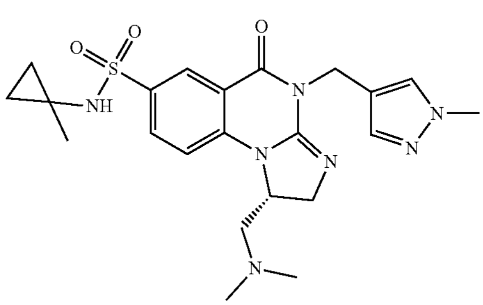 [SMILES: CN(C)C[C@H]1CN=C2N(Cc3cnn(C)c3)C(=O)c3cc(S(=O)(=O)NC4(C)CC4)ccc3N21] | (S)-1-((dimethylamino)methyl)-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |

TABLE 1-continued

| Synthetic Chemistry Example | Compound Structure | Compound Name |
|---|---|---|
| 97 | 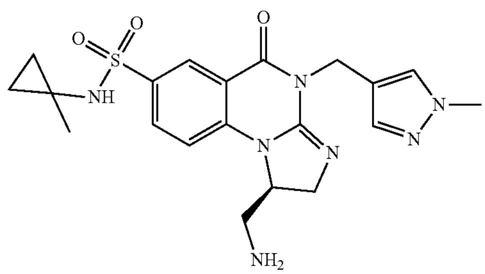 [SMILES: Cn1cc(CN2C(=O)c3cc(S(=O)(=O)NC4(C)CC4)ccc3N3C2=NC[C@H]3CN)cn1] | (R)-1-(aminomethyl)-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 98 | 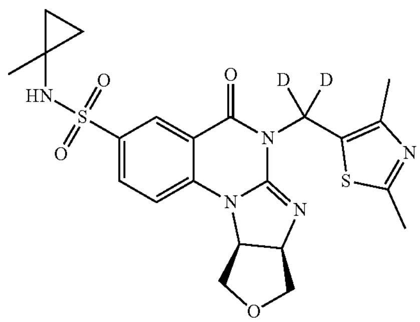 [SMILES: [2H]C([2H])(c1sc(C)nc1C)N1C(=O)c2cc(S(=O)(=O)NC3(C)CC3)ccc2N2C1=N[C@H]1COC[C@H]12] | (7aR,10aS)-6-(dideutero(2,4-dimethylthiazol-5-yl)methyl)-N-(1-methylcyclopropyl)-5-oxo-5,6,7a,8,10,10a-hexahydro-furo[3',4':4,5]imidazo-[1,2-a]quinazoline-3-sulfonamide |
| 99 | 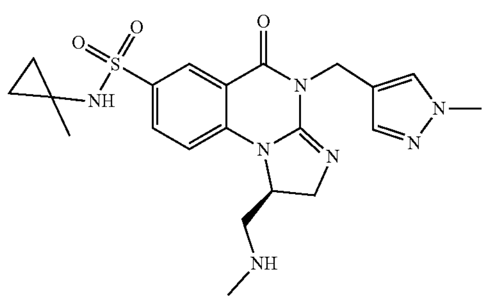 [SMILES: CNC[C@@H]1CN=C2N(Cc3cnn(C)c3)C(=O)c3cc(S(=O)(=O)NC4(C)CC4)ccc3N21] | (R)-4-((1-methyl-1H-pyrazol-4-yl)methyl)-1-((methylamino)-methyl)-N-(1-methylcyclopropyl)-5-oxo-1,2,4,5-tetrahydroimidazo[1,2-a]quinazoline-7-sulfonamide |
| 100 | 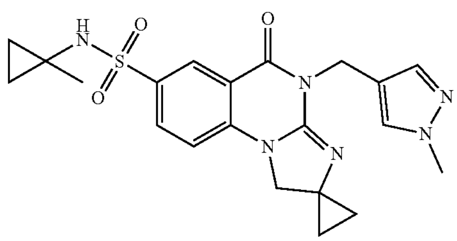 [SMILES: Cn1cc(CN2C(=O)c3cc(S(=O)(=O)NC4(C)CC4)ccc3N3CC4(CC4)N=C23)cn1] | 4'-((1-methyl-1H-pyrazol-4-yl)methyl)-N-(1-methylcyclopropyl)-5'-oxo-4',5'-dihydro-1'H-spiro[cyclopropane-1,2'-imidazo[1,2-a]quinazoline]-7'-sulfonamide |
| 101 | 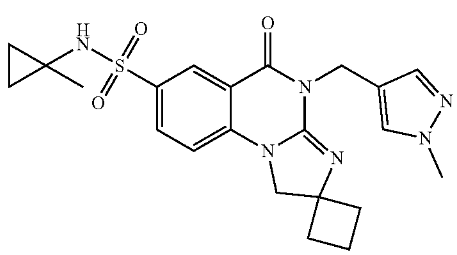 [SMILES: Cn1cc(CN2C(=O)c3cc(S(=O)(=O)NC4(C)CC4)ccc3N3CC4(CCC4)N=C23)cn1] | 4'-((1-methyl-1H-pyrazol-4-yl)methyl)-N-(1-methylcyclopropyl)-5'-oxo-4',5'-dihydro-1'H-spiro[cyclobutane-1,2'-imidazo[1,2-a]quinazoline]-7'-sulfonamide |

TABLE 1-continued

| Synthetic Chemistry Example | Compound Structure | Compound Name |
|---|---|---|
| 102 | 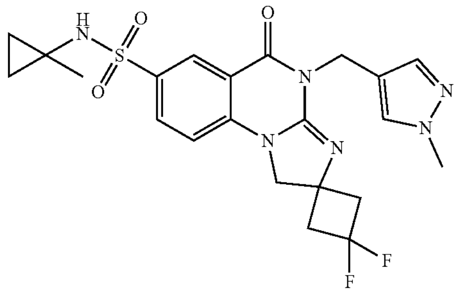 [SMILES: Cn1cc(CN2C(=O)c3cc(S(=O)(=O)NC4(C)CC4)ccc3N3CC4(CC(F)(F)C4)N=C23)cn1] | 3,3-difluoro-4'-((1-methyl-1H-pyrazol-4-yl)methyl)-N-(1-methylcyclopropyl)-5'-oxo-4',5'-dihydro-1'H-spiro[cyclobutane-1,2'-imidazo[1,2-a]quinazoline]-7'-sulfonamide |
| 103 | 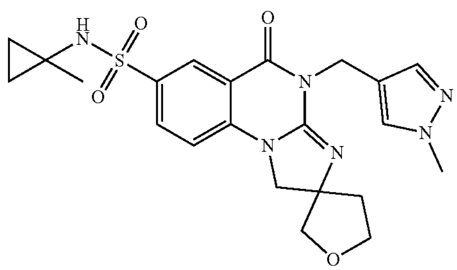 [SMILES: Cn1cc(CN2C(=O)c3cc(S(=O)(=O)NC4(C)CC4)ccc3N3CC4(CCOC4)N=C23)cn1] | 4'-((1-methyl-1H-pyrazol-4-yl)methyl)-N-(1-methylcyclopropyl)-5'-oxo-4,4',5,5'-tetrahydro-1'H,2H-spiro[furan-3,2'-imidazo[1,2-a]quinazoline]-7'-sulfonamide |
| 104 | 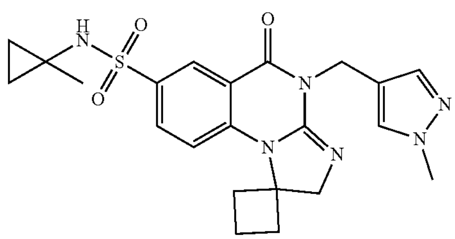 [SMILES: Cn1cc(CN2C(=O)c3cc(S(=O)(=O)NC4(C)CC4)ccc3N3C2=NCC32CCC2)cn1] | 4'-((1-methyl-1H-pyrazol-4-yl)methyl)-N-(1-methylcyclopropyl)-5'-oxo-4',5'-dihydro-2'H-spiro[cyclobutane-1,1'-imidazo[1,2-a]quinazoline]-7'-sulfonamide |
| 105 | 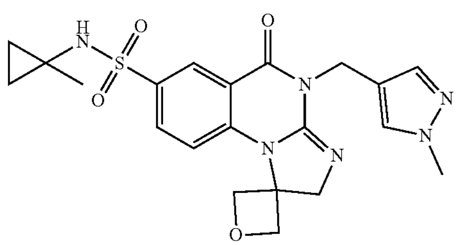 [SMILES: Cn1cc(CN2C(=O)c3cc(S(=O)(=O)NC4(C)CC4)ccc3N3C2=NCC32COC2)cn1] | 4-((1-methyl-1H-pyrazol-4-yl)methyl)-N-(1-methylcyclopropyl)-5-oxo-4,5-dihydro-2H-spiro[imidazo[1,2-a]quinazoline-1,3'-oxetane]-7-sulfonamide |
| 106 | 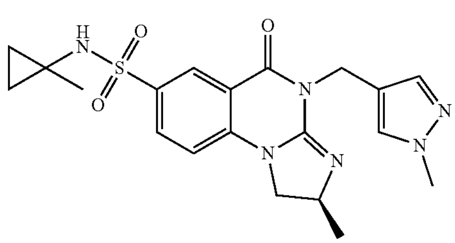 [SMILES: C[C@H]1CN2C(=N1)N(Cc1cnn(C)c1)C(=O)c1cc(S(=O)(=O)NC3(C)CC3)ccc12] | (S)-2-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 107 | 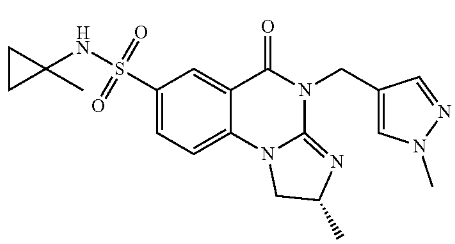 [SMILES: C[C@@H]1CN2C(=N1)N(Cc1cnn(C)c1)C(=O)c1cc(S(=O)(=O)NC3(C)CC3)ccc12] | (R)-2-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |

TABLE 1-continued

| Synthetic Chemistry Example | Compound Structure | Compound Name |
|---|---|---|
| 108 | 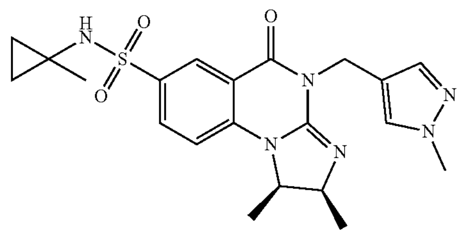 [SMILES: C[C@@H]1N=C2N(Cc3cnn(C)c3)C(=O)c3cc(S(=O)(=O)NC4(C)CC4)ccc3N2[C@@H]1C] | (1R,2S)-1,2-dimethyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 109 | 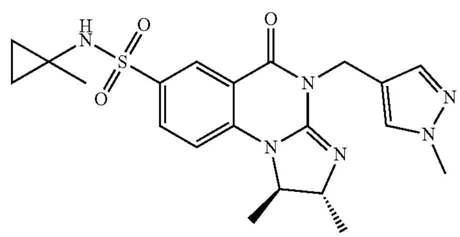 [SMILES: C[C@@H]1[C@@H](C)N=C2N(Cc3cnn(C)c3)C(=O)c3cc(S(=O)(=O)NC4(C)CC4)ccc3N21] | (1R,2R)-1,2-dimethyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 110 | 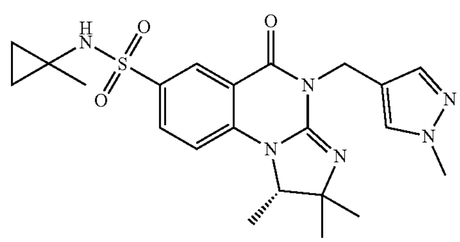 [SMILES: C[C@@H]1N2C(=NC1(C)C)N(Cc1cnn(C)c1)C(=O)c1cc(S(=O)(=O)NC3(C)CC3)ccc12] | (S)-1,2,2-trimethyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 111 | 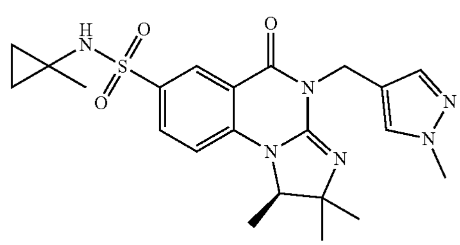 [SMILES: C[C@H]1N2C(=NC1(C)C)N(Cc1cnn(C)c1)C(=O)c1cc(S(=O)(=O)NC3(C)CC3)ccc12] | (R)-1,2,2-trimethyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 112 | 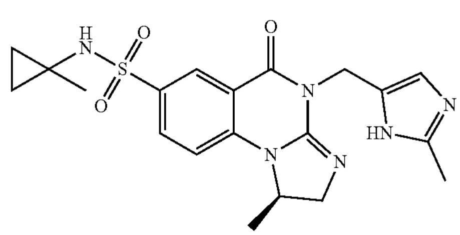 [SMILES: Cc1ncc(CN2C(=O)c3cc(S(=O)(=O)NC4(C)CC4)ccc3N3C2=NC[C@H]3C)[nH]1] | (R)-1-methyl-4-((2-methyl-1H-imidazol-5-yl)methyl)-N-(1-methylcyclopropyl)-5-oxo-1,2,4,5-tetrahydroimidazo[1,2-a]quinazoline-7-sulfonamide |
| 113 | 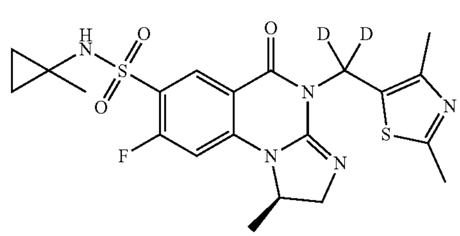 [SMILES: [2H]C([2H])(c1sc(C)nc1C)N1C(=O)c2cc(S(=O)(=O)NC3(C)CC3)c(F)cc2N2C1=NC[C@H]2C] | (R)-4-(dideutero(2,4-dimethylthiazol-5-yl)methyl)-8-fluoro-1-methyl-N-(1-methylcyclopropyl)-5-oxo-1,2,4,5-tetrahydroimidazo[1,2-a]quinazoline-7-sulfonamide |

TABLE 1-continued

| Synthetic Chemistry Example | Compound Structure | Compound Name |
|---|---|---|
| 114 | 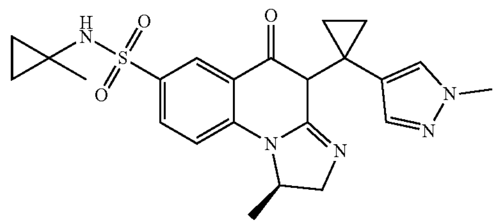 [SMILES: C[C@@H]1CN=C2C(C3(c4cnn(C)c4)CC3)C(=O)c3cc(S(=O)(=O)NC4(C)CC4)ccc3N21] | (R)-1-methyl-4-(1-(1-methyl-1H-pyrazol-4-yl)cyclopropyl)-N-(1-methylcyclopropyl)-5-oxo-1,2,4,5-tetrahydroimidazo[1,2-a]quinazoline-7-sulfonamide |
| 115 | 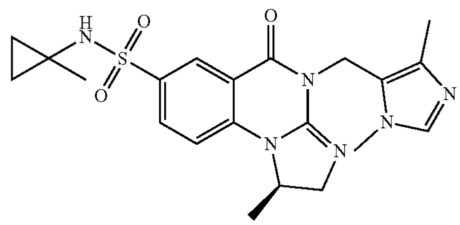 [SMILES: Cc1ncn(C)c1CN1C(=O)c2cc(S(=O)(=O)NC3(C)CC3)ccc2N2C1=NC[C@H]2C] | (R)-4-((1,4-dimethyl-1H-imidazol-5-yl)methyl)-1-methyl-N-(1-methylcyclopropyl)-5-oxo-1,2,4,5-tetrahydroimidazo[1,2-a]quinazoline-7-sulfonamide |
| 116 | 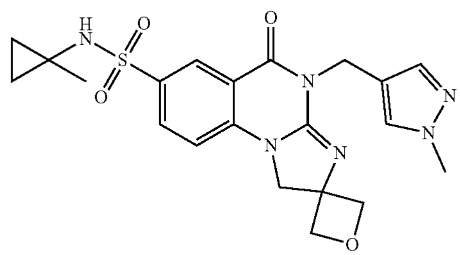 [SMILES: Cn1cc(CN2C(=O)c3cc(S(=O)(=O)NC4(C)CC4)ccc3N3CC4(COC4)N=C23)cn1] | 4-((1-methyl-1H-pyrazol-4-yl)methyl)-N-(1-methylcyclopropyl)-5-oxo-4,5-dihydro-1H-spiro[imidazo[1,2-a]quinazoline-2,3'-oxetane]-7-sulfonamide |
| 117 | 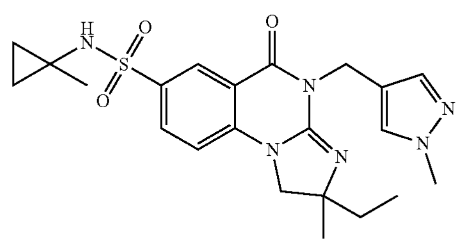 [SMILES: CCC1(C)CN2C(=N1)N(Cc1cnn(C)c1)C(=O)c1cc(S(=O)(=O)NC3(C)CC3)ccc12] | 2-ethyl-2-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 118 | 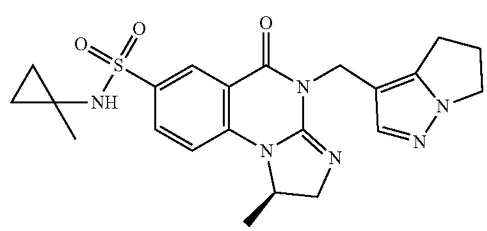 [SMILES: C[C@@H]1CN=C2N(Cc3cnn4c3CCC4)C(=O)c3cc(S(=O)(=O)NC4(C)CC4)ccc3N21] | (R)-4-((5,6-dihydro-4H-pyrrolo[1,2-b]pyrazol-3-yl)methyl)-1-methyl-N-(1-methylcyclopropyl)-5-oxo-1,2,4,5-tetrahydroimidazo[1,2-a]quinazoline-7-sulfonamide |
| 119 | 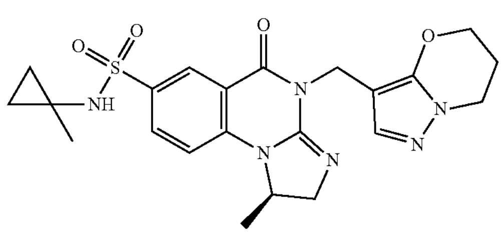 [SMILES: C[C@@H]1CN=C2N(Cc3cnn4c3OCCC4)C(=O)c3cc(S(=O)(=O)NC4(C)CC4)ccc3N21] | (R)-4-((6,7-dihydro-5H-pyrazolo[5,1-b][1,3]oxazin-3-yl)methyl)-1-methyl-N-(1-methylcyclopropyl)-5-oxo-1,2,4,5-tetrahydroimidazo[1,2-a]quinazoline-7-sulfonamide |

TABLE 1-continued

| Synthetic Chemistry Example | Compound Structure | Compound Name |
|---|---|---|
| 120 | 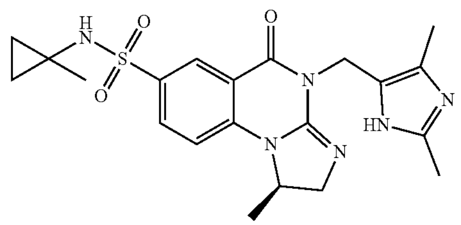 [SMILES: Cc1nc(C)c(CN2C(=O)c3cc(S(=O)(=O)NC4(C)CC4)ccc3N3C2=NC[C@H]3C)[nH]1] | (R)-4-((2,4-dimethyl-1H-imidazol-5-yl)methyl)-1-methyl-N-(1-methylcyclopropyl)-5-oxo-1,2,4,5-tetrahydroimidazo[1,2-a]quinazoline-7-sulfonamide |
| 121 | 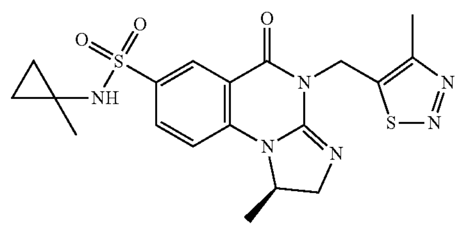 [SMILES: Cc1nnsc1CN1C(=O)c2cc(S(=O)(=O)NC3(C)CC3)ccc2N2C1=NC[C@H]2C] | (R)-1-methyl-4-((4-methyl-1,2,3-thiadiazol-5-yl)methyl)-N-(1-methylcyclopropyl)-5-oxo-1,2,4,5-tetrahydroimidazo[1,2-a]quinazoline-7-sulfonamide |
| 122 | 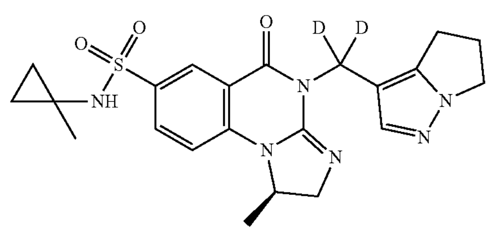 [SMILES: [2H]C([2H])(c1cnn2c1CCC2)N1C(=O)c2cc(S(=O)(=O)NC3(C)CC3)ccc2N2C1=NC[C@H]2C] | (R)-4-(dideutero(5,6-dihydro-4H-pyrrolo[1,2-b]pyrazol-3-yl)methyl)-1-methyl-N-(1-methylcyclopropyl)-5-oxo-1,2,4,5-tetrahydroimidazo[1,2-a]quinazoline-7-sulfonamide |
| 123 | 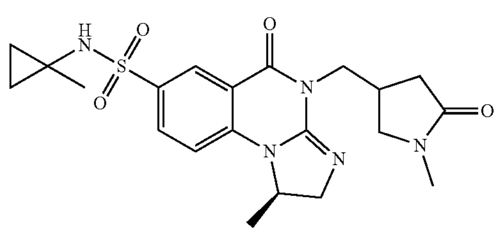 [SMILES: C[C@@H]1CN=C2N(CC3CC(=O)N(C)C3)C(=O)c3cc(S(=O)(=O)NC4(C)CC4)ccc3N21] | (R)-1-methyl-4-((1-methyl-5-oxopyrrolidin-3-yl)methyl)-N-(1-methylcyclopropyl)-5-oxo-1,2,4,5-tetrahydroimidazo[1,2-a]quinazoline-7-sulfonamide Absolute stereochemistry not assigned (Isomer B) |
| 124 | 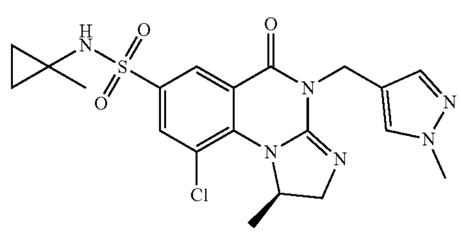 [SMILES: C[C@@H]1CN=C2N(Cc3cnn(C)c3)C(=O)c3cc(S(=O)(=O)NC4(C)CC4)cc(Cl)c3N21] | (R)-9-chloro-1-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 125 | 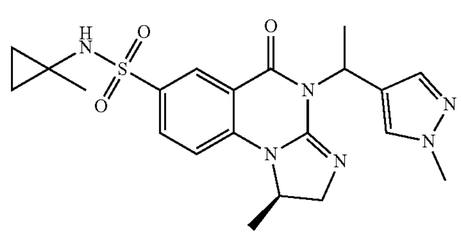 [SMILES: CC(c1cnn(C)c1)N1C(=O)c2cc(S(=O)(=O)NC3(C)CC3)ccc2N2C1=NC[C@H]2C] | (R)-1-methyl-4-((1-(1-methyl-1H-pyrazol-4-yl)ethyl)-N-(1-methylcyclopropyl)-5-oxo-1,2,4,5-tetrahydroimidazo[1,2-a]quinazoline-7-sulfonamide Absolute stereochemistry not assigned (Isomer A) |

TABLE 1-continued

| Synthetic Chemistry Example | Compound Structure | Compound Name |
|---|---|---|
| 126 | 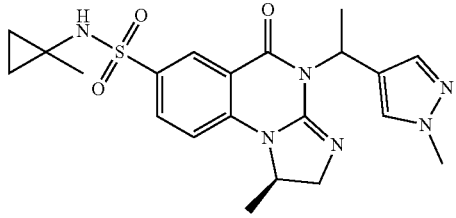 [SMILES: CC(c1cnn(C)c1)N1C(=O)c2cc(S(=O)(=O)NC3(C)CC3)ccc2N2C1=NC[C@H]2C] | (R)-1-methyl-4-((1-(1-methyl-1H-pyrazol-4-yl)ethyl)-N-(1-methylcyclopropyl)-5-oxo-1,2,4,5-tetrahydroimidazo[1,2-a]quinazoline-7-sulfonamide Absolute stereochemistry not assigned (Isomer B) |
| 127 | 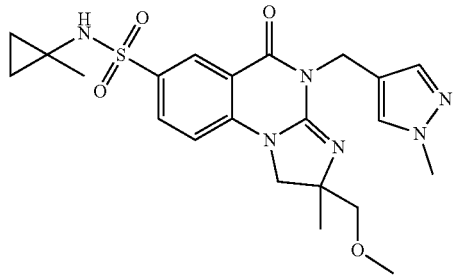 [SMILES: COCC1(C)CN2C(=N1)N(Cc1cnn(C)c1)C(=O)c1cc(S(=O)(=O)NC3(C)CC3)ccc12] | 2-(methoxymethyl)-2-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 128 | 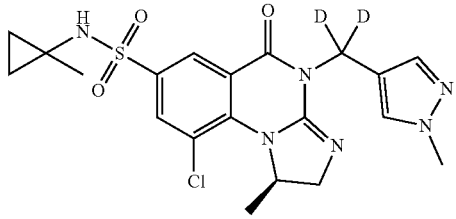 [SMILES: [2H]C([2H])(c1cnn(C)c1)N1C(=O)c2cc(S(=O)(=O)NC3(C)CC3)cc(Cl)c2N2C1=NC[C@H]2C] | (R)-9-chloro-4-(dideutero(1-methyl-1H-pyrazol-4-yl)methyl)-1-methyl-N-(1-methylcyclopropyl)-5-oxo-1,2,4,5-tetrahydroimidazo[1,2-a]quinazoline-7-sulfonamide |
| 129 | 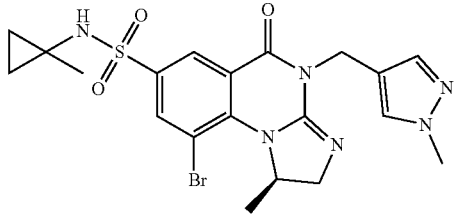 | (R)-9-bromo-1-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 130 | 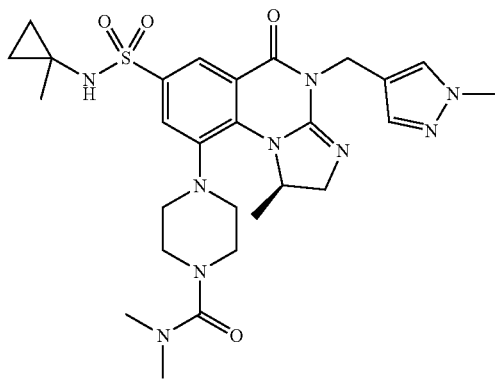 [SMILES: C[C@@H]1CN=C2N(Cc3cnn(C)c3)C(=O)c3cc(S(=O)(=O)NC4(C)CC4)cc(N4CCN(C(=O)N(C)C)CC4)c3N21] | (R)-N,N-dimethyl-4-(1-methyl-4-((1-methyl-1H-pyrazol-4-yl)methyl)-7-(N-(1-methylcyclopropyl)sulfamoyl)-5-oxo-1,2,4,5-tetrahydroimidazo[1,2-a]quinazolin-9-yl)piperazine-1-carboxamide |

TABLE 1-continued

| Synthetic Chemistry Example | Compound Structure | Compound Name |
|---|---|---|
| 131 | 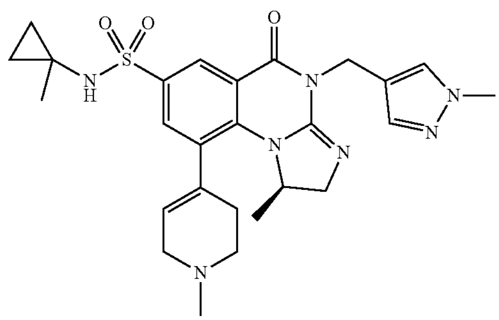 [SMILES: C[C@@H]1CN=C2N(Cc3cnn(C)c3)C(=O)c3cc(S(=O)(=O)NC4(C)CC4)cc(C4=CCN(C)CC4)c3N21] | (R)-1-methyl-9-(1-methyl-1,2,3,6-tetrahydropyridin-4-yl)-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 132 | 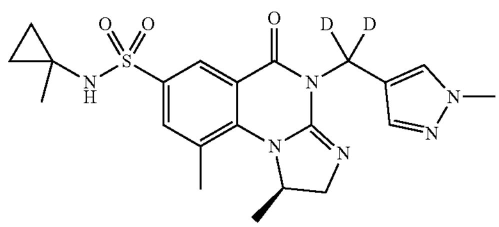 [SMILES: [2H]C([2H])(c1cnn(C)c1)N1C(=O)c2cc(S(=O)(=O)NC3(C)CC3)cc(C)c2N2C1=NC[C@H]2C] | (R)-1,9-dimethyl-4-((1-methyl-1H-pyrazol-4-yl)methyl-d2)-N-(1-methylcyclopropyl)-5-oxo-1,2,4,5-tetrahydroimidazo[1,2-a]quinazoline-7-sulfonamide |
| 133 | 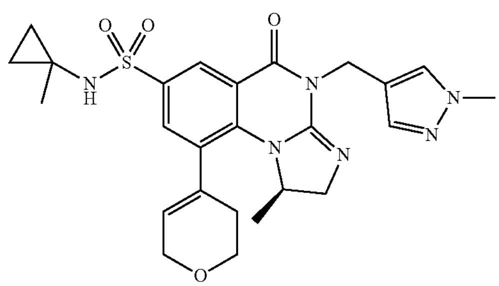 [SMILES: C[C@@H]1CN=C2N(Cc3cnn(C)c3)C(=O)c3cc(S(=O)(=O)NC4(C)CC4)cc(C4=CCOCC4)c3N21] | (R)-9-(3,6-dihydro-2H-pyran-4-yl)-1-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 134 | 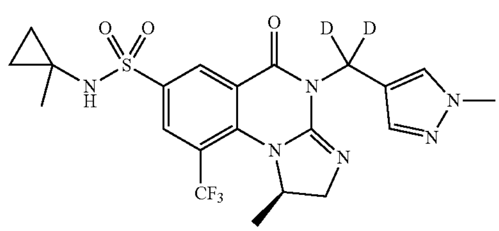 [SMILES: [2H]C([2H])(c1cnn(C)c1)N1C(=O)c2cc(S(=O)(=O)NC3(C)CC3)cc(C(F)(F)F)c2N2C1=NC[C@H]2C] | (R)-1-methyl-4-((1-methyl-1H-pyrazol-4-yl)methyl-d2)-N-(1-methylcyclopropyl)-5-oxo-9-(trifluoromethyl)-1,2,4,5-tetrahydroimidazo[1,2-a]quinazoline-7-sulfonamide |
| 135 | 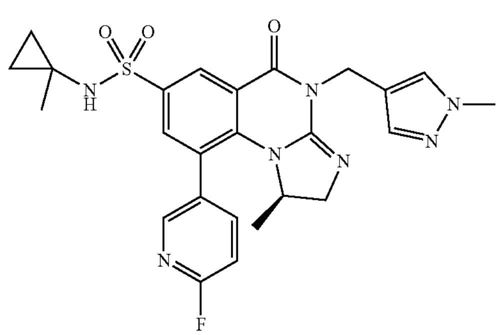 [SMILES: C[C@@H]1CN=C2N(Cc3cnn(C)c3)C(=O)c3cc(S(=O)(=O)NC4(C)CC4)cc(-c4ccc(F)nc4)c3N21] | (R)-9-(6-fluoropyridin-3-yl)-1-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |

TABLE 1-continued

| Synthetic Chemistry Example | Compound Structure | Compound Name |
|---|---|---|
| 136 | 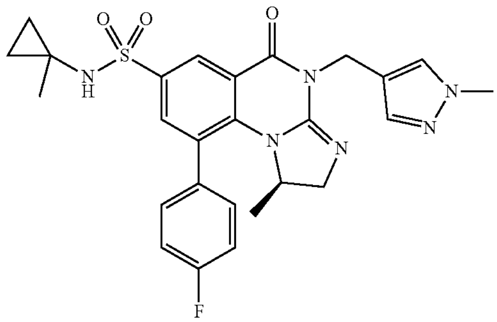 [SMILES: C[C@@H]1CN=C2N(Cc3cnn(C)c3)C(=O)c3cc(S(=O)(=O)NC4(C)CC4)cc(-c4ccc(F)cc4)c3N21] | (R)-9-(4-fluorophenyl)-1-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |
| 137 | 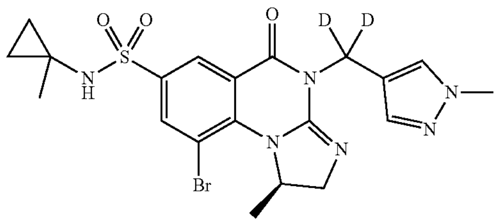 [SMILES: [2H]C([2H])(c1cnn(C)c1)N1C(=O)c2cc(S(=O)(=O)NC3(C)CC3)cc(Br)c2N2C1=NC[C@H]2C] | (R)-9-bromo-1-methyl-4-((1-methyl-1H-pyrazol-4-yl)methyl-d2)-N-(1-methylcyclopropyl)-5-oxo-1,2,4,5-tetrahydroimidazo-[1,2-a]quinazoline-7-sulfonamide |
| 138 | 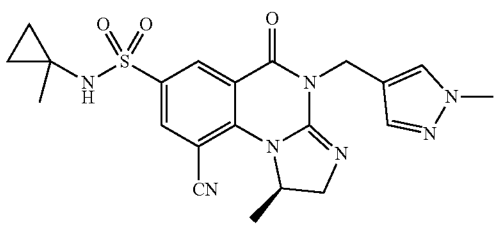 [SMILES: C[C@@H]1CN=C2N(Cc3cnn(C)c3)C(=O)c3cc(S(=O)(=O)NC4(C)CC4)cc(C#N)c3N21] | (R)-9-cyano-1-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide |

Another embodiment provides an PARG inhibitory compound, or a pharmaceutically acceptable salt or solvate thereof, having a structure presented in Tables 2A-2I.

TABLE 2A

TABLE 2A-continued

TABLE 2A-continued
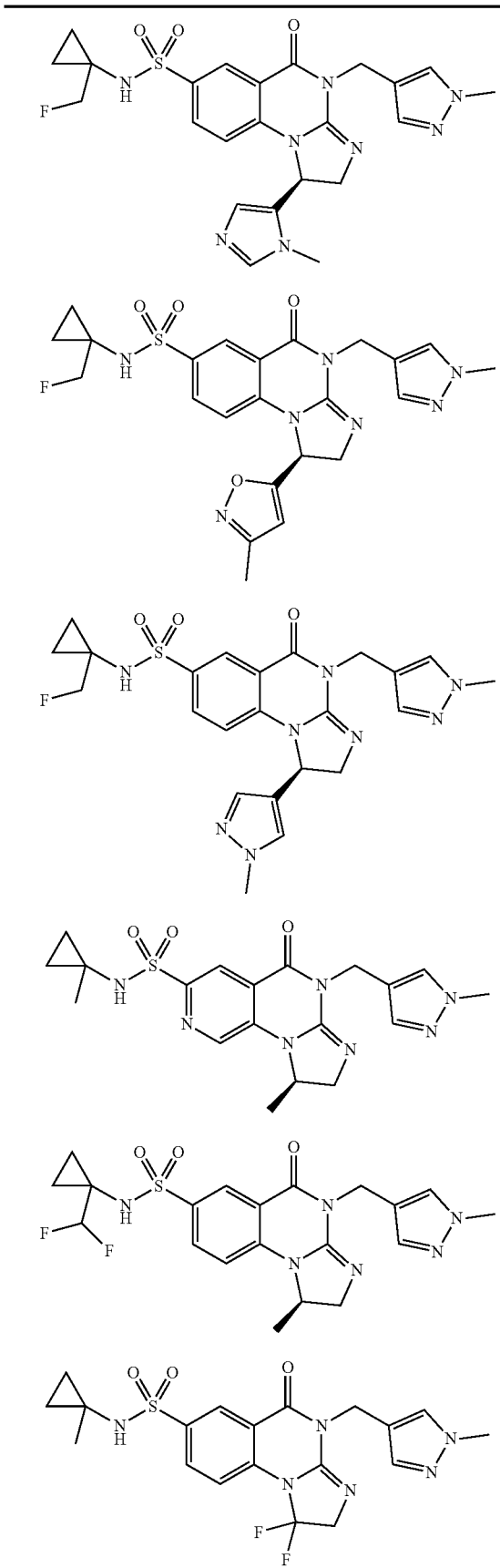
TABLE 2A-continued
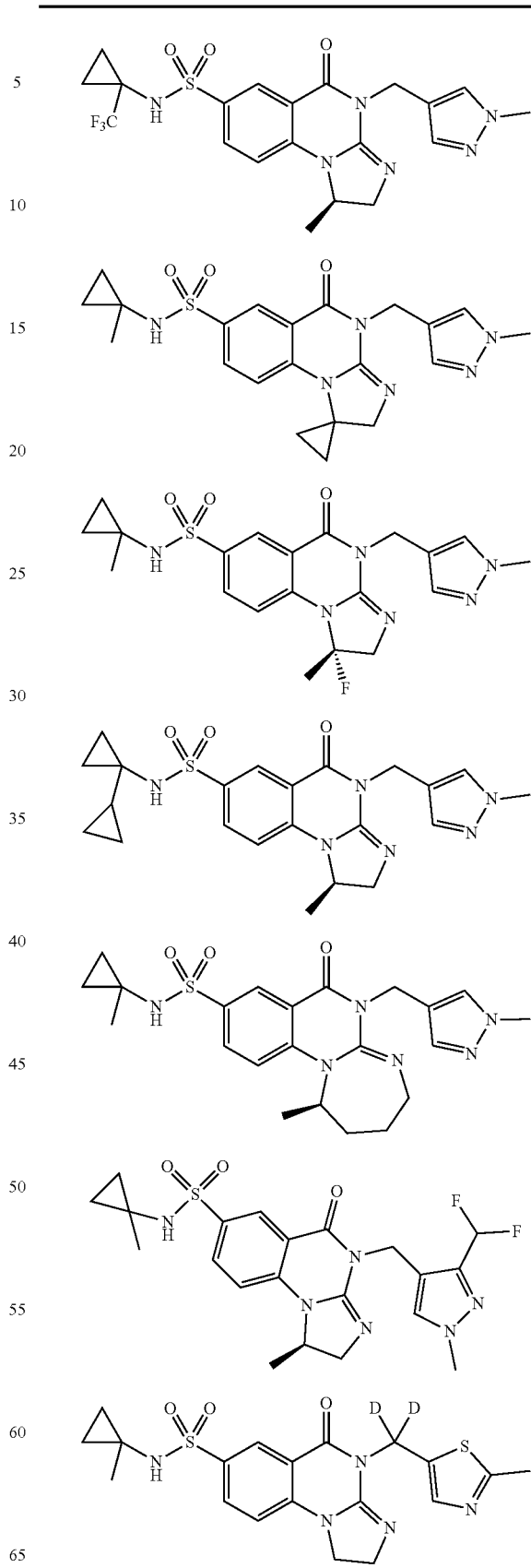

TABLE 2A-continued
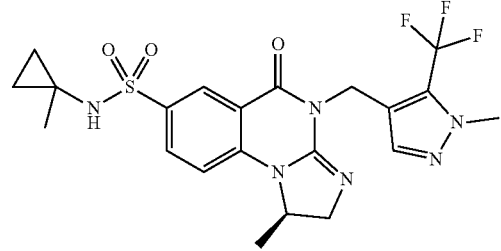 [SMILES: C[C@@H]1CN=C2N(Cc3cnn(C)c3C(F)(F)F)C(=O)c3cc(S(=O)(=O)NC4(C)CC4)ccc3N21]
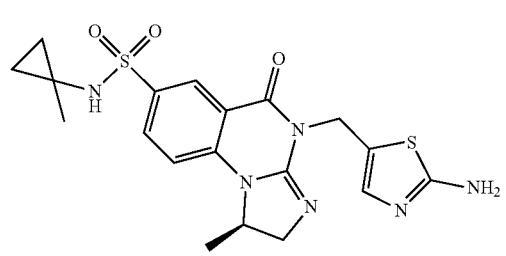 [SMILES: C[C@@H]1CN=C2N(Cc3cnc(N)s3)C(=O)c3cc(S(=O)(=O)NC4(C)CC4)ccc3N21]
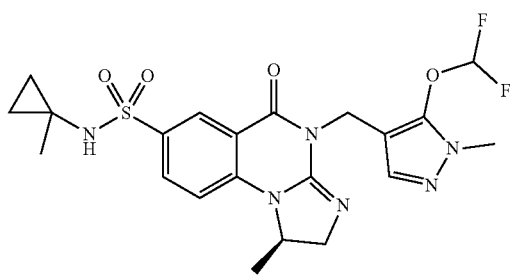 [SMILES: C[C@@H]1CN=C2N(Cc3cnn(C)c3OC(F)F)C(=O)c3cc(S(=O)(=O)NC4(C)CC4)ccc3N21]
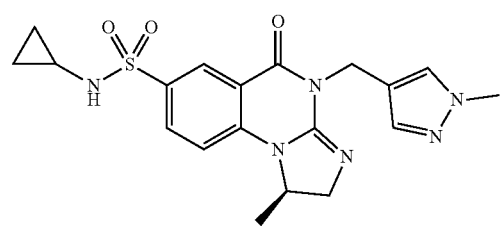 [SMILES: C[C@@H]1CN=C2N(Cc3cnn(C)c3)C(=O)c3cc(S(=O)(=O)NC4CC4)ccc3N21]
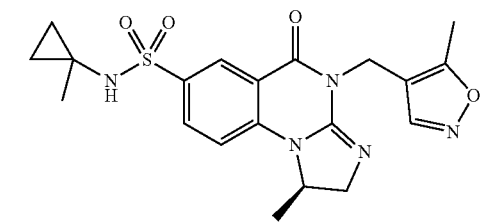
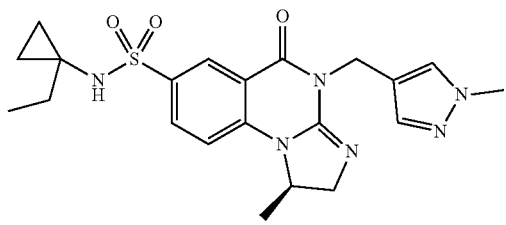 [SMILES: CCC1(NS(=O)(=O)c2ccc3c(c2)C(=O)N(Cc2cnn(C)c2)C2=NC[C@@H](C)N23)CC1]
TABLE 2A-continued
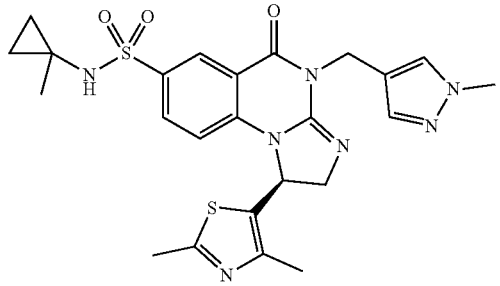 [SMILES: Cc1nc(C)c([C@@H]2CN=C3N(Cc4cnn(C)c4)C(=O)c4cc(S(=O)(=O)NC5(C)CC5)ccc4N32)s1]
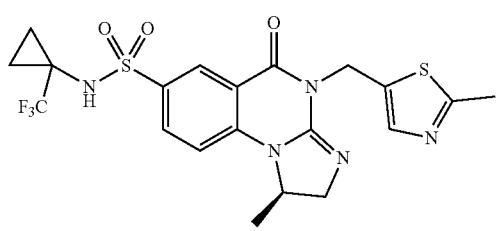 [SMILES: Cc1ncc(CN2C(=O)c3cc(S(=O)(=O)NC4(C(F)(F)F)CC4)ccc3N3C2=NC[C@H]3C)s1]
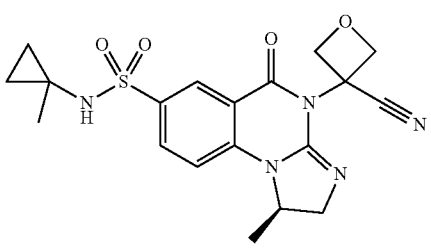 [SMILES: C[C@@H]1CN=C2N1c1ccc(S(=O)(=O)NC3(C)CC3)cc1C(=O)N2C1(C#N)COC1]
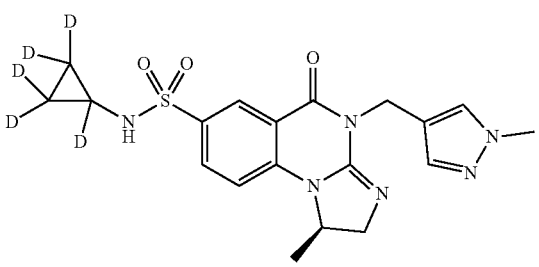 [SMILES: [2H]C1([2H])C([2H])([2H])C1([2H])NS(=O)(=O)c1ccc2c(c1)C(=O)N(Cc1cnn(C)c1)C1=NC[C@@H](C)N12]
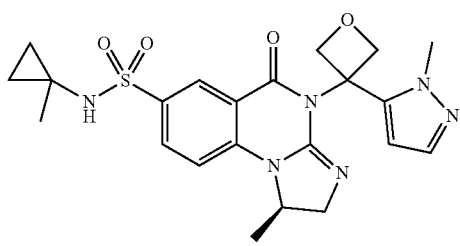 [SMILES: C[C@@H]1CN=C2N1c1ccc(S(=O)(=O)NC3(C)CC3)cc1C(=O)N2C1(c2ccnn2C)COC1]
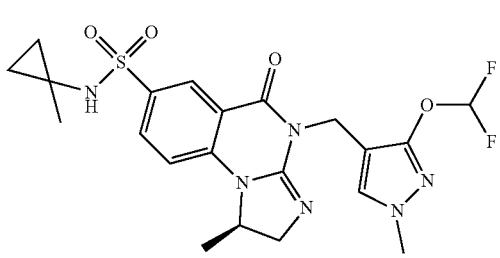 [SMILES: C[C@@H]1CN=C2N(Cc3cn(C)nc3OC(F)F)C(=O)c3cc(S(=O)(=O)NC4(C)CC4)ccc3N21]

TABLE 2A-continued
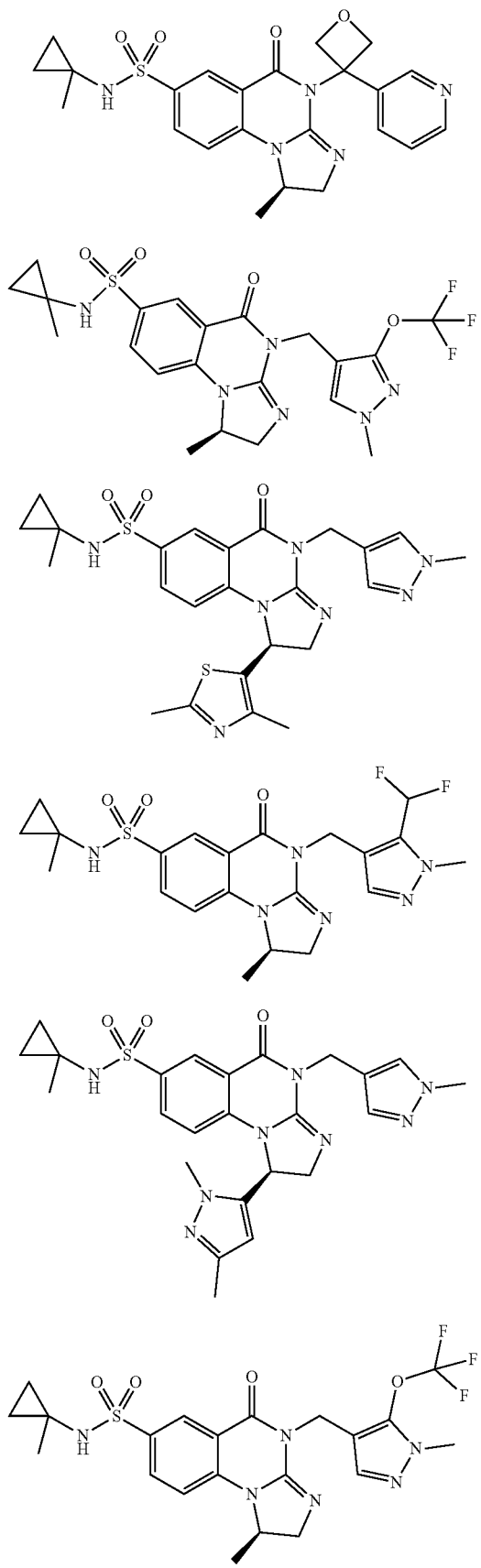
TABLE 2A-continued
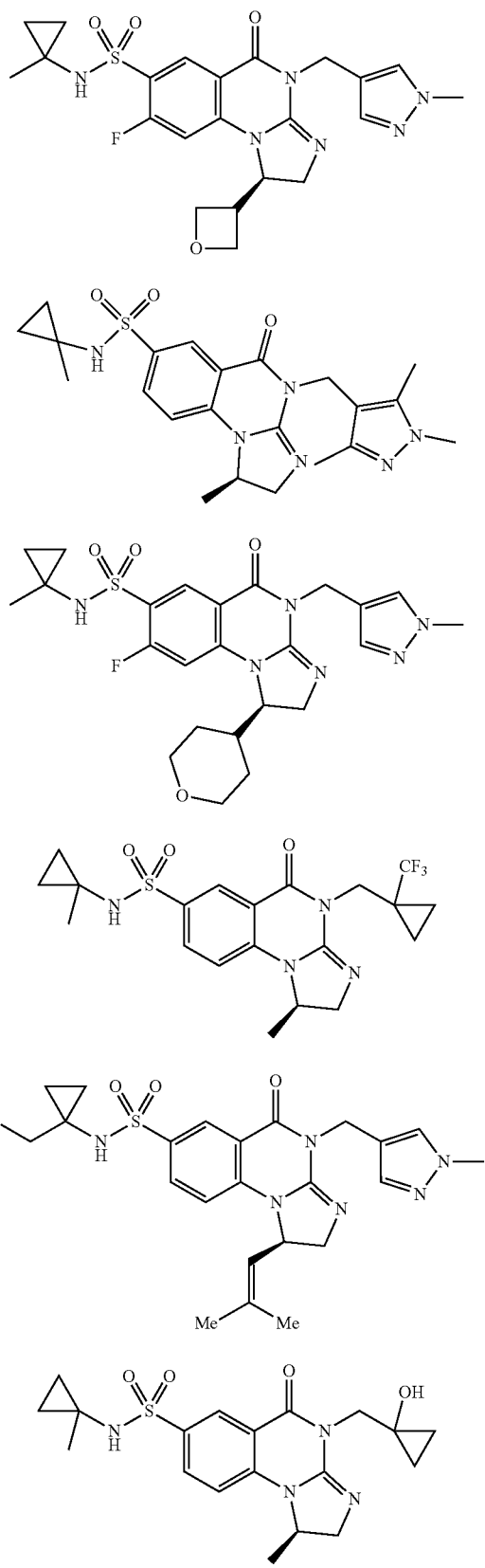

TABLE 2A-continued
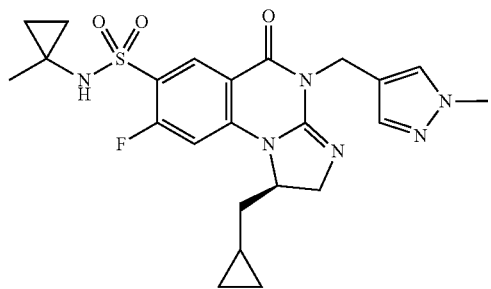
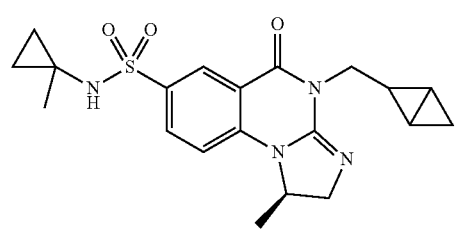 [SMILES: C[C@@H]1CN=C2N(CC3C4CC43)C(=O)c3cc(S(=O)(=O)NC4(C)CC4)ccc3N21]
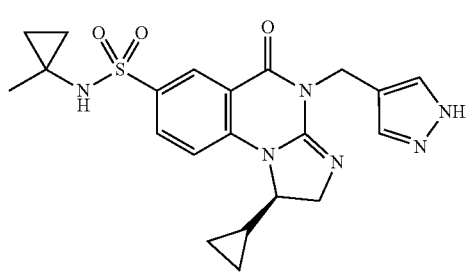 [SMILES: CC1(NS(=O)(=O)c2ccc3c(c2)C(=O)N(Cc2cn[nH]c2)C2=NC[C@@H](C4CC4)N23)CC1]
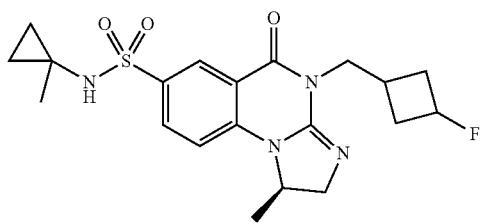 [SMILES: C[C@@H]1CN=C2N(CC3CC(F)C3)C(=O)c3cc(S(=O)(=O)NC4(C)CC4)ccc3N21]
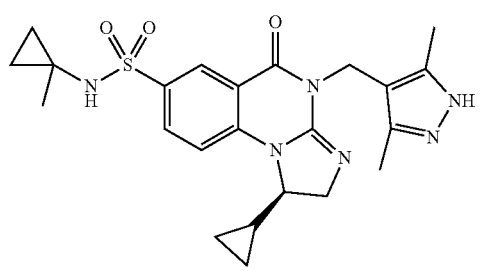 [SMILES: Cc1n[nH]c(C)c1CN1C(=O)c2cc(S(=O)(=O)NC3(C)CC3)ccc2N2C1=NC[C@H]2C1CC1]
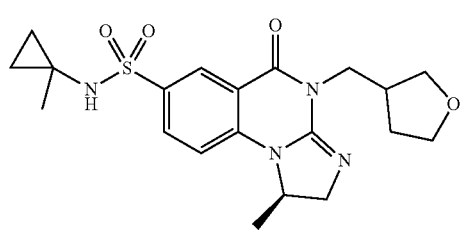 [SMILES: C[C@@H]1CN=C2N(CC3CCOC3)C(=O)c3cc(S(=O)(=O)NC4(C)CC4)ccc3N21]
TABLE 2A-continued
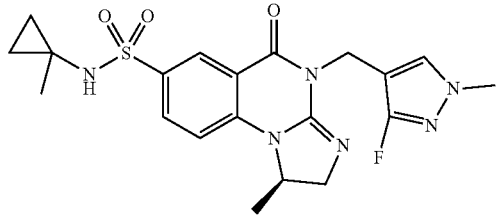 [SMILES: C[C@@H]1CN=C2N(Cc3cn(C)nc3F)C(=O)c3cc(S(=O)(=O)NC4(C)CC4)ccc3N21]
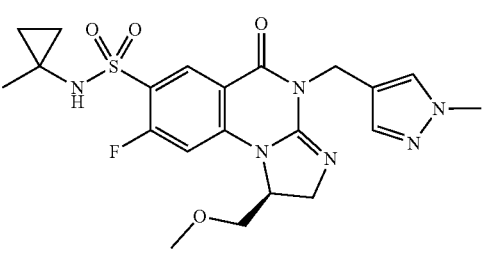
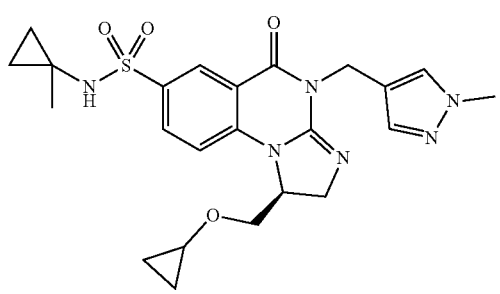 [SMILES: Cn1cc(CN2C(=O)c3cc(S(=O)(=O)NC4(C)CC4)ccc3N3C2=NC[C@H]3COC2CC2)cn1]
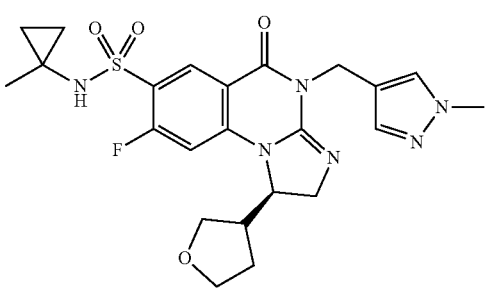
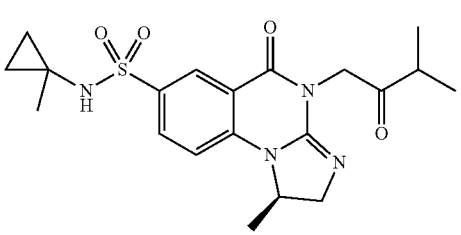 [SMILES: CC(C)C(=O)CN1C(=O)c2cc(S(=O)(=O)NC3(C)CC3)ccc2N2C1=NC[C@H]2C]
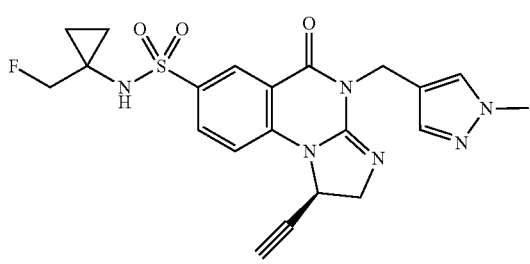 [SMILES: C#C[C@@H]1CN=C2N(Cc3cnn(C)c3)C(=O)c3cc(S(=O)(=O)NC4(CF)CC4)ccc3N21]

TABLE 2A-continued
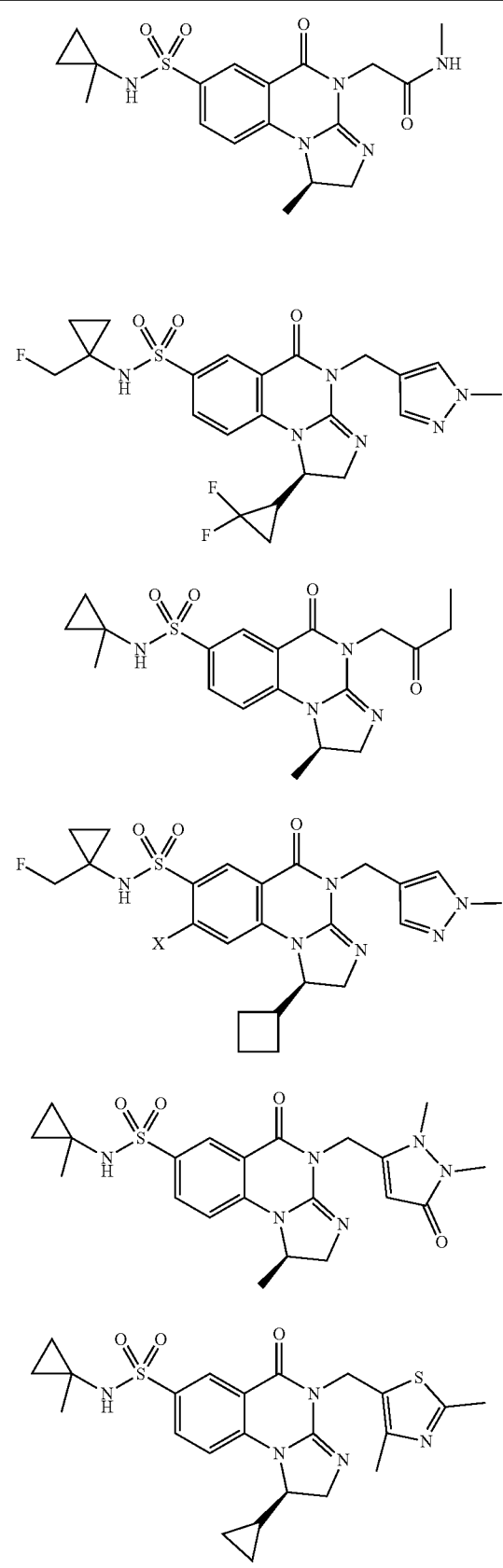
TABLE 2A-continued
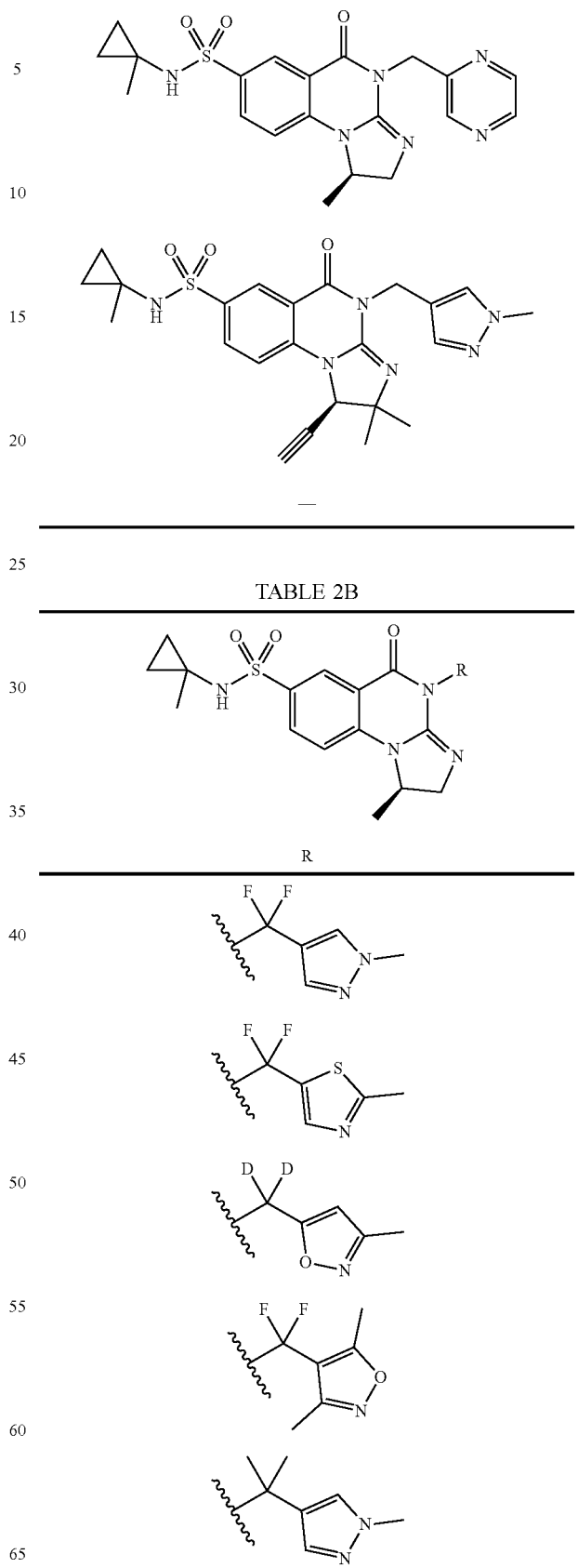

TABLE 2B-continued
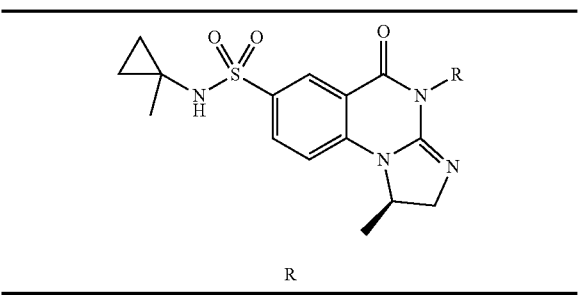
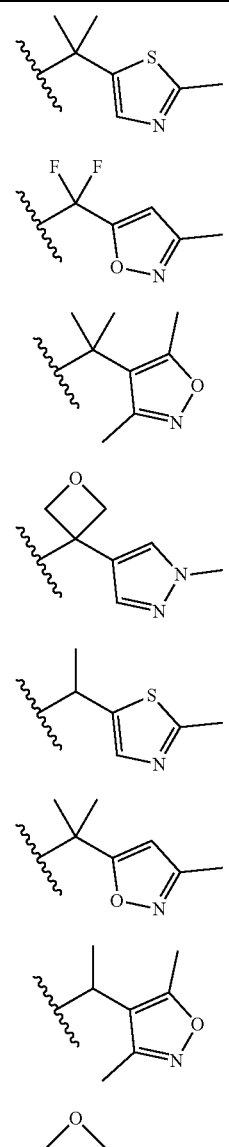
TABLE 2B-continued
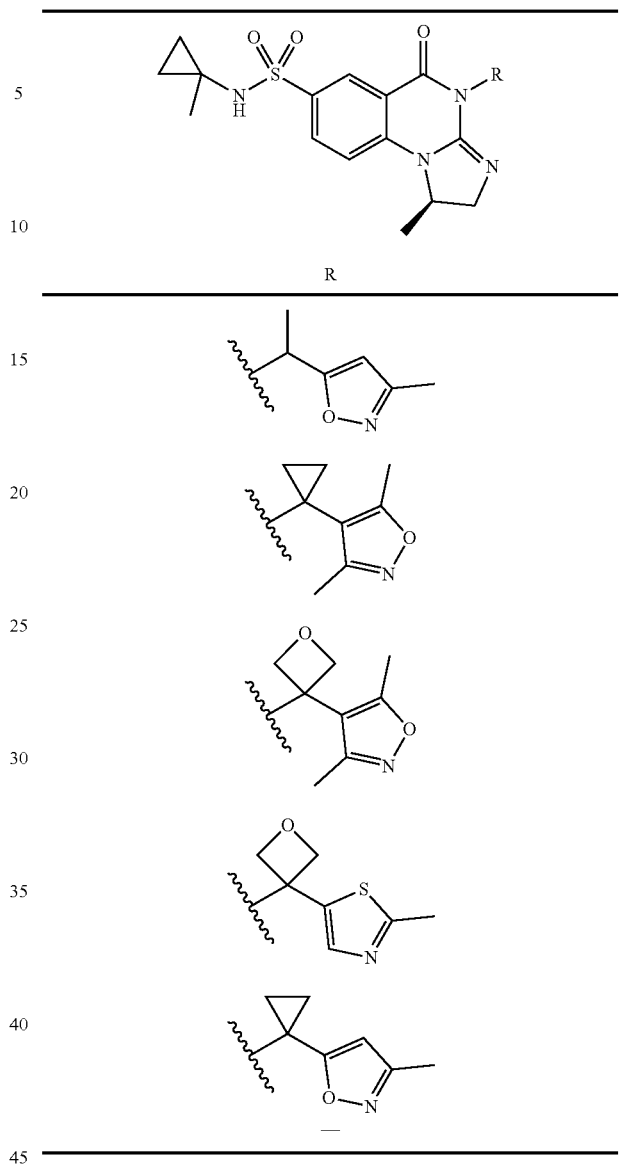
TABLE 2C
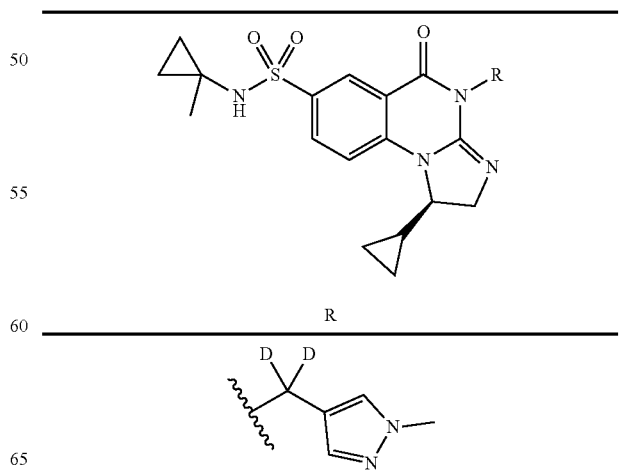

TABLE 2C-continued
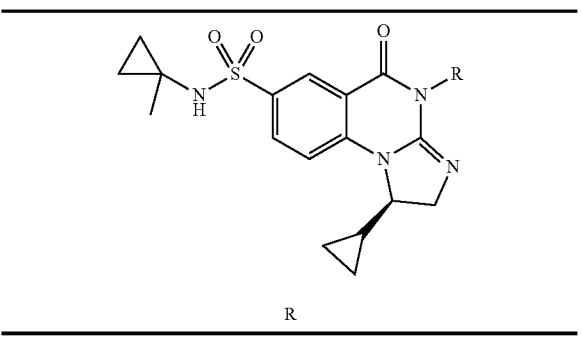
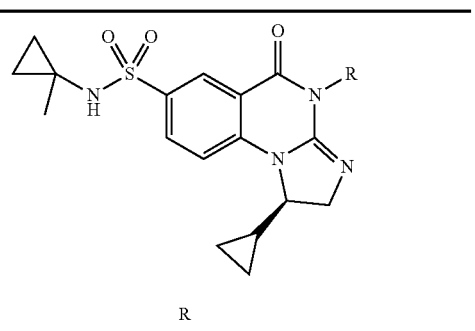
| R | R |
|---|---|
| 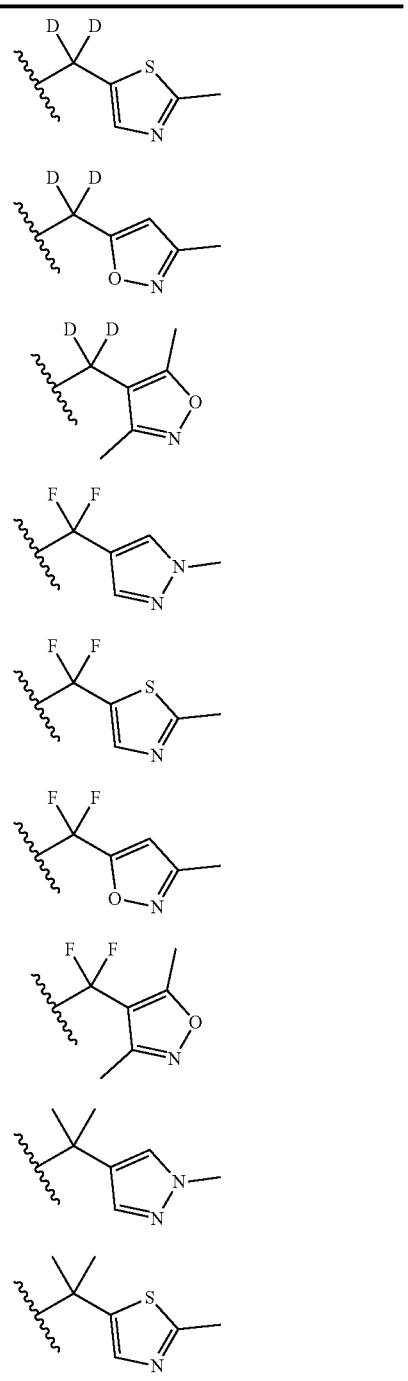 | 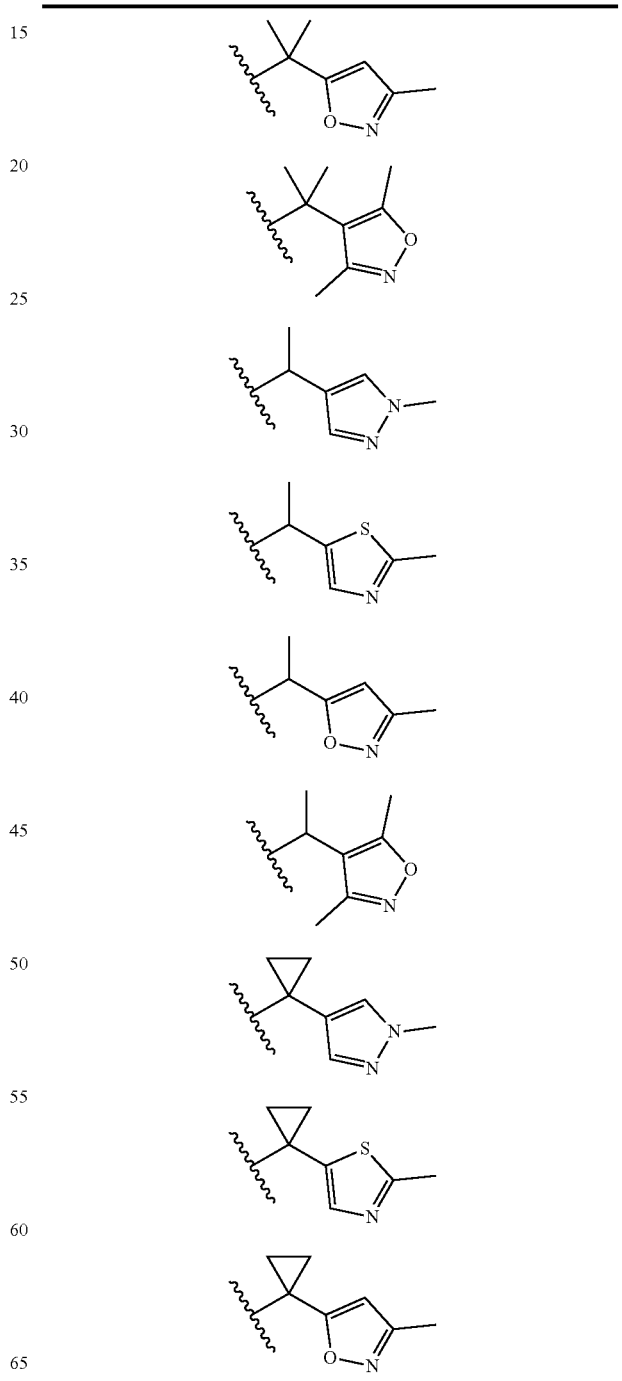 |

TABLE 2C-continued
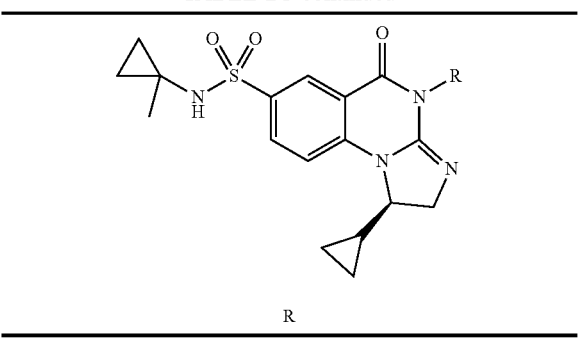
| R |
|---|
|  |
|  |
|  |
|  |
|  |
TABLE 2D
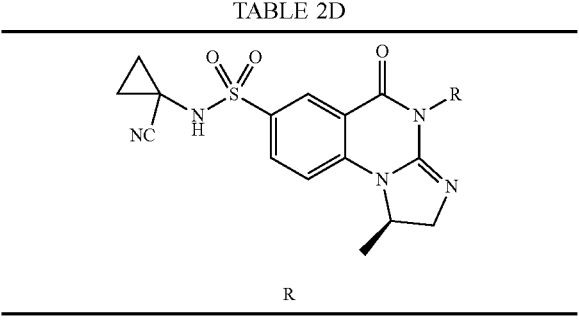
| R |
|---|
|  |
TABLE 2D-continued
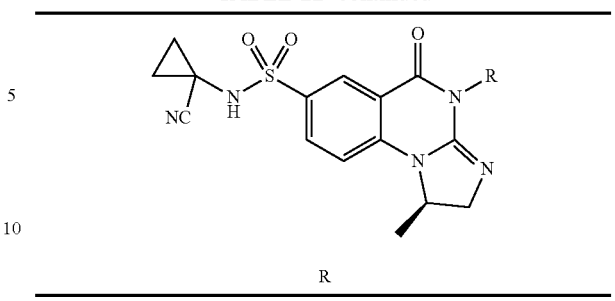
| R |
|---|
|  |
|  |
|  |
|  |

TABLE 2D-continued
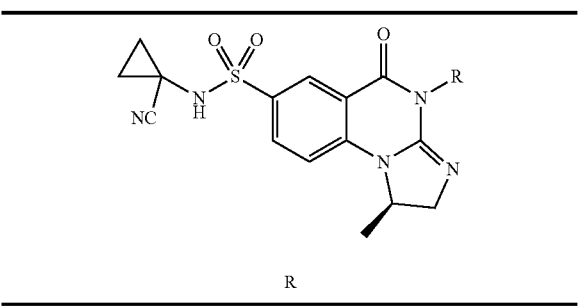
R
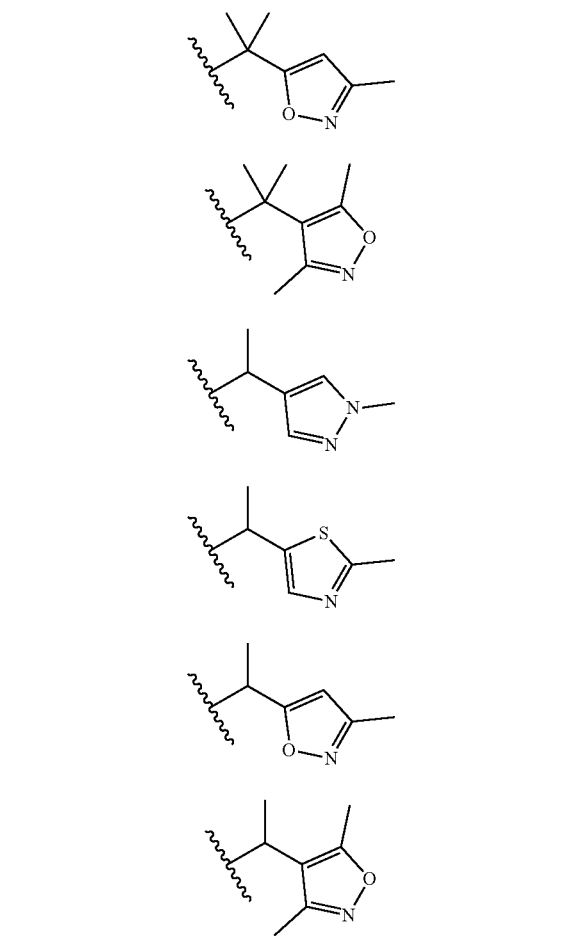
TABLE 2D-continued
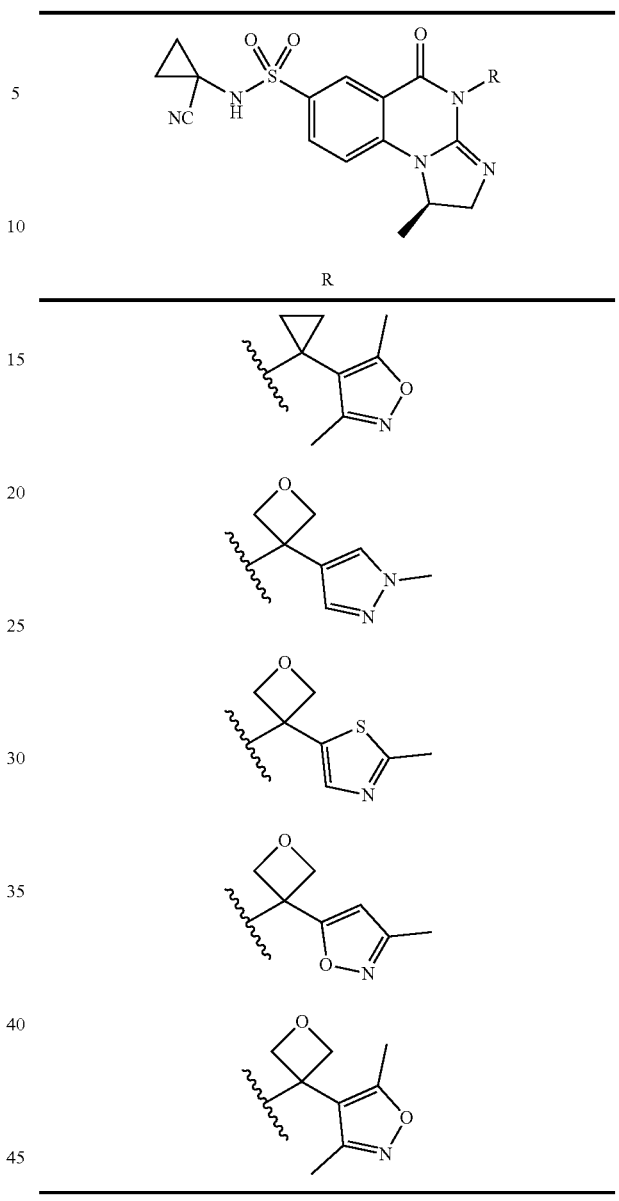
R
TABLE 2E
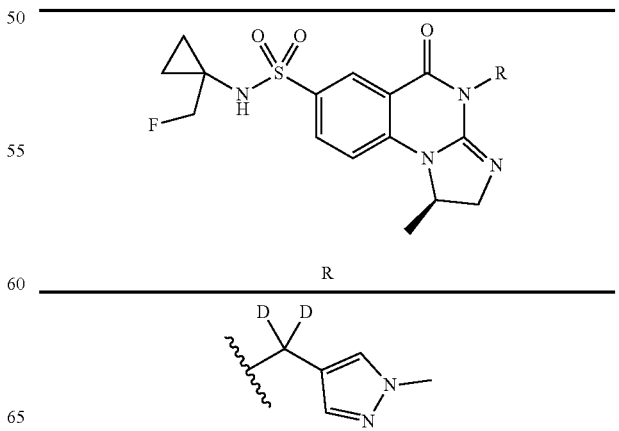
R TABLE 2E-continued
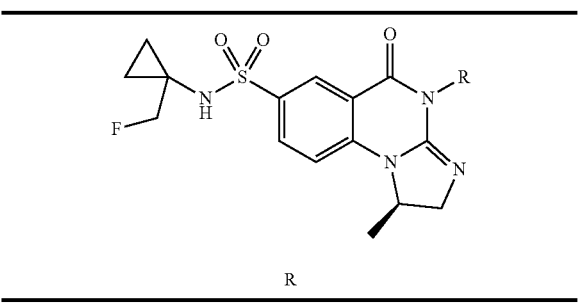
R
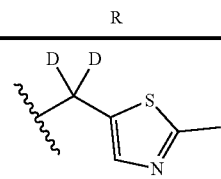
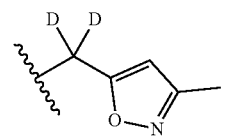
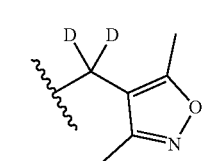
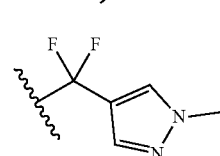
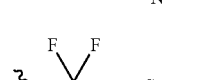
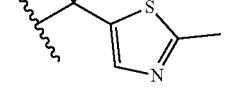
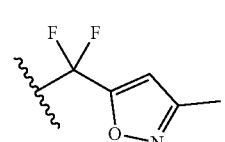
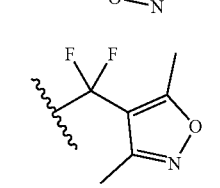
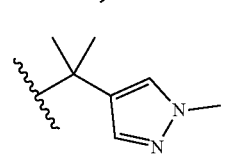
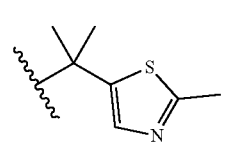 [SMILES: *C(C)(C)c1cnc(C)s1]
TABLE 2E-continued
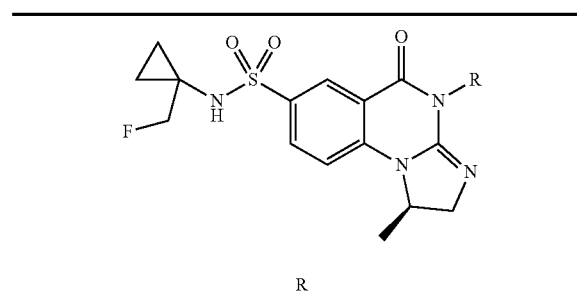
R
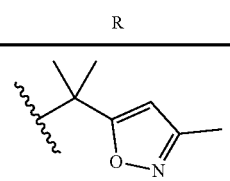
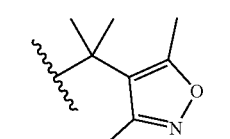
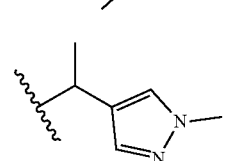
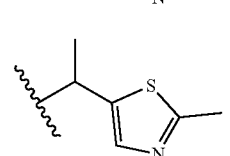
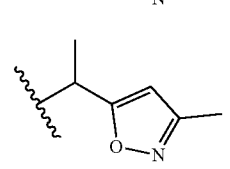
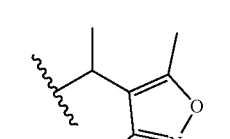
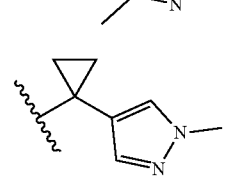
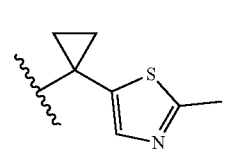 [SMILES: *C1(c2cnc(C)s2)CC1]
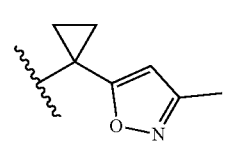 [SMILES: *C1(c2cc(C)no2)CC1]

TABLE 2E-continued
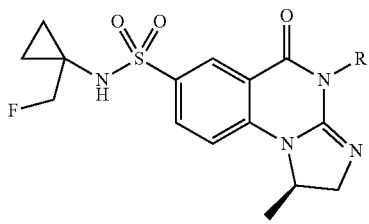
| R |
|---|
| 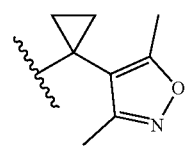 [SMILES: *C1(c2c(C)noc2C)CC1] |
| 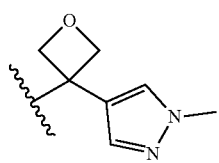 [SMILES: *C1(c2cnn(C)c2)COC1] |
| 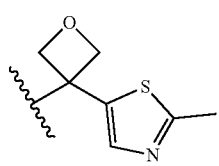 [SMILES: *C1(c2cnc(C)s2)COC1] |
| 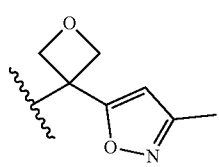 [SMILES: *C1(c2cc(C)no2)COC1] |
| 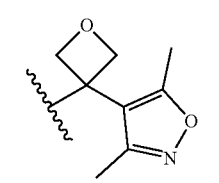 [SMILES: *C1(c2c(C)noc2C)COC1] |
TABLE 2F
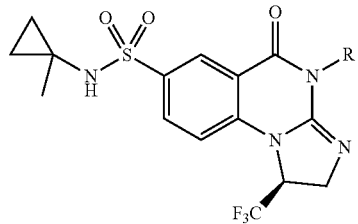
| R |
|---|
| 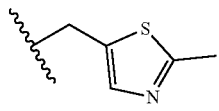 |
TABLE 2F-continued
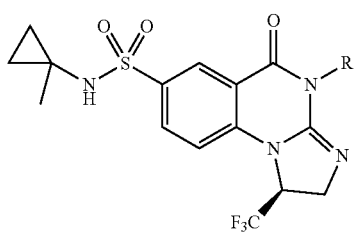
| R |
|---|
| 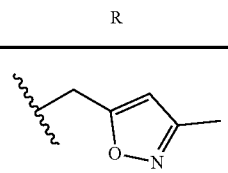 |
| 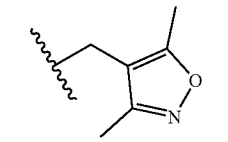 |
TABLE 2G
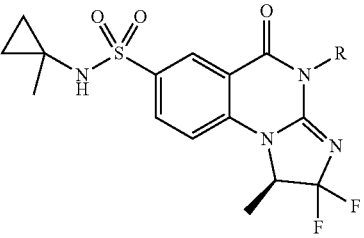
| R |
|---|
| 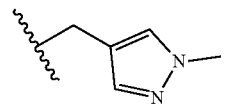 [SMILES: *Cc1cnn(C)c1] |
| 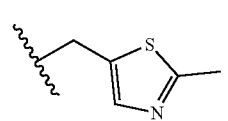 [SMILES: *Cc1cnc(C)s1] |
| 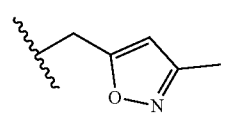 [SMILES: *Cc1cc(C)no1] |
| 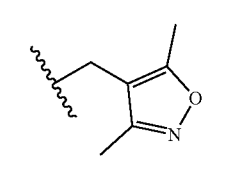 [SMILES: *Cc1c(C)noc1C] |

TABLE 2H
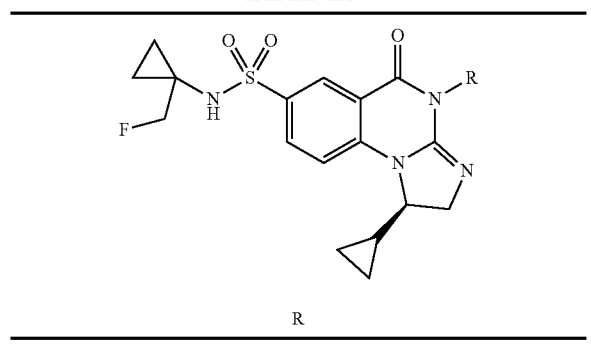
| R |
|---|
| 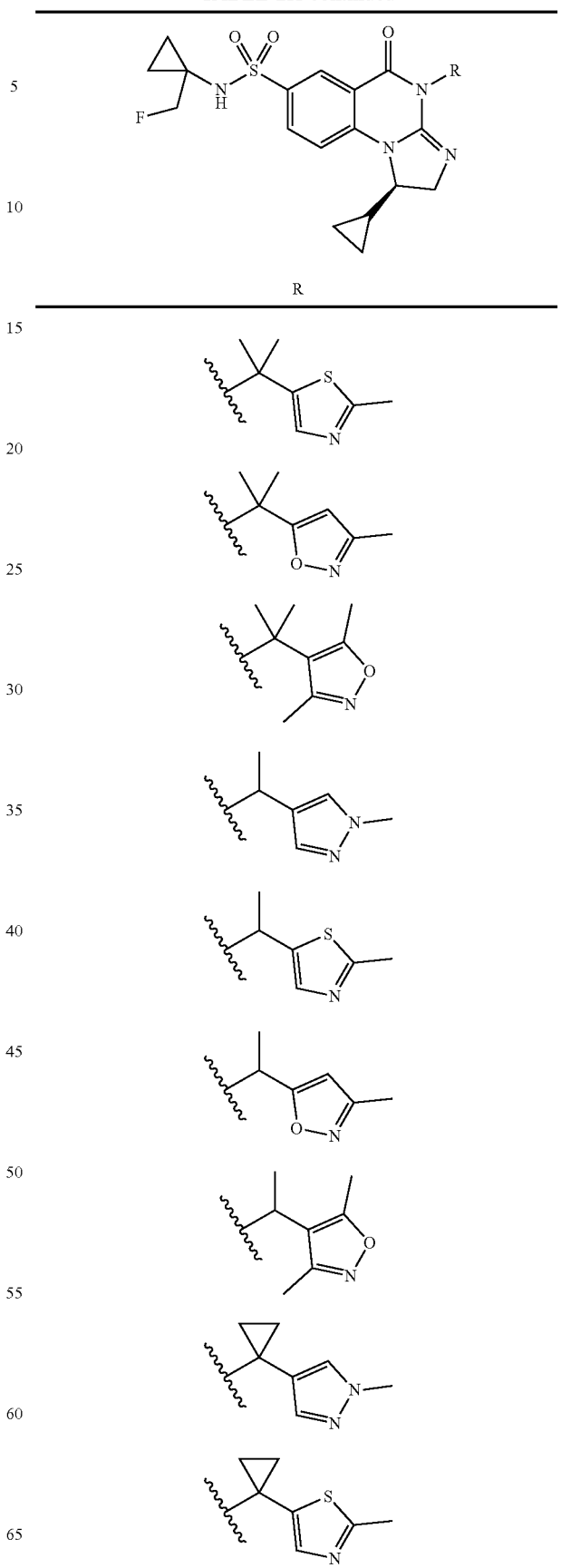 |

| TABLE 2H-continued | TABLE 2I |
|---|---|
| 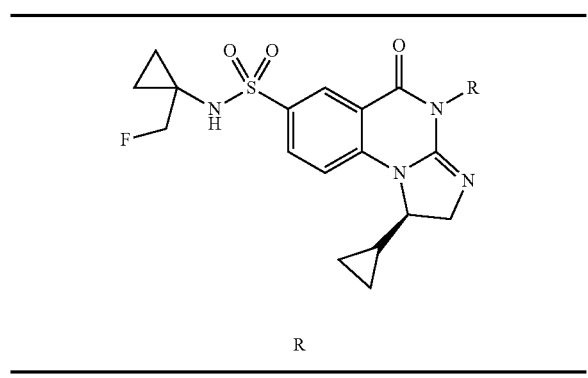 | 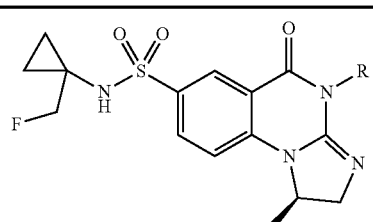 |
| R | R |
| 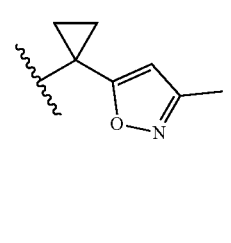 | 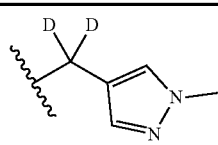 |
| 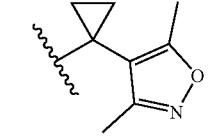 | 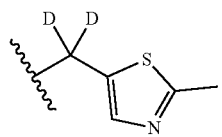 [SMILES: *C([2H])([2H])c1cnc(C)s1] |
| 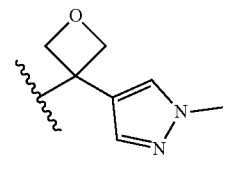 | 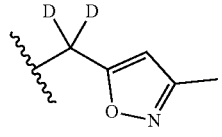 [SMILES: *C([2H])([2H])c1cc(C)no1] |
| 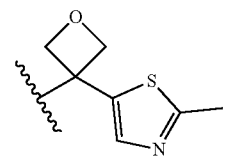 [SMILES: *C1(c2cnc(C)s2)COC1] | 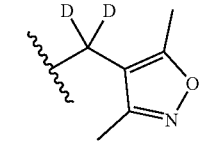 |
| 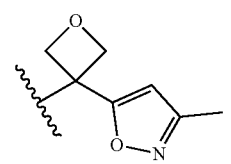 [SMILES: *C1(c2cc(C)no2)COC1] | 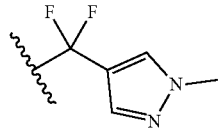 |
| 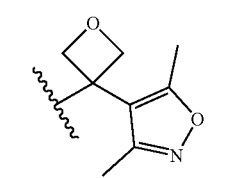 [SMILES: *C1(c2c(C)noc2C)COC1] | 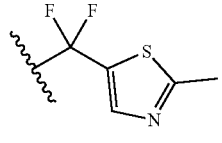 [SMILES: *C(F)(F)c1cnc(C)s1] |
| | 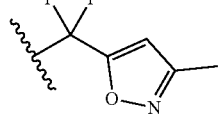 |
| | 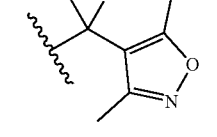 |
| | 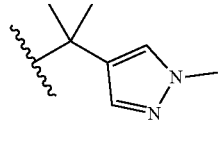 [SMILES: *C(C)(C)c1cnn(C)c1] |

TABLE 2I-continued

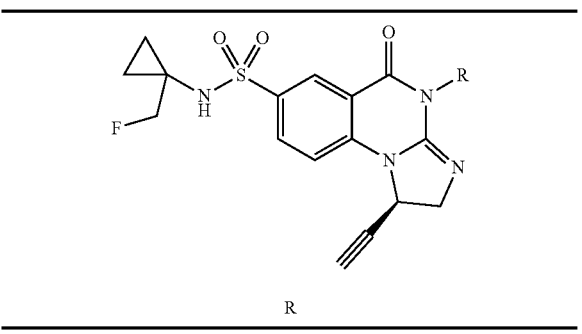

| R |
|---|
| 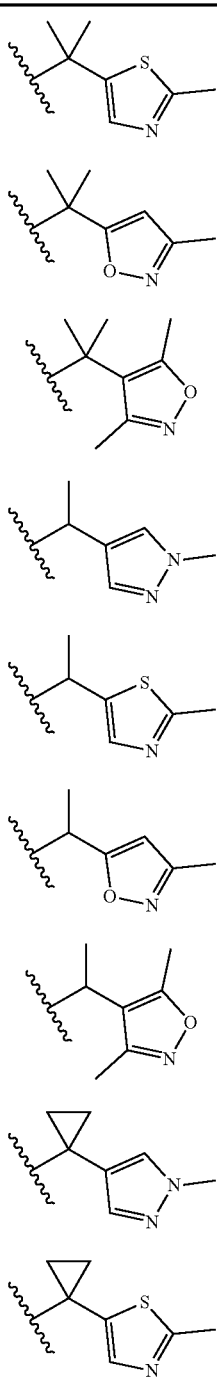 |

TABLE 2I-continued

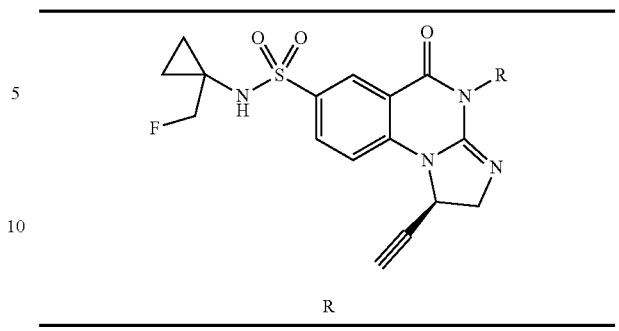

| R |
|---|
| 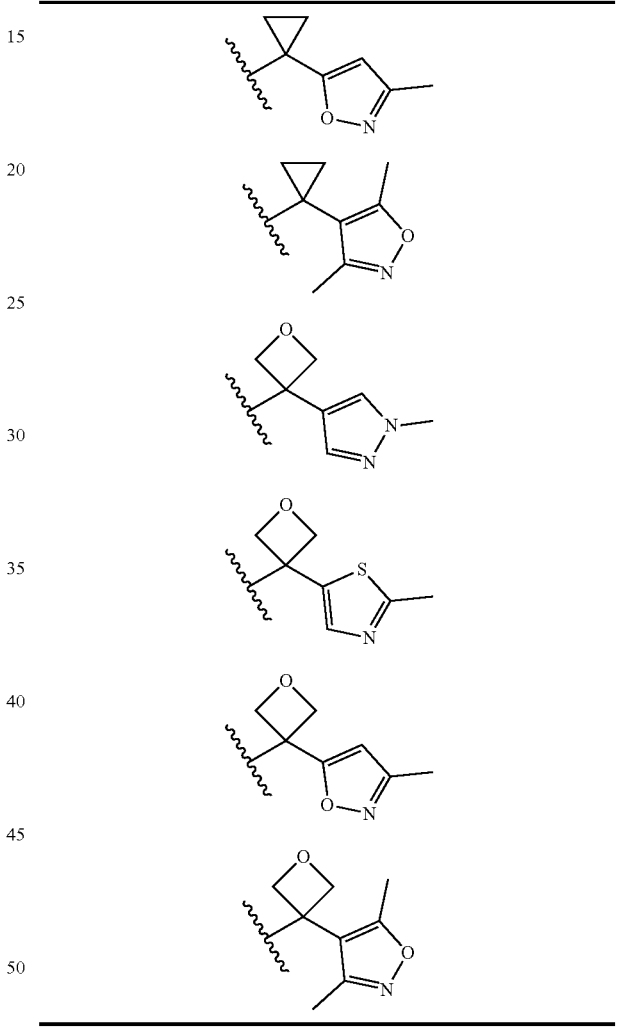 |

Preparation of Compounds

The compounds used in the synthetic chemistry reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CN), Poly organix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference useful for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

General Synthetic Schemes

The PARG inhibitory compound disclosed herein can be prepared by a variety of synthetic routes including, but not limited to, the routes described below in Scheme I or II.

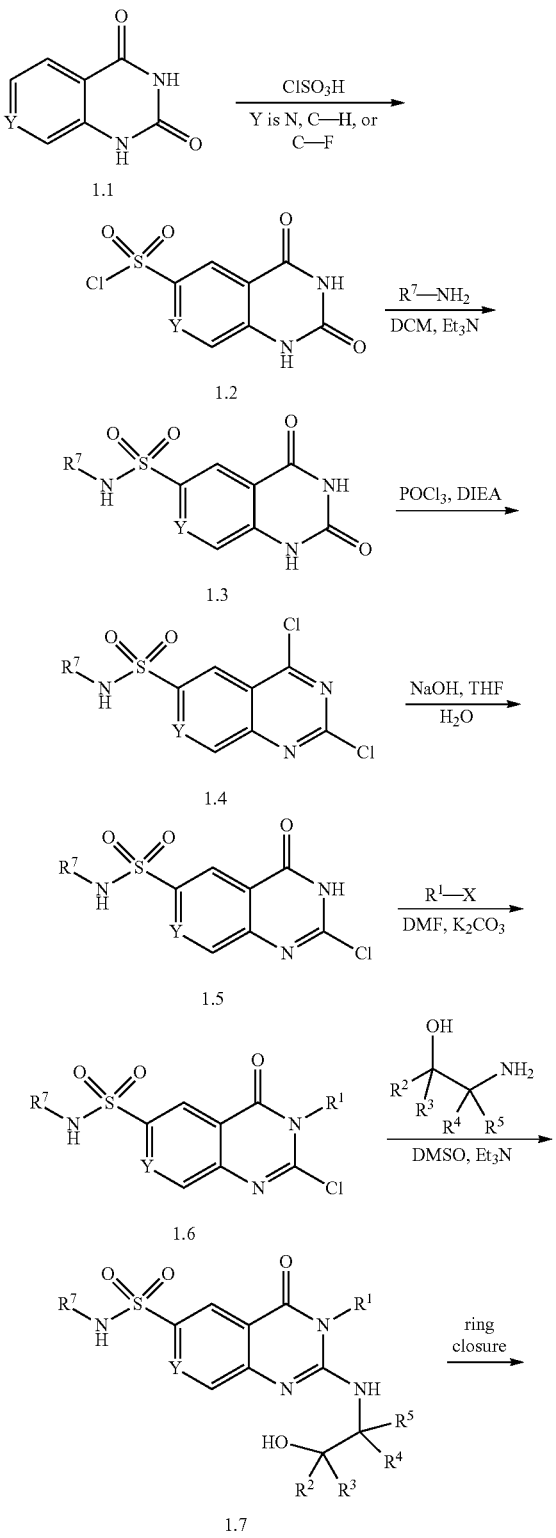

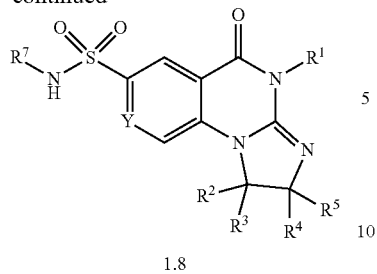

1.8

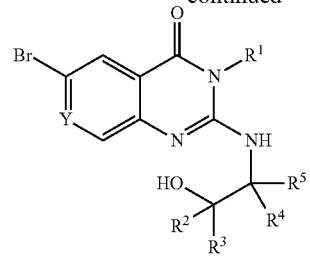

2.4

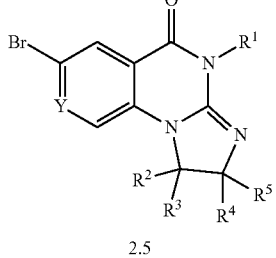

2.5

Reaction of 2,4-quinazolinedione derivative 1.1 with chlorosulfonic acid affords the chlorosulfonyl derivative 1.2. Reaction of compound 1.2 with a substituted amine provides sulfonamide 1.3. Chlorination of compound 1.3 affords the dichloroquinazoline derivative 1.4, which undergoes selective hydrolysis at the 4-position upon treatment with aqueous base. 2-chloroquinazolinone 1.5 is substituted on the amide nitrogen by treatment with a suitable electrophile under basic conditions to afford compound 1.6. Annulation of the 5-membered imidazo ring begins with substitution of the chloro group by reaction with a suitable amino alcohol to yield 2-aminoquinazolinone derivative 1.7. Closure of the imidazo ring to obtain target compound 1.8 is accomplished under Mitsunobu conditions (e.g., DEAD, PPh₃), or, alternatively, by activating the alcohol as a suitable leaving group, such as conversion to methanesulfonate or chlorination with SOCl₂, followed by treatment with base to effect ring closure. Persons of skill in the art will recognize that use of a 1,2-amino alcohol will afford the 5-membered imidazo compound 1.8, whereas use of a 1,3-amino alcohol will afford the analogous 6-membered compound. Likewise, use of a 1,4-amino alcohol will afford the analogous 7-membered compound. In the event a single stereoisomer of the target compound is desired, chiral chromatography with supercritical fluid chromatography can be employed.

Alternatively, non-racemic, chiral starting materials, such as the amino alcohol may be employed, as appropriate.

Scheme II

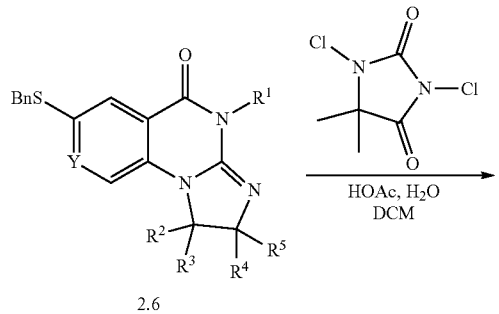

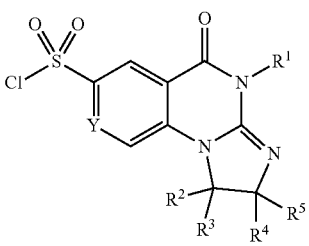

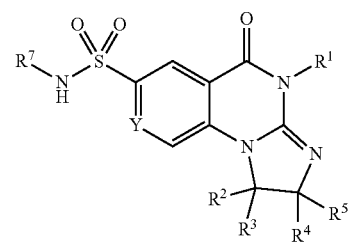

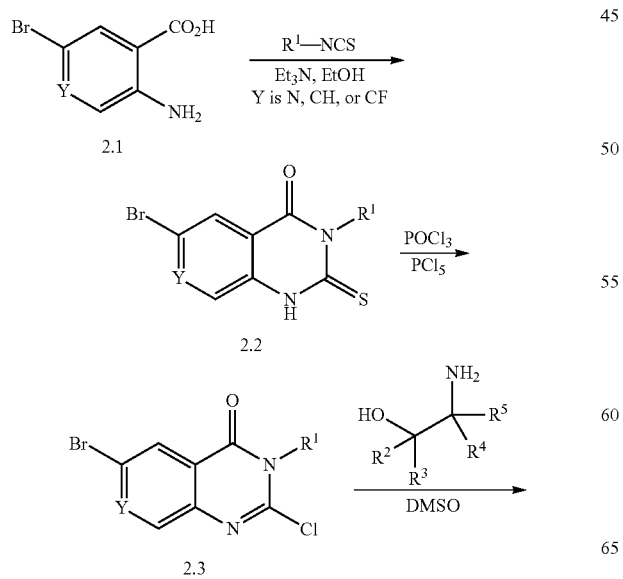

2.8

Anthranilic acid derivative 2.1 can be condensed with an alkyl isothiocyanate to afford the 2-thioxo-2,3-dihydroquinazolin-4(1H)-one derivative 2.2. Chlorination provides compound 2.3 which undergoes substitution with an amino alcohol to afford quinazolinone derivative 2.4. Closure of the imidazo ring to obtain compound 2.5 is accomplished under Mitsunobu conditions (e.g., DIAD, PPh₃), or, alternatively, by activating the alcohol as a suitable leaving group, effected by reagents such as conversion to methanesulfonyl chloride (MeSO₂Cl) or thionyl chloride (SOCl₂), followed by treatment with base to effect ring closure.

Persons of skill in the art will recognize that use of a 1,2-amino alcohol will afford the 5-membered imidazo compound 2.5, whereas use of a 1,3-amino alcohol will afford the analogous 6-membered compound. Likewise, use of a 1,4-amino alcohol will afford the analogous 7-membered compound. Palladium-catalyzed thiolation of imidazo compound 2.5 affords sulfide 2.6 which undergoes oxidative chlorination to afford sulfonyl chloride 2.7. Reaction of the sulfonyl chloride with an appropriate amine affords target compound 2.8.

Persons of skill in the art of organic synthesis will recognize that variation of Scheme I or II may be necessitated by the nature of the substituents in groups $R^1$-$R^5$ and $R^7$. Such modifications may include, for example, the use of protecting groups to alter the reactivity of substituents, or altered time and temperature for reaction. Additionally, further modification of compounds of formula 1.8 or 2.8 may be performed to arrive upon the desired PARG inhibitory compound. In the event a single stereoisomer of the target compound is desired, chiral chromatography with supercritical fluid chromatography can be employed. Alternatively, non-racemic, chiral starting materials, such as the amino alcohol may be employed, as appropriate.

Using appropriate starting materials, the PARG inhibitory compounds described herein by Formula (I) or (Ia), or within Tables 1 or Table 2A-2I, can be synthesized using the methods described above in Scheme I or II.

Pharmaceutical Compositions

In certain embodiments, the PARG inhibitory compound described herein is administered as a pure chemical. In other embodiments, the PARG inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, PA (2005)).

Provided herein is a pharmaceutical composition comprising at least one PARG inhibitory compound as described herein, or a stereoisomer, a pharmaceutically acceptable salt, hydrate, or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject or the patient) of the composition.

One embodiment provides a pharmaceutical composition comprising a pharmaceutically acceptable excipient and a compound of Formula (I) or (Ia), or a pharmaceutically acceptable salt or solvate thereof.

One embodiment provides a method of preparing a pharmaceutical composition comprising mixing a compound of Formula (I) or (Ia), or a pharmaceutically acceptable salt or solvate thereof, and a pharmaceutically acceptable carrier.

In certain embodiments, the PARG inhibitory compound as described by Formula (I) or (Ia), or a pharmaceutically acceptable salt or solvate thereof, is substantially pure, in that it contains less than about 5%, or less than about 2%, or less than about 1%, or less than about 0.5%, or less than about 0.10%, of other organic small molecules, such as unreacted intermediates or synthesis by-products that are created, for example, in one or more of the steps of a synthesis method.

One embodiment provides a pharmaceutical composition comprising a pharmaceutically acceptable excipient and a compound of Table 1 or Table 2A-2I, or a pharmaceutically acceptable salt or solvate thereof.

One embodiment provides a method of preparing a pharmaceutical composition comprising mixing a compound of Table 1 or Table 2A-2I, or a pharmaceutically acceptable salt or solvate thereof, and a pharmaceutically acceptable carrier.

In certain embodiments, the PARG inhibitory compound as described by Table 1 or Table 2A-2I, or a pharmaceutically acceptable salt or solvate thereof, is substantially pure, in that it contains less than about 5%, or less than about 2%, or less than about 1%, or less than about 0.5%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, 21$^{st}$ Ed. Mack Pub. Co., Easton, PA (2005)).

In some embodiments, the PARG inhibitory compound as described by Formula (I) or (Ia) or Table 1 or Table 2A-2I, or a pharmaceutically acceptable salt or solvate thereof, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one PARG inhibitory compound as described herein differs depending upon the subject or patient's (e.g., human) condition. In some embodiments, such factors include general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Methods of Treatment

One embodiment provides a compound of Formula (I) or (Ia), or a pharmaceutically acceptable salt or solvate thereof, for use in a method of treatment of the human or animal body.

One embodiment provides a compound of Formula (I) or (Ia), or a pharmaceutically acceptable salt or solvate thereof, for use in a method of treatment of cancer or neoplastic disease.

One embodiment provides a pharmaceutical composition comprising a compound of Formula (I) or (Ia), or a pharmaceutically acceptable salt or solvate thereof, and a pharmaceutically acceptable excipient for use in a method of treatment of cancer or neoplastic disease.

One embodiment provides a use of a compound of Formula (I) or (Ia), or a pharmaceutically acceptable salt or solvate thereof, in the manufacture of a medicament for the treatment of cancer or neoplastic disease.

In some embodiments is provided a method of treating cancer, in a patient in need thereof, comprising administering to the patient a compound of Formula (I) or (Ia), or a pharmaceutically acceptable salt or solvate thereof. In some embodiments is provided a method of treating cancer, in a patient in need thereof, comprising administering to the patient a pharmaceutical composition comprising a compound of Formula (I) or (Ia), or a pharmaceutically acceptable salt or solvate thereof, and a pharmaceutically acceptable excipient.

One embodiment provides a compound of Table 1 or Table 2A-2I, or a pharmaceutically acceptable salt or solvate thereof, for use in a method of treatment of the human or animal body.

One embodiment provides a compound of Table 1 or Table 2A-2I, or a pharmaceutically acceptable salt or solvate thereof, for use in a method of treatment of cancer or neoplastic disease.

One embodiment provides a pharmaceutical composition comprising a compound of Table 1 or Table 2A-2I, or a pharmaceutically acceptable salt or solvate thereof, and a pharmaceutically acceptable excipient for use in a method of treatment of cancer or neoplastic disease.

One embodiment provides a use of a compound of Table 1 or Table 2A-2I, or a pharmaceutically acceptable salt or solvate thereof, in the manufacture of a medicament for the treatment of cancer or neoplastic disease.

In some embodiments is provided a method of treating cancer, in a patient in need thereof, comprising administering to the patient a compound of Table 1 or Table 2A-2I, or a pharmaceutically acceptable salt or solvate thereof. In some embodiments is provided a method of treating cancer, in a patient in need thereof, comprising administering to the patient a pharmaceutical composition comprising a compound of Table 1 or Table 2A-2I, or a pharmaceutically acceptable salt or solvate thereof, and a pharmaceutically acceptable excipient.

Provided herein is the method wherein the pharmaceutical composition is administered orally. Provided herein is the method wherein the pharmaceutical composition is administered by injection.

One embodiment provides a method of inhibiting a PARG enzyme comprising contacting the PARG enzyme with a compound of Formula (I) or (Ia) or Table 1 or Table 2A-2I.

Another embodiment provides the method of inhibiting a PARG enzyme, wherein the PARG enzyme is contacted in an in vivo setting. Another embodiment provides the method of inhibiting a PARG enzyme, wherein the PARG enzyme is contacted in an in vitro setting.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

In some embodiments, the PARG inhibitory compounds disclosed herein are synthesized according to the following examples. As used below, and throughout the description of the invention, the following abbreviations, unless otherwise indicated, shall be understood to have the following meanings:

ACN acetonitrile

° C. degrees Celsius $\delta_H$ chemical shift in parts per million downfield from tetramethylsilane DCM dichloromethane ($CH_2C2$)

DIAD diisopropyl azodicarboxylate

DIEA diisopropylethylamine

DMF dimethylformamide

DMSO dimethylsulfoxide

EA ethyl acetate

EtOAc ethyl acetate

ESI electrospray ionization

Et ethyl g gram(s)

h hour(s)

HPLC high performance liquid chromatography

Hz hertz

J coupling constant (in NMR spectrometry)

LCMS liquid chromatography mass spectrometry

µ micro m multiplet (spectral); meter(s); milli

M molar

M+ parent molecular ion

Me methyl

MsCl methanesulfonyl chloride

MHz megahertz min minute(s)

mol mole(s); molecular (as in mol wt)

mL milliliter

MS mass spectrometry nm nanometer(s)

NMR nuclear magnetic resonance pH potential of hydrogen; a measure of the acidity or basicity of an aqueous solution PE petroleum ether RT room temperature s singlet (spectral)

t triplet (spectral)

SFC Supercritical fluid chromatography

T temperature

TFA trifluoroacetic acid

THF tetrahydrofuran

TPP Triphenylphosphine

Representative Synthesis Route 1

Example 46: (R)-1-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide

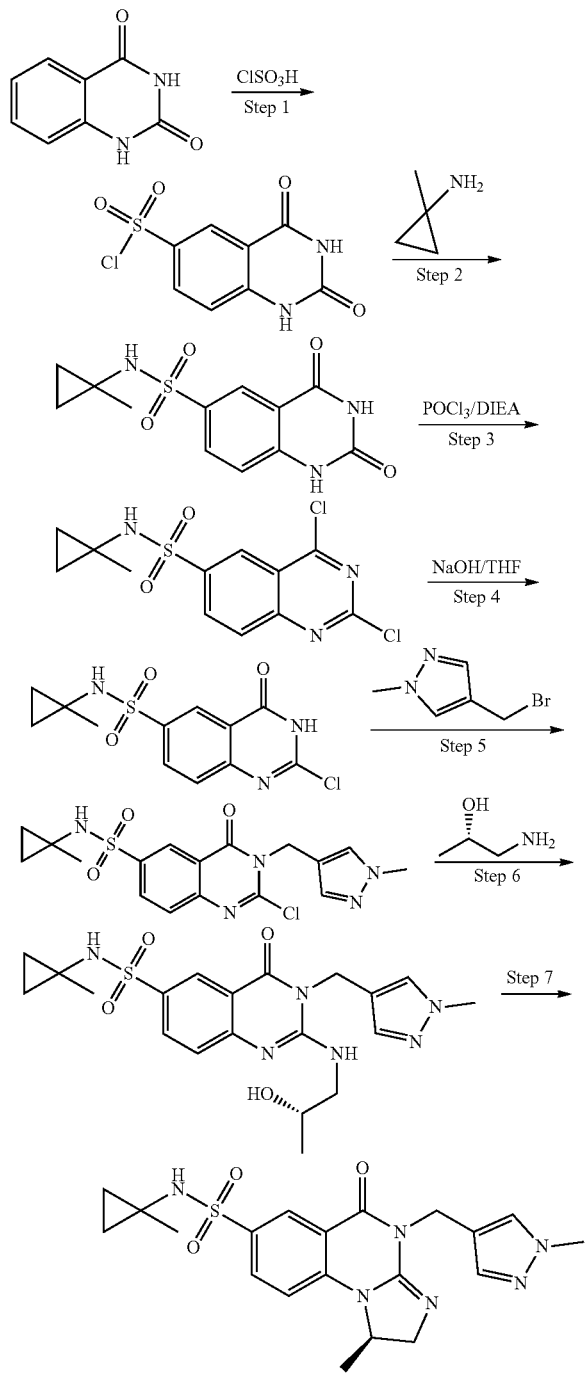

Step 1

A solution of 1,3-dihydroquinazoline-2,4-dione (15.0 g, 92.5 mmol) in chlorosulfonic acid (50 mL) was stirred for 4 h at 60° C. The mixture was allowed to cool to room temperature and then poured onto water/ice. The precipitated solids were collected by filtration and washed with water (2×100 mL). The resulting solid was dried under vacuum to afford 2,4-dioxo-1,3-dihydroquinazoline-6-sulfonyl chloride (16.0 g, 66%) as a white solid. LCMS (ESI) m/z: 259 (M−H).

Step 2

To a solution of 1-methylcyclopropan-1-amine hydrochloride (7.92 g, 73.6 mmol) in DCM (100 mL) was added TEA (37.2 g, 368 mmol), followed by the addition of 2,4-dioxo-1,3-dihydroquinazoline-6-sulfonyl chloride (16.0 g, 61.3 mmol) in portions at room temperature. The resulting mixture was stirred for 2 h at room temperature. The resulting mixture was filtered. The precipitated solids were collected by filtration and washed with water (3×50 mL). The resulting solid was dried under vacuum to afford N-(1-methylcyclopropyl)-2,4-dioxo-1,3-dihydroquinazoline-6-sulfonamide (17.5 g, 82%) as a light yellow solid. LCMS (ESI) m/z: 294 (M−H).

Step 3

To a stirred mixture of N-(1-methylcyclopropyl)-2,4-dioxo-1,3-dihydroquinazoline-6-sulfonamide (17 g, 57.5 mmol) in $POCl_3$ (50.0 mL) was added DIEA (18.6 g, 1434 mmol) dropwise at 0° C. The resulting mixture was stirred for 6 h at 105° C. The resulting mixture was concentrated under reduced pressure. The reaction was diluted with cold water (200 mL) at 0° C. The resulting mixture was extracted with EtOAc (3×200 mL). The combined organic layers were washed with saturated $NaHCO_3$ aqueous (3×200 mL) and dried over anhydrous $Na_2SO_4$. After filtration, the filtrate was concentrated under reduced pressure. The residue was purified by silica gel column chromatography, eluted with PE/EtOAc (1:1) to afford 2,4-dichloro-N-(1-methylcyclopropyl)quinazoline-6-sulfonamide (8.00 g, 42%) as a light yellow solid. LCMS (ESI) m/z: 332 [M+H]+.

Step 4

To a solution of 2,4-dichloro-N-(1-methylcyclopropyl)quinazoline-6-sulfonamide (8 g, 24.0 mmol) in THF (60 mL) and water (60 mL), was added NaOH (4.58 g, 114 mmol). The solution was stirred for 1 h at room temperature. The mixture was acidified to pH 3 with HCl (aq). The precipitated solids were collected by filtration and washed with water (3×50 mL). The filtrate was concentrated under reduced pressure to afford 2-chloro-N-(1-methylcyclopropyl)-4-oxo-3H-quinazoline-6-sulfonamide (6.5 g, 86%) as a light yellow solid. LCMS (ESI) m/z: 314 [M+H]+.

Step 5

A solution of 2-chloro-N-(1-methylcyclopropyl)-4-oxo-3H-quinazoline-6-sulfonamide (1.00 g, 2.81) in DMF (10 mL) and DME (10 mL), was treated with $K_2CO_3$ (0.78 g, 5.62 mmol), followed by the addition of LiBr (0.49 g, 5.62 mmol) and 4-(bromomethyl)-1-methylpyrazole hydrobromide (0.72 g, 2.81 mmol). The resulting mixture was stirred for 5 h at room temperature. The reaction was quenched with water (50 mL) at room temperature. The resulting mixture was extracted with EtOAc (3×50 mL). The combined organic layers were washed with brine (50 mL) and dried over anhydrous $Na_2SO_4$. After filtration, the filtrate was concentrated under reduced pressure. The residue was purified by silica gel column chromatography, eluted with DCM/MeOH (9:1) to afford 2-chloro-N-(1-methylcyclopropyl)-3-[(1-methylpyrazol-3-yl)methyl]-4-oxoquinazoline-6-sulfonamide (430 mg, 37%) as a white solid. LCMS (ESI) m/z: 408 [M+H]+.

Step 6

To a solution of 2-chloro-N-(1-methylcyclopropyl)-3-[(1-methylpyrazol-3-yl)methyl]-4-oxoquinazoline-6-sulfonamide (400 mg, 0.98 mmol) in DMSO (4 mL) were added (S)-1-aminopropan-2-ol (105 mg, 1.40 mmol) and Et$_3$N (298 mg, 2.94 mmol) at room temperature. The resulting mixture was stirred for 2 h at 100° C. The reaction was quenched by water (20 mL) at room temperature. The resulting mixture was extracted with EtOAc (3×30 mL). The combined organic layers were washed with brine (30 mL), and dried over anhydrous Na$_2$SO$_4$. After filtration, the filtrate was concentrated under reduced pressure. The residue was purified by silica gel column chromatography, eluted with DCM/MeOH (9:1) to afford (S)-2-((2-hydroxypropyl)amino)-3-((1-methyl-1H-pyrazol-4-yl)methyl)-N-(1-methylcyclopropyl)-4-oxo-3,4-dihydroquinazoline-6-sulfonamide (300 mg, 66%) as an off-white solid. LCMS (ESI) m/z: 447 [M+H]+.

Step 7

To a solution of (S)-2-((2-hydroxypropyl)amino)-3-((1-methyl-1H-pyrazol-4-yl)methyl)-N-(1-methylcyclopropyl)-4-oxo-3,4-dihydroquinazoline-6-sulfonamide (100 mg, 0.22 mmol) in DCM (5 mL), was added Et$_3$N (67.7 mg, 0.67 mmol) followed by the addition of CH$_3$SO$_2$Cl (51.9 mg, 0.45 mmol). The resulting mixture was stirred for 3 h at room temperature. The reaction was quenched with water (10 mL) at room temperature. The resulting mixture was extracted with DCM (3×20 mL). The combined organic layers were washed with brine (20 mL), dried over anhydrous Na$_2$SO$_4$. After filtration, the filtrate was concentrated under reduced pressure. The resulting mixture was concentrated under reduced pressure. The residue was purified by prep-HPLC [Column: XBridge Shield RP18 OBD Column, 19*150 mm, 5 μm; Mobile Phase A: Water (10 mmol/L NH$_4$HCO$_3$), Mobile Phase B: ACN; Flow rate: 25 mL/min; Gradient: 18% B to 45% B in 7 min, 45% B; Wave Length: 220 nm] to afford (R)-1-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide (35 mg, 36%). LCMS (ESI) m/z: 429.10 [M+H]+. $^1$H NMR (400 MHz, CD$_3$OD): 8.42 (s, 1H), 8.00 (dd, J$_1$=8.8, 2.0 Hz, 1H), 7.67 (s, 1H), 7.54 (s, 1H), 7.20 (d, J=8.8 Hz, 1H), 5.03-4.96 (m, 2H), 4.78-4.73 (m, 1H), 4.19-4.11 (m, 1H), 13.83 (s, 3H), 3.65-3.62 (m, 1H), 1.40 (d, J=6.0 Hz, 3H), 1.16 (s, 3H), 0.72-0.69 (2H), 0.45-0.39 (in, 2H).

The following compounds in Table 3 were prepared using procedures similar to those described in Representative Synthesis Route 1 for Example 46 using appropriate starting materials.

TABLE 3

| Example No. | Name | [M + H]+ |
|---|---|---|
| 3 | (R)-4-(cyclopropylmethyl)-1-methyl-N-(1-methylcyclopropyl)-5-oxo-1,2,4,5-tetrahydroimidazo[1,2-a]quinazoline-7-sulfonamide | 389.05 |
| 4 | (R)-1-methyl-N-(1-methylcyclopropyl)-5-oxo-4-(pyridin-3-ylmethyl)-1,2,4,5-tetrahydroimidazo[1,2-a]quinazoline-7-sulfonamide | 426.00 |
| 5 | (R)-1-methyl-4-((5-methyl-1H-pyrazol-3-yl)methyl)-N-(1-methylcyclopropyl)-5-oxo-1,2,4,5-tetrahydroimidazo[1,2-a]quinazoline-7-sulfonamide | 429.05 |
| 6 | (R)-4-((1H-pyrazol-4-yl)methyl)-1-methyl-N-(1-methylcyclopropyl)-5-oxo-1,2,4,5-tetrahydroimidazo[1,2-a]quinazoline-7-sulfonamide | 415.05 |
| 7 | 4-((1-methyl-1H-pyrazol-3-yl)methyl)-N-(1-methylcyclopropyl)-5-oxo-1,2,4,5-tetrahydroimidazo[1,2-a]quinazoline-7-sulfonamide | 415.05 |
| 8 | (R)-4-((3,5-dimethylisoxazol-4-yl)methyl)-1-methyl-N-(1-methylcyclopropyl)-5-oxo-1,2,4,5-tetrahydroimidazo[1,2-a]quinazoline-7-sulfonamide | 444.05 |
| 9 | (S)-1-ethynyl-N-(1-methylcyclopropyl)-4-((3-methylisoxazol-5-yl)methyl)-5-oxo-1,2,4,5-tetrahydroimidazo[1,2-a]quinazoline-7-sulfonamide | 440.00 |
| 10 | (R)-1-ethynyl-N-(1-methylcyclopropyl)-4-((3-methylisoxazol-5-yl)methyl)-5-oxo-1,2,4,5-tetrahydroimidazo[1,2-a]quinazoline-7-sulfonamide | 439.95 |
| 11 | (S)-1-isopropyl-N-(1-methylcyclopropyl)-4-((3-methylisoxazol-5-yl)methyl)-5-oxo-1,2,4,5-tetrahydroimidazo[1,2-a]quinazoline-7-sulfonamide | 458.05 |
| 12 | (R)-1-isopropyl-N-(1-methylcyclopropyl)-4-((3-methylisoxazol-5-yl)methyl)-5-oxo-1,2,4,5-tetrahydroimidazo[1,2-a]quinazoline-7-sulfonamide | 458.05 |
| 13 | (S)-4-((3,5-dimethylisoxazol-4-yl)methyl)-1-ethyl-N-(1-methylcyclopropyl)-5-oxo-1,2,4,5-tetrahydroimidazo[1,2-a]quinazoline-7-sulfonamide | 458.05 |
| 14 | (R)-4-((3,5-dimethylisoxazol-4-yl)methyl)-1-ethyl-N-(1-methylcyclopropyl)-5-oxo-1,2,4,5-tetrahydroimidazo[1,2-a]quinazoline-7-sulfonamide | 458.00 |
| 15 | (S)-1-ethynyl-N-(1-methylcyclopropyl)-4-((2-methylthiazol-5-yl)methyl)-5-oxo-1,2,4,5-tetrahydroimidazo[1,2-a]quinazoline-7-sulfonamide | 455.95 |
| 16 | (R)-1-ethynyl-N-(1-methylcyclopropyl)-4-((2-methylthiazol-5-yl)methyl)-5-oxo-1,2,4,5-tetrahydroimidazo[1,2-a]quinazoline-7-sulfonamide | 456.00 |
| 17 | (S)-1-cyclopropyl-N-(1-methylcyclopropyl)-4-((2-methylthiazol-5-yl)methyl)-5-oxo-1,2,4,5-tetrahydroimidazo[1,2-a]quinazoline-7-sulfonamide | 472.00 |
| 18 | (R)-1-cyclopropyl-N-(1-methylcyclopropyl)-4-((2-methylthiazol-5-yl)methyl)-5-oxo-1,2,4,5-tetrahydroimidazo[1,2-a]quinazoline-7-sulfonamide | 472.00 |
| 19 | (S)-1-isopropyl-N-(1-methylcyclopropyl)-4-((2-methylthiazol-5-yl)methyl)-5-oxo-1,2,4,5-tetrahydroimidazo[1,2-a]quinazoline-7-sulfonamide | 474.05 |

TABLE 3-continued

| Example No. | Name | [M + H]+ |
|---|---|---|
| 20 | (R)-1-isopropyl-N-(1-methylcyclopropyl)-4-((2-methylthiazol-5-yl)methyl)-5-oxo-1,2,4,5-tetrahydroimidazo[1,2-a]quinazoline-7-sulfonamide | 474.00 |
| 21 | (S)-1-cyclopropyl-N-(1-methylcyclopropyl)-4-((3-methylisoxazol-5-yl)methyl)-5-oxo-1,2,4,5-tetrahydroimidazo[1,2-a]quinazoline-7-sulfonamide | 456.05 |
| 22 | (R)-1-cyclopropyl-N-(1-methylcyclopropyl)-4-((3-methylisoxazol-5-yl)methyl)-5-oxo-1,2,4,5-tetrahydroimidazo[1,2-a]quinazoline-7-sulfonamide | 456.05 |
| 23 | (S)-1-ethyl-N-(1-methylcyclopropyl)-4-((3-methylisoxazol-5-yl)methyl)-5-oxo-1,2,4,5-tetrahydroimidazo[1,2-a]quinazoline-7-sulfonamide | 444.00 |
| 24 | (R)-1-ethyl-N-(1-methylcyclopropyl)-4-((3-methylisoxazol-5-yl)methyl)-5-oxo-1,2,4,5-tetrahydroimidazo[1,2-a]quinazoline-7-sulfonamide | 444.05 |
| 25 | (S)-1-cyclopropyl-4-ethyl-N-(1-methylcyclopropyl)-5-oxo-1,2,4,5-tetrahydroimidazo[1,2-a]quinazoline-7-sulfonamide | 389.00 |
| 26 | (R)-1-cyclopropyl-4-ethyl-N-(1-methylcyclopropyl)-5-oxo-1,2,4,5-tetrahydroimidazo[1,2-a]quinazoline-7-sulfonamide | 389.05 |
| 27 | (S)-4-ethyl-1-ethynyl-N-(1-methylcyclopropyl)-5-oxo-1,2,4,5-tetrahydroimidazo[1,2-a]quinazoline-7-sulfonamide | 373.05 |
| 28 | (R)-4-ethyl-1-ethynyl-N-(1-methylcyclopropyl)-5-oxo-1,2,4,5-tetrahydroimidazo[1,2-a]quinazoline-7-sulfonamide | 373.05 |
| 29 | (S)-1-ethyl-N-(1-methylcyclopropyl)-4-((2-methylthiazol-5-yl)methyl)-5-oxo-1,2,4,5-tetrahydroimidazo[1,2-a]quinazoline-7-sulfonamide | 460.05 |
| 30 | (R)-1-ethyl-N-(1-methylcyclopropyl)-4-((2-methylthiazol-5-yl)methyl)-5-oxo-1,2,4,5-tetrahydroimidazo[1,2-a]quinazoline-7-sulfonamide | 460.05 |
| 31 | (R)-1-methyl-N-(1-methylcyclopropyl)-4-((2-methylthiazol-5-yl)methyl)-5-oxo-1,2,4,5-tetrahydroimidazo[1,2-a]quinazoline-7-sulfonamide | 446.00 |
| 32 | (R)-1-methyl-N-(1-methylcyclopropyl)-4-((3-methylisoxazol-5-yl)methyl)-5-oxo-1,2,4,5-tetrahydroimidazo[1,2-a]quinazoline-7-sulfonamide | 430.10 |
| 33 | (S)-1-ethynyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 439.05 |
| 34 | (R)-1-ethynyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 439.05 |
| 35 | (R)-1-cyclopropyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 455.10 |
| 36 | (S)-1-cyclopropyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 455.10 |
| 37 | (S)-4-ethyl-1-isopropyl-N-(1-methylcyclopropyl)-5-oxo-1,2,4,5-tetrahydroimidazo[1,2-a]quinazoline-7-sulfonamide | 391.05 |
| 38 | (R)-4-ethyl-1-isopropyl-N-(1-methylcyclopropyl)-5-oxo-1,2,4,5-tetrahydroimidazo[1,2-a]quinazoline-7-sulfonamide | 391.10 |
| 39 | (S)-1-isopropyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 457.15 |
| 40 | (R)-1-isopropyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 457.10 |
| 41 | (S)-1,4-diethyl-N-(1-methylcyclopropyl)-5-oxo-1,2,4,5-tetrahydroimidazo[1,2-a]quinazoline-7-sulfonamide | 377.10 |
| 42 | (R)-1,4-diethyl-N-(1-methylcyclopropyl)-5-oxo-1,2,4,5-tetrahydroimidazo[1,2-a]quinazoline-7-sulfonamide | 377.10 |
| 43 | 1-ethynyl-4-methyl-N-(1-methylcyclopropyl)-5-oxo-1,2,4,5-tetrahydroimidazo[1,2-a]quinazoline-7-sulfonamide | 359.00 |
| 47 | (R)-4-ethyl-1-methyl-N-(1-methylcyclopropyl)-5-oxo-1,2,4,5-tetrahydroimidazo[1,2-a]quinazoline-7-sulfonamide | 363.10 |
| 48 | 1-cyclopropyl-4-methyl-N-(1-methylcyclopropyl)-5-oxo-1,2,4,5-tetrahydroimidazo[1,2-a]quinazoline-7-sulfonamide | 375.10 |
| 54 | (R)-1-methyl-N-(1-methylcyclopropyl)-4-(oxetan-3-ylmethyl)-5-oxo-1,2,4,5-tetrahydroimidazo[1,2-a]quinazoline-7-sulfonamide | 405.05 |
| 55 | (R)-1-methyl-4-((1-methyl-3-(trifluoromethyl)-1H-pyrazol-4-yl)methyl)-N-(1-methylcyclopropyl)-5-oxo-1,2,4,5-tetrahydroimidazo[1,2-a]quinazoline-7-sulfonamide | 497.00 |
| 56 | (R)-1-methyl-4-((5-methyl-1,3,4-thiadiazol-2-yl)methyl)-N-(1-methylcyclopropyl)-5-oxo-1,2,4,5-tetrahydroimidazo[1,2-a]quinazoline-7-sulfonamide | 447.05 |
| 58 | (R)-1-methyl-N-(1-methylcyclopropyl)-5-oxo-4-(prop-2-yn-1-yl)-1,2,4,5-tetrahydroimidazo[1,2-a]quinazoline-7-sulfonamide | 373.05 |
| 59 | (R)-4-((1-methyl-1H-pyrazol-4-yl)methyl)-N-(1-methylcyclopropyl)-5-oxo-1-(prop-1-yn-1-yl)-1,2,4,5-tetrahydroimidazo[1,2-a]quinazoline-7-sulfonamide | 453.00 |
| 60 | (S)-4-((1-methyl-1H-pyrazol-4-yl)methyl)-N-(1-methylcyclopropyl)-5-oxo-1-(prop-1-yn-1-yl)-1,2,4,5-tetrahydroimidazo[1,2-a]quinazoline-7-sulfonamide | 453.05 |

TABLE 3-continued

| Example No. | Name | [M + H]+ |
|---|---|---|
| 64 | 2,2-dimethyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 443.05 |
| 65 | (S)-1-trifluoromethyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 482.95 |
| 66 | (R)-1-methyl-4-((1-cyanomethyl-1H-pyrazol-4-yl)methyl)-N-(1-methylcyclopropyl)-5-oxo-1,2,4,5-tetrahydroimidazo[1,2-a]quinazoline-7-sulfonamide | 454.05 |
| 67 | (R)-4-((3,5-dimethylisoxazol-4-yl)methyl)-1-isopropyl-N-(1-methylcyclopropyl)-5-oxo-1,2,4,5-tetrahydroimidazo[1,2-a]quinazoline-7-sulfonamide | 472.00 |
| 68 | (S)-4-((3,5-dimethylisoxazol-4-yl)methyl)-1-isopropyl-N-(1-methylcyclopropyl)-5-oxo-1,2,4,5-tetrahydroimidazo[1,2-a]quinazoline-7-sulfonamide | 472.05 |
| 69 | (R)-1-cyclopropyl-4-((3,5-dimethylisoxazol-4-yl)methyl)-N-(1-methylcyclopropyl)-5-oxo-1,2,4,5-tetrahydroimidazo[1,2-a]quinazoline-7-sulfonamide | 470.00 |
| 70 | (S)-1-cyclopropyl-4-((3,5-dimethylisoxazol-4-yl)methyl)-N-(1-methylcyclopropyl)-5-oxo-1,2,4,5-tetrahydroimidazo[1,2-a]quinazoline-7-sulfonamide | 469.95 |
| 71 | (R)-4-((3,5-dimethylisoxazol-4-yl)methyl)-1-ethynyl-N-(1-methylcyclopropyl)-5-oxo-1,2,4,5-tetrahydroimidazo[1,2-a]quinazoline-7-sulfonamide | 454.00 |
| 72 | (S)-4-((3,5-dimethylisoxazol-4-yl)methyl)-1-ethynyl-N-(1-methylcyclopropyl)-5-oxo-1,2,4,5-tetrahydroimidazo[1,2-a]quinazoline-7-sulfonamide | 454.00 |
| 73 | (R)-4-((2,4-dimethylthiazol-5-yl)methyl)-1-methyl-N-(1-methylcyclopropyl)-5-oxo-1,2,4,5-tetrahydroimidazo[1,2-a]quinazoline-7-sulfonamide | 460.05 |
| 74 | (R)-8-fluoro-1-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 447.00 |
| 75 | (S)-1-methyl-5-((1-methyl-1H-pyrazol-4-yl)methyl)-N-(1-methylcyclopropyl)-6-oxo-2,3,5,6-tetrahydro-1H-pyrimido[1,2-a]quinazoline-8-sulfonamide | 443.00 |
| 76 | (R)-1-methyl-5-((1-methyl-1H-pyrazol-4-yl)methyl)-N-(1-methylcyclopropyl)-6-oxo-2,3,5,6-tetrahydro-1H-pyrimido[1,2-a]quinazoline-8-sulfonamide | 443.00 |
| 77 | (S)-1-(methoxymethyl)-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 459.05 |
| 78 | (R)-1-(methoxymethyl)-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 459.00 |
| 79 | (7aS,10aR)-6-((1-methyl-1H-pyrazol-4-yl)methyl)-N-(1-methylcyclopropyl)-5-oxo-6,7a,8,9,10,10a-hexahydro-5H-cyclopenta[4,5]imidazo[1,2-a]quinazoline-3-sulfonamide | 455.10 |
| 80 | (R)-4-((1,3-dimethyl-1H-pyrazol-4-yl)methyl)-1-methyl-N-(1-methylcyclopropyl)-5-oxo-1,2,4,5-tetrahydroimidazo[1,2-a]quinazoline-7-sulfonamide | 443.20 |
| 81 | (R)-4-((1,5-dimethyl-1H-pyrazol-4-yl)methyl)-1-methyl-N-(1-methylcyclopropyl)-5-oxo-1,2,4,5-tetrahydroimidazo[1,2-a]quinazoline-7-sulfonamide | 443.05 |
| 82 | (S)-4-(cyclopropylmethyl)-1-(2,4-dimethylthiazol-5-yl)-N-(1-methylcyclopropyl)-5-oxo-1,2,4,5-tetrahydroimidazo[1,2-a]quinazoline-7-sulfonamide | 486.05 |
| 83 | (R)-1-(cyclopropylethynyl)-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 479.25 |
| 84 | (S)-1-(cyclopropylethynyl)-4-((1-methyl-1H-pyrazol-4-y]methyl)-N-(1-methylcyclopropyl)-5-oxo-1,2,4,5-tetrahydroimidazo[1,2-a]quinazoline-7-sulfonamide | 479.25 |
| 90 | (R)-1-methyl-4-((1-methyl-1H-1,2,3-triazol-4-yl)methyl)-N-(1-methylcyclopropyl)-5-oxo-1,2,4,5-tetrahydroimidazo[1,2-a]quinazoline-7-sulfonamide | 430.30 |
| 93 | (7aR,10aS)-6-((1-methyl-1H-pyrazol-4-yl)methyl)-N-(1-methylcyclopropyl)-5-oxo-5,6,7a,8,10,10a-hexahydrofuro[3',4':4,5]imidazo[1,2-a]quinazoline-3-sulfonamide | 456.95 |
| 94 | (R)-N-cyclopropyl-4-((2,4-dimethylthiazol-5-yl)methyl)-1-methyl-5-oxo-1,2,4,5-tetrahydroimidazo[1,2-a]quinazoline-7-sulfonamide | 446.05 |
| 95 | (R)-1-((dimethylamino)methyl)-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 472.10 |
| 96 | (S)-1-((dimethylamino)methyl)-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 472.05 |

TABLE 3-continued

| Example No. | Name | [M + H]+ |
|---|---|---|
| 97 | (R)-1-(aminomethyl)-4-((1-methyl-1H-pyrazol-4-y])methyl)-N-(1-methylcyclopropyl)-5-oxo-1,2,4,5-tetrahydroimidazo[1,2-a]quinazoline-7-sulfonamide | 444.00 |
| 99 | (R)-4-((1-methyl-1H-pyrazol-4-yl)methyl)-1-((methylamino)methyl)-N-(1-methylcyclopropyl)-5-oxo-1,2,4,5-tetrahydroimidazo[1,2-a]quinazoline-7-sulfonamide | 458.15 |
| 100 | 4'-((1-methyl-1H-pyrazol-4-yl)methyl)-N-(1-methylcyclopropyl)-5'-oxo-4',5'-dihydro-1'H-spiro[cyclopropane-1,2'-imidazo[1,2-a]quinazoline]-7'-sulfonamide | 441.25 |
| 101 | 4'-((1-methyl-1H-pyrazol-4-yl)methyl)-N-(1-methylcyclopropyl)-5'-oxo-4',5'-dihydro-1'H-spiro[cyclobutane-1,2'-imidazo[1,2-a]quinazoline]-7'-sulfonamide | 455.15 |
| 102 | 3,3-difluoro-4'-((1-methyl-1H-pyrazol-4-yl)methyl)-N-(1-methylcyclopropyl)-5'-oxo-4',5'-dihydro-1'H-spiro[cyclobutane-1,2'-imidazo[1,2-a]quinazoline]-7'-sulfonamide | 491.30 |
| 103 | 4'-((1-methyl-1H-pyrazol-4-yl)methyl)-N-(1-methylcyclopropyl)-5'-oxo-4,4',5,5'-tetrahydro-1'H,2H-spiro[furan-3,2'-imidazo[1,2-a]quinazoline]-7'-sulfonamide | 471.25 |
| 104 | 4'-((1-methyl-1H-pyrazol-4-yl)methyl)-N-(1-methylcyclopropyl)-5'-oxo-4',5'-dihydro-2'H-spiro[cyclobutane-1,1'-imidazo[1,2-a]quinazoline]-7'-sulfonamide | 455.25 |
| 105 | 4-((1-methyl-1H-pyrazol-4-yl)methyl)-N-(1-methylcyclopropyl)-5-oxo-4,5-dihydro-2H-spiro[imidazo[1,2-a]quinazoline-1,3'-oxetane]-7-sulfonamide | 457.10 |
| 106 | (S)-2-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 429.25 |
| 107 | (R)-2-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 429.30 |
| 108 | (1R,2S)-1,2-dimethyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 443.30 |
| 109 | (1R,2R)-1,2-dimethyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 443.30 |
| 110 | (S)-1,2,2-trimethyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 457.30 |
| 111 | (R)-1,2,2-trimethyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 457.20 |
| 112 | (R)-1-methyl-4-((2-methyl-1H-imidazol-5-yl)methyl)-N-(1-methylcyclopropyl)-5-oxo-1,2,4,5-tetrahydroimidazo[1,2-a]quinazoline-7-sulfonamide | 429.20 |
| 115 | (R)-4-((1,4-dimethyl-1H-imidazol-5-yl)methyl)-1-methyl-N-(1-methylcyclopropyl)-5-oxo-1,2,4,5-tetrahydroimidazo[1,2-a]quinazoline-7-sulfonamide | 443.15 |
| 116 | 4-((1-methyl-1H-pyrazol-4-yl)methyl)-N-(1-methylcyclopropyl)-5-oxo-4,5-dihydro-1H-spiro[imidazo[1,2-a]quinazoline-2,3'-oxetane]-7-sulfonamide | 457.15 |
| 117 | 2-ethyl-2-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 457.05 |
| 118 | (R)-4-((5,6-dihydro-4H-pyrrolo[1,2-b]pyrazol-3-yl)methyl)-1-methyl-N-(1-methylcyclopropyl)-5-oxo-1,2,4,5-tetrahydroimidazo[1,2-a]quinazoline-7-sulfonamide | 455.20 |
| 119 | (R)-4-((6,7-dihydro-5H-pyrazolo[5,1-b][1,3]oxazin-3-yl)methyl)-1-methyl-N-(1-methylcyclopropyl)-5-oxo-1,2,4,5-tetrahydroimidazo[1,2-a]quinazoline-7-sulfonamide | 471.15 |
| 120 | (R)-4-((2,4-dimethyl-1H-imidazol-5-yl)methyl)-1-methyl-N-(1-methylcyclopropyl)-5-oxo-1,2,4,5-tetrahydroimidazo[1,2-a]quinazoline-7-sulfonamide | 443.20 |
| 121 | (R)-1-methyl-4-((4-methyl-1,2,3-thiadiazol-5-yl)methyl)-N-(1-methylcyclopropyl)-5-oxo-1,2,4,5-tetrahydroimidazo[1,2-a]quinazoline-7-sulfonamide | 447.10 |
| 124 | (R)-9-chloro-1-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 463.05 |
| 127 | 2-(methoxymethyl)-2-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 473.15 |
| 129 | (R)-9-bromo-1-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 507.05, 509.05 |

Example 61: (R)-1-methyl-4-((1-methyl-1H-pyrazol-4-yl)methyl-d2)-N-(1-methylcyclopropyl)-5-oxo-1,2,4,5-tetrahydroimidazo[1,2-a]quinazoline-7-sulfonamide

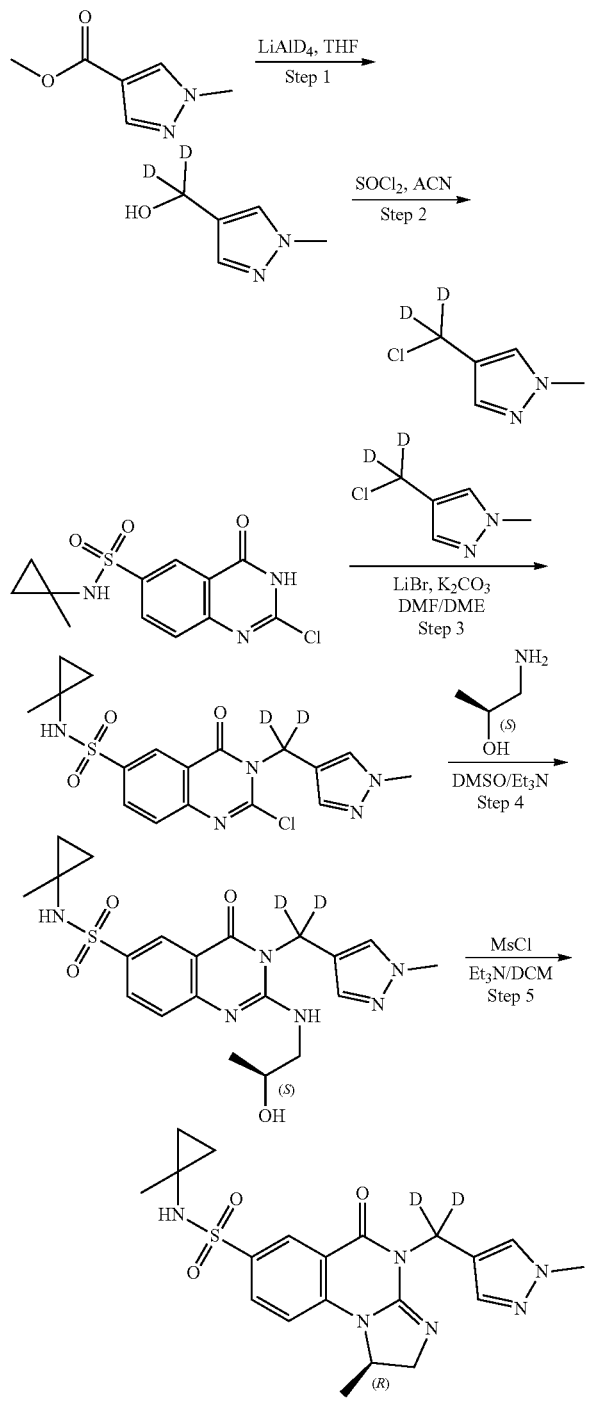

Step 1

To a stirred solution of methyl 1-methylpyrazole-4-carboxylate (1.0 g, 7.1 mmol) in THF (20 mL) was added LiAlD$_4$ (0.6 g, 14.3 mmol) in portions at 0° C. under nitrogen atmosphere. The resulting mixture was stirred for 1 h at 0° C. under nitrogen atmosphere. The reaction was quenched with Na$_2$SO$_4$·10H$_2$O (1 g) at room temperature. The resulting mixture was filtered, the filter cake was washed with MeCN (3×10 mL). The resulting mixture was concentrated under reduced pressure to afford (1-methylpyrazol-4-yl) (2H$_2$) methanol (757 mg, 93%). LCMS (ESI) m/z: 115.0 [M+H]$^+$.

Step 2

To a stirred solution of (1-methylpyrazol-4-yl) (2H$_2$) methanol (600 mg, 5.3 mmol) in MeCN (10 mL) was added thionyl chloride (2501.3 mg, 21 mmol) in portions at room temperature. The resulting mixture was stirred for 20 h at 50° C. The resulting mixture was concentrated under reduced pressure to afford 4-[chloro (2H$_2$) methyl]-3,5-dimethyl-1,2-oxazole (360 mg, 52%). LCMS (ESI) m/z: 133.0 [M+H]$^+$.

Step 3

To a stirred solution of 2-chloro-N-(1-methylcyclopropyl)-4-oxo-3H-quinazoline-6-sulfonamide (150 mg, 0.48 mmol) and 4-[chloro (2H$_2$) methyl]-1-methylpyrazole (126.8 mg, 0.96 mmol) in DME (4 mL) and DMF (1 mL) were added K$_2$CO$_3$ (132 mg, 0.96 mmol) and LiBr (83 mg, 0.96 mmol) in portions at room temperature. The resulting mixture was stirred for 2 h at 50° C. The reaction was quenched with water (40 mL) at room temperature. The resulting mixture was extracted with EtOAc (3×30 mL). The combined organic layers were washed with brine (2×20 mL), dried over anhydrous Na$_2$SO$_4$. After filtration, the filtrate was concentrated under reduced pressure. The residue was purified by silica gel column chromatography, eluted with EA/PE (50%-70%) to afford 2-chloro-N-(1-methylcyclopropyl)-3-[(1-methylpyrazol-4-yl) (2H$_2$) methyl]-4-oxoquinazoline-6-sulfonamide (138 mg, 70%). LCMS (ESI) m/z: 410.0 [M+H]$^+$.

Step 4

To a stirred solution of 2-chloro-N-(1-methylcyclopropyl)-3-[(1-methylpyrazol-4-yl) (2H$_2$) methyl]-4-oxoquinazoline-6-sulfonamide (138 mg, 0.34 mmol) in DMSO (6 mL) was added (S)-1-amino-2-propanol (30.3 mg, 0.41 mmol) and TEA (102.2 mg, 1 mmol) in portions at room temperature. The resulting mixture was stirred for 2 h at 50° C. The reaction was quenched with water (40 mL) at room temperature. The resulting mixture was extracted with EtOAc (3×30 mL). The combined organic layers were washed with brine (2×30 mL), dried over anhydrous Na$_2$SO$_4$. After filtration, the filtrate was concentrated under reduced pressure. The residue was purified by silica gel column chromatography, eluted with MeOH/CH$_2$Cl$_2$ (10%-20%) to afford 2-{[(2S)-2-hydroxypropyl]amino}-N-(1-methylcyclopropyl)-3-[(1-methylpyrazol-4-yl) (2H$_2$) methyl]-4-oxoquinazoline-6-sulfonamide (122 mg, 81%). LCMS (ESI) m/z: 449.0 [M+H]$^+$.

Step 5

To a stirred solution of 2-{[(2S)-2-hydroxypropyl]amino}-N-(1-methylcyclopropyl)-3-[(1-methylpyrazol-4-yl)(2H2)methyl]-4-oxoquinazoline-6-sulfonamide (120 mg, 0.27 mmol,) in DCM (5 mL) was added MsCl (92 mg, 0.81 mmol) and TEA (81.2 mg, 0.81 mmol) in portions at room temperature. The resulting mixture was stirred for 2 h at 35° C. The reaction was quenched with water (20 mL) at room temperature. The resulting mixture was extracted with CH$_2$Cl$_2$ (3×20 mL). The combined organic layers were washed with brine (2×20 mL), dried over anhydrous Na$_2$SO$_4$. After filtration, the filtrate was concentrated under reduced pressure. The crude product was purified by Prep-HPLC with the following conditions (Column: XBridge Prep OBD C18 Column, 30*150 mm, 5 μm; Mobile Phase A: water (10 mmol/L NH$_4$HCO$_3$), Mobile Phase B: ACN; Flow rate: 60 mL/min; Gradient: 30% B to 55% B in 8 min, 55% B; Wave Length: 220 nm; to afford (R)-1-methyl-4-((1-methyl-1H-pyrazol-4-yl)methyl-d2)-N-(1-methylcyclopropyl)-5-oxo-1,2,4,5-tetrahydroimidazo[1,2-a]quinazoline-7-sulfonamide (30 mg, 26%). LCMS (ESI) m/z: 431.00 [M+H]$^+$. $^1$H NMR (400 M z, CD$_3$OD) δ 8.42 (d, J=2.4 Hz, 1H), 7.99 (dd, J=8.8, 2.4 Hz, 1H), 7.68 (s, 1H), 7.55 (s, 1H), 7.20 (d, J=8.8 Hz, 1H), 4.77-4.71 (m, 1H), 4.18-4.13 (m, 1H), 3.82 (s, 3H), 3.65-3.61 (m, 1H), 1.40 (d, J=6.4 Hz, 3H), 1.16 (s, 3H), 0.74-0.67 (m, 2H), 0.46-0.39 (i, 2H).

The following compounds in Table 4 were prepared using procedures similar to those described for Example 61 using appropriate starting materials.

TABLE 4

| Example No. | Name | [M + H]$^+$ |
|---|---|---|
| 62 | (R)-4-((3,5-dimethylisoxazol-4-yl)methyl-d2)-1-methyl-N-(1-methylcyclopropyl)-5-oxo-1,2,4,5-tetrahydroimidazo[1,2-a]quinazoline-7-sulfonamide | 446.00 |
| 63 | (R)-1-methyl-N-(1-methylcyclopropyl)-4-((2-methylthiazol-5-yl)methyl-d2)-5-oxo-1,2,4,5-tetrahydroimidazo[1,2-a]quinazoline-7-sulfonamide | 448.05 |
| 85 | (7aS,10aR)-6-(dideutero(1-methyl-1H-pyrazol-4-yl)methyl)-N-(1-methylcyclopropyl)-5-oxo-6,7a,8,9,10,10a-hexahydro-5H-cyclopenta[4,5]imidazo[1,2-a]quinazoline-3-sulfonamide | 457.00 |
| 86 | (R)-4-(dideutero(1-methyl-1H-pyrazol-4-yl)methyl)-8-fluoro-1-methyl-N-(1-methylcyclopropyl)-5-oxo-1,2,4,5-tetrahydroimidazo[1,2-a]quinazoline-7-sulfonamide | 449.00 |
| 87 | (S)-4-(dideutero(1-methyl-1H-pyrazol-4-yl)methyl)-N-(1-methylcyclopropyl)-5-oxo-1-(trifluoromethyl)-1,2,4,5-tetrahydroimidazo[1,2-a]quinazoline-7-sulfonamide | 484.95 |
| 89 | (R)-4-(dideutero(2,4-dimethylthiazol-5-yl)methyl)-1-methyl-N-(1-methylcyclopropyl)-5-oxo-1,2,4,5-tetrahydroimidazo[1,2-a]quinazoline-7-sulfonamide | 462.00 |
| 91 | (S)-4-(dideutero(1-methyl-1H-pyrazol-4-yl)methyl)-1-methyl-N-(1-methylcyclopropyl)-5-oxo-1,2,4,5-tetrahydroimidazo[1,2-a]quinazoline-7-sulfonamide | 431.00 |
| 98 | (7aR,10aS)-6-(dideutero(2,4-dimethylthiazol-5-yl)methyl)-N-(1-methylcyclopropyl)-5-oxo-5,6,7a,8,10,10a-hexahydrofuro[3',4':4,5]imidazo[1,2-a]quinazoline-3-sulfonamide | 490.05 |
| 113 | (R)-4-(dideutero(2,4-dimethylthiazol-5-yl)methyl)-8-fluoro-1-methyl-N-(1-methylcyclopropyl)-5-oxo-1,2,4,5-tetrahydroimidazo[1,2-a]quinazoline-7-sulfonamide | 480.20 |
| 122 | (R)-4-(dideutero(5,6-dihydro-4H-pyrrolo[1,2-b]pyrazol-3-yl)methyl)-1-methyl-N-(1-methylcyclopropyl)-5-oxo-1,2,4,5-tetrahydroimidazo[1,2-a]quinazoline-7-sulfonamide | 457.30 |
| 128 | (R)-9-chloro-4-(dideutero(1-methyl-1H-pyrazol-4-yl)methyl)-1-methyl-N-(1-methylcyclopropyl)-5-oxo-1,2,4,5-tetrahydroimidazo[1,2-a]quinazoline-7-sulfonamide | 465.20 |

Representative Synthesis Route 2

Example 45: (R)-1-ethyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide

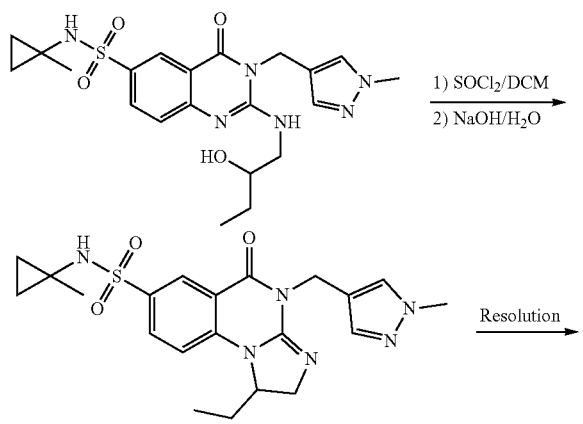

To a mixture of 2-{[2-hydroxybutyl]amino}-N-(1-methylcyclopropyl)-3-[(1-methylpyrazol-3-yl)methyl]-4-oxoquinazoline-6-sulfonamide (130 mg, 0.28 mmol) in DCM (2 mL) was added SOCl$_2$ (167 mg, 1.40 mmol). The mixture was stirred for 2 h at room temperature. To the above mixture was added NaOH (226 mg, 5.63 mmol) in water (1 mL) dropwise over 10 min at 0° C. The resulting mixture was stirred for additional 2 h at room temperature. The aqueous layer was extracted with DCM (3×15 mL). The resulting mixture was concentrated under reduced pressure. The crude product was purified by Prep-HPLC with the following conditions (Column: Sunfire prep C18 column, 30*150 mm, 5 m; Mobile Phase A: water (0.1% FA), Mobile Phase B: ACN; Flow rate: 60 mL/min; Gradient: 7% B to 21% B in 11 min, 21% B; Wave Length: 254/220 nm) to afford 22 mg of racemic (1-ethyl-N-(1-methylcyclopropyl)-4-[(1-methylpyrazol-4-yl)methyl]-5-oxo-1H,2H-imidazo[1,2-a]quinazoline-7-sulfonamide.

The racemate was separated by Chiral HPLC[Column: Lux 5 um Cellulose-4, 2.12*25 cm, 5 m; Mobile Phase A: Hex (10 mM NH$_3$-MeOH), Mobile Phase B: EtOH:ACN=5:1; Flow rate: 20 mL/min; Gradient: 30% B in 28 min; Wave Length: 220/286 nm; RT1(min): 18.325; RT2 (min): 23.1] to afford (1R)-1-ethyl-N-(1-methylcyclopropyl)-4-[(1-methylpyrazol-4-yl)methyl]-5-oxo-1H,2H-imidazo[1,2-a]quinazoline-7-sulfonamide (6.2 mg, 32%) and (1S)-1-ethyl-N-(1-methylcyclopropyl)-4-[(1-methylpyrazol-4-yl)methyl]-5-oxo-1H,2H-imidazo[1,2-a]quinazoline-7-sulfonamide (10.7 mg, 56%). LCMS (ESI) m/z: 443.25 [M+H]$^+$.

The following compounds in Table 5 were prepared using procedures similar to those described in Representative Synthesis Route 2 for Example 45 using appropriate starting materials.

TABLE 5

| Example No. | Name | [M + H]$^+$ |
|---|---|---|
| 49 | 1-isopropyl-4-methyl-N-(1-methylcyclopropyl)-5-oxo-1,2,4,5-tetrahydroimidazo[1,2-a]quinazoline-7-sulfonamide | 377.10 |
| 50 | 1-ethyl-4-methyl-N-(1-methylcyclopropyl)-5-oxo-1,2,4,5-tetrahydroimidazo[1,2-a]quinazoline-7-sulfonamide | 363.05 |

-continued

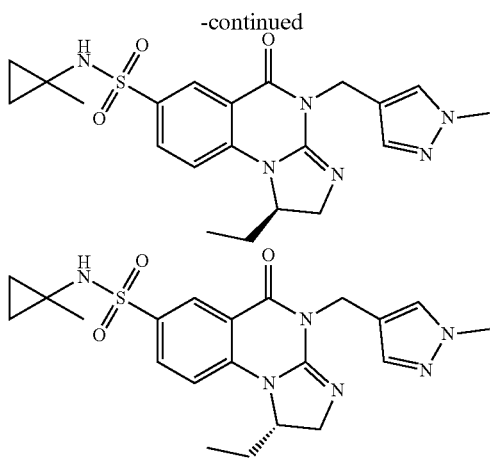

Representative Synthesis Route 3

Example 46: (R)-1-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide

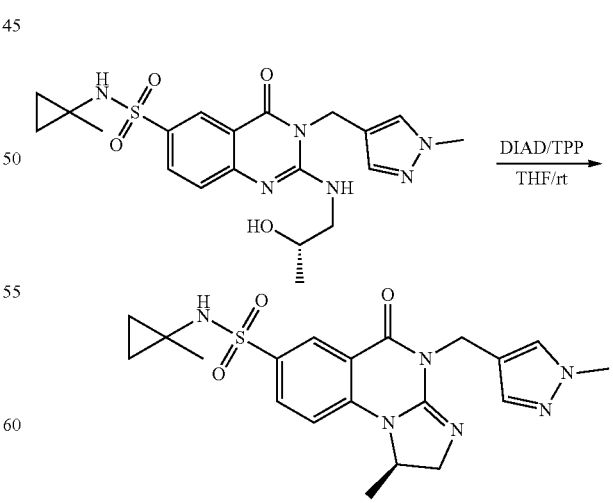

An alternative route to Example 46 which exemplifies an alternative ring closure method is also provided herein. To a solution of (S)-2-((2-hydroxypropyl)amino)-3-((1-methyl- 1H-pyrazol-4-yl)methyl)-N-(1-methylcyclopropyl)-4-oxo-3,4-dihydroquinazoline-6-sulfonamide (85 mg, 0.19 mmol) in THF (2 mL) was added triphenylphosphine (96 mg, 0.36 mmol). The solution was cooled to 0° C. and DIAD (73 mg, 0.36 mmol) was added dropwise. The reaction was stirred for 16 h at room temperature. The mixture was concentrated under vacuum. The residue was purified by silica gel column, eluted with MeOH/DCM (0-15%) to afford a crude product which was further purified by HPLC.

The following compound in Table 6 was prepared using procedures similar to those described in Representative Synthesis Route 3 for Example 46 using appropriate starting materials.

TABLE 6

| Example No. | Name | [M + H]+ |
|---|---|---|
| 134 | (R)-1-methyl-4-((1-methyl-1H-pyrazol-4-yl)methyl-d2)-N-(1-methylcyclopropyl)-5-oxo-9-(trifluoromethyl)-1,2,4,5-tetrahydroimidazo[1,2-a]quinazoline-7-sulfonamide | 499.05 |

Representative Synthesis Route 4

Example 52: (R)-1,4-dimethyl-N-(1-methylcyclopropyl)-5-oxo-1,2,4,5-tetrahydroimidazo[1,2-a]quinazoline-7-sulfonamide

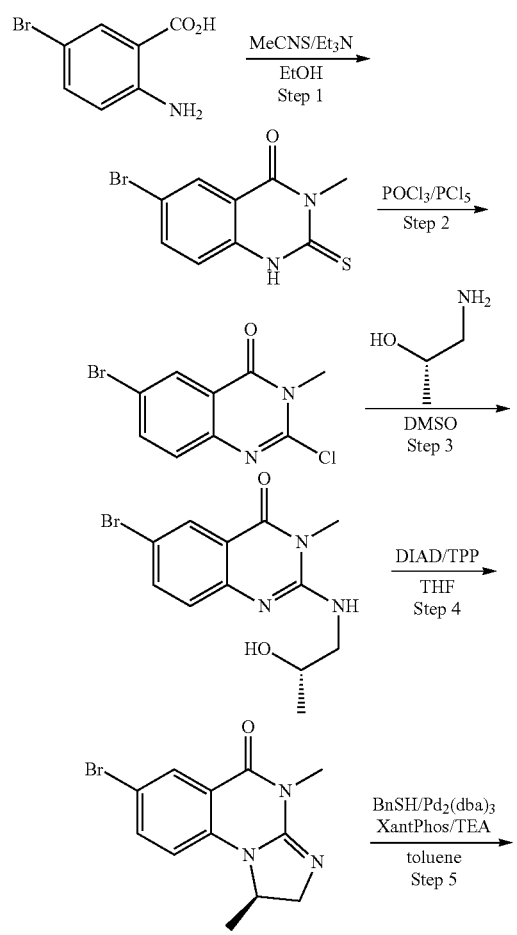

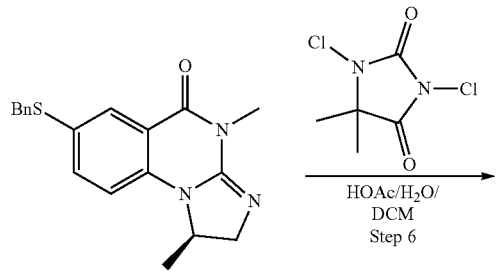

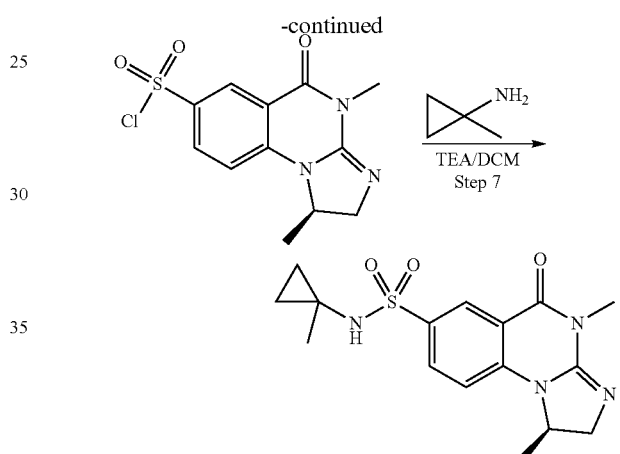

Step 1
To a stirred solution of 5-bromoanthranilic acid (10 g, 46.3 mmol) and methyl isothiocyanate (4.1 g, 55.5 mmol) in ethanol (200 mL) was added Et$_3$N (4.7 g, 46.3 mmol). The reaction was stirred at 80° C. for 2 h. The reaction was poured into water (500 mL). The aqueous layer was extracted with EtOAc (2×200 mL), and the combined organic layers were concentrated under reduced pressure. The residue was purified by silica gel column chromatography, eluting with CH$_2$Cl$_2$/MeOH (6:1), to afford 6-bromo-3-methyl-2-sulfanylidene-1H-quinazolin-4-one (5.6 g, 45%) as a white solid.

Step 2:
To a mixture of 6-bromo-3-methyl-2-sulfanylidene-1H-quinazolin-4-one (5.6 g, 20.7 mmol) in POCl$_3$ (50 mL) was added PCl$_5$ (6.4 g, 31.1 mmol) at room temperature. The reaction was heated to reflux and stirred for 2 h. The reaction was concentrated under reduced pressure. The solid was rinsed with hexanes (50 mL) and dried under vacuum to afford 6-bromo-2-chloro-3-methylquinazolin-4-one (2.6 g, 46%) as a brown solid.

Step 3:
To a stirred solution of 6-bromo-2-chloro-3-methylquinazolin-4-one (2.6 g, 9.36 mmol) and (2S)-1-aminopropan-2-ol (0.84 g, 11.2 mmol) in DMSO (50 mL) was added Et$_3$N (2.8 g, 28.1 mmol). The solution was stirred at 100° C. for 2 h. The reaction was quenched by water (100 mL). The aqueous layer was extracted with EtOAc (2×100 mL), the combined organic layers were washed with brine (100 mL) and concentrated under reduced pressure. The residue was purified by silica gel column chromatography, eluting with $CH_2Cl_2$/MeOH (5:1), to afford 6-bromo-2-{[(2S)-2-hydroxypropyl]amino}-3-methylquinazolin-4-one (2.2 g, 74%) as a brown solid.

Step 4

To a stirred solution of 6-bromo-2-{[(2S)-2-hydroxypropyl]amino}-3-methylquinazolin-4-one (2.2 g, 7.07 mmol) and $PPh_3$ (2.8 g, 10.6 mmol) in THF (50 mL), was added DIAD (2.1 g, 10.6 mmol) dropwise at 0° C. The solution was stirred at 0° C. for 2 h. The resulting mixture was concentrated under reduced pressure. The residue was purified by silica gel column chromatography, eluted with PE/EA (1:1) to afford (1R)-7-bromo-1,4-dimethyl-1H,2H-imidazo[1,2-a]quinazolin-5-one (1.0 g, 48%) as a yellow solid.

Step 5

To a stirred mixture of (1R)-7-bromo-1,4-dimethyl-1H,2H-imidazo[1,2-a]quinazolin-5-one (1 g, 3.4 mmol) and benzyl mercaptan (0.51 g, 4.08 mmol) in toluene (20 mL) were added TEA (1 g, 10.2 mmol), XantPhos (0.39 g, 0.68 mmol) and $Pd_2(dba)_3$ (0.31 g, 0.34 mmol). The resulting mixture was stirred for 3 h at 90° C. under nitrogen atmosphere. The reaction was quenched with water (120 mL) at room temperature. The resulting mixture was extracted with EtOAc (3×120 mL). The combined organic layers were washed with brine (2×150 mL), dried over anhydrous $Na_2SO_4$. After filtration, the filtrate was concentrated under reduced pressure. The residue was purified by silica gel column chromatography, eluted with DCM/EA (3:2) to afford (1R)-7-(benzylsulfanyl)-1,4-dimethyl-1H,2H-imidazo[1,2-a]quinazolin-5-one (700 mg, 61%) as a yellow solid. LCMS (ESI) m/z: 338.0 $[M+H]^+$.

Step 6

To a mixture of (1R)-7-(benzylsulfanyl)-1,4-dimethyl-1H,2H-imidazo[1,2-a]quinazolin-5-one (700 mg, 2.07 mmol) in DCM (10 mL), were added 1,3-dichloro-5,5-dimethyl-2-methylideneimidazolidin-4-one (809 mg, 4.15 mmol), acetic acid (0.15 mL) and $H_2O$ (0.1 mL). The mixture was stirred for 3 h at room temperature. The reaction was quenched with water (30 mL) at room temperature. The resulting mixture was extracted with $CH_2Cl_2$ (3×30 mL). The combined organic layers were dried over anhydrous $Na_2SO_4$ and concentrated under reduced pressure. The residue was purified by silica gel column chromatography, eluted with PE/EA (1:2) to afford (1R)-1,4-dimethyl-5-oxo-1H,2H-imidazo[1,2-a]quinazoline-7-sulfonyl chloride (210 mg, 32%) as a brown solid. LCMS (ESI) m/z: 314.0 $[M+H]^+$.

Step 7

To a solution of 1-methylcyclopropan-1-amine hydrochloride (86.4 mg, 0.80 mmol) in DCM (10 mL), was added TEA (203 mg, 2.0 mmol) at room temperature. The mixture was stirred for 15 min and then (1R)-1,4-dimethyl-5-oxo-1H,2H-imidazo[1,2-a]quinazoline-7-sulfonyl chloride (210 mg, 0.67 mmol) was added. The solution was stirred for 3 h at room temperature. The reaction was quenched with water (30 mL) at room temperature. The resulting mixture was extracted with $CH_2Cl_2$ (3×40 mL). The combined organic layers were dried over anhydrous $Na_2SO_4$ and concentrated under reduced pressure. The crude product was purified by Prep-HPLC with the following conditions (Column: XBridge Shield RP18 OBD Column, 19*150 mm, 5 m; Mobile Phase A: water (10 mmol/L $NH_4HCO_3$), Mobile Phase B: ACN; Flow rate: 25 mL/min; Gradient: 25% B to 60% B in 10 min Wave Length: 220 nm) to afford (1R)-1,4-dimethyl-N-(1-methylcyclopropyl)-5-oxo-1H,2H-imidazo[1,2-a]quinazoline-7-sulfonamide (26.0 mg, 11%). LCMS (ESI) m/z: 349.00 $[M+H]^+$. $^1$H NMR (400 MHz, $CD_3OD$) δ 8.41 (s, 1H), 8.01 (d, J=8.8 Hz, 1H), 7.05 (d, J=8.8 Hz, 1H), 4.37-4.29 (m, 1H), 4.26 (t, J=9.2 Hz, 1H), 3.70-3.64 (m, 1H), 3.41 (s, 3H), 1.38 (d, J=6.4 Hz, 3H), 1.15 (d, J=0.8 Hz, 3H), 0.73-0.67 (m, 2H), 0.44-0.38 (m, 2H).

The following compound in Table 7 was prepared using procedures similar to those described in Representative Synthesis Route 4 for Example 52 using appropriate starting materials.

TABLE 7

| Example No. | Name | $[M + H]^+$ |
|---|---|---|
| 51 | (R)-4-benzyl-1-methyl-N-(1-methylcyclopropyl)-5-oxo-1,2,4,5-tetrahydroimidazo[1,2-a]quinazoline-7-sulfonamide | 425.15 |

The following compound in Table 8 was prepared using procedures similar to those described in Representative Synthesis Route 4 for Example 52 (Steps 5-7) using appropriate starting materials.

TABLE 8

| Example No. | Name | $[M + H]^+$ |
|---|---|---|
| 92 | (R)-4-(dideutero(1-methyl-1H-pyrazol-4-yl)methyl)-9-methoxy-1-methyl-N-(1-methylcyclopropyl)-5-oxo-1,2,4,5-tetrahydroimidazo[1,2-a]quinazoline-7-sulfonamide | 461.30 |

Representative Synthesis Route 5

Example 1: (R)-4-((1-(2-hydroxyethyl)-1H-pyrazol-4-yl)methyl)-1-methyl-N-(1-methylcyclopropyl)-5-oxo-1,2,4,5-tetrahydroimidazo[1,2-a]quinazoline-7-sulfonamide

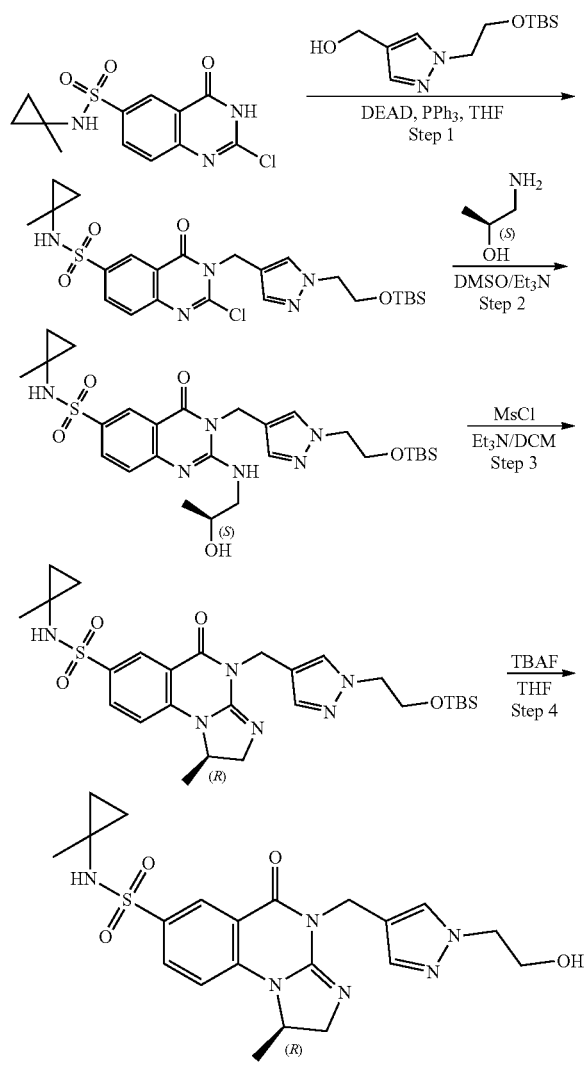

Step 1

To a stirred mixture of 2-chloro-N-(1-methylcyclopropyl)-4-oxo-3H-quinazoline-6-sulfonamide (170 mg, 0.54 mmol) and (1-{2-[(tert-butyldimethylsilyl)oxy]ethyl}pyrazol-4-yl)methanol (166 mg, 0.65 mmol) in THF (10 mL) were added PPh₃ (213 mg, 0.81 mmol) and DEAD (164 mg, 0.81 mmol) in portions at room temperature. The resulting mixture was stirred for 12 h at room temperature. The resulting mixture was concentrated under reduced pressure. The residue was purified by reverse flash chromatography with the following conditions: column, C18 silica gel; mobile phase, MeCN in Water (0.1% FA), 60% to 80% gradient in 10 min; detector, UV 254 nm to afford 3-[(1-{2-[(tert-butyldimethylsilyl)oxy]ethyl}pyrazol-4-yl)methyl]-2-chloro-N-(1-methylcyclopropyl)-4-oxoquinazoline-6-sulfonamide (100 mg, 33%). LCMS (ESI) m/z: 552 [M+H]⁺.

Step 2

To a stirred mixture of 3-[(1-{2-[(tert-butyldimethylsilyl)oxy]ethyl}pyrazol-4-yl)methyl]-2-chloro-N-(1-methylcyclopropyl)-4-oxoquinazoline-6-sulfonamide (100 mg, 0.18 mmol) and (2S)-1-aminopropan-2-ol (16.3 mg, 0.22 mmol) in DMSO (10 mL) was added TEA (54.9 mg, 0.54 mmol) in portions at room temperature. The resulting mixture was stirred for 2 h at 100° C. The mixture was purified by reverse flash chromatography with the following conditions: column, C18 silica gel; mobile phase, MeCN in Water (10 mmol/L NH₄HCO₃), 50% to 70% gradient in 10 min; detector, UV 254 nm to afford 3-[(1-{2-[(tert-butyldimethylsilyl)oxy]ethyl}pyrazol-4-yl)methyl]-2-{[(2S)-2-hydroxypropyl]amino}-N-(1-methylcyclopropyl)-4-oxoquinazoline-6-sulfonamide (50 mg, 47%). LCMS (ESI) m/z: 591 [M+H]⁺.

Step 3

To a stirred mixture of 3-[(1-{2-[(tert-butyldimethylsilyl)oxy]ethyl}pyrazol-4-yl)methyl]-2-{[(2S)-2-hydroxypropyl]amino}-N-(1-methylcyclopropyl)-4-oxoquinazoline-6-sulfonamide (50 mg, 0.08 mmol) and MsCl (24 mg, 0.21 mmol) in DCM (5 mL) was added TEA (21.4 mg, 0.21 mmol) in portions at room temperature. The resulting mixture was stirred for 2 h at 35° C. The resulting mixture was concentrated under reduced pressure. The residue was purified by reverse flash chromatography with the following conditions: column, C18 silica gel; mobile phase, MeCN in water (10 mmol/L NH₄HCO₃), 40% to 60% gradient in 10 min; detector, UV 254 nm to afford (1R)-4-[(1-{2-[(tert-butyldimethylsilyl)oxy]ethyl}pyrazol-4-yl)methyl]-1-methyl-N-(1-methylcyclopropyl)-5-oxo-1H,2H-imidazo[1,2-a]quinazoline-7-sulfonamide (30 mg, 65%). LCMS (ESI) m/z: 573 [M+H]⁺.

Step 4

To a stirred mixture of (1R)-4-[(1-{2-[(tert-butyldimethylsilyl)oxy]ethyl}pyrazol-4-yl)methyl]-1-methyl-N-(1-methylcyclopropyl)-5-oxo-1H,2H-imidazo[1,2-a]quinazoline-7-sulfonamide (30 mg, 0.05 mmol) in THF (5 mL) was added TBAF (13.7 mg, 0.05 mmol) in portions at room temperature. The resulting mixture was stirred for 2 h at room temperature. The crude product was purified by Prep-HPLC with the following conditions (Column: YMC-Actus Triart C18 ExRS, 30*150 mm, 5 μm; Mobile Phase A: Water (10 mmol/L NH₄HCO₃), Mobile Phase B: ACN; Flow rate: 60 mL/min; Gradient: 20% B to 35% B in 7 min, 35% B; Wave Length: 220 nm; RT1(min): 6.45; afford (1R)-4-{[1-(2-hydroxyethyl)pyrazol-4-yl]methyl}-1-methyl-N-(1-methylcyclopropyl)-5-oxo-1H,2H-imidazo[1,2-a]quinazoline-7-sulfonamide (12.3 mg, 54%). LCMS (ESI) m/z: 459.10 [M+H]⁺. ¹H-NMR (300 MHz, DMSO-d₆) δ: 8.25 (d, J=2.1 Hz, 1H), 8.07 (s, 1H), 7.93 (dd, J₁=8.4, 2.1 Hz, 1H), 7.71 (s, 1H), 7.45 (s, 1H), 7.28 (d, J=9.0 Hz, 1H), 4.99-4.85 (m, 3H), 4.75 (s, 1H), 4.11-4.01 (m, 3H), 3.68-3.67 (m, 2H), 3.57-3.55 (m, 1H), 1.32 (d, J=6.3 Hz, 3H), 1.06 (s, 3H), 0.61-0.59 (m, 2H), 0.37-0.34 (m, 2H).

Representative Synthesis Route 6

Example 53: (R)-4-((1-(2-(dimethylamino)ethyl)-1H-pyrazol-4-yl)methyl)-1-methyl-N-(1-m ethylcyclopropyl)-5-oxo-1,2,4,5-tetrahydroimidazo[1,2-a]quinazoline-7-sulfonamide

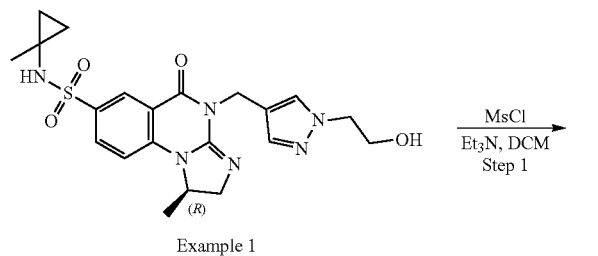

Example 1

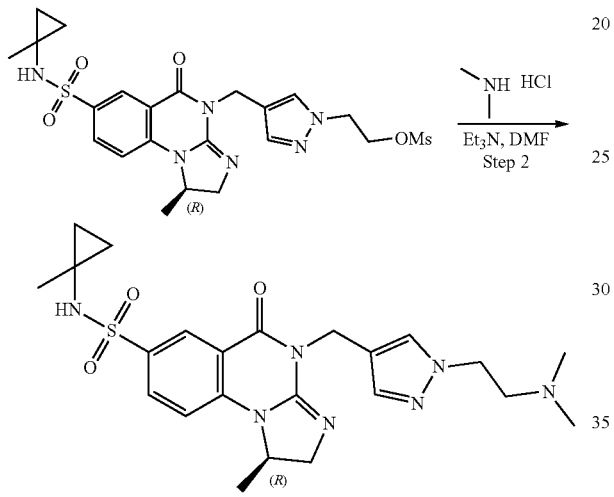

Step 1

To a stirred mixture of (1R)-4-{[1-(2-hydroxyethyl)pyrazol-4-yl]methyl}-N-isopropyl-1-methyl-5-oxo-1H,2H-imidazo[1,2-a]quinazoline-7-sulfonamide (40 mg, 0.09 mmol) an d MsCl (25.7 mg, 0.22 mmol) in DCM (5 mL) was added TEA (27.2 mg, 0.27 mmol) in portions at room temperature. The resulting mixture was stirred for 16 h at 35° C. The resulting mixture was concentrated under reduced pressure. The residue was purified by silica gel column chromatography, eluted with MeOH in $CH_2Cl_2$ (10%-15%) to afford 2-(4-{[(1R)-1-methyl-7-[(1-methylcyclopropyl)sulfamoyl]-5-oxo-1H,2H-imidazo[1,2-a]quinazolin-4-yl]methyl}pyrazol-1-yl)eth yl methanesulfonate (10 mg, 21%). LCMS (ESI) m/z: 537 [M+H]$^+$.

Step 2

To a stirred mixture of 2-(4-{[(1R)-1-methyl-7-[(1-methylcyclopropyl)sulfamoyl]-5-oxo-1H,2H-imidazo[1,2-a]quinazolin-4-yl]methyl}pyrazol-1-yl)ethyl methanesulfonate (10 mg, 0.02 mmol) and dimethylamine hydrochloride (1.8 mg, 0.023 mmol) in DMF (2 mL) was added $K_2CO_3$ (7.7 mg, 0.057 mmol) in portions at room temperature. The resulting mixture was stirred for 16 h at 70° C. After filtration, the filtrate was concentrated under reduced pressure. The crude product was purified by Prep-HPLC with the following conditions (Column: YMC-Actus Triart C18 ExRS, 30*150 mm, 5 m; Mobile Phase A: water (10 mmol/L $NH_4HCO_3$), Mobile Phase B: ACN; Flow rate: 60 mL/min; Gradient: 25% B to 55% B in 7 min, 55% B; Wave Length: 220 nm; RT1(min): 6.23; to afford (1R)-4-({1-[2-(dimethylamino)ethyl]pyrazol-4-yl}methyl)-1-methyl-N-(1-methylcyclopropyl)-5-oxo-1H,2H-imidazo[1,2-a]quinazoline-7-sulfonamide (3.9 mg, 40%). LCMS (ESI) m/z: 486.30 [M+H]$^+$. $^1$H-NMR (400 MHz, DMSO-d$_6$) δ: 8.24 (d, J=2.4 Hz, 1H), 8.03 (s, 1H), 7.90 (dd, J=8.4, 2.0 Hz, 1H), 7.72 (s, 1H), 7.41 (s, 1H), 7.23 (d, J=8.8 Hz, 1H), 4.97-4.85 (m, 2H), 4.75-4.66 (m, 1H), 4.14-4.01 (m, 3H), 3.51 (dd, J=13.6, 3.6 Hz, 1H), 2.58 (t, J=6.4 Hz, 2H), 2.12 (s, 6H), 1.31 (d, J=6.4 Hz, 3H), 1.07 (s, 3H), 0.62-0.57 (m, 2H), 0.40-0.35 (m, 2H).

Representative Synthesis Route 7

Example 57: (R)-4-((1-(difluoromethyl)-1H-pyrazol-4-yl)methyl)-1-methyl-N-(1-methylcyclopropyl)-5-oxo-1,2,4,5-tetrahydroimidazo[1,2-a]quinazoline-7-sulfonamide

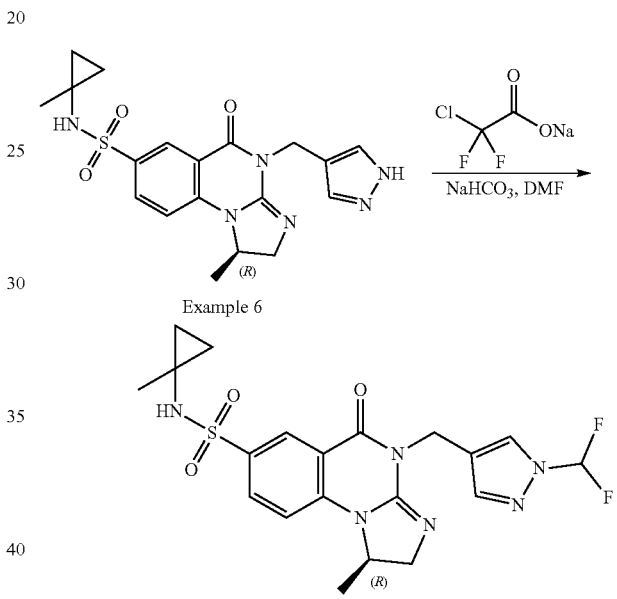

Example 6

A solution of Example 6 (20 mg, 0.05 mmol) in DMF (5 mL) was treated with $NaHCO_3$ (8 mg, 0.1 mmol) for 5 min at room temperature under nitrogen atmosphere followed by the addition of difluoro methyl sodium carbonochloridate (8 mg, 0.05 mmol) dropwise at room temperature. The reaction mixture was stirred at 100° C. for 16 h. The reaction was quenched by the addition of water (5 mL) at room temperature. The resulting mixture was extracted with EtOAc (3×50 mL). The combined organic layers were washed with brine (3×50 mL), dried over anhydrous $Na_2SO_4$. After filtration, the filtrate was concentrated under reduced pressure. The crude product was purified by reverse phase flash with the following conditions (Column: YMC-Actus Triart C18, 30*150 mm, 5 m; Mobile Phase A: water (0.1% FA), Mobile Phase B: ACN; Flow rate: 60 mL/min; Gradient: 25% B to 45% B in 7 min, 45% B; Wave Length: 254/220 nm; RT1(min): 5.92; to afford (1R)-4-{[1-(difluoromethyl) pyrazol-4-yl] methyl}-1-methyl-N-(1-methylcyclopropyl)-5-oxo-1H,2H-imidazo[1,2-a] quinazoline-7-sulfonamide (2.3 mg, 10%). LCMS (ESI) m/z: 465.00 [M+H]$^+$. $^1$H NMR (400 MHz, DMSO-d$_6$) δ 8.28-8.19 (m, 2H), 8.05 (s, 1H), 7.91 (dd, J=9.2, 6.9 Hz, 1H), 7.77 (d, J=21.3 Hz, 1H), 7.25 (d, J=8.7 Hz, 1H), 4.99 (q, J=14.5 Hz, 2H), 4.73 (ddp, J=8.9, 6.1, 3.1, 2.6 Hz, 1H), 4.06 (dd, J=13.7, 9.3 Hz, 1H), 3.52 (dd, J=13.7, 3.6 Hz, 1H), 1.33 (d, J=6.2 Hz, 3H), 1.08 (s, 3H), 0.61 (q, J=4.0 Hz, 2H), 0.39 (dd, J=5.0, 2.2 Hz, 2H).

Representative Synthesis Route 8

Example 2: (R)-N-(1-cyanocyclopropyl)-1-methyl-4-((1-methyl-1H-pyrazol-4-yl)methyl)-5-oxo-1,2,4,5-tetrahydroimidazo[1,2-a]quinazoline-7-sulfonamide

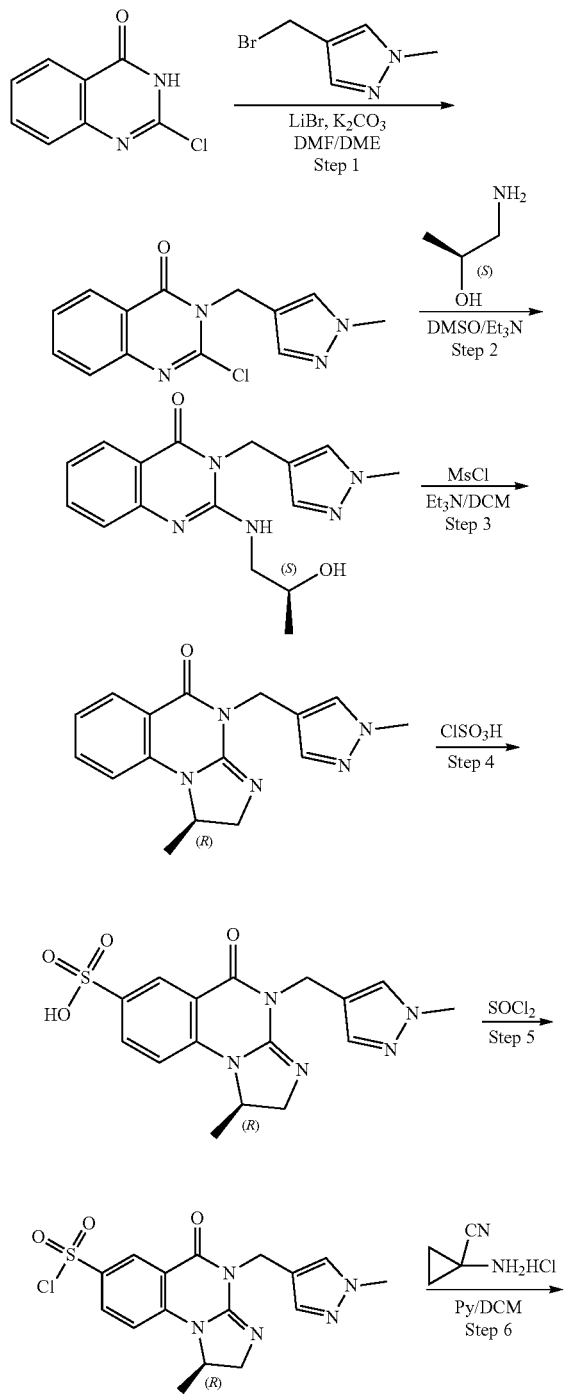

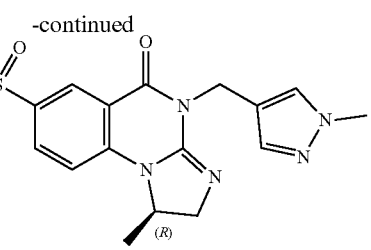
-continued

Step 1

To a stirred solution of 2-chloro-3H-quinazolin-4-one (1 g, 5.53 mmol) and 4-(bromomethyl)-1-methylpyrazole (0.97 g, 5.54 mmol) in DMF (1 mL) and DME (4 mL) was added $K_2CO_3$ (1.53 g, 11.1 mmol) in portions at room temperature. The resulting mixture was stirred for 3 h at room temperature. The resulting mixture was diluted with water (100 mL). The aqueous layer was extracted with EtOAc (2×200 mL), combined organic phase was concentrated under reduced pressure. The crude product was used in the next step directly without further purification. LCMS (ESI) m/z: 275 [M+H]$^+$.

Step 2

To a stirred solution of 2-chloro-3-[(1-methylpyrazol-4-yl)methyl]quinazolin-4-one (1 g, 3.64 mmol) and (2S)-1-aminopropan-2-ol (0.27 g, 3.64 mmol) in DMSO was added $Et_3N$ (1.1 g, 10.9 mmol) in portions at room temperature. The resulting mixture was stirred for 1 h at 100° C. The resulting mixture was extracted with EtOAc (2×100 mL). The combined organic layers were washed with water (20 mL), dried over anhydrous $Na_2SO_4$. After filtration, the filtrate was concentrated under reduced pressure. The crude product was used in the next step directly without further purification. LCMS (ESI) m/z: 314 [M+H]$^+$.

Step 3

To a stirred solution of 2-{[(2S)-2-hydroxypropyl]amino}-3-[(1-methylpyrazol-4-yl)methyl]quinazolin-4-one (500 mg, 1.59 mmol) and MsCl (457 mg, 3.99 mmol) in DCM was added TEA (484 mg, 4.78 mmol) in portions at room temperature. The resulting mixture was stirred for 5 h at 35° C. The resulting mixture was diluted with water (20 mL), concentrated under reduced pressure. The residue was purified by silica gel column chromatography, eluted with $CH_2Cl_2$/MeOH (10:1) to afford (1R)-1-methyl-4-[(1-methylpyrazol-4-yl)methyl]-1H,2H-imidazo[1,2-a]quinazolin-5-one (200 mg, 42%). LCMS (ESI) m/z: 296 [M+H]$^+$.

Step 4

A mixture of (1R)-1-methyl-4-[(1-methylpyrazol-4-yl)methyl]-1H,2H-imidazo[1,2-a]quinazolin-5-one (200 mg, 0.67 mmol) and chlorosulfonic acid (2 mL) was stirred for 1 h at 60° C. The reaction was quenched with water/ice at room temperature. The resulting mixture was concentrated under reduced pressure. The crude product was used in the next step directly without further purification.

Step 5

A solution of (1R)-1-methyl-4-[(1-methylpyrazol-4-yl)methyl]-5-oxo-1H,2H-imidazo[1,2-a]quinazoline-7-sulfonic acid (100 mg, 0.26 mmol) and DMF (0.1 mL) in $SOCl_2$ (3 mL) was stirred for 1 h at 60° C. The resulting mixture was concentrated under reduced pressure. The crude product was used in the next step directly without further purification. LCMS (ESI) m/z: 394 [M+H]$^+$.

Step 6

To a stirred solution of (1R)-1-methyl-4-[(1-methylpyrazol-4-yl)methyl]-5-oxo-1H,2H-imidazo[1,2-a]quinazoline-7-sulfonyl chloride (50 mg, 0.13 mmol) and 1-aminocyclopropane-1-carbonitrile (12.5 mg, 0.15 mmol) in DCM (2 mL) was added Pyridine (30 mg, 0.38 mmol) in portions at room temperature. The resulting mixture was stirred for 1 h at room temperature. The resulting mixture was diluted with water (10 mL), and extracted with DCM (2×10 mL). The combined organic layers were washed with acetic acid (2×10 mL), dried over anhydrous Na$_2$SO$_4$. After filtration, the filtrate was concentrated under reduced pressure. The crude product (10 mg) was purified by Prep-HPLC (Column: Sunfire prep C18 column, 30*150 mm, 5 m; Mobile Phase A: water (0.1% FA), Mobile Phase B: ACN; Flow rate: 60 mL/min; Gradient: 11% B to 19% B in 7 min, 19% B; Wave Length: 254/220 nm; RT1(min): 4.82) to afford (1R)-N-(1-cyanocyclopropyl)-1-methyl-4-[(1-methylpyrazol-4-yl)methyl]-5-oxo-1H, 2H-imidazo[1,2-a]quinazoline-7-sulfonamide (1.7 mg, 3%). LCMS (ESI) m/z: 440.05 [M+H]$^+$. $^1$H NMR (400 MHz, CD$_3$OD) δ 8.38 (d, J=2.2 Hz, 1H), 7.96 (dd, J=8.8, 2.2 Hz, 1H), 7.58 (s, 1H), 7.46 (s, 1H), 7.18 (d, J=8.8 Hz, 1H), 4.98-4.85 (m, 2H), 4.08 (dd, J=13.3, 9.4 Hz, 1H), 3.95 (q, J=7.2 Hz, 1H), 3.73 (s, 3H), 3.57-3.54 (m, 1H), 1.35-1.27 (m, 5H), 1.18 (t, J=7.2 Hz, 2H).

The following compound in Table 9 was prepared using procedures similar to those described in Representative Synthesis Route 8 for Example 2 using appropriate starting materials

TABLE 9

| Example No. | Name | [M + H]$^+$ |
|---|---|---|
| 88 | (7aS,10aR)-N-(1-cyanocyclopropyl)-6-(dideutero(1-methyl-1H-pyrazol-4-yl)methyl)-5-oxo-6,7a,8,9,10,10a-hexahydro-5H-cyclopenta[4,5]imidazo[1,2-a]quinazoline-3-sulfonamide | 468.10 |

Representative Synthesis Route 9

Example 114: (R)-1-methyl-4-(1-(1-methyl-1H-pyrazol-4-yl)cyclopropyl)-N-(1-methylcyclopropyl)-5-oxo-1,2,4,5-tetrahydroimidazo[1,2-a]quinazoline-7-sulfonamide

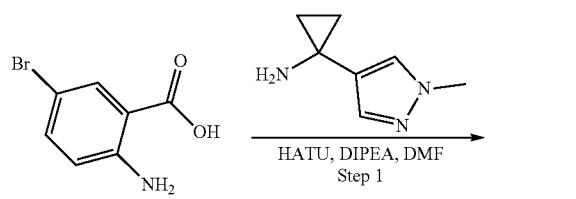

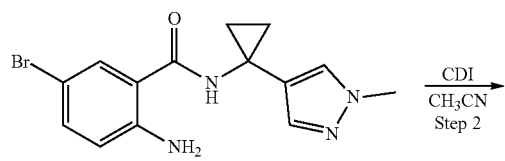

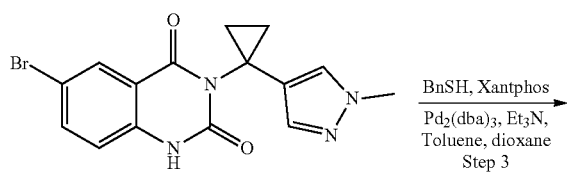

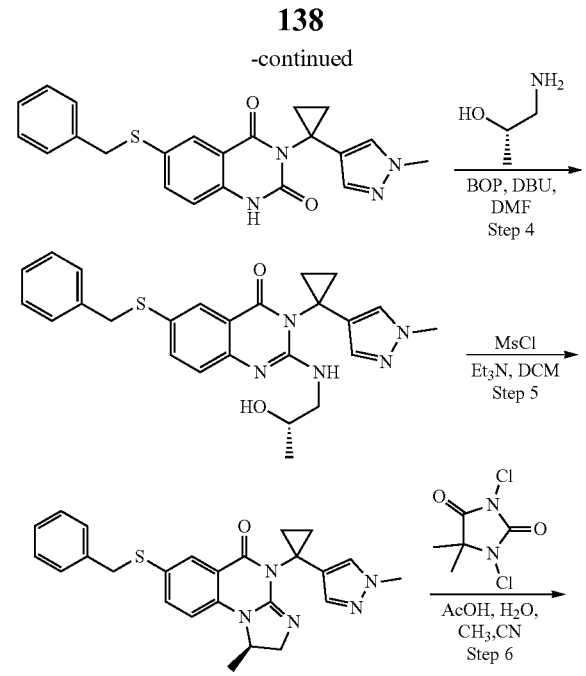

Step 1

To a solution of 2-amino-5-bromobenzoic acid (1.5 g, 7.17 mmol) in DMF (40 mL) was added HATU (3 g, 7.89 mmol), DIPEA (1.7 mL, 10 mmol) and 1-(1-methyl-1H-pyrazol-4-yl) cyclopropan-1-amine (984 mg, 7.17 mmol) and reacted at room temperature for 1.10 h. Water was added and the formed ppt was filtered. Filtrate was extracted with EtOAc. Organic layer was concentrated and purified by silica gel chromatography (0-18% MeOH/DCM) to obtain product (2.3 g, 96%).

Step 2

To a mixture of 2-amino-5-bromo-N-[1-(1-methyl-1H-pyrazol-4-yl)cyclopropyl]benzamide (1 g, 2.98 mmol) in CH$_3$CN (13.6 mL) was added CDI (869 mg, 5.36 mmol) and DMAP (36.4 mg, 0.3 mmol). Reaction was stirred at room temperature for 20 min and then at 55° C. for 5.45 h. Solvent was evaporated in vacuo, added water and the formed white ppt was filtered. The precipitate was washed with 1M HCl and then with water, dried to obtain the product (681.2 mg, 63%).

Step 3

To a solution of 6-bromo-3-[1-(1-methyl-1H-pyrazol-4-yl)cyclopropyl]-1,2,3,4-tetrahydroquinazoline-2,4-dione (601 mg, 1.66 mmol) in Toluene (9.6 mL) was added Et₃N (0.7 mL, 5 mmol), BnSH (0.2 mL, 2 mmol), dioxane (0.4 mL) and the reaction was degassed and back filled with N₂. Next added Xantphos (193 mg, 0.33 mmol), Pd₂(dba)₃ (152 mg, 0.16 mmol), degassed and back filled with N₂, and heated at 90° C. for 1.45 h. Crude reaction mixture was purified by silica gel chromatography (0-100% EtOAc/hex and then 100% MeOH/DCM) to obtain product (599 mg, 89%). LCMS (ESI) m/z: 405 [M+H]⁺.

Step 4

Into a microwave vial added 6-(benzylsulfanyl)-3-[1-(1-methyl-1H-pyrazol-4-yl)cyclopropyl]-1,2,3,4-tetrahydroquinazoline-2,4-dione (300 mg, 0.74 mmol), DMF (0.3 mL), BOP (590 mg, 1.34 mmol), DBU (0.2 mL, 1.48 mmol) and the reaction mixture was stirred at room temperature for 2 h. Additional BOP (165 mg), DBU (65 ul) was added and reacted at room temperature for 1 h. Further addition of BOP (211.4 mg), DBU (0.1 mL) and reaction was stirred for another 1.20 h. To this reaction mixture added (2S)-1-aminopropan-2-ol (0.5 mL, 6.5 mmol) and reacted at room temperature for 10 min and then heated in the microwave at 80° C. for 1 h. Water was added to the reaction mixture and extracted with EtOAc. Crude was purified by silica gel chromatography (0-100% EtOAc/hex then 0-100% MeOH/DCM) to obtain product (239.1 mg, 70%). LCMS (ESI) m/z: 462 [M+H]⁺.

Step 5

To a mixture of 2-{[(2S)-2-hydroxypropyl]amino}-3-[1-(1-methyl-1H-pyrazol-4-yl)ethyl]-3,4-dihydroquinazolin-4-one (239 mg, 0.52 mmol) in DCM (10.7 mL) was added Et₃N (0.2 mL, 1.5 mmol) and MsCl (0.1 mL, 1.29 mmol). The reaction mixture was stirred at room temperature for 1.10 h and then heated at 35° C. for 2.20 h. Water was added and extracted with DCM and EtOAc. Crude was purified by silica gel chromatography (0-37% MeOH/DCM) to obtain product (95.1 mg, 41%). LCMS (ESI) m/z: 444 [M+H]⁺.

Step 6

To a solution of (1R)-7-(benzylsulfanyl)-1-methyl-4-[1-(1-methyl-1H-pyrazol-4-yl)cyclopropyl]-1H,2H,4H,5H-imidazo[1,2-a]quinazolin-5-one (45 mg, 0.1 mmol) in CH₃CN (0.4 mL) at 0° C. added 1 drop of H₂O, 1 drop of AcOH, 1,3-dichloro-5,5-dimethylimidazolidine-2,4-dione (22 mg, 0.1 mmol) and reacted at 0° C. for 2.30 h. The reaction mixture was directly used for the next step. LCMS (ESI) m/z: 420 [M+H]⁺.

Step 7

The crude reaction mixture from the previous step was cooled to 0° C., added 1-methylcyclopropan-1-amine hydrochloride (30 mg, 0.28 mmol) and Et₃N (0.2 mL, 1.43 mmol). The reaction was stirred at 0° C. for 1 h. Solvent was evaporated in vacuo and the crude reaction mixture was purified by prep-HPLC to obtain product (5.1 mg, 13%). LCMS (ESI) m/z: 455.00 [M+H]⁺. ¹H NMR (400 MHz, CD₃OD) δ 8.43 (s, 1H), 8.03-8.00 (m, 1H), 7.64 (d, J=8.0 Hz, 1H), 7.50 (d, J=8.0 Hz, 1H), 7.28-7.24 (m, 1H), 4.76-4.74 (m, 1H), 4.20-4.16 (m, 1H), 3.81 (s, 3H), 3.69-3.63 (m, 1H), 1.51-1.45 (m, 5H), 1.41-1.38 (m, 2H), 1.16 (s, 3H), 0.71-0.69 (m, 2H), 0.45-0.42 (m, 2H).

Representative Synthesis Route 10

Example 123: (R)-1-methyl-4-((1-methyl-5-oxopyrrolidin-3-yl)methyl)-N-(1-methylcyclopropyl)-5-oxo-1,2,4,5-tetrahydroimidazo[1,2-a]quinazoline-7-sulfonamide

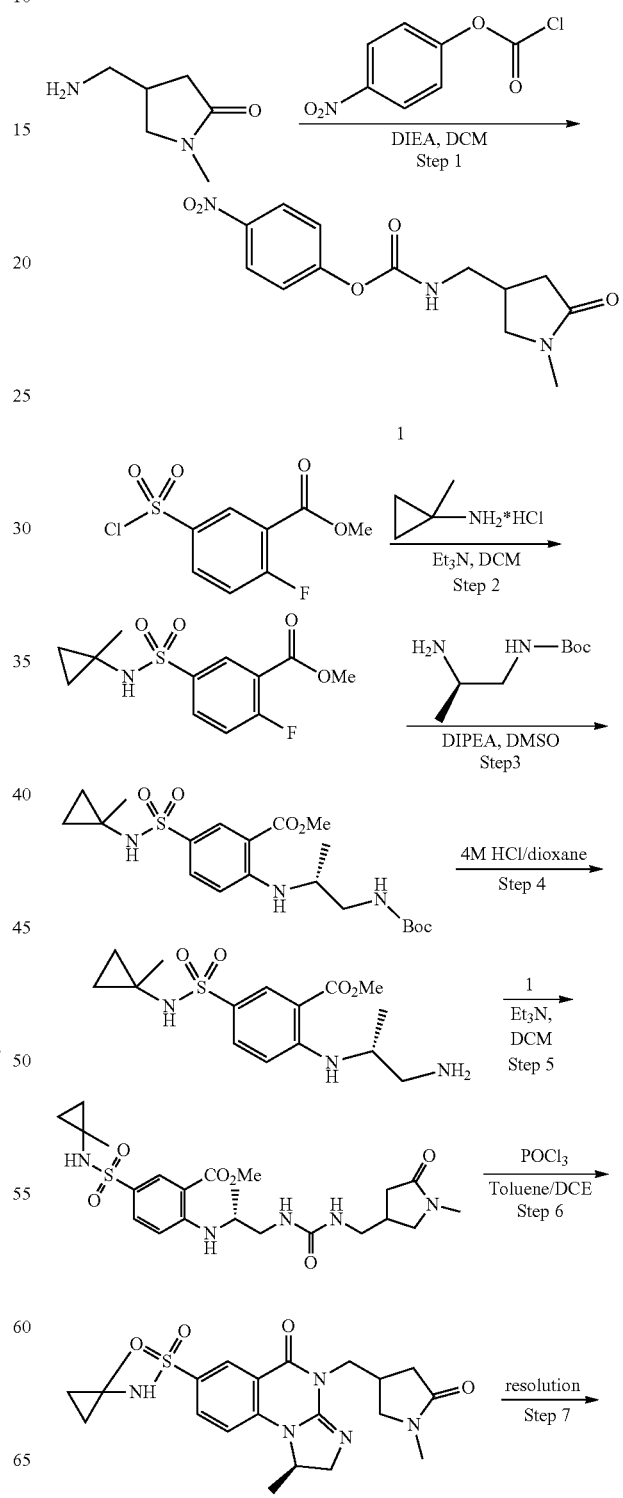

-continued

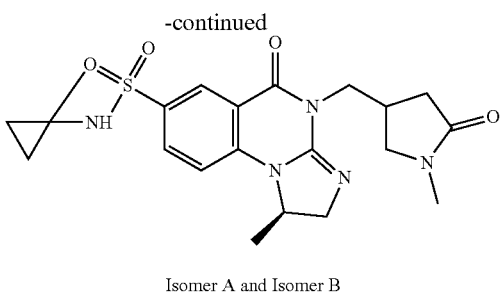

Isomer A and Isomer B

Step 1

A solution of 4-(aminomethyl)-1-methylpyrrolidin-2-one (100 mg, 0.78 mmol) in DCM (10 mL) was treated with 4-nitrophenyl carbonochloridate (173 mg, 0.86 mmol) for 2 min followed by the addition of DIEA (111 mg, 0.86 mmol) in portions at −60° C. The resulting mixture was stirred for 30 min at −20° C. The reaction was quenched by the addition of Water (30 mL) at room temperature. The resulting mixture was extracted with $CH_2Cl_2$ (3×30 mL). The combined organic layers were washed with brine (1×50 mL), dried over anhydrous $Na_2SO_4$. After filtration, the filtrate was concentrated under reduced pressure to obtain 4-nitrophenyl N-[(1-methyl-5-oxopyrrolidin-3-yl)methyl]carbamate (212 mg, 93%). LCMS (ESI) m/z: 294.0 $[M+H]^+$.

Step 2

To a stirred mixture of methyl 5-(chlorosulfonyl)-2-fluorobenzoate (2.5 g, 9.90 mmol) and 1-methylcyclopropan-1-amine hydrochloride (1.17 g, 10.9 mmol) in DCM (50 mL) was added $Et_3N$ (3.00 g, 29.7 mmol) dropwise at room temperature. The resulting mixture was stirred overnight at room temperature. The resulting mixture was concentrated under reduced pressure. The residue was purified by silica gel column chromatography, eluted with PE/EA (5:1) to afford methyl 2-fluoro-5-[(1-methylcyclopropyl)sulfamoyl]benzoate (2.6 g, 92%). LCMS (ESI) m/z: 288.0 $[M+H]^+$.

Step 3

To a stirred mixture of methyl 2-fluoro-5-[(1-methylcyclopropyl)sulfamoyl]benzoate (2.63 g, 9.14 mmol) and tert-butyl N-[(2R)-2-aminopropyl]carbamate (1.75 g, 10 mmol) in DMSO (50 mL) was added DIEA (3.54 g, 27.4 mmol) dropwise at room temperature. The resulting mixture was stirred overnight at 60° C. The reaction was quenched by the addition of Water (200 mL) at room temperature. The resulting mixture was extracted with EtOAc (3×200 mL). The combined organic layers were washed with brine (1×300 mL), dried over anhydrous $Na_2SO_4$. After filtration, the filtrate was concentrated under reduced pressure to obtain methyl 2-{[(2R)-1-[(tert-butoxycarbonyl)amino]propan-2-yl]amino}-5-[(1-methylcyclopropyl)sulfamoyl]benzoate (3.5 g 87%). LCMS (ESI) m/z: 442.0 $[M+H]^+$.

Step 4

A mixture of methyl 2-{[(2R)-1-[(tert-butoxycarbonyl)amino]propan-2-yl]amino}-5-[(1-methylcyclopropyl)sulfamoyl]benzoate (500 mg, 1.13 mmol) and HCl in 1,4-dioxane (1032 mg, 11.32 mmol) in THF (10 mL) was stirred overnight at room temperature. The resulting mixture was concentrated under reduced pressure. The residue was purified by silica gel column chromatography, eluted with $CH_2Cl_2$/MeOH (4:1) to afford methyl 2-{[(2R)-1-aminopropan-2-yl]amino}-5-[(1-methylcyclopropyl)sulfamoyl]benzoate (322 mg, 83%). LCMS (ESI) m/z: 342.0 $[M+H]^+$.

Step 5

To a stirred mixture of methyl 2-{[(2R)-1-aminopropan-2-yl]amino}-5-[(1-methylcyclopropyl)sulfamoyl]benzoate (212 mg, 0.62 mmol) and 4-nitrophenyl N-[(1-methyl-5-oxopyrrolidin-3-yl)methyl]carbamate (218.5 mg, 0.74 mmol) in DCM (10 mL) was added $Et_3N$ (138.2 mg, 1.37 mmol) dropwise at room temperature. The resulting mixture was stirred overnight at 40° C. The resulting mixture was concentrated under reduced pressure. The residue was purified by silica gel column chromatography, eluted with $CH_2Cl_2$/MeOH (12:1) to afford methyl 2-{[(2R)-1-({[(1-methyl-5-oxopyrrolidin-3-yl)methyl]carbamoyl}amino)propan-2-yl]amino}-5-[(1-methylcyclopropyl)sulfamoyl]benzoate (275 mg, 89%). LCMS (ESI) m/z: 496.0 $[M+H]^+$.

Step 6

A mixture of methyl 2-{[(2R)-1-({[(1-methyl-5-oxopyrrolidin-3-yl)methyl]carbamoyl}amino)propan-2-yl]amino}-5-[(1-methylcyclopropyl)sulfamoyl]benzoate (200 mg, 0.40 mmol) and $POCl_3$ (309.4 mg, 2.02 mmol) in Toluene (8 mL) and DCE (2 mL) was stirred overnight at 60° C. The reaction mixture was purified by Prep-HPLC with the following conditions (Column: XBridge Prep OBD C18 Column 30*150 mm, 5 m; Mobile Phase A: Water (10 mmol/L $NH_4HCO_3$), Mobile Phase B: ACN; Flow rate: 60 mL/min mL/min; Gradient: 9% B to 27% B in 10 min; Wave Length: 254 nm/220 nm nm; RT1(min): 12.4) to afford (1R)-1-methyl-4-[(1-methyl-5-oxopyrrolidin-3-yl)methyl]-N-(1-methylcyclopropyl)-5-oxo-1H,2H-imidazo[1,2-a]quinazoline-7-sulfonamide (60 mg, 33%). LCMS (ESI) m/z: 446.0 $[M+H]^+$.

Step 7

The racemate (60 mg) was purified by Prep-CHIRAL-HPLC with the following conditions (Column: CHIRAL-PAK IA, 2*25 cm, 5 m; Mobile Phase A: MtBE (10 mM $NH_3$-MeOH), Mobile Phase B: MeOH-HPLC; Flow rate: 20 mL/min; Gradient: isocratic 30; Wave Length: 220/286 nm; RT1(min): 6; RT2(min): 10; Sample Solvent: MeOH-HPLC; Injection Volume: 0.5 mL) to afford Isomer A (7.6 mg, 13%) and Isomer B (15.5 mg, 26%). LCMS (ESI) m/z: 446.25 $[M+H]^+$.

Isomer A: $^1$H NMR (400 MHz, Methanol-$d_4$) δ 8.40 (m, 1H), 7.22 (m, 1H), 4.76 (m, 1H), 4.72-4.80 (m, 1H), 4.18-4.02 (m, 3H), 3.64-3.51 (m, 2H), 3.33 (d, J=14.2, 7.0 Hz, 1H), 2.94-3.04 (m, 3H), 2.84 (s, 1H), 2.52 (dd, J=16.9, 8.8 Hz, 1H), 2.32 (dd, J=17.0, 6.4 Hz, 1H), 1.43 (dd, J=6.2, 0.8 Hz, 3H), 1.21-1.10 (m, 3H), 0.68-0.74 (m, 2H), 0.41-0.46 (m, 2H).

Isomer B: $^1$H NMR (400 MHz, DMSO-$d_6$) δ 8.24 (d, J=2.2 Hz, 1H), 8.03 (s, 1H), 7.92 (dd, J=8.7, 2.3 Hz, 1H), 7.25 (d, J=8.8 Hz, 1H), 4.66-4.76 (m, 1H), 4.06-3.95 (m, 3H), 3.47 (dd, J=13.7, 3.5 Hz, 1H), 3.40 (dd, J=9.8, 7.8 Hz, 1H), 3.22-3.14 (m, 1H), 2.93-2.83 (m, 1H), 2.69 (s, 3H), 2.34 (dd, J=16.7, 8.8 Hz, 1H), 2.17-2.05 (m, 1H), 1.32 (d, J=6.1 Hz, 3H), 1.09 (s, 3H), 0.58-0.64 (m, 2H), 0.44-0.35 (m, 2H).

The following compounds in Table 10 were prepared using procedures similar to those described in Representative Synthesis Route 10 for Example 123 using appropriate starting materials.

TABLE 10

| Example No. | Name | [M + H]+ |
|---|---|---|
| 125 | (R)-1-methyl-4-((1-(1-methyl-1H-pyrazol-4-yl)ethyl)-N-(1-methylcyclopropyl)-5-oxo-1,2,4,5-tetrahydroimidazo[1,2-a]quinazoline-7-sulfonamide (Isomer A) | 443.25 |
| 126 | (R)-1-methyl-4-((1-(1-methyl-1H-pyrazol-4-yl)ethyl)-N-(1-methylcyclopropyl)-5-oxo-1,2,4,5-tetrahydroimidazo[1,2-a]quinazoline-7-sulfonamide (Isomer B) | 443.25 |

Representative Synthesis Route 11

Example 130: (R)-N,N-dimethyl-4-(1-methyl-4-((1-methyl-1H-pyrazol-4-yl)methyl)-7-(N-(1-methylcyclopropyl)sulfamoyl)-5-oxo-1,2,4,5-tetrahydroimidazo[1,2-a]quinazolin-9-yl)piperazine-1-carboxamide

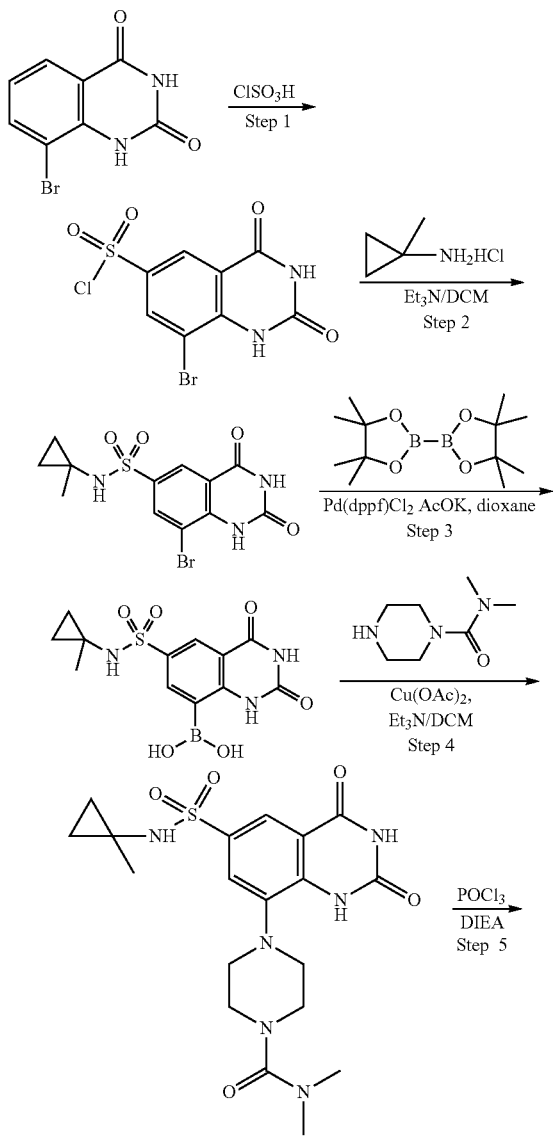

-continued

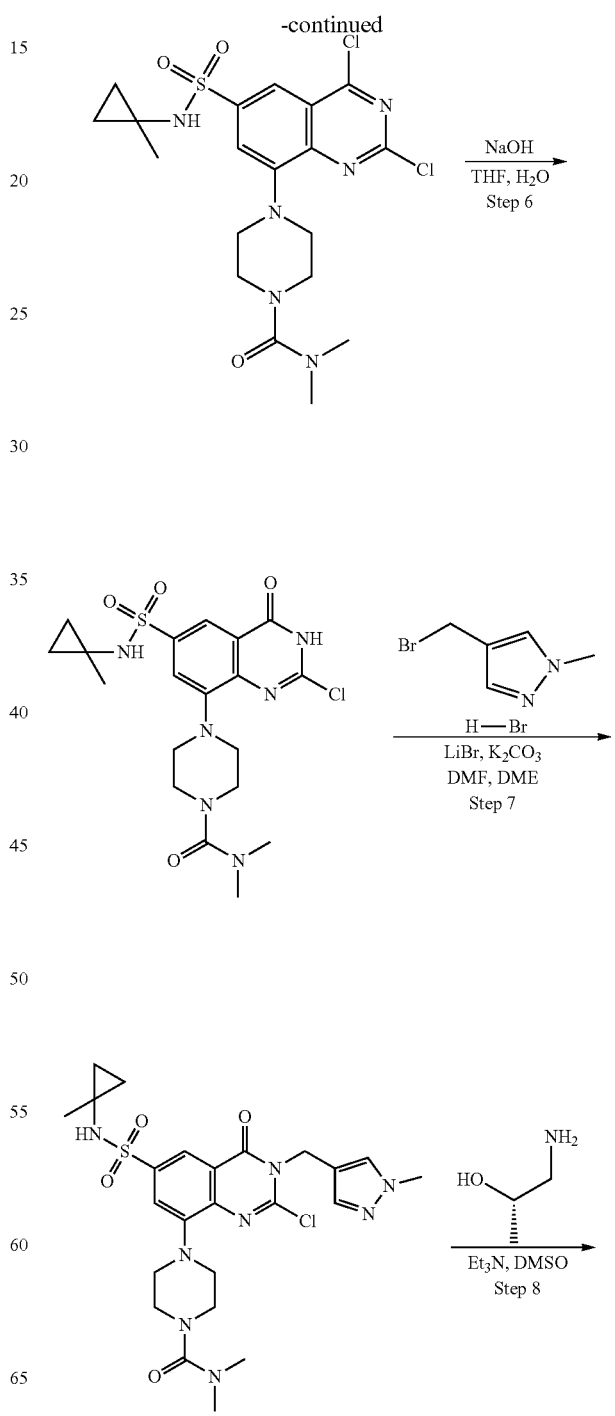

-continued

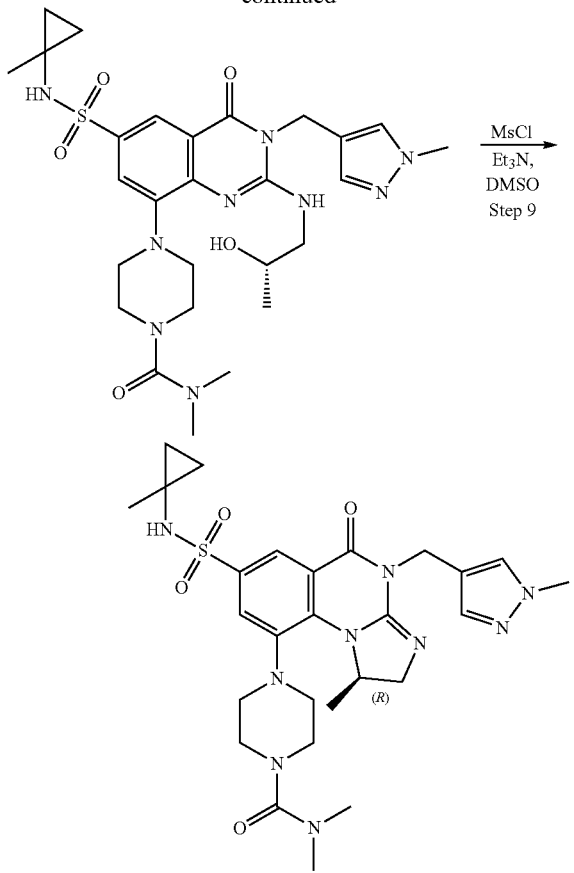

Step 1

A solution of 8-bromo-1,3-dihydroquinazoline-2,4-dione (20 g, 82.9 mmol) in chlorosulfonic acid (200 mL) was stirred overnight at 80° C. The reaction was quenched by the addition of ice (1000 g) at 0° C. The precipitated solids were collected by filtration and washed with water (3×100 mL). The resulting solid was dried under vacuum to obtain 8-bromo-2,4-dioxo-1,3-dihydroquinazoline-6-sulfonyl chloride (30 g) as a white solid. The crude product was used in the next step directly without further purification. LCMS (ESI) m/z: 339, 341 [M+H]$^+$.

Step 2

A solution of 8-bromo-2,4-dioxo-1,3-dihydroquinazoline-6-sulfonyl chloride (30 g, 88.3 mmol), 1-methylcyclopropan-1-amine hydrochloride (11.4 g, 106 mmol) and TEA (26.8 g, 265 mmol) in DCM (500 mL) was stirred for 2 h at room temperature. The resulting mixture was concentrated under reduced pressure. The residue was purified by silica gel column chromatography, eluted with $CH_2Cl_2$/EA (1:1) to afford 8-bromo-N-(1-methylcyclopropyl)-2,4-dioxo-1,3-dihydroquinazoline-6-sulfonamide (25 g, 76%). LCMS (ESI) m/z: 374, 376 [M+H]$^+$.

Step 3

A solution of 8-bromo-N-(1-methylcyclopropyl)-2,4-dioxo-1,3-dihydroquinazoline-6-sulfonamide (25 g, 66.8 mmol), bis(pinacolato)diboron (33.9 g, 133.6 mmol), AcOK (19.7 g, 200.4 mmol) and Pd(dppf)Cl$_2$ (4.89 g, 6.68 mmol) in 1,4-dioxane (300 mL) was stirred overnight at 90° C. under nitrogen atmosphere. The resulting mixture was concentrated under reduced pressure. The residue was purified by silica gel column chromatography, eluted with $CH_2Cl_2$/PE (1:1) to afford 6-[(1-methylcyclopropyl)sulfamoyl]-2,4-dioxo-1,3-dihydroquinazolin-8-ylboronic acid (17 g, 75%). LCMS (ESI) m/z: 340 [M+H]$^+$.

Step 4

A solution of 6-[(1-methylcyclopropyl)sulfamoyl]-2,4-dioxo-1,3-dihydroquinazolin-8-ylboronic acid (8 g, 23.6 mmol), N,N-dimethylpiperazine-1-carboxamide (3.71 g, 23.6 mmol), copper (II) acetate (4.28 g, 23.6 mmol) and DIEA (9.15 g, 70.8 mmol) in DCM (200 mL) was stirred for 2 h at room temperature. The resulting mixture was concentrated under reduced pressure. The residue was purified by silica gel column chromatography, eluted with $CH_2Cl_2$/MeOH (9:1) to afford N,N-dimethyl-4-{6-[(1-methylcyclopropyl)sulfamoyl]-2,4-dioxo-1,3-dihydroquinazolin-8-yl}piperazine-1-carboxamide as a white solid which was further purified by Prep-HPLC with the following conditions (Column: XBridge Prep OBD C18 Column 30*150 mm, 5 m; Mobile Phase A: water (0.1% FA), Mobile Phase B: ACN; Flow rate: 60 mL/min mL/min; Gradient: 26% B to 40% B in 10 min; Wave Length: 254 nm/220 nm; RT1(min): 12.97) to afford N,N-dimethyl-4-{6-[(1-methylcyclopropyl)sulfamoyl]-2,4-dioxo-1,3-dihydroquinazolin-8-yl}piperazine-1-carboxamide (300 mg, 3%). LCMS (ESI) m/z: 451[M+H]$^+$.

Step 5

A mixture of N,N-dimethyl-4-{6-[(1-methylcyclopropyl)sulfamoyl]-2,4-dioxo-1,3-dihydroquinazolin-8-yl}piperazine-1-carboxamide (300 mg, 0.67 mmol) and DIEA (172.1 mg, 1.33 mmol) in POCl$_3$ (20 mL) was stirred overnight at 105° C. The resulting mixture was concentrated under reduced pressure. The reaction was quenched by the addition of water/ice (150 mL) at 0° C. The resulting mixture was extracted with EtOAc (3×200 mL). The combined organic layers were washed with brine (2×10 mL), dried over anhydrous Na$_2$SO$_4$. After filtration, the filtrate was concentrated under reduced pressure. This resulted in 4-{2,4-dichloro-6-[(1-methylcyclopropyl)sulfamoyl]quinazolin-8-yl}-N,N-dimethylpiperazine-1-carboxamide (260 mg). The crude product was used in the next step directly without further purification.

Step 6

A mixture of 4-{2,4-dichloro-6-[(1-methylcyclopropyl)sulfamoyl]quinazolin-8-yl}-N,N-dimethylpiperazine-1-carboxamide (260 mg, 0.53 mmol) and NaOH (42.7 mg, 1.1 mmol) in THF (10 mL) and H$_2$O (10 mL) was stirred for 30 min at 0° C. The mixture was acidified to pH 2 with conc. HCl. The resulting mixture was extracted with EtOAc (3×200 mL). The combined organic layers were washed with brine (3×50 mL), dried over anhydrous Na$_2$SO$_4$. After filtration, the filtrate was concentrated under reduced pressure to obtain 4-{2-chloro-6-[(1-methylcyclopropyl)sulfamoyl]-4-oxo-3H-quinazolin-8-yl}-N,N-dimethylpiperazine-1-carboxamide (110 mg, 44%).

Step 7

A mixture of 4-{2-chloro-6-[(1-methylcyclopropyl)sulfamoyl]-4-oxo-3H-quinazolin-8-yl}-N,N-dimethylpiperazine-1-carboxamide (110 mg, 0.23 mmol), 4-(bromomethyl)-1-methyl-1H-pyrazole hydrobromide (60 mg, 0.23 mmol), K$_2$CO$_3$ (64.8 mg, 0.47 mmol) and LiBr (40.7 mg, 0.47 mmol) in DME (10 mL) and DMF (2.5 mL) was stirred overnight at room temperature. The reaction was quenched by the addition of water (100 mL) at room temperature. The resulting mixture was extracted with EtOAc (3×150 mL). The combined organic layers were washed with brine (4×50 mL), dried over anhydrous Na$_2$SO4. After filtration, the filtrate was concentrated under reduced pressure to obtain 4-{2-chloro-6-[(1-methylcyclopropyl)sulfamoyl]-3-[(1- methylpyrazol-4-yl)methyl]-4-oxoquinazolin-8-yl}-N,N-dimethylpiperazine-1-carboxamide (80 mg, 61%). LCMS (ESI) m/z: 564 [M+H]+.

Step 8

A mixture of 4-{2-chloro-6-[(1-methylcyclopropyl)sulfamoyl]-3-[(1-methylpyrazol-4-yl)methyl]-4-oxoquinazolin-8-yl}-N,N-dimethylpiperazine-1-carboxamide (80 mg, 0.14 mmol), (2S)-1-aminopropan-2-ol (12.8 mg, 0.17 mmol) and TEA (43.1 mg, 0.43 mmol) in DMSO (5 mL) was stirred for 30 min at 50° C. The reaction was quenched by the addition of water (100 mL) at room temperature. The resulting mixture was extracted with EtOAc (3×100 mL). The combined organic layers were washed with brine (5×50 mL), dried over anhydrous Na₂SO₄. After filtration, the filtrate was concentrated under reduced pressure to obtain 4-(2-{[(2S)-2-hydroxypropyl]amino}-6-[(1-methylcyclopropyl)sulfamoyl]-3-[(1-methylpyrazol-4-yl)methyl]-4-oxoquinazolin-8-yl)-N,N-dimethylpiperazine-1-carboxamide (50 mg, 59%). LCMS (ESI) m/z: 602 [M+H]+.

Step 9

A solution of 4-(2-{[(2S)-2-hydroxypropyl]amino}-6-[(1-methylcyclopropyl)sulfamoyl]-3-[(1-methylpyrazol-4-yl)methyl]-4-oxoquinazolin-8-yl)-N,N-dimethylpiperazine-1-carboxamide (50 mg, 0.08 mmol), MsCl (28.5 mg, 0.25 mmol) and TEA (42 mg, 0.41 mmol) in DCM (5 mL) was stirred overnight at room temperature. The reaction was quenched by the addition of water (5 mL) at room temperature. The resulting mixture was concentrated under reduced pressure. The crude product was purified by Prep-HPLC with the following conditions (Column: Xselect CSH F-Phenyl OBD column 30*250 mm, 5 μm; Mobile Phase A: water (0.1% FA), Mobile Phase B: ACN; Flow rate: 60 mL/min mL/min; Gradient: 2% B to 19% B in 10 min; Wave Length: 254 nm/220 nm; RT1(min): 12.57) to afford N,N-dimethyl-4-[(1R)-1-methyl-7-[(1-methylcyclopropyl)sulfamoyl]-4-[(1-methylpyrazol-4-yl)methyl]-5-oxo-1H,2H-imidazo[1,2-a]quinazolin-9-yl]piperazine-1-carboxamide (10.1 mg, 21%). LCMS (ESI) m/z: 584.30 [M+H]+. ¹H NMR (400 MHz, DMSO-d₆) δ 8.11 (d, J=2.2 Hz, 1H), 8.01 (s, 1H), 7.79 (d, J=2.2 Hz, 1H), 7.68 (s, 1H), 7.41 (s, 1H), 5.29-5.20 (m, 1H), 5.00-4.90 (m, 2H), 3.93 (dd, J=13.6, 8.4 Hz, 1H), 3.77 (s, 3H), 3.69 (d, J=12.4 Hz, 1H), 3.47 (dd, J=17.1, 12.9 Hz, 2H), 3.16 (q, J=10.8 Hz, 2H), 3.06-2.93 (m, 3H), 2.79 (s, 6H), 2.35-2.26 (m, 1H), 1.08-1.02 (m, 6H), 0.61 (q, J=10.8 Hz, 2H), 0.38 (s, 2H).

Representative Synthesis Route 12

Example 131: (R)-1-methyl-9-(1-methyl-1,2,3,6-tetrahydropyridin-4-yl)-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide

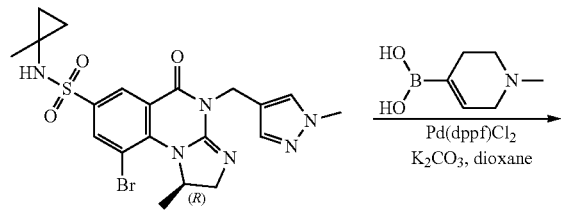

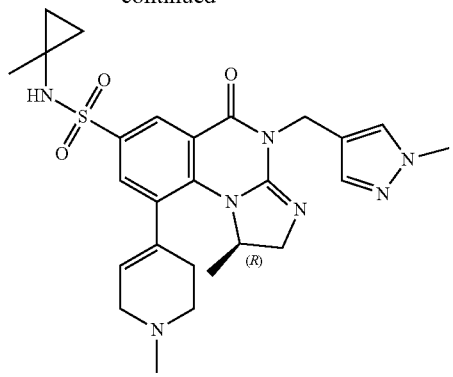

To a stirred mixture of (1R)-9-bromo-1-methyl-N-(1-methylcyclopropyl)-4-[(1-methylpyrazol-4-yl)methyl]-5-oxo-1H,2H-imidazo[1,2-a]quinazoline-7-sulfonamide (50 mg, 0.099 mmol) and 1-methyl-3,6-dihydro-2H-pyridin-4-ylboronic acid (20.8 mg, 0.15 mmol) in 1,4-dioxane (4 mL) and H₂O (0.4 mL) were added K₂CO₃ (40.9 mg, 0.3 mmol) and Pd(dppf)Cl₂ (7.21 mg, 0.010 mmol) in portions at room temperature. The resulting mixture was stirred for 2 h at 80° C. under nitrogen atmosphere. The residue was purified by Prep-TLC (10% MeOH/CH₂C2) and further purified by Prep-HPLC with the following conditions (Column: XBridge Shield RP18 OBD Column 30*150 mm, 5 m; Mobile Phase A: water (10 mmol/L NH₄HCO₃), Mobile Phase B: ACN; Flow rate: 60 mL/min mL/min; Gradient: 15% B to 35% B in 10 min; Wave Length: 254 nm/200 nm; RT1(min): 10.78) to afford (1R)-1-methyl-9-(1-methyl-3,6-dihydro-2H-pyridin-4-yl)-N-(1-methylcyclopropyl)-4-[(1-methylpyrazol-4-yl)methyl]-5-oxo-1H,2H-imidazo[1,2-a]quinazoline-7-sulfonamide (2 mg, 4%). LCMS (ESI) m/z: 524.35 [M+H]+. ¹H NMR (400 MHz, DMSO-d₆) δ 8.22 (d, J=2.3 Hz, 1H), 8.03 (s, 1H), 7.69 (d, J=2.2 Hz, 1H), 7.59 (d, J=2.3 Hz, 1H), 7.41 (d, J=2.3 Hz, 1H), 6.00 (s, 1H), 4.95 (q, J=14.2 Hz, 2H), 4.58 (d, J=7.9 Hz, 1H), 3.88 (dd, J=13.4, 8.1 Hz, 1H), 3.77 (d, J=2.2 Hz, 3H), 3.48 (d, J=13.6 Hz, 1H), 3.17 (d, J=17.5 Hz, 1H), 2.90 (d, J=17.4 Hz, 1H), 2.66 (d, J=11.6 Hz, 2H), 2.41 (d, J=18.0 Hz, 1H), 2.29 (s, 3H), 2.05 (s, 1H), 1.07-0.96 (m, 6H), 0.59 (d, J=5.8 Hz, 2H), 0.38 (d, J=2.1 Hz, 2H).

The following compounds in Table 11 were prepared using procedures similar to those described in Representative Synthesis Route 12 for Example 131 using appropriate starting materials.

TABLE 11

| Example No. | Name | [M + H]⁺ |
| --- | --- | --- |
| 133 | (R)-9-(3,6-dihydro-2H-pyran-4-yl)-1-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 511.05 |
| 135 | (R)-9-(6-fluoropyridin-3-yl)-1-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 524.15 |
| 136 | (R)-9-(4-fluorophenyl)-1-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide | 523.05 |

Representative Synthesis Route 13

Example 132: (R)-1,9-dimethyl-4-((1-methyl-1H-pyrazol-4-yl)methyl-d2)-N-(1-methylcyclopropyl)-5-oxo-1,2,4,5-tetrahydroimidazo[1,2-a]quinazoline-7-sulfonamide

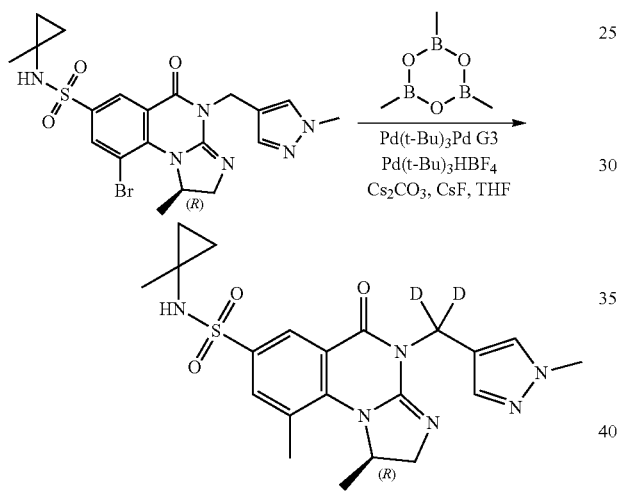

A solution of (1R)-9-bromo-1-methyl-N-(1-methylcyclopropyl)-4-[(1-methylpyrazol-4-yl)(2H2)methyl]-5-oxo-1H,2H-imidazo[1,2-a]quinazoline-7-sulfonamide (50 mg, 0.098 mmol) trimethyl-1,3,5,2,4,6-trioxatriborinane (14.8 mg, 0.12 mmol), P(t-Bu)₃ Pd G 3 (5.61 mg, 0.01 mmol), P(t-Bu)₃·HBF₄ (3.1 mg, 0.010 mmol), Cs₂CO₃ (64 mg, 0.2 mmol) and CsF (29.8 mg, 0.2 mmol) in THF (2 mL) was stirred overnight at 80° C. The resulting mixture was diluted with water (50 mL) then extracted with EtOAc (200 mL). The combined organic layers were washed with water (50 mL), dried over anhydrous Na₂SO₄. After filtration, the filtrate was concentrated under reduced pressure. The crude product was purified by Prep-HPLC with the following conditions (Column: Sunfire prep C18 column, 30*150 mm, 5 m; Mobile Phase A: Water (0.1% FA), Mobile Phase B: ACN; Flow rate: 60 mL/min mL/min; Gradient: isocratic 11% B to 31% B in 10 min; Wave Length: 254 nm/220 nm; RT1(min): 12.48) to afford (1R)-1,9-dimethyl-N-(1-methylcyclopropyl)-4-[(1-methylpyrazol-4-yl)(2H2)methyl]-5-oxo-1H,2H-imidazo[1,2-a]quinazoline-7-sulfonamide (1.4 mg, 3%). LCMS (ESI) m/z: 445.05 [M+H]⁺. ¹H NMR (400 MHz, Methanol-d₄) δ 8.38 (d, J=2.3 Hz, 1H), 7.84 (d, J=2.3 Hz, 1H), 7.70 (s, 1H), 7.56 (s, 1H), 5.18 (m, 1H), 4.01 (dd, J=13.2, 8.2 Hz, 1H), 3.83 (s, 3H), 3.59 (d, J=13.3 Hz, 1H), 2.61 (s, 3H), 1.19 (d, J=6.3 Hz, 3H), 1.15 (s, 3H), 0.75-0.67 (m, 2H), 0.46-0.39 (m, 2H).

Representative Synthesis Route 14

Example 137: (R)-9-bromo-1-methyl-4-((1-methyl-1H-pyrazol-4-yl)methyl-d2)-N-(1-methylcyclopropyl)-5-oxo-1,2,4,5-tetrahydroimidazo[1,2-a]quinazoline-7-sulfonamide

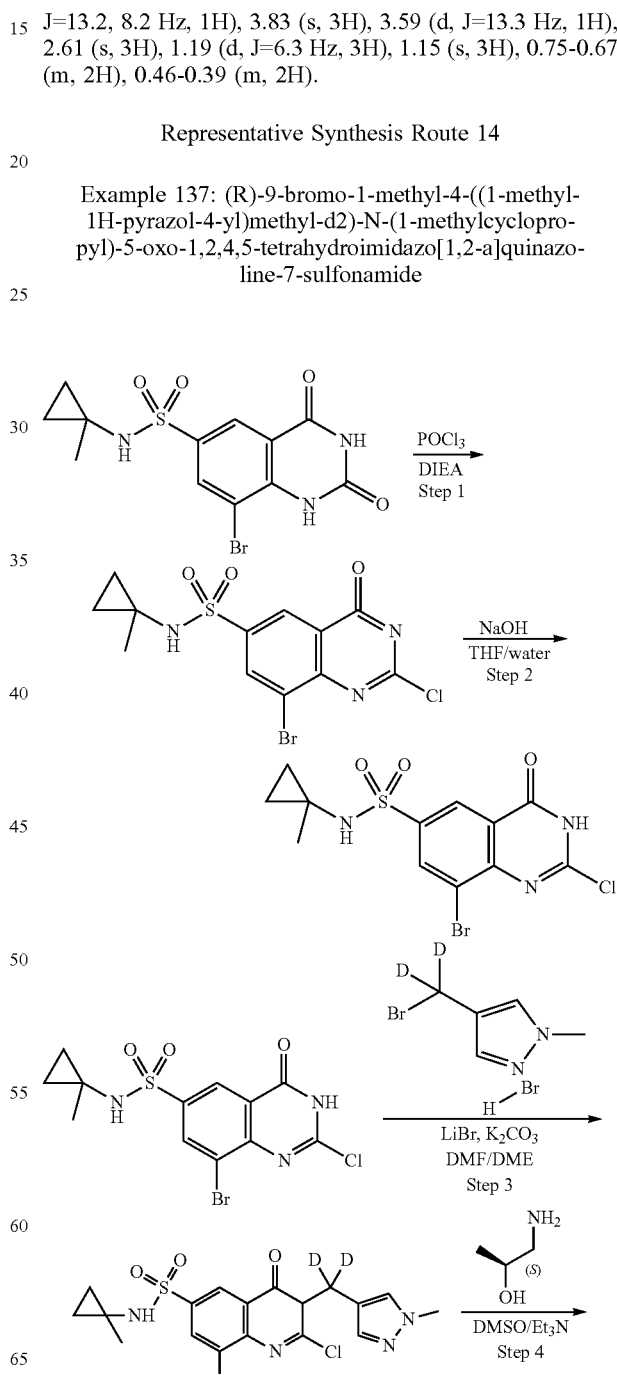

151

-continued

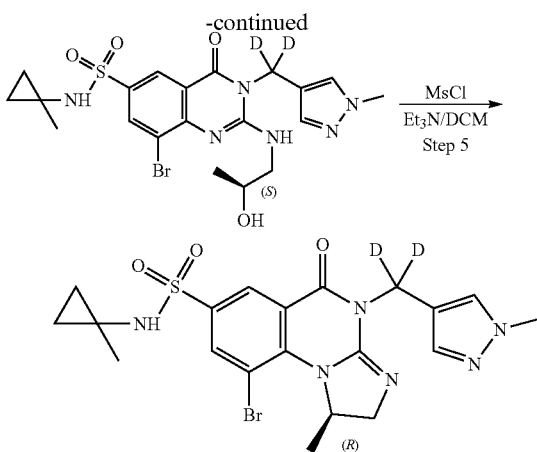

Step 1

A mixture of 8-bromo-N-(1-methylcyclopropyl)-2,4-dioxo-1,3-dihydroquinazoline-6-sulfonamide (5 g, 13.4 mmol) and DIEA (3.45 g, 26.7 mmol) in POCl₃ (100 mL) was stirred overnight at 105° C. The resulting mixture was concentrated under reduced pressure. The reaction was quenched by the addition of water/ice (150 mL) at room temperature. The resulting mixture was extracted with EtOAc (3×200 mL). The combined organic layers were washed with brine (2×50 mL), dried over anhydrous Na₂SO₄. After filtration, the filtrate was concentrated under reduced pressure. This resulted in 8-bromo-2,4-dichloro-N-(1-methylcyclopropyl)quinazoline-6-sulfonamide (5 g) which was used in the next step directly without further purification.

Step 2

To a stirred mixture of 8-bromo-2,4-dichloro-N-(1-methylcyclopropyl)quinazoline-6-sulfonamide (2 g, 4.86 mmol) in THF (20 mL) and H₂O (20 mL) was added NaOH (0.39 g, 9.7 mmol) dropwise at 0° C. The resulting mixture was stirred for 30 min at 0° C. The mixture was acidified to pH 6 with conc. HCl. The reaction was quenched by the addition of water (200 mL) at 0° C. The resulting mixture was extracted with EtOAc (3×250 mL). The combined organic layers were washed with brine (2×50 mL), dried over anhydrous Na₂SO₄. After filtration, the filtrate was concentrated under reduced pressure. The residue was purified by silica gel column chromatography, eluted with PE/EA (45%-55%) to afford 8-bromo-2-chloro-N-(1-methylcyclopropyl)-4-oxo-3H-quinazoline-6-sulfonamide (500 mg). LCMS (ESI) m/z: 392, 394 [M+H]⁺.

Step 3

A solution of 8-bromo-2-chloro-N-(1-methylcyclopropyl)-4-oxo-3H-quinazoline-6-sulfonamide (300 mg, 0.76 mmol), 4-[bromo(2H2)methyl]-1-methylpyrazole (270.5 mg, 1.53 mmol), LiBr (132.7 mg, 1.53 mmol) and K₂CO₃ (316.8 mg, 2.29 mmol) in DME (10 mL) and DMF (2.5 mL) was stirred overnight at room temperature. The resulting mixture was diluted with water (100 mL) then extracted with EtOAc (300 mL). The combined organic layers were washed with water (100 mL), dried over anhydrous Na₂SO₄. After filtration, the filtrate was concentrated under reduced pressure to obtain 8-bromo-2-chloro-N-(1-methylcyclopropyl)-3-[(1-methylpyrazol-4-yl)(2H2)methyl]-4-oxoquinazoline-6-sulfonamide (300 mg). LCMS (ESI) m/z: 488, 490 [M+H]⁺.

152

Step 4

A solution of 8-bromo-2-chloro-N-(1-methylcyclopropyl)-3-[(1-methylpyrazol-4-yl)(2H2)methyl]-4-oxoquinazoline-6-sulfonamide (300 mg, 0.61 mmol), (2S)-1-aminopropan-2-ol (55.3 mg, 0.74 mmol) and Et₃N (186.3 mg, 1.84 mmol) in DMSO (20 mL) was stirred for 30 min at 50° C. The resulting mixture was diluted with water (100 mL) then extracted with EtOAc (300 mL). The combined organic layers were washed with water (100 mL), dried over anhydrous Na₂SO₄. After filtration, the filtrate was concentrated under reduced pressure to afford 8-bromo-2-{[(2S)-2-hydroxypropyl]amino}-N-(1-methylcyclopropyl)-3-[(1-methylpyrazol-4-yl)(2H2)methyl]-4-oxoquinazoline-6-sulfonamide (250 mg). LCMS (ESI) m/z: 527, 529 [M+H]⁺.

Step 5

A solution of 8-bromo-2-{[(2S)-2-hydroxypropyl]amino}-N-(1-methylcyclopropyl)-3-[(1-methylpyrazol-4-yl)(2H2)methyl]-4-oxoquinazoline-6-sulfonamide (300 mg, 0.57 mmol) MsCl (130.3 mg, 1.14 mmol) and Et₃N (172.7 mg, 1.71 mmol) in DCM (20 mL) was stirred overnight at room temperature. The resulting mixture was diluted with water (100 mL) then extracted with EtOAc (300 mL). The combined organic layers were washed with water (100 mL), dried over anhydrous Na₂SO₄. After filtration, the filtrate was concentrated under reduced pressure. The residue was purified by silica gel column chromatography, eluted with CH₂Cl₂/MeOH (10:1) to afford (1R)-9-bromo-1-methyl-N-(1-methylcyclopropyl)-4-[(1-methylpyrazol-4-yl)(2H2)methyl]-5-oxo-1H,2H-imidazo[1,2-a]quinazoline-7-sulfonamide (150 mg, 52%). LCMS (ESI) m/z: 509.05, 511.00 [M+H]⁺. ¹H NMR (400 MHz, DMSO-d₆) δ 8.29 (d, J=2.0 Hz, 1H), 8.18 (s, 1H), 8.11 (d, J=2.0 Hz, 1H), 7.68 (s, 1H), 7.41 (s, 1H), 5.73-5.64 (m, 1H), 3.97-3.91 (m, 1H), 3.75 (s, 3H), 3.54-3.51 (m, 1H), 1.21 (d, J=6.4 Hz, 3H), 1.09 (s, 3H), 0.64-0.59 (m, 2H), 0.44-0.39 (m, 2H).

Representative Synthesis Route 15

Example 138: (R)-9-cyano-1-methyl-4-((1-methyl-1H-pyrazol-4-yl)methyl)-N-(1-methylcyclopropyl)-5-oxo-1,2,4,5-tetrahydroimidazo[1,2-a]quinazoline-7-sulfonamide

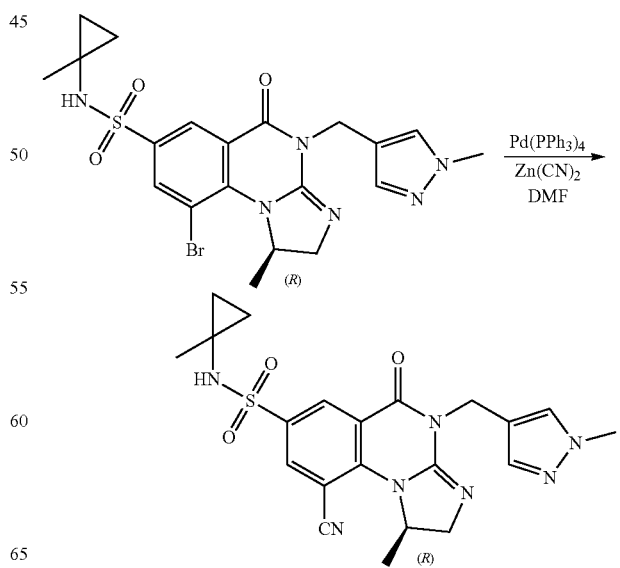

To a stirred mixture of (1R)-9-bromo-1-methyl-N-(1-methylcyclopropyl)-4-[(1-methylpyrazol-4-yl)methyl]-5-oxo-1H,2H-imidazo[1,2-a]quinazoline-7-sulfonamide (50 mg, 0.1 mmol) and Zn(CN)$_2$ (13.9 mg, 0.12 mmol) in DMF (2 mL) was added Pd(PPh$_3$)$_4$ (11.4 mg, 0.01 mmol) in portions at room temperature. The resulting mixture was stirred for 12 h at 100° C. under nitrogen atmosphere. The reaction was quenched with water at room temperature. The resulting mixture was extracted with EtOAc (2×50 mL). The combined organic layers were washed with brine (2×30 mL), dried over anhydrous Na$_2$SO$_4$. After filtration, the filtrate was concentrated under reduced pressure. The crude product was purified by Prep-HPLC with the following conditions (Column: XBridge Prep Phenyl OBD Column 19*250 mm, 5 m; Mobile Phase A: water (0.1% FA), Mobile Phase B: ACN; Flow rate: 60 mL/min mL/min; Gradient: 23% B to 40% B in 10 min; Wave Length: 254 nm/220 nm; RT1(min): 10.54) to afford (1R)-9-cyano-1-methyl-N-(1-methylcyclopropyl)-4-[(1-methylpyrazol-4-yl)methyl]-5-oxo-1H,2H-imidazo[1,2-a]quinazoline-7-sulfonamide (0.7 mg, 1.5%). LCMS (ESI) m/z: 454.10 [M+H]$^+$. $^1$H NMR (400 MHz, DMSO-d$_6$) δ 8.41 (d, J=2.4 Hz 1H), 8.22 (s, J=2.4 Hz 1H), 7.68 (s, 1H), 7.41 (m, 1H), 5.35-5.25 (m, 1H), 5.02-4.84 (m, 2H), 4.09-4.02 (m, 1H), 3.76 (s, 3H), 3.63-3.55 (m, 1H), 1.42-1.30 (m, 3H), 1.11 (s, 3H), 0.66-0.57 (m, 2H), 0.47-0.38 (m, 2H).

Synthesis of Intermediates

Intermediate 1—Tert-butyl 4-(bromomethyl)pyrazole-1-carboxylate

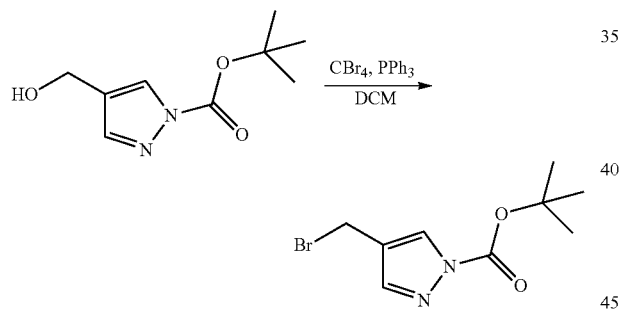

To a stirred mixture of tert-butyl 4-(hydroxymethyl)pyrazole-1-carboxylate (2.00 g, 10.1 mmol) and CBr$_4$ (6.7 g, 20.2 mmol) in DCM (100 mL) was added PPh$_3$ (5.3 g, 20.2 mmol) in portions at room temperature. The resulting mixture was stirred for 2 h at room temperature. The resulting mixture was concentrated under reduced pressure. The residue was purified by silica gel column chromatography, eluted with EtOAc in PE (40%-45%) to afford tert-butyl 4-(bromomethyl)pyrazole-1-carboxylate (0.80 g) as a light yellow liquid.

Intermediate 1 was used for the synthesis of Example 6.

Intermediate 2—1-Aminobut-3-yn-2-ol hydrochloride

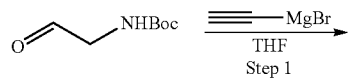

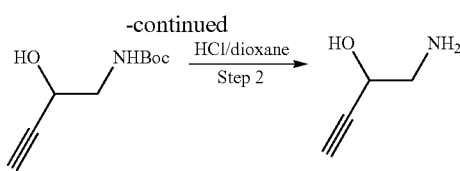

Step 1

To a solution of tert-butyl (2-oxoethyl)carbamate (5 g, 31.4 mmol) in THF (50 mL) was added bromo(ethynyl)magnesium (0.5 M in THF, 157 mL, 78.5 mmol) dropwise at −78° C. under N$_2$ atmosphere. The reaction mixture was stirred at −78° C. for 20 mins. The resulting mixture was stirred for 1 h at room temperature under nitrogen atmosphere. The reaction was quenched with saturated NH$_4$Cl aqueous solution (20 mL), and then the mixture was extracted with EtOAc (500 mL). The combined organic extracts were washed with brine (200 mL), dried over anhydrous Na$_2$SO$_4$. After filtration, the filtrate was concentrated under reduced pressure to obtain tert-butyl N-(2-hydroxybut-3-yn-1-yl)carbamate (4.5 g, 77%) as a light yellow oil. LCMS (ESI) m/z: 186 [M+H]$^+$.

Step 2

A mixture of tert-butyl N-(2-hydroxybut-3-yn-1-yl)carbamate (4.5 g, 24.3 mmol), HCl in 1,4-dioxane (40 ml) was stirred for 2 h at room temperature. The resulting mixture was concentrated under reduced pressure to obtain 1-aminobut-3-yn-2-ol hydrochloride (3 g) as a light yellow solid. LCMS (ESI) m/z: 86 [M+H]$^+$.

Intermediate 2 was used for the synthesis of Examples 9, 10, 15, 16, 27, 28, 33, 34, 43, 71, 72. Examples 59, 60 were synthesized using appropriate starting material similar to intermediate 2.

Intermediate 3—4-(Chloromethyl)-1-methyl-3-(trifluoromethyl)-1H-pyrazole

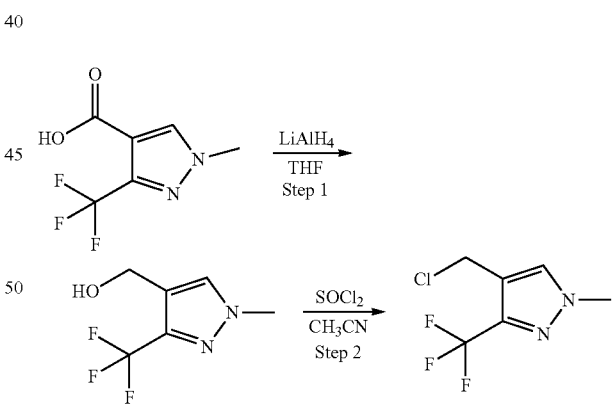

Step 1

To a solution of 1-methyl-3-(trifluoromethyl)pyrazole-4-carboxylic acid (2 g, 10.3 mmol) in THF (20 mL) was added LiAlH$_4$ (0.78 g, 20.6 mmol) in portions at room temperature. The resulting mixture was stirred for 2 h at room temperature. The reaction was quenched with Na$_2$SO$_4$·10H$_2$O at room temperature. The resulting mixture was filtered, the filter cake was washed with THF (3×10 mL). The filtrate was concentrated under reduced pressure. The residue was purified by silica gel column chromatography, eluted with MeOH in CH$_2$Cl$_2$ (0%-10%) to afford [1-methyl-3-(trifluoromethyl)pyrazol-4-yl]methanol (300 mg) as a yellow liquid. LCMS (ESI) m/z: 181 [M+H]+.
Step 2
To a solution of [1-methyl-3-(trifluoromethyl)pyrazol-4-yl]methanol (300 mg, 1.67 mmol) in acetonitrile (10 mL) was added thionyl chloride (396 mg, 3.33 mmol) in portions at room temperature. The resulting mixture was stirred for 4 h at room temperature. The resulting mixture was concentrated under reduced pressure to afford 4-(chloromethyl)-1-methyl-3-(trifluoromethyl)-1H-pyrazole (200 mg) which was used in the next step directly without further purification. LCMS (ESI) m/z: 199 [M+H]+.

Intermediate 3 was used for the synthesis of Example 55.

Intermediate 4—2-chloro-N-(1-methylcyclopropyl)-4-oxo-3-(3-(trimethylsilyl) prop-2-yn-1-yl)-3,4-dihydroquinazoline-6-sulfonamide

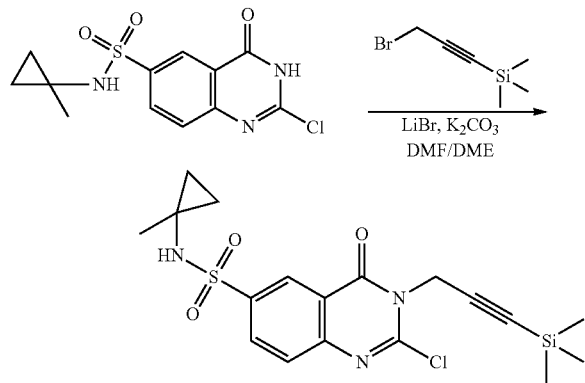

To a stirred mixture of 2-chloro-N-(1-methylcyclopropyl)-4-oxo-3,4-dihydroquinazoline-6-sulfonamide (0.3 g, 0.96 mmol) and K₂CO₃ (264 mg, 1.91 mmol) in DMF (8 mL) were added LiBr (166 mg, 1.91 mmol) and (3-bromoprop-1-yn-1-yl) trimethylsilane (219 mg, 1.15 mmol) dropwise at room temperature. The mixture was stirred for 2 h at 50° C. The resulting mixture was extracted with PE (3×50 mL). The combined organic layers were washed with brine (20 mL), dried over anhydrous Na₂SO₄. After filtration, the filtrate was concentrated under reduced pressure. The residue was purified by silica gel column chromatography, eluted with PE/EA (5:1) to afford 2-chloro-N-(1-methylcyclopropyl)-4-oxo-3-(3-(trimethylsilyl) prop-2-yn-1-yl)-3,4-dihydroquinazoline-6-sulfonamide (0.12 g, 29%) as a white solid. LCMS (ESI) m/z: 424 [M+H]+.

Example 58 was synthesized using intermediate 4 and Representative Synthesis Route 1, steps 6-7 for Example 46.

Intermediate 5—2-(4-(Chloromethyl)-1H-pyrazol-1-yl)acetonitrile

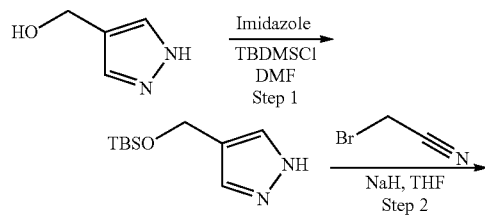

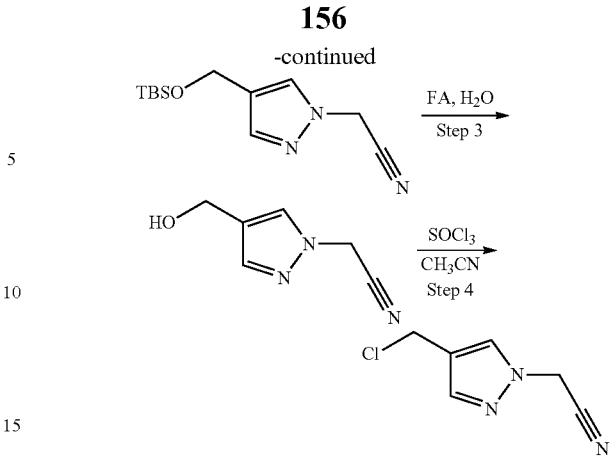

Step 1
To a stirred mixture of 1H-pyrazol-4-ylmethanol (1.2 g, 12.2 mmol) and TBDMSCl (2.8 g, 18.3 mmol) in DMF (20 mL) was added Imidazole (1.7 g, 24.5 mmol) in portions at 0° C. under nitrogen atmosphere. The mixture was stirred for 1 h at room temperature. The reaction was quenched by the addition of Water (50 mL) at room temperature. The resulting mixture was extracted with EtOAc (3×50 mL). The combined organic layers were washed with brine (3×10 mL), dried over anhydrous Na₂SO₄. After filtration, the filtrate was concentrated under reduced pressure. The residue was purified by silica gel column chromatography, eluted with PE/EA (5:1) concentrated under reduced pressure to afford 4-(((tert-butyldimethylsilyl)oxy)methyl)-1H-pyrazole (1.2 g, 46%) as a colorless oil.
Step 2
A solution of 4-(((tert-butyldimethylsilyl)oxy)methyl)-1H-pyrazole (1.2 g, 5.6 mmol) in THF (10 mL) was treated with NaH (0.16 g, 6.8 mmol) for 30 min at 0° C. under nitrogen atmosphere followed by the addition of 2-bromoacetonitrile (1 g, 8.5 mmol) dropwise at room temperature. The mixture was stirred for overnight at room temperature under nitrogen atmosphere. The resulting mixture was extracted with EtOAc (3×50 mL). The combined organic layers were washed with brine (3×5 mL), dried over anhydrous Na2SO₄. After filtration, the filtrate was concentrated under reduced pressure. The residue was purified by silica gel column chromatography, eluted with PE/EA (5:1) concentrated under reduced pressure to afford 2-(4-(((tert-butyldimethylsilyl)oxy)methyl)-1H-pyrazol-1-yl)acetonitrile (850 mg, 60%) as a colorless oil.
Step 3
A mixture of 2-(4-(((tert-butyldimethylsilyl)oxy)methyl)-1H-pyrazol-1-yl)acetonitrile (310 mg, 1.23 mmol) and formic acid (1.5 mL) in water (10 mL) was stirred for 2 h at room temperature under nitrogen atmosphere. The resulting mixture was concentrated under reduced pressure. The residue was dissolved in EtOAc (5 mL). The resulting mixture was concentrated under reduced pressure to obtain 2-(4-(hydroxymethyl)-1H-pyrazol-1-yl)acetonitrile (210 mg, 17%) as a white solid. The crude product was used in the next step directly without further purification.
Step 4
A mixture of 2-(4-(hydroxymethyl)-1H-pyrazol-1-yl)acetonitrile (90 mg, 0.66 mmol) and thionyl chloride (156 mg, 1.31 mmol) in MeCN (2 mL) was stirred for overnight at room temperature under nitrogen atmosphere. The resulting mixture was concentrated under reduced pressure to obtain 2-(4-(chloromethyl)-1H-pyrazol-1-yl)acetonitrile (40 mg, 39%) as a white solid. The crude product was used in the next step directly without further purification.

Intermediate 5 was used for the synthesis of Example 66.

Intermediate 6—2-amino-1-(2,4-dimethyl-1,3-thiazol-5-yl)ethanol

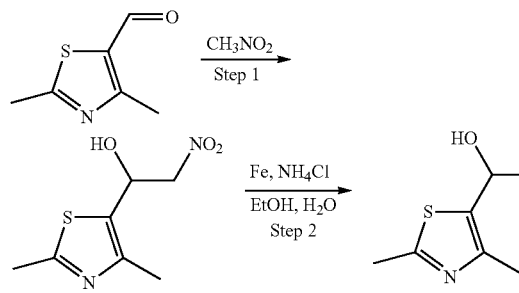

Step 1

A mixture of 2,4-dimethyl-1,3-thiazole-5-carbaldehyde (1 g, 7.1 mmol) in nitromethane (20 mL) was stirred for 12 h at room temperature. The reaction was quenched by the addition of Water/Ice (50 mL) at room temperature. The resulting mixture was extracted with EtOAc (3×80 mL). The combined organic layers were washed with brine (2×80 mL), dried over anhydrous $Na_2SO_4$. After filtration, the filtrate was concentrated under reduced pressure. The residue was purified by reversed-phase flash chromatography with the following conditions: column, C18 silica gel; mobile phase, MeCN in Water (0.1% FA), 10% to 50% gradient in 10 min; detector, UV 254 nm. To obtain 1-(2,4-dimethyl-1,3-thiazol-5-yl)-2-nitroethanol (1.0 g, 70%) as an orange solid. LCMS (ESI) m/z: 203.0 $[M+H]^+$.

Step 2

A mixture of 1-(2,4-dimethyl-1,3-thiazol-5-yl)-2-nitroethanol (250 mg, 1.2 mmol), $NH_4Cl$ (331 mg, 6.2 mmol) and Fe (69 mg, 1.2 mmol) in $CH_3CH_2OH$ (5.0 mL), $H_2O$ (0.5 mL) was stirred for 2 h at 80° C. The reaction was quenched by the addition of Water/Ice (20 mL) at room temperature. The resulting mixture was filtered, the filter cake was washed with MeCN (3×50 mL). The filtrate was concentrated under reduced pressure. The residue was purified by reversed-phase flash chromatography with the following conditions: column, C18 silica gel; mobile phase, MeCN in Water (0.1% FA), 10% to 50% gradient in 10 min; detector, UV 254 nm to obtain 2-amino-1-(2,4-dimethyl-1,3-thiazol-5-yl)ethanol (150 mg, 70%) as a white solid. LCMS (ESI) m/z: 173.0 $[M+H]^+$.

Intermediate 6 was used for the synthesis of Example 82.

Intermediate 7—1-amino-4-cyclopropylbut-3-yn-2-ol

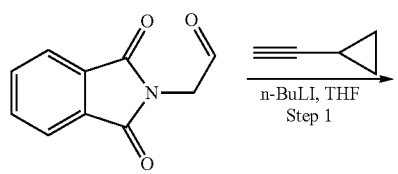

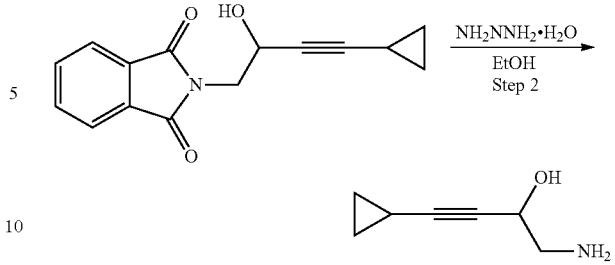

Step 1

To a stirred solution of ethynylcyclopropane (1 g, 15 mmol) in anhydrous THF (20 mL) was added n-BuLi (1.1 g, 16.6 mmol) at −78° C. for 30 min. To the above mixture was added Phthalimidoacetaldehyde (3.15 g, 16.6 mmol) dropwise over 15 min at −78° C. The resulting mixture was stirred for additional 2 h at room temperature. After completion of reaction, the reaction mixture was quenched by addition of saturated $NH_4Cl$ solution (20 mL) The aqueous layer was extracted with ethyl acetate (300 mL). The combined organic phase was washed with brine (100 mL), dried over anhydrous sodium sulfate and concentrated under reduced pressure to give crude product which was further purified by silica gel column chromatography using 10 to 30% ethyl acetate in PE gradient to afford desired compound 2-(4-cyclopropyl-2-hydroxybut-3-yn-1-yl) isoindole-1,3-dione (0.8 g). LCMS (ESI) m/z: 256 $[M+H]^+$.

Step 2

To a stirred solution of 2-(4-cyclopropyl-2-hydroxybut-3-yn-1-yl) isoindole-1,3-dione (800 mg, 3.1 mmol) in anhydrous EtOH (25 mL) was added hydrazine hydrate (307 mg, 6.3 mmol) at room temperature. The reaction mixture was stirred at 70° C. for 2 h. After completion of reaction, the reaction mixture was quenched by addition of water (10 mL). The aqueous layer was extracted with ethyl acetate (200 mL), dried over anhydrous sodium sulfate and concentrated under reduced pressure to give crude product which was further purified by column chromatography using 10 to 30% MeOH in DCM gradient to afford desired compound 1-amino-4-cyclopropylbut-3-yn-2-ol (200 mg). LCMS (ESI) m/z: 126 $[M+H]^+$.

Intermediate 7 was used for the synthesis of Examples 83 and 84.

Intermediate 8—4-(Chloromethyl)-1-methyl-1,2,3-triazole

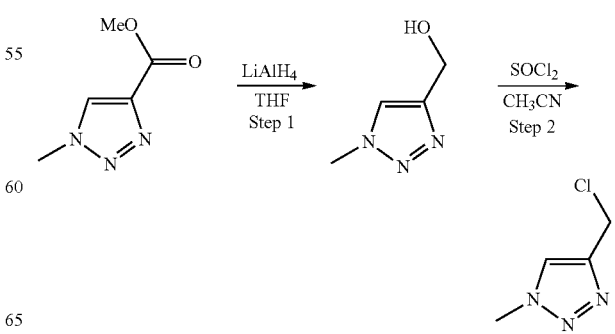

Step 1

A solution of methyl 1-methyl-1,2,3-triazole-4-carboxylate (400 mg, 2.8 mmol) and LiAlH$_4$ (215 mg, 5.7 mmol) in THF (4 mL) was stirred for 1 h at room temperature. The reaction was quenched with sat. sodium hyposulfite at room temperature. The resulting mixture was filtered, the filter cake was washed with THF (2×20 mL). The filtrate was concentrated under reduced pressure. The crude product was used in the next step directly without further purification. LCMS (ESI) m/z: 114 [M+H]$^+$.

Step 2

A solution of (1-methyl-1,2,3-triazol-4-yl) methanol (30 mg, 0.26 mmol) in SOCl$_2$ (2 mL) was stirred for 1 h at 70° C. The resulting mixture was concentrated under reduced pressure and was used in the next step directly without further purification. LCMS (ESI) m/z: 132 [M+H]$^+$.

Intermediate 8 was used for the synthesis of Example 90.

Intermediate 9—3-(bromomethyl)-5H,6H,7H-pyrazolo[3,2-b][1,3]oxazine

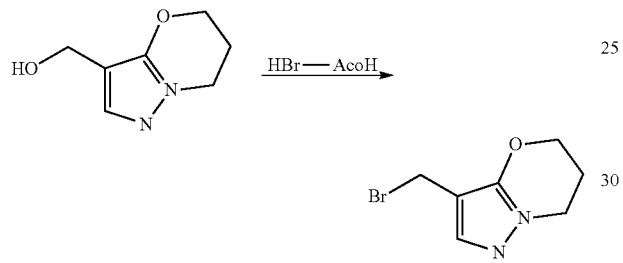

A solution of 5H,6H,7H-pyrazolo[3,2-b][1,3]oxazin-3-ylmethanol (800 mg, 5.2 mmol) in HBr in AcOH (10 mL) was stirred overnight at 90° C. under nitrogen atmosphere. Addition of Et$_2$O formed a precipitate which was dried to obtain desired product as a brown solid (700 mg). The crude product was used in the next step directly without further purification.

Intermediate 9 was used for the synthesis of Example 119. In a similar manner using appropriate starting materials Examples 118, 120, 121 and 122 were synthesized.

II. Biological Evaluation

Example 1: Nuclear PAR Accumulation Assay

Compound IC$_{50}$ values for inhibition of cellular PARG were determined using an immunofluorescence high-content imaging assay for nuclear PAR accumulation. HeLa cells were plated at 15,000 cells/well in a 96-well plate the day before compound treatment and then treated with varying concentrations of test compound and incubated for 1 hour at 37° C.±5% CO$_2$. Following test compound treatment, methylmethane sulfonate (MMS) was added to a final concentration of 50 μg/mL and the cells were incubated for an additional hour. Following treatment, the cells were fixed with ice cold 95% methanol and the plates sealed and placed at −20° C. for 15 minutes. The cells were then washed once with phosphate buffered saline (PBS) and permeabilized with 0.10% Triton-X 100 for 20 minutes at room temperature. The cells were again washed once with PBS and incubated with an anti-poly-ADP ribose (PAR) monoclonal antibody (Millipore Part #AM80 clone 10H) diluted 1:1,000 in 5% fetal bovine serum+0.1% Tween-20+PBS overnight at 4° C. The cells were then washed three times with PBS before incubation with a fluorescently conjugated goat anti-mouse antibody (Invitrogen A32723) diluted 1:500 in 5% FBS+0.1% Tween-20+PBS for 1 hour at room temperature. The cells were again washed three times with PBS and the nuclei labeled by incubating with 1 μg/mL DAPI (4',6-diamidino-2-phenylindole). Nuclear PAR accumulation was evaluated using high-content fluorescence microscopy. Four fields for each well were acquired at 20× magnification resulting in at least 1,000 cells analyzed per well. Using high-content software (CellReporterXpress) the nuclei were detected and segmented using the DAPI channel and the fluorescence intensity of the PAR-Alexa 488 channel was quantified within the nuclei regions. Both the average intensity per nucleus and percent PAR positive cells were quantified. Percent PAR positive cells were identified by having greater anti-PAR labeling above the threshold set with vehicle DMSO treated control cells. Percent inhibition of PARG by test compounds was calculated by normalizing the data to the 0.1% DMSO and reference compound control values, which represent 0% and 100% inhibition of enzymatic activity, respectively. Concentration-response-curves and IC$_{50}$ values were generated using four parameter logistic curve fit software.

Representative data for exemplary compounds is presented in Table 12.

TABLE 12

| Example | PAR Accumulation IC$_{50}$ (μM) |
|---|---|
| 1 | B |
| 2 | B |
| 3 | B |
| 4 | B |
| 5 | B |
| 6 | B |
| 7 | A |
| 8 | A |
| 9 | B |
| 10 | A |
| 11 | D |
| 12 | B |
| 13 | C |
| 14 | A |
| 15 | B |
| 16 | A |
| 17 | B |
| 18 | A |
| 19 | D |
| 20 | A |
| 21 | B |
| 22 | A |
| 23 | C |
| 24 | A |
| 25 | D |
| 26 | B |
| 27 | C |
| 28 | B |
| 29 | C |
| 30 | A |
| 31 | A |
| 32 | A |
| 33 | B |
| 34 | A |
| 35 | A |
| 36 | B |
| 37 | D |
| 38 | B |
| 39 | C |
| 40 | A |
| 41 | D |
| 42 | B |
| 43 | B |

TABLE 12-continued

| Example | PAR Accumulation IC$_{50}$ (μM) |
|---|---|
| 44 | B |
| 45 | A |
| 46 | A |
| 47 | B |
| 48 | B |
| 49 | C |
| 50 | B |
| 51 | C |
| 52 | B |
| 53 | B |
| 54 | D |
| 55 | A |
| 56 | A |
| 57 | A |
| 58 | A |
| 59 | A |
| 60 | B |
| 61 | A |
| 62 | A |
| 63 | A |
| 64 | A |
| 65 | A |
| 66 | A |
| 67 | A |
| 68 | C |
| 69 | A |
| 70 | B |
| 71 | A |
| 72 | A |
| 73 | A |
| 74 | A |
| 75 | A |
| 76 | A |
| 77 | A |
| 78 | B |
| 79 | A |
| 80 | A |
| 81 | A |
| 82 | B |
| 83 | A |
| 84 | C |
| 85 | A |
| 86 | A |
| 87 | A |
| 88 | A |
| 89 | A |
| 90 | B |
| 91 | B |
| 92 | B |
| 93 | A |
| 94 | A |
| 95 | A |
| 96 | C |
| 97 | B |
| 98 | A |
| 99 | B |
| 100 | A |
| 101 | A |
| 102 | A |
| 103 | A |
| 104 | A |
| 105 | B |
| 106 | A |
| 107 | B |
| 108 | A |
| 109 | A |
| 110 | B |
| 111 | A |
| 112 | C |
| 113 | A |
| 114 | C |
| 115 | B |
| 116 | B |
| 117 | A |
| 118 | A |
| 119 | A |
| 120 | C |
| 121 | A |
| 122 | A |
| 123 | C |
| 124 | A |
| 125 | C |
| 126 | C |
| 127 | B |
| 128 | A |
| 129 | A |
| 130 | A |
| 131 | A |
| 132 | A |
| 133 | A |
| 134 | A |
| 135 | A |
| 136 | A |
| 137 | A |
| 138 | B |

Note:
PAR accumulation assay IC$_{50}$ data are designated within the following ranges:
A: ≤0.1 μM
B: >0.1 μM to ≤1.0 μM
C: >1.0 μM to ≤10 μM
D: >10 μM

III. Preparation of Pharmaceutical Dosage Forms

Example 1: Oral Capsule

The active ingredient is a compound of Table 1, or a pharmaceutically acceptable salt or solvate thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

Example 2: Solution for Injection

The active ingredient is a compound of Table 1, or a pharmaceutically acceptable salt or solvate thereof, and is formulated as a solution in sesame oil at a concentration of 50 mg-eq/mL.

The examples and embodiments described herein are for illustrative purposes only and various modifications or changes suggested to persons skilled in the art are to be included within the spirit and purview of this application and scope of the appended claims.

We claim:
1. A compound having the structure of Formula (I):

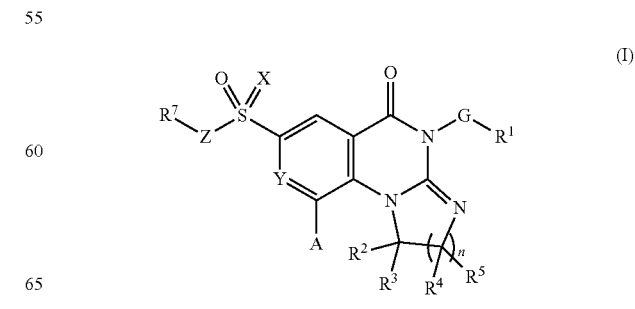

or a pharmaceutically acceptable salt, deuteroisotope, or stereoisomer thereof, wherein:

Z is —NH—;

$R^7$ is alkyl, cycloalkyl, or 1,1'-bi(cyclopropan)-1-yl;
  wherein the alkyl is optionally substituted with one or more substituents independently selected from the group consisting of D, halo, CN, $NO_2$, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl; and
  wherein the cycloalkyl or 1,1'-bi(cyclopropan)-1-yl is optionally substituted with one or more substituents independently selected from the group consisting of D, halo, CN, $NO_2$, alkyl, haloalkyl, alkenyl, haloalkenyl, alkynyl, haloalkynyl, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl;

X is O;

Y is CH, CF, or N;

A is H, halo, CN, C1-C6 alkyl, alkyl(carbocyclyl), alkyl(heterocyclyl), C2-C6 alkenyl, C2-C6 alkynyl, alkynyl(carbocyclyl), $NR^9R^9$, OH, OC1-C6 alkyl, C3-C7 carbocyclyl, heterocyclyl, aryl, or heteroaryl;
  wherein the C1-C6 alkyl, alkyl portion of alkyl(carbocyclyl), alkyl portion of alkyl(heterocyclyl), C2-C6 alkenyl, C2-C6 alkynyl, alkynyl portion of alkynyl(carbocyclyl), or OC1-C6 alkyl is optionally substituted with one or more substituents independently selected from the group consisting of D, halo, CN, $NO_2$, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl; and
  wherein the carbocyclyl portion of alkyl(carbocyclyl), heterocyclyl portion of alkyl(heterocyclyl), carbocyclyl portion of alkynyl(carbocyclyl), C3-C7 carbocyclyl, heterocyclyl, aryl, or heteroaryl is optionally substituted with one or more substituents independently selected from the group consisting of halo, CN, $NO_2$, alkyl, haloalkyl, alkenyl, haloalkenyl, alkynyl, haloalkynyl, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl;

each $R^9$ is independently H or C1-C6 alkyl, wherein each C1-C6 alkyl is optionally and independently substituted with one or more substituents independently selected from the group consisting of D, halo, CN, $NO_2$, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl;

G is a bond, cycloalkylene, or heterocycloalkylene, wherein the cycloalkylene or heterocycloalkylene is optionally substituted with one or more substituents independently selected from the group consisting of D, halo, CN, $NO_2$, alkyl, haloalkyl, alkenyl, haloalkenyl, alkynyl, haloalkynyl, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl;

$R^1$ is alkyl, alkyl(cycloalkyl), alkyl(heterocyclyl), aralkyl, alkyl(heteroaryl), alkenyl, or alkynyl;
  wherein the alkyl, alkyl portion of alkyl(cycloalkyl), alkyl portion of alkyl(heterocyclyl), alkyl portion of aralkyl, alkyl portion of alkyl(heteroaryl), alkenyl, or alkynyl is optionally substituted with one or more substituents independently selected from the group consisting of D, halo, CN, $NO_2$, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl; and
  wherein the cycloalkyl portion of alkyl(cycloalkyl), heterocyclyl portion of alkyl(heterocyclyl), aryl portion of aralkyl, or heteroaryl portion of alkyl(heteroaryl) is optionally substituted with one or more substituents independently selected from the group consisting of D, halo, CN, $NO_2$, alkyl, haloalkyl, alkenyl, haloalkenyl, alkynyl, haloalkynyl, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl;

$R^2$ is H, halo, CN, alkyl, alkyl(cycloalkyl), alkyl(heterocyclyl), alkenyl, alkynyl, alkynyl(cycloalkyl), OH, cycloalkyl, heterocyclyl, aryl, or heteroaryl;
  wherein the alkyl, alkyl portion of alkyl(cycloalkyl), alkyl portion of alkyl(heterocyclyl), alkenyl, alkynyl, or alkynyl portion of alkynyl(cycloalkyl) is optionally substituted with one or more substituents independently selected from the group consisting of D, halo, CN, $NO_2$, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl; and
  wherein the cycloalkyl portion of alkyl(cycloalkyl), heterocyclyl portion of alkyl(heterocyclyl), cycloalkyl portion of alkynyl(cycloalkyl), cycloalkyl, heterocyclyl, aryl, or heteroaryl is optionally substituted with one or more substituents independently selected from the group consisting of D, halo, CN, $NO_2$, alkyl, haloalkyl, alkenyl, haloalkenyl, alkynyl, haloalkynyl, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl;

$R^3$ is H, halo, CN, alkyl, alkyl(cycloalkyl), alkyl(heterocyclyl), alkenyl, alkynyl, alkynyl(cycloalkyl), OH, cycloalkyl, heterocyclyl, aryl, or heteroaryl;
  wherein the alkyl, alkyl portion of alkyl(cycloalkyl), alkyl portion of alkyl(heterocyclyl), alkenyl, alkynyl, or alkynyl portion of alkynyl(cycloalkyl) is optionally substituted with one or more substituents independently selected from the group consisting of D, halo, CN, $NO_2$, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl; and wherein the cycloalkyl portion of alkyl(cycloalkyl), heterocyclyl portion of alkyl(heterocyclyl), cycloalkyl portion of alkynyl(cycloalkyl), cycloalkyl, heterocyclyl, aryl, or heteroaryl is optionally substituted with one or more substituents independently selected from the group consisting of D, halo, CN, $NO_2$, alkyl, haloalkyl, alkenyl, haloalkenyl, alkynyl, haloalkynyl, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl; or $R^2$ and $R^3$, taken together with the carbon atom to which they are attached, form a carbocyclyl or heterocyclyl, wherein the carbocyclyl or heterocyclyl is optionally substituted with one or more substituents independently selected from the group consisting of D, halo, CN, $NO_2$, alkyl, haloalkyl, alkenyl, haloalkenyl, alkynyl, haloalkynyl, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl;

$R^4$ is H, halo, CN, alkyl, alkyl(cycloalkyl), alkyl(heterocyclyl), alkenyl, alkynyl, alkynyl(cycloalkyl), OH, cycloalkyl, heterocyclyl, aryl, or heteroaryl;

wherein the alkyl, alkyl portion of alkyl(cycloalkyl), alkyl portion of alkyl(heterocyclyl), alkenyl, alkynyl, or alkynyl portion of alkynyl(cycloalkyl) is optionally substituted with one or more substituents independently selected from the group consisting of D, halo, CN, $NO_2$, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl; and wherein the cycloalkyl portion of alkyl(cycloalkyl), heterocyclyl portion of alkyl(heterocyclyl), cycloalkyl portion of alkynyl(cycloalkyl), cycloalkyl, heterocyclyl, aryl, or heteroaryl is optionally substituted with one or more substituents independently selected from the group consisting of D, halo, CN, $NO_2$, alkyl, haloalkyl, alkenyl, haloalkenyl, alkynyl, haloalkynyl, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl;

$R^5$ is H, halo, CN, alkyl, alkyl(cycloalkyl), alkyl(heterocyclyl), alkenyl, alkynyl, alkynyl(cycloalkyl), OH, cycloalkyl, heterocyclyl, aryl, or heteroaryl;

wherein the alkyl, alkyl portion of alkyl(cycloalkyl), alkyl portion of alkyl(heterocyclyl), alkenyl, alkynyl, or alkynyl portion of alkynyl(cycloalkyl) is optionally substituted with one or more substituents independently selected from the group consisting of D, halo, CN, $NO_2$, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl; and wherein the cycloalkyl portion of alkyl(cycloalkyl), heterocyclyl portion of alkyl(heterocyclyl), cycloalkyl portion of alkynyl(cycloalkyl), cycloalkyl, heterocyclyl, aryl, or heteroaryl is optionally substituted with one or more substituents independently selected from the group consisting of D, halo, CN, $NO_2$, alkyl, haloalkyl, alkenyl, haloalkenyl, alkynyl, haloalkynyl, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl; or any $R^4$ and $R^5$, taken together with the carbon atom to which they are attached, independently forms a carbocyclyl or heterocyclyl, wherein each carbocyclyl or heterocyclyl is optionally and independently substituted with one or more substituents independently selected from the group consisting of D, halo, CN, $NO_2$, alkyl, haloalkyl, alkenyl, haloalkenyl, alkynyl, haloalkynyl, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl; or $R^3$ and $R^4$, taken together with the carbon atoms to which they are attached, form a carbocyclyl or heterocyclyl, wherein the carbocyclyl or heterocyclyl is optionally substituted with one or more substituents independently selected from the group consisting of D, halo, CN, $NO_2$, alkyl, haloalkyl, alkenyl, haloalkenyl, alkynyl, haloalkynyl, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl;

each $R^a$ is independently H, D, alkyl, alkyl(cycloalkyl), alkyl(heterocycloalkyl), aralkyl, alkyl(heteroaryl), cycloalkyl, heterocycloalkyl, aryl, or heteroaryl;

each $R^c$ is independently alkylene or alkenylene;

n is 1, 2, or 3; and each t is independently 1 or 2.

2. The compound of claim 1, or a pharmaceutically acceptable salt, deuteroisotope, or stereoisomer thereof, wherein $R^7$ is C3-C5 cycloalkyl, wherein the C3-C5 cycloalkyl is optionally substituted with one or more substituents independently selected from the group consisting of D, halo, CN, $NO_2$, alkyl, haloalkyl, alkenyl, haloalkenyl, alkynyl, haloalkynyl, $C(O)R^a$, $C(O)N(R^a)_2$, $C(O)OR^a$, $N(R^a)_2$, $NR^aC(O)R^a$, $NR^aC(O)OR^a$, $NR^aS(O)_tR^a$, $OR^a$, $OC(O)R^a$, $OC(O)N(R^a)_2$, $OC(O)OR^a$, $OR^cC(O)N(R^a)_2$, =O, $S(O)_tR^a$, $S(O)_tN(R^a)_2$, $S(O)_tOR^a$, =S, cycloalkyl, heterocycloalkyl, aryl, and heteroaryl.

3. The compound of claim 1, or a pharmaceutically acceptable salt, deuteroisotope, or stereoisomer thereof, wherein:
R$^7$ is

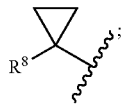

R$^8$ is H, CN, CH$_3$, CH$_2$F, CHF$_2$, CF$_3$, CH$_2$CH$_3$, CH(CH$_3$)$_2$, C(CH$_3$)$_3$, or cyclopropyl.

4. The compound of claim 1, or a pharmaceutically acceptable salt, deuteroisotope, or stereoisomer thereof, wherein Y is CH.

5. The compound of claim 1, or a pharmaceutically acceptable salt, deuteroisotope, or stereoisomer thereof, wherein A is H.

6. The compound of claim 1, or a pharmaceutically acceptable salt, deuteroisotope, or stereoisomer thereof, wherein A is halo.

7. The compound of claim 1, or a pharmaceutically acceptable salt, deuteroisotope, or stereoisomer thereof, wherein G is a bond.

8. The compound of claim 1, or a pharmaceutically acceptable salt, deuteroisotope, or stereoisomer thereof, wherein R$^1$ is alkyl(heteroaryl);
wherein the alkyl portion of alkyl(heteroaryl) is optionally substituted with one or more substituents independently selected from the group consisting of D, halo, CN, NO$_2$, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl; and
wherein the heteroaryl portion of alkyl(heteroaryl) is optionally substituted with one or more substituents independently selected from the group consisting of D, halo, CN, NO$_2$, alkyl, haloalkyl, alkenyl, haloalkenyl, alkynyl, haloalkynyl, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, S(O)$_t$R$^a$, S(O)$_t$N(R$^a$)$_2$, S(O)$_t$OR$^a$, cycloalkyl, heterocycloalkyl, aryl, and heteroaryl.

9. The compound of claim 1, or a pharmaceutically acceptable salt, deuteroisotope, or stereoisomer thereof, wherein R$^1$ is C1-C4 alkyl(heteroaryl);
wherein the C1-C4 alkyl portion of C1-C4 alkyl(heteroaryl) is optionally substituted with one or more substituents independently selected from the group consisting of D, halo, CN, NO$_2$, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl; and
wherein the heteroaryl portion of C1-C4 alkyl(heteroaryl) is optionally substituted with one or more substituents independently selected from the group consisting of D, halo, CN, NO$_2$, alkyl, haloalkyl, alkenyl, haloalkenyl, alkynyl, haloalkynyl, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, S(O)$_t$R$^a$, S(O)$_t$N(R$^a$)$_2$, S(O)$_t$OR$^a$, cycloalkyl, heterocycloalkyl, aryl, and heteroaryl.

10. The compound of claim 9, or a pharmaceutically acceptable salt, deuteroisotope, or stereoisomer thereof, wherein R$^1$ is CH$_2$(heteroaryl), wherein the heteroaryl portion of CH$_2$(heteroaryl) is optionally substituted with one or more substituents independently selected from the group consisting of D, halo, CN, NO$_2$, alkyl, haloalkyl, alkenyl, haloalkenyl, alkynyl, haloalkynyl, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, S(O)$_t$R$^a$, S(O)$_t$N(R$^a$)$_2$, S(O)$_t$OR$^a$, cycloalkyl, heterocycloalkyl, aryl, and heteroaryl.

11. The compound of claim 9, or a pharmaceutically acceptable salt, deuteroisotope, or stereoisomer thereof, wherein R$^1$ is CD$_2$(heteroaryl), wherein the heteroaryl portion of CD$_2$(heteroaryl) is optionally substituted with one or more substituents independently selected from the group consisting of D, halo, CN, NO$_2$, alkyl, haloalkyl, alkenyl, haloalkenyl, alkynyl, haloalkynyl, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, S(O)$_t$R$^a$, S(O)$_t$N(R$^a$)$_2$, S(O)$_t$OR$^a$, cycloalkyl, heterocycloalkyl, aryl, and heteroaryl.

12. The compound of claim 1, or a pharmaceutically acceptable salt, deuteroisotope, or stereoisomer thereof, wherein R$^1$ is alkyl(heteroaryl);
wherein the heteroaryl is 5-membered and contains at least one nitrogen heteroatom;
wherein the alkyl portion of alkyl(heteroaryl) is optionally substituted with one or more substituents independently selected from the group consisting of D, halo, CN, NO$_2$, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl; and
wherein the heteroaryl portion of alkyl(heteroaryl) is optionally substituted with one or more substituents independently selected from the group consisting of D, halo, CN, NO$_2$, alkyl, haloalkyl, alkenyl, haloalkenyl, alkynyl, haloalkynyl, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, S(O)$_t$R$^a$, S(O)$_t$N(R$^a$)$_2$, S(O)$_t$OR$^a$, cycloalkyl, heterocycloalkyl, aryl, and heteroaryl.

13. The compound of claim 12, or a pharmaceutically acceptable salt, deuteroisotope, or stereoisomer thereof, wherein R$^1$ is alkyl(heteroaryl);
wherein the heteroaryl is pyrrolyl, pyrazolyl, imidazolyl, isoxazolyl, oxazolyl, isothiazolyl, thiazolyl, triazolyl, oxadiazolyl, or thiadiazolyl;
wherein the alkyl portion of alkyl(heteroaryl) is optionally substituted with one or more substituents independently selected from the group consisting of D, halo, CN, NO$_2$, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl; and
wherein the pyrrolyl, pyrazolyl, imidazolyl, isoxazolyl, oxazolyl, isothiazolyl, thiazolyl, triazolyl, oxadiazolyl, or thiadiazolyl is optionally substituted with one or more substituents independently selected from the group consisting of D, halo, CN, NO$_2$, alkyl, haloalkyl, alkenyl, haloalkenyl, alkynyl, haloalkynyl, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, S(O)$_t$R$^a$, S(O)$_t$N(R$^a$)$_2$, S(O)$_t$OR$^a$, cycloalkyl, heterocycloalkyl, aryl, and heteroaryl.

14. The compound of claim 13, or a pharmaceutically acceptable salt, deuteroisotope, or stereoisomer thereof, wherein R$^1$ is alkyl(pyrazolyl);
  wherein the alkyl portion of alkyl(pyrazolyl) is optionally substituted with one or more substituents independently selected from the group consisting of D, halo, CN, NO$_2$, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl; and
  wherein the pyrazolyl is optionally substituted with one or more substituents independently selected from the group consisting of D, halo, CN, NO$_2$, alkyl, haloalkyl, alkenyl, haloalkenyl, alkynyl, haloalkynyl, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, S(O)$_t$R$^a$, S(O)$_t$N(R$^a$)$_2$, S(O)$_t$OR$^a$, cycloalkyl, heterocycloalkyl, aryl, and heteroaryl.

15. The compound of claim 13, or a pharmaceutically acceptable salt, deuteroisotope, or stereoisomer thereof, wherein R$^1$ is alkyl(pyrazolyl);
  wherein the alkyl portion of alkyl(pyrazolyl) is optionally substituted with one or more substituents independently selected from the group consisting of D, halo, CN, NO$_2$, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl; and
  wherein the pyrazolyl is optionally substituted with one or more independently selected C1-C5 alkyl substituents.

16. The compound of claim 1, or a pharmaceutically acceptable salt, deuteroisotope, or stereoisomer thereof, wherein R$^2$ is H.

17. The compound of claim 1, or a pharmaceutically acceptable salt, deuteroisotope, or stereoisomer thereof, wherein R$^2$ is C1-C5 alkyl, wherein the C1-C5 alkyl is optionally substituted with one or more substituents independently selected from the group consisting of D, halo, CN, NO$_2$, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl.

18. The compound of claim 17, or a pharmaceutically acceptable salt, deuteroisotope, or stereoisomer thereof, wherein R$^2$ is C1-C5 alkyl, wherein the C1-C2 alkyl is optionally substituted with one or more substituents independently selected from the group consisting of D, halo, CN, NO$_2$, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl.

19. The compound of claim 1, or a pharmaceutically acceptable salt, deuteroisotope, or stereoisomer thereof, wherein R$^2$ is C2-C5 alkynyl, wherein the C2-C5 alkynyl is optionally substituted with one or more substituents independently selected from the group consisting of D, halo, CN, NO$_2$, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl.

20. The compound of claim 1, or a pharmaceutically acceptable salt, deuteroisotope, or stereoisomer thereof, wherein R$^3$ is H.

21. The compound of claim 1, or a pharmaceutically acceptable salt, deuteroisotope, or stereoisomer thereof, wherein R$^2$ and R$^3$, taken together with the carbon atom to which they are attached, form a carbocyclyl or heterocyclyl, wherein the carbocyclyl or heterocyclyl is optionally substituted with one or more substituents independently selected from the group consisting of D, halogen, CN, NO$_2$, alkyl, haloalkyl, alkenyl, haloalkenyl, alkynyl, haloalkynyl, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl.

22. The compound of claim 1, or a pharmaceutically acceptable salt, deuteroisotope, or stereoisomer thereof, wherein R$^4$ is H.

23. The compound of claim 1, or a pharmaceutically acceptable salt, deuteroisotope, or stereoisomer thereof, wherein R$^4$ is C1-C5 alkyl, wherein the C1-C5 alkyl is optionally substituted with one or more substituents independently selected from the group consisting of D, halo, CN, NO$_2$, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl.

24. The compound of claim 1, or a pharmaceutically acceptable salt, deuteroisotope, or stereoisomer thereof, wherein:
  R$^4$ is C1-C5 alkyl, wherein the C1-C5 alkyl is optionally substituted with one or more substituents independently selected from the group consisting of D, halo, CN, NO$_2$, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl; and
  R$^5$ is C1-C5 alkyl, wherein the C1-C5 alkyl is optionally substituted with one or more substituents independently selected from the group consisting of D, halo, CN, NO$_2$, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl.

25. The compound of claim 1, or a pharmaceutically acceptable salt, deuteroisotope, or stereoisomer thereof, wherein any R$^4$ and R$^5$, taken together with the carbon atom to which they are attached, independently forms a carbocyclyl or heterocyclyl, wherein each carbocyclyl or heterocyclyl is optionally and independently substituted with one or more substituents independently selected from the group consisting of D, halo, CN, NO$_2$, alkyl, haloalkyl, alkenyl, haloalkenyl, alkynyl, haloalkynyl, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl.

26. The compound of claim 1, or a pharmaceutically acceptable salt, deuteroisotope, or stereoisomer thereof, wherein n is 1.

27. A pharmaceutical composition comprising a pharmaceutically acceptable excipient and a compound of claim 1, or a pharmaceutically acceptable salt, deuteroisotope, or stereoisomer thereof.

28. A compound having the structure of Formula (Ia):

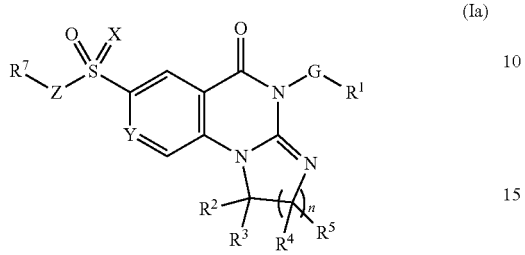

(Ia)

or a pharmaceutically acceptable salt, deuteroisotope, or stereoisomer thereof,
wherein:
Z is —NH—;
$R^7$ is alkyl, cycloalkyl, or 1,1'-bi(cyclopropan)-1-yl;
 wherein the alkyl is optionally substituted with one or more substituents independently selected from the group consisting of D, halo, CN, $NO_2$, C(O)$R^a$, C(O)N($R^a$)$_2$, C(O)O$R^a$, N($R^a$)$_2$, $NR^aC(O)R^a$, $NR^aC(O)OR^a$, $NR^aS(O)_tR^a$, O$R^a$, OC(O)$R^a$, OC(O)N($R^a$)$_2$, OC(O)O$R^a$, O$R^c$C(O)N($R^a$)$_2$, =O, S(O)$_t R^a$, S(O)$_t$N($R^a$)$_2$, S(O)$_t$O$R^a$, =S, cycloalkyl, heterocycloalkyl, aryl, and heteroaryl; and
 wherein the cycloalkyl or 1,1'-bi(cyclopropan)-1-yl is optionally substituted with one or more substituents independently selected from the group consisting of D, halo, CN, $NO_2$, alkyl, haloalkyl, alkenyl, haloalkenyl, alkynyl, haloalkynyl, C(O)$R^a$, C(O)N($R^a$)$_2$, C(O)O$R^a$, N($R^a$)$_2$, $NR^aC(O)R^a$, $NR^aC(O)OR^a$, $NR^aS(O)_tR^a$, O$R^a$, OC(O)$R^a$, OC(O)N($R^a$)$_2$, OC(O)O$R^a$, O$R^c$C(O)N($R^a$)$_2$, =O, S(O)$_t R^a$, S(O)$_t$N($R^a$)$_2$, S(O)$_t$O$R^a$, =S, cycloalkyl, heterocycloalkyl, aryl, and heteroaryl;
X is O;
Y is CH, CF, or N;
G is a bond, cycloalkylene, or heterocycloalkylene,
 wherein the cycloalkylene or heterocycloalkylene is optionally substituted with one or more substituents independently selected from the group consisting of D, halo, CN, $NO_2$, alkyl, haloalkyl, alkenyl, haloalkenyl, alkynyl, haloalkynyl, C(O)$R^a$, C(O)N($R^a$)$_2$, C(O)O$R^a$, N($R^a$)$_2$, $NR^aC(O)R^a$, $NR^aC(O)OR^a$, $NR^aS(O)_tR^a$, O$R^a$, OC(O)$R^a$, OC(O)N($R^a$)$_2$, OC(O)O$R^a$, O$R^c$C(O)N($R^a$)$_2$, =O, S(O)$_t R^a$, S(O)$_t$N($R^a$)$_2$, S(O)$_t$O$R^a$, =S, cycloalkyl, heterocycloalkyl, aryl, and heteroaryl;
$R^1$ is alkyl, alkyl(cycloalkyl), alkyl(heterocyclyl), aralkyl, alkyl(heteroaryl), alkenyl, or alkynyl;
 wherein the alkyl, alkyl portion of alkyl(cycloalkyl), alkyl portion of alkyl(heterocyclyl), alkyl portion of aralkyl, alkyl portion of alkyl(heteroaryl), alkenyl, or alkynyl is optionally substituted with one or more substituents independently selected from the group consisting of D, halo, CN, $NO_2$, C(O)$R^a$, C(O)N($R^a$)$_2$, C(O)O$R^a$, N($R^a$)$_2$, $NR^aC(O)R^a$, $NR^aC(O)OR^a$, $NR^aS(O)_tR^a$, O$R^a$, OC(O)$R^a$, OC(O)N($R^a$)$_2$, OC(O)O$R^a$, O$R^c$C(O)N($R^a$)$_2$, =O, S(O)$_t R^a$, S(O)$_t$N($R^a$)$_2$, S(O)$_t$O$R^a$, =S, cycloalkyl, heterocycloalkyl, aryl, and heteroaryl; and
 wherein the cycloalkyl portion of alkyl(cycloalkyl), heterocyclyl portion of alkyl(heterocyclyl), aryl portion of aralkyl, or heteroaryl portion of alkyl(heteroaryl) is optionally substituted with one or more substituents independently selected from the group consisting of D, halo, CN, $NO_2$, alkyl, haloalkyl, alkenyl, haloalkenyl, alkynyl, haloalkynyl, C(O)$R^a$, C(O)N($R^a$)$_2$, C(O)O$R^a$, N($R^a$)$_2$, $NR^aC(O)R^a$, $NR^aC(O)OR^a$, $NR^aS(O)_tR^a$, O$R^a$, OC(O)$R^a$, OC(O)N($R^a$)$_2$, OC(O)O$R^a$, O$R^c$C(O)N($R^a$)$_2$, =O, S(O)$_t R^a$, S(O)$_t$N($R^a$)$_2$, S(O)$_t$O$R^a$, =S, cycloalkyl, heterocycloalkyl, aryl, and heteroaryl;
$R^2$ is H, halo, CN, alkyl, alkyl(cycloalkyl), alkyl(heterocyclyl), alkenyl, alkynyl, alkynyl(cycloalkyl), OH, cycloalkyl, heterocyclyl, aryl, or heteroaryl;
 wherein the alkyl, alkyl portion of alkyl(cycloalkyl), alkyl portion of alkyl(heterocyclyl), alkenyl, alkynyl, or alkynyl portion of alkynyl(cycloalkyl) is optionally substituted with one or more substituents independently selected from the group consisting of D, halo, CN, $NO_2$, C(O)$R^a$, C(O)N($R^a$)$_2$, C(O)O$R^a$, N($R^a$)$_2$, $NR^aC(O)R^a$, $NR^aC(O)OR^a$, $NR^aS(O)_tR^a$, O$R^a$, OC(O)$R^a$, OC(O)N($R^a$)$_2$, OC(O)O$R^a$, O$R^c$C(O)N($R^a$)$_2$, =O, S(O)$_t R^a$, S(O)$_t$N($R^a$)$_2$, S(O)$_t$O$R^a$, =S, cycloalkyl, heterocycloalkyl, aryl, and heteroaryl; and
 wherein the cycloalkyl portion of alkyl(cycloalkyl), heterocyclyl portion of alkyl(heterocyclyl), cycloalkyl portion of alkynyl(cycloalkyl), cycloalkyl, heterocyclyl, aryl, or heteroaryl is optionally substituted with one or more substituents independently selected from the group consisting of D, halo, CN, $NO_2$, alkyl, haloalkyl, alkenyl, haloalkenyl, alkynyl, haloalkynyl, C(O)$R^a$, C(O)N($R^a$)$_2$, C(O)O$R^a$, N($R^a$)$_2$, $NR^aC(O)R^a$, $NR^aC(O)OR^a$, $NR^aS(O)_tR^a$, O$R^a$, OC(O)$R^a$, OC(O)N($R^a$)$_2$, OC(O)O$R^a$, O$R^c$C(O)N($R^a$)$_2$, =O, S(O)$_t R^a$, S(O)$_t$ N($R^a$)$_2$, S(O)$_t$O$R^a$, =S, cycloalkyl, heterocycloalkyl, aryl, and heteroaryl;
$R^3$ is H, halo, CN, alkyl, alkyl(cycloalkyl), alkyl(heterocyclyl), alkenyl, alkynyl, alkynyl(cycloalkyl), OH, cycloalkyl, heterocyclyl, aryl, or heteroaryl;
 wherein the alkyl, alkyl portion of alkyl(cycloalkyl), alkyl portion of alkyl(heterocyclyl), alkenyl, alkynyl, or alkynyl portion of alkynyl(cycloalkyl) is optionally substituted with one or more substituents independently selected from the group consisting of D, halo, CN, $NO_2$, C(O)$R^a$, C(O)N($R^a$)$_2$, C(O)O$R^a$, N($R^a$)$_2$, $NR^aC(O)R^a$, $NR^aC(O)OR^a$, $NR^aS(O)_tR^a$, O$R^a$, OC(O)$R^a$, OC(O)N($R^a$)$_2$, OC(O)O$R^a$, O$R^c$C(O)N($R^a$)$_2$, =O, S(O)$_t R^a$, S(O)$_t$N($R^a$)$_2$, S(O)$_t$O$R^a$, =S, cycloalkyl, heterocycloalkyl, aryl, and heteroaryl; and
 wherein the cycloalkyl portion of alkyl(cycloalkyl), heterocyclyl portion of alkyl(heterocyclyl), cycloalkyl portion of alkynyl(cycloalkyl), cycloalkyl, heterocyclyl, aryl, or heteroaryl is optionally substituted with one or more substituents independently selected from the group consisting of D, halo, CN, $NO_2$, alkyl, haloalkyl, alkenyl, haloalkenyl, alkynyl, haloalkynyl, C(O)$R^a$, C(O)N($R^a$)$_2$, C(O)O$R^a$, N($R^a$)$_2$, $NR^aC(O)R^a$, $NR^aC(O)OR^a$, $NR^aS(O)_tR^a$, O$R^a$, OC(O)$R^a$, OC(O)N($R^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl; or R$^2$ and R$^3$, taken together with the carbon atom to which they are attached, form a carbocyclyl or heterocyclyl, wherein the carbocyclyl or heterocyclyl is optionally substituted with one or more substituents independently selected from the group consisting of D, halo, CN, NO$_2$, alkyl, haloalkyl, alkenyl, haloalkenyl, alkynyl, haloalkynyl, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl;

R$^4$ is H, halo, CN, alkyl, alkyl(cycloalkyl), alkyl(heterocyclyl), alkenyl, alkynyl, alkynyl(cycloalkyl), OH, cycloalkyl, heterocyclyl, aryl, or heteroaryl;
wherein the alkyl, alkyl portion of alkyl(cycloalkyl), alkyl portion of alkyl(heterocyclyl), alkenyl, alkynyl, or alkynyl portion of alkynyl(cycloalkyl) is optionally substituted with one or more substituents independently selected from the group consisting of D, halo, CN, NO$_2$, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl; and
wherein the cycloalkyl portion of alkyl(cycloalkyl), heterocyclyl portion of alkyl(heterocyclyl), cycloalkyl portion of alkynyl(cycloalkyl), cycloalkyl, heterocyclyl, aryl, or heteroaryl is optionally substituted with one or more substituents independently selected from the group consisting of D, halo, CN, NO$_2$, alkyl, haloalkyl, alkenyl, haloalkenyl, alkynyl, haloalkynyl, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl;

R$^5$ is H, halo, CN, alkyl, alkyl(cycloalkyl), alkyl(heterocyclyl), alkenyl, alkynyl, alkynyl(cycloalkyl), OH, cycloalkyl, heterocyclyl, aryl, or heteroaryl;
wherein the alkyl, alkyl portion of alkyl(cycloalkyl), alkyl portion of alkyl(heterocyclyl), alkenyl, alkynyl, or alkynyl portion of alkynyl(cycloalkyl) is optionally substituted with one or more substituents independently selected from the group consisting of D, halo, CN, NO$_2$, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl; and
wherein the cycloalkyl portion of alkyl(cycloalkyl), heterocyclyl portion of alkyl(heterocyclyl), cycloalkyl portion of alkynyl(cycloalkyl), cycloalkyl, heterocyclyl, aryl, or heteroaryl is optionally substituted with one or more substituents independently selected from the group consisting of D, halo, CN, NO$_2$, alkyl, haloalkyl, alkenyl, haloalkenyl, alkynyl, haloalkynyl, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl; or any R$^4$ and R$^5$, taken together with the carbon atom to which they are attached, independently forms a carbocyclyl or heterocyclyl, wherein each carbocyclyl or heterocyclyl is optionally and independently substituted with one or more substituents independently selected from the group consisting of D, halo, CN, NO$_2$, alkyl, haloalkyl, alkenyl, haloalkenyl, alkynyl, haloalkynyl, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl; or R$^3$ and R$^4$, taken together with the carbon atom to which they are attached, form a carbocyclyl or heterocyclyl, wherein the carbocyclyl or heterocyclyl is optionally substituted with one or more substituents independently selected from the group consisting of D, halo, CN, NO$_2$, alkyl, haloalkyl, alkenyl, haloalkenyl, alkynyl, haloalkynyl, C(O)R$^a$, C(O)N(R$^a$)$_2$, C(O)OR$^a$, N(R$^a$)$_2$, NR$^a$C(O)R$^a$, NR$^a$C(O)OR$^a$, NR$^a$S(O)$_t$R$^a$, OR$^a$, OC(O)R$^a$, OC(O)N(R$^a$)$_2$, OC(O)OR$^a$, OR$^c$C(O)N(R$^a$)$_2$, =O, S(O)$_t$R$^a$, S(O)$_t$N(R$^a$)$_2$, S(O)$_t$OR$^a$, =S, cycloalkyl, heterocycloalkyl, aryl, and heteroaryl;

each R$^a$ is independently H, D, alkyl, alkyl(cycloalkyl), alkyl(heterocycloalkyl), aralkyl, alkyl(heteroaryl), cycloalkyl, heterocycloalkyl, aryl, or heteroaryl;

each R$^c$ is independently alkylene or alkenylene;

n is 1, 2, or 3; and each t is independently 1 or 2.

* * * * *

UNITED STATES PATENT AND TRADEMARK OFFICE
CERTIFICATE OF CORRECTION

PATENT NO. : 11,939,335 B2
APPLICATION NO. : 18/199900
DATED : March 26, 2024
INVENTOR(S) : Veal et al.

It is certified that error appears in the above-identified patent and that said Letters Patent is hereby corrected as shown below:

On the Title Page

Item (54) and in the Specification, Column 1; Lines 1-5; Title; delete: "IMIDAZO[1,2-A]QUINAZOLINES AND IMIDAZO[1,2-A]PYRIDO[4,3-E]PYRIMIDINES" and replace with -- IMIDAZO[1,2-$a$]QUINAZOLINES AND IMIDAZO[1,2-$a$]PYRIDO[4,3-$e$]PYRIMIDINES --

In the Claims

Column 163; Line 49; Claim 1, delete: "consisting of halo " and replace with: -- consisting of D, halo --

Column 164; Lines 3-4; Claim 1, delete: "CN, NO$_2$, alkyl, haloalkyl, alkenyl, haloalkenyl, alkynyl, haloalkynyl," and replace with: -- CN, NO$_2$, --

Column 167; Line 45; Claim 8, delete: "S(O)$_t$R$^a$, S(O)$_t$N(R$^a$)$_2$, S(O)$_t$(O)R$^a$," and replace with: -- =O, S(O)$_t$R$^a$, S(O)$_t$N(R$^a$)$_2$, S(O)$_t$(O)R$^a$, =S, --

Column 167; Line 66; Claim 9, delete: "S(O)$_t$R$^a$, S(O)$_t$N(R$^a$)$_2$, S(O)$_t$(O)R$^a$," and replace with: -- =O, S(O)$_t$R$^a$, S(O)$_t$N(R$^a$)$_2$, S(O)$_t$(O)R$^a$, =S, --

Column 168; Line 10; Claim 10, delete: "S(O)$_t$R$^a$, S(O)$_t$N(R$^a$)$_2$, S(O)$_t$(O)R$^a$," and replace with: -- =O, S(O)$_t$R$^a$, S(O)$_t$N(R$^a$)$_2$, S(O)$_t$(O)R$^a$, =S, --

Column 168; Line 21; Claim 11, delete: "S(O)$_t$R$^a$, S(O)$_t$N(R$^a$)$_2$, S(O)$_t$(O)R$^a$," and replace with: -- =O, S(O)$_t$R$^a$, S(O)$_t$N(R$^a$)$_2$, S(O)$_t$(O)R$^a$, =S, --

Column 168; Line 44; Claim 12, delete: "S(O)$_t$R$^a$, S(O)$_t$N(R$^a$)$_2$, S(O)$_t$(O)R$^a$," and replace with: -- =O, S(O)$_t$R$^a$, S(O)$_t$N(R$^a$)$_2$, S(O)$_t$(O)R$^a$, =S, --

Column 169; Lines 1-2; Claim 13, delete: "S(O)$_t$R$^a$, S(O)$_t$N(R$^a$)$_2$, S(O)$_t$(O)R$^a$," and replace with:

Signed and Sealed this
Ninth Day of July, 2024

Katherine Kelly Vidal
*Director of the United States Patent and Trademark Office*

-- =O, S(O)$_t$R$^a$, S(O)$_t$N(R$^a$)$_2$, S(O)$_t$(O)R$^a$, =S, --

Column 169; Lines 22-23; Claim 14, delete: "S(O)$_t$R$^a$, S(O)$_t$N(R$^a$)$_2$, S(O)$_t$(O)R$^a$," and replace with:
-- =O, S(O)$_t$R$^a$, S(O)$_t$N(R$^a$)$_2$, S(O)$_t$(O)R$^a$, =S, --

Column 169; Line 46; Claim 17, delete: "NO$_2$, C(O)R$^a$," and replace with: -- NO$_2$, alkyl, haloalkyl, alkenyl, haloalkenyl, alkynyl, haloalkynyl, C(O)R$^a$, --

Column 169; Line 53; Claim 18, delete: "R$^2$ is C1-C5 alkyl" and replace with: -- R$^2$ is C1-C2 alkyl --

Column 169; Line 56; Claim 18, delete: "NO$_2$, C(O)R$^a$," and replace with: -- NO$_2$, alkyl, haloalkyl, alkenyl, haloalkenyl, alkynyl, haloalkynyl, C(O)R$^a$, --

Column 169; Line 66; Claim 19, delete: "NO$_2$, C(O)R$^a$," and replace with: -- NO$_2$, alkyl, haloalkyl, alkenyl, haloalkenyl, alkynyl, haloalkynyl, C(O)R$^a$, --

Column 170; Line 28; Claim 23, delete: "NO$_2$, C(O)R$^a$," and replace with: -- NO$_2$, alkyl, haloalkyl, alkenyl, haloalkenyl, alkynyl, haloalkynyl, C(O)R$^a$, --

Column 170; Line 39; Claim 24, delete: "NO$_2$, C(O)R$^a$," and replace with: -- NO$_2$, alkyl, haloalkyl, alkenyl, haloalkenyl, alkynyl, haloalkynyl, C(O)R$^a$, --

Column 170; Line 47; Claim 24, delete: "NO$_2$, C(O)R$^a$," and replace with: -- NO$_2$, alkyl, haloalkyl, alkenyl, haloalkenyl, alkynyl, haloalkynyl, C(O)R$^a$, --

Column 171; Lines 50-51; Claim 28, delete: "NO$_2$, alkyl, haloalkyl, alkenyl, haloalkenyl, alkynyl, haloalkynyl, C(O)R$^a$," and replace with: -- NO$_2$, C(O)R$^a$, --